US009181330B2

(12) United States Patent
Marks et al.

(10) Patent No.: US 9,181,330 B2
(45) Date of Patent: Nov. 10, 2015

(54) THERAPEUTIC MONOCLONAL ANTIBODIES THAT NEUTRALIZE BOTULINUM NEUROTOXINS

(71) Applicant: The Regents of the University of California, Oakland, CA (US)

(72) Inventors: James D. Marks, Kensington, CA (US); Maria Consuelo Garcia, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/035,619

(22) Filed: Sep. 24, 2013

(65) Prior Publication Data

US 2014/0105910 A1    Apr. 17, 2014

Related U.S. Application Data

(63) Continuation of application No. 12/528,601, filed as application No. PCT/US2008/003767 on Mar. 21, 2008, now Pat. No. 8,598,321.

(60) Provisional application No. 60/942,173, filed on Jun. 5, 2007, provisional application No. 60/896,332, filed on Mar. 22, 2007.

(51) Int. Cl.
C07K 16/12 (2006.01)

(52) U.S. Cl.
CPC ......... *C07K 16/1282* (2013.01); *C07K 2316/96* (2013.01); *C07K 2317/21* (2013.01); *C07K 2317/56* (2013.01); *C07K 2317/565* (2013.01); *C07K 2317/622* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,689,299 A | 8/1987 | Insel et al. | |
| 5,231,003 A | 7/1993 | Coughlin et al. | |
| 5,306,730 A | 4/1994 | Nagai et al. | |
| 5,599,539 A | 2/1997 | Carroll et al. | |
| 5,719,267 A | 2/1998 | Carroll et al. | |
| 5,731,161 A | 3/1998 | Aoki et al. | |
| 5,807,741 A | 9/1998 | Brown et al. | |
| 5,919,665 A | 7/1999 | Williams | |
| 5,932,449 A | 8/1999 | Emanuel et al. | |
| 6,331,402 B1 | 12/2001 | Nussbaum et al. | |
| 6,416,947 B1 | 7/2002 | Balasubramanian et al. | |
| 6,461,617 B1 | 10/2002 | Shone et al. | |
| 6,495,143 B2 | 12/2002 | Lee et al. | |
| 6,656,468 B1 | 12/2003 | Carroll et al. | |
| 6,667,158 B1 | 12/2003 | Bavari et al. | |
| 6,730,324 B2 | 5/2004 | Troczynski et al. | |
| 6,762,280 B2 | 7/2004 | Schmidt et al. | |
| 6,794,128 B2 | 9/2004 | Marks et al. | |
| 6,841,156 B2 | 1/2005 | Aoki et al. | |
| 6,932,449 B2 | 8/2005 | Collins et al. | |
| 7,049,085 B2 | 5/2006 | Bavari et al. | |
| 7,081,529 B2 | 7/2006 | Smith et al. | |
| 7,157,562 B1 | 1/2007 | Olsen, II et al. | |
| 7,192,596 B2 | 3/2007 | Shone et al. | |
| 7,214,787 B1 | 5/2007 | Smith et al. | |
| 7,244,826 B1 | 7/2007 | Marks et al. | |
| 7,332,580 B2 | 2/2008 | Adams et al. | |
| 7,332,585 B2 | 2/2008 | Adams et al. | |
| 7,341,843 B2 | 3/2008 | Atassi | |
| 7,563,874 B2 | 7/2009 | Marks et al. | |
| 7,700,738 B2 | 4/2010 | Marks et al. | |
| 7,999,079 B2 | 8/2011 | Marks et al. | |
| 8,198,034 B2 | 6/2012 | Fernandez-Salas et al. | |
| 8,263,747 B2 | 9/2012 | Marks et al. | |
| 8,299,218 B2 | 10/2012 | Marks et al. | |
| 8,329,873 B2 | 12/2012 | Adams et al. | |
| 8,476,024 B2 | 7/2013 | Mahrhold et al. | |
| 8,598,321 B2 | 12/2013 | Marks et al. | |
| 8,618,261 B2 * | 12/2013 | Ester et al. | 530/387.1 |
| 9,000,131 B2 * | 4/2015 | Marks et al. | 530/388.15 |
| 9,023,352 B2 * | 5/2015 | Shoemaker et al. | 424/133.1 |
| 2004/0009172 A1 | 1/2004 | Fischkoff et al. | |
| 2004/0137601 A1 | 7/2004 | Von Eichel-Streiber et al. | |
| 2004/0265935 A1 | 12/2004 | Atassi | |
| 2005/0147610 A1 | 7/2005 | Ghayur et al. | |
| 2006/0147471 A1 | 7/2006 | Borodic et al. | |

(Continued)

FOREIGN PATENT DOCUMENTS

| | | |
|---|---|---|
| EP | 0578515 | 1/1994 |
| WO | WO 9410332 | 5/1994 |

(Continued)

OTHER PUBLICATIONS

Przedpelski, Amanda, et al., "Ehancing the Protective Immune Response against Botulism", Infection and Immunity, 2013, 81(7):2638-2644.

Zhang, Yanfeng, et al., "Simultaneous and sensitive detection of six serotypes of botulinum neurotoxin using enzyme-linked immunosorbent assay-based protein antibody microarrays", Analytical Biochemistry, 2012, 430:185-192.

Arnon (1993) "Clinical Trial of Human Botulism" *Botulinum and Tetanus Neurotoxins: Neurotransmission and Biomedical Aspects*, ed. DasGupta, B. R. Plenum, New York., pp. 477-482.

Arnon et al. (2001) "Botulinum toxin as a biological weapon: medical and public health management" *JAMA* 285(8):1059-1070.

(Continued)

*Primary Examiner* — Nita M Minnifield
(74) *Attorney, Agent, or Firm* — Carl L. Francis; Bozicevic, Field & Francis LLP

(57) ABSTRACT

This invention provides antibodies that specifically bind to and typically neutralize *botulinum* neurotoxins (e.g., BoNT/A, BoNT/B, BoNT/E, etc.) and the epitopes bound by those antibodies. The antibodies and derivatives thereof and/or other antibodies that specifically bind to the neutralizing epitopes provided herein can be used to neutralize *botulinum* neurotoxin and are therefore also useful in the treatment of botulism.

25 Claims, 8 Drawing Sheets

(56) References Cited

U.S. PATENT DOCUMENTS

| | | |
|---|---|---|
| 2006/0177881 A1 | 8/2006 | Bavari et al. |
| 2006/0246071 A1 | 11/2006 | Green et al. |
| 2006/0251658 A1 | 11/2006 | Ledbetter et al. |
| 2008/0125328 A1 | 5/2008 | Wyrick et al. |
| 2010/0222555 A1 | 9/2010 | Dessain et al. |
| 2011/0059079 A1 | 3/2011 | Babuka et al. |
| 2011/0200615 A1 | 8/2011 | Marks et al. |
| 2012/0121581 A1 | 5/2012 | Babuka et al. |
| 2012/0177663 A1 | 7/2012 | Marks et al. |
| 2012/0225436 A1 | 9/2012 | Fernandez-Salas et al. |
| 2012/0269822 A1 | 10/2012 | Marks et al. |
| 2013/0040368 A1 | 2/2013 | Fernandez-Salas et al. |
| 2015/0030600 A1* | 1/2015 | Marks et al. ............... 424/139.1 |

FOREIGN PATENT DOCUMENTS

| | | |
|---|---|---|
| WO | WO 9625669 | 8/1996 |
| WO | WO 9956129 | 11/1999 |
| WO | WO 0069891 | 11/2000 |
| WO | WO 0069895 | 11/2000 |
| WO | WO 0119992 | 3/2001 |
| WO | WO 03057857 | 7/2003 |
| WO | WO 2004106376 | 12/2004 |
| WO | WO 2005084361 | 9/2005 |
| WO | WO 2005118635 | 12/2005 |
| WO | WO 2008097866 | 8/2008 |
| WO | WO 2009105150 | 8/2009 |
| WO | WO 2009131605 | 10/2009 |
| WO | WO 2011028961 | 3/2011 |
| WO | WO 2011028962 | 3/2011 |
| WO | 2012047427 | 4/2012 |

OTHER PUBLICATIONS

Black & Gunn (1980) "Hypersensitivity reactions associated with botulinal antitoxin" *Am. J. Med.* 69(4): 567-570.

Franz, et al. (1993) "Efficacy of Prophylactic and Therapeutic Administration of Antitoxin for Inhalation Botulism" *Botulinum and Tetanus Neurotoxins: Neurotransmission and Biomedical Aspects*, ed. DasGupta, B. R. Plenum, New York., pp. 473-476.

Hatheway (1995) "Botulism: the present status of the disease" *Curr Top. Microbiol. Immunol*, 195:55-75.

Hibbs, et al. (1996) "Experience with the use of an investigational F(ab')2 heptavalent botulism immune globulin of equine origin during an outbreak of type E botulism in Egypt" *Clin. Infect. Dis.* 23(2):337-340.

Kozaki, et al. (1998) "Characterization of *Clostridium botulinum* type B neurotoxin associated with infant botulism in japan" *Infect. Immun.* 66(10):4811-4816.

Lacy & Stevens (1999) "Sequence homology and structural analysis of the clostridial neurotoxins" *J. Mol. Biol.* 291 (5): 1091-1104.

Middlebrook & Franz (1997) "Botulinum Toxins" *Medical Aspects of Chemical and Biological Warfare* Ed. Sidell, et al. TMM publications, Washington, D.C., Chapter 33, pp. 643-654.

Siegel (1988) "Human immune response to botulinum pentavalent (ABCDE) toxoid determined by a neutralization test and by an enzyme-linked immunosorbent assay" *J Clin. Microbiol.* 26(11):2351-2356.

Sonnabend, et al. (1981) "Isolation of *Clostridium botulinum* type G and identification of type G botulinal toxin in humans: report of five sudden unexpected deaths" *J. Infect. Dis.* 143(1):22-27.

U.S. Appl. No. 13/614,771, filed Sep. 13, 2012, Marks, et al.

U.S. Appl. No. 13/813,623, filed Aug. 9, 2013, Marks, et al.

Paul, Wlilliam, E., (1993), "Fundamental Immunology", Raven Press, 9:292-295.

Almquist, et al. (2006) "Expression of an anti-botulinum toxin A neutralizing single-chain Fv recombinant antibody in transgenic tobacco" *Vaccine* 24(12):2079-2086.

Amersdorfer & Marks (2000) "Phage libraries for generation of anti-botulinum scFv antibodies" *Meth. Mol. Biol.* 145:219-240.

Amersdorfer (1997) "Molecular Characterization of Murine Humoral Immune Response to Botulinum Neurotoxin Type A Binding Domain as Assessed by Using Phage Antibody Libraries" *Infect. Immun.* 65(9):3743-3752.

Amersdorfer, et al. (2002) "Genetic and Immunological Comparison of Anti-Botulinum Type A Antibodies from Immune and Non-Immune Human Phage Libraries" *Vaccine* 20(11-12):1640-1648.

Arndt, et al. (2005) "The structure of the neurotoxin-associated protein HA33/A from *Clostridium botulinum* suggests a reoccurring beta-trefoil fold in the progenitor toxin complex" *J. Mol. Biol.* 346(4):1083-1093.

Atassi, et al. (1996) "Mapping of the Antibody-Binding Regions on Botulinum Neurotoxin H-Chain Domain 855-1296 with Antitoxin Antibodies from Three Host Species" *J. Protein Chem.* 15(7):691-699.

Baldwin, et al. (2005) "Characterization of the antibody response to the receptor binding domain of botulinum neurotoxin serotypes A and E" *Infect. Immun.* 73(10): 6998-7005.

Bartels et al. (1994) "Specific Antibodies against the Zn(2+)-Binding Domain of Clostridial Neurotoxins Restore Exocytosis in Chromaffin Cells Treated with Tetanus or Botulinum A Neurotoxin" *J Biol Chem* 269(11):8122-8127.

Bavari, et al. (1998) "Identifying the principal protective antigenic determinants of type A botulinum neurotoxin" *Vaccine* 16(19):1850-1856.

Bendig (1995) "Humanization of Rodent Monoclonal Antibodies by CDR Grafting" *METHODS: Companion to Methods in Enzymology* 8:83-93.

Berzofsky, et al. (1993) "Immunogenicity and Antigen Structure" *Fundamental Immunology* 3rd edition, Ed. William E. Paul, Chapter 8, p. 242.

Black & Dolly (1986) "Interaction of 125I-labeled botulinum neurotoxins with nerve terminals. I. Ultrastructural autoradiographic localization and quantitation of distinct membrane acceptors for types A and B on motor nerves" *J. Cell Biol.* 103(2):521-534.

Boder, et al. (2000) "Directed Evolution of Antibody Fragments withMonovalent Femtomolar Antigen-Binding Affinity" *PNAS USA* 97(20):10701-10705.

Boles, et al. (2006) "Recombinant C Fragment of Botulinum Neurotoxin B Serotype (rBoNTB (HC)) Immune Response and Protection in the Rhesus Monkey" *Toxicon* 47(8):877-884.

Bowmer (1963) "Preparation and Assay of the International Standards for *Clostridium botulinum* Types A, B, C, D and E Antitoxins" *Bull. World Health Organ.* 29:701-709.

Brown, et al. (1997) "Identification and Characterization of a Neutralizing Monoclonal Antibody against Botulinum Neurotoxin Serotype F, Following Vaccination with Active Toxin" *Hybridoma* 16(5):447-456.

Byrne & Smith (2000) "Development of vaccines for prevention of botulism" *Biochimie* 82(9-10): 955-966.

Casset, et al. (2003) "A peptide mimetic of an anti-CD4 monoclonal antibody by rational design" *Biochem Biophys. Res Comm.* 307(1): 198-205.

Caton, et al. (1986) "Structural and functional implications of a restricted antibody response to a defined antigenic region on the influenza virus hemagglutinin" *EMBO J.* 5(7):1577-1587.

Cenci Di Bello, et al. (1994) "Antagonism of the Intracellular Action of Botulinum Neurotoxin Type A with Monoclonal Antibodies That Map to Light-Chain Epitopes" *Eur. J. Biochem.* 219(1-2):161-169.

Chen, et al. (1997) "Antibody Mapping to Domains of Botulinum Neurotoxin Serotype A in the Complexed and Uncomplexed Forms" *Infect. Immun.* 65(5):1626-1630.

Chen, et al. (1998) "Biophysical characterization of the stability of the 150-kilodalton botulinum toxin, the nontoxic component, and the 900-kilodalton botulinum toxin complex species" *Infect. Immun.* 66(6):2420-2425.

Colcher et al. (1990) "In vivo tumor targeting of a recombinant single-chain antigen-binding protein" *J. Natl. Cancer Inst.* 82(14):1191-1197.

Coleman et al. (2004) "Methods: Recombinant DNA Technology" *FASEB Journal* 18(8):Suppl. S:C174, Meeting abstract, Abstract Only.

(56) References Cited

OTHER PUBLICATIONS

Colman (1994) "Effects of Amino Acid Sequence Changes on Antibody-Antigen Interactions" *Res. Immunol.* 145(1):33-36.
Daniels-Holgate & Dolly (1996) "Productive and non-productive binding of botulinum neurotoxin A to motor nerve endings are distinguished by its heavy chain" *J. Neurosci. Res.* 44(3):263-271.
Dixit et al. (2005) "Characterization of *Clostridium sp.* RKD producing botulinum-like Neurotoxin" *Syst. Appl. Microbiol.* 28(5):405-414.
Dixit et al. (2006) Development of an immunodetection test for a botulinum-like neurotoxin produced by *Clostridium sp. Indian J Med Res.* 124(3):355-362.
Doellgast, et al. (1993) "Sensitive enzyme-linked immunosorbent assay for detection of *Clostridium botulinum* neurotoxins A, B, and E using signal amplification via enzyme-linked coagulation assay" *J. Clin. Microbiol.* 31(9):2402-2409.
Doellgast, et al. (1997) "Sensitive assay for measurement of antibodies to *Clostridium botulinum* neurotoxins A, B, and E: use of hapten-labeled-antibody elution to isolate specific complexes" *J. Clin. Microbiol.* 35(3):578-583.
Dolimbek, et al. (2008) "Immune recognition of botulinum neurotoxin B: Antibody binding regions on the heavy chain of the toxin" *Mol. Immunol.* 45(4):910-924.
Dolly, et al. (1984) "Acceptors for botulinum neurotoxin reside on motor nerve terminals and mediate its internalization" *Nature (London)* 307(5950):457-460.
Dong et al. (2010) "A Single-Domain Llama Antibody Potently Inhibits the Enzymatic Activity of Botulinum Neurotoxin by Binding to the Non-Catalytic Alpha-Exosite Binding Region" *J Mol Biol* 397(4):1106-1118.
Emanuel, et al. (1996) "Directing antigen specificity towards botulinum neurotoxin with combinatorial phage display libraries" *J. Immunol. Meth.* 193(2):189-197.
Emanuel, et al. (2000) "Recombinant antibodies: a new reagent for biological agent detection" *Biosen. Bioelectron.* 14(10-11):751-759.
Ferreira, et al. (1987) "Monoclonal Antibody for the Detection of *Clostridium botulinum* Type A toxin" *Mol. Cell Probes* 1(4):337-345.
Ferreira, et al. (1990) "Monoclonal antibody to type F *Clostridium botulinum* toxin" *Appl. Environ Microbiol.* 56(3):808-811.
Fitzsimmons, et al. (2000) "Inhibition of tetanus toxin fragment C binding to ganglioside G(T1b) by monoclonal antibodies recognizing different epitopes" *Vaccine* 19(1):114-121.
Foote & Milstein (1991) "Kinetic maturation of an immune response" *Nature* 352(6335):530-532.
Fotinou, et al. (2001) "The crystal structure of tetanus toxin Hc fragment complexed with a synthetic GT1b analogue suggests cross-linking between ganglioside receptors and the toxin" *J. Biol. Chem.* 276(34):32274-32281.
Garcia-Rodriguez, et al. (2007) "Molecular evolution of antibody specificity and cross reactivity for type A botulinum neurotoxins" *Nature Biotech.* 25(1):107-116.
Gibson, et al. (1988) "Evaluation of a monoclonal antibody-based immunoassay for detecting type B *Clostridium botulinum* toxin produced in pure culture and an inoculated model cured meat system" *J. Appl. Bacterial.* 64(4):285-291.
Gill (1982) "Bacterial Toxins: A Table of Lethal Amounts" *Mol. Biol. Rev.* 46(1):86-94.
Gilsdorf et al. (2006) "Expression Purification, and Characterization of *Clostridium Botulinum* Type B Light Chain" *Protein Expr Purif* 46(2):256-267.
Goldman et al. (2008) "Thermostable Llama Single Domain Antibodies for Detection of Botulinum A Neurotoxin Complex" *Anal Chem* 80(22):8583-8591.
Gonzales, et al. (2005) "Minimizing the Immunogenicity of Antibodies for Clinical Application" *Tumour Biol.* 26(1):31-43.
Hall (2004) "Novel Application of an In Vitro Technique to the Detection and Quantification of Botulinum Neurotoxin Antibodies" *J. Immunol. Methods* 288(1-2):55-60.
Hallis, et al. (1993) "Characterization of Monoclonal Antibodies to Botulinum" *Botulinum and Tetanus Neurotoxins: Neurotransmission and Biomedical Aspects,* ed. DasGupta, B. R. Plenum, New York., pp. 433-436.
Hathaway, et al. (1984) "Antitoxin levels in botulism patients treated with trivalent equine botulism antitoxin to toxin types A, B, and E" *J. Infect. Dis.* 150(3):407-412.
Hatheway & Dang (1994) "Immunogenicity of the Neurotoxins of *Clostridium botulinum*" *Therapy with Botulinum Toxin* ed. Jankovic & Hallet, Marcel Dekker, New York, pp. 93-107.
Hildebrand & Archer (1961) "Evidence Concerning Liquid Structure" *PNAS USA* 47(12):1881-1882.
Hildebrand, et al. (1961) "Distribution and Particle Size of Type A Botulinum Toxin in Body Fluids of Intravenously Injected Rabbits" *Proc. Soc. Exp. Biol. Med.* 107(2):284-289.
Huston, et al. (1996) "Single-chain Fv radioimmunotargeting" *Q. J. Nucl. Med.* 40(3):320-333.
Jung & Plückthun (1997) "Improving In Vivo Folding and Stability of a Single-Chain Fv Antibody Fragment by Loop Grafting" *Protein Eng.* 10(8):959-66.
Koriazova & Montal (2003) "Translocation of botulinum neurotoxin light chain protease through the heavy chain channel" *Nat. Struct. Biol.* 10(1):13-18.
Kozaki, et al. (1986) "The use of monoclonal antibodies to analyze the structure of *Clostridium botulinum* type E derivative toxin" *Infect Immun.* 52(3):786-791.
Kozaki, et al. (1995) "Immunological characterization of the neurotoxin produced by *Clostridium botulinum* type A associated with infant botulism in Japan" *Microbiol. Immunol.* 39(10):767-774.
Lacy, et al. (1998) "Crystal structure of botulinum neurotoxin type A and implications for toxicity" *Nat. Struct. Biol.* 5(10): 898-902.
Lang, et al. (1993) "Immunotherapy with human monoclonal antibodies. Fragment A specificity of polyclonal and monoclonal antibodies is crucial for full protection against tetanus toxin" *J. Immunol.* 151(13):466-472.
Lebecque & Gearhart (1990) "Boundaries of somatic mutation in rearranged immunoglobulin genes: 5' boundary is near the promoter, and 3' boundary is approximately 1 kb from V(D)J gene" *J. Exp. Med.* 172(6):1717-1727.
Lee et al. (2008) "Production and characterization of monoclonal antibody to botulinum neurotoxin type B light chain by phage display" *Hybridoma (Larchmt)* 27(1):18-24.
Levy, et al. (1989) "Early onset of somatic mutation in immunoglobulin VH genes during the primary immune response" *J. Exp. Med.* 169(6):2007-2019.
Levy, et al. (2007) "Fine and domain-level epitope mapping of botulinum neurotoxin type A neutralizing antibodies by yeast surface display" *J. Mol. Biol.* 365(1):196-210.
Lipps & Khan (2000) "Antigenic cross reactivity among the venoms and toxins from unrelated diverse sources" *Toxicon.* 38(7):973-980.
Liu et al. (2007) "Isolation of Anti-Toxin Single Domain Antibodies from a Semi-Synthetic Spiny Dogfish Shark Display Library" *BMC Biotechnol* 7:78.
MacCallum, et al. (1996) "Antibody-antigen Interactions: Contact Analysis and Binding Site Topography" *J. Mol. Biol.* 262(5):732-45.
Mah, et al. (2003) "Recombinant anti-botulinum neurotoxin A single-chain variable fragment antibody generated using a phage display system" *Hybrid Hybridomics.* 22(5):277-283.
Mahant, et al. (2000) "The current use of botulinum toxin" *J. Clin. Neurosci.* 7(5):389-394.
Marchev & Marcheva (1982) "[Production of MonoSpecific Type A Botulinum Toxin and Antiserum Using a Column Chromatographic Method]" *Vet. Med. Nauki.* 19(1):57-63.
Marks (2004) "Deciphering antibody properties that lead to potent botulinum neurotoxin neutralization" *Mov. Disord.* 19(Suppl. 8):S101-S108.
McHeyzer-Williams (1993) "B Lymphocyte Biology" *Fundamental Immunology,* 3rd Edition, Ed. William E. Paul Raven Press: NY, Chapter 9, pp. 292-295.
McKean, et al. (1978) "Mechanisms of antibody diversity: multiple genes encode structurally related mouse κ variable regions" *PNAS USA* 75(8):3913-3917.

(56) References Cited

OTHER PUBLICATIONS

Meng et al. (2012) "Engineered domain-based assays to identify individual antibodies in oligoclonal combinations targeting the same protein" *Anal Biochem* 430(2):141-150.

Middlebrook & Brown (1995) "Immunodiagnosis and immunotherapy of tetanus and botulinum neurotoxins" *Curr. Top. Microbiol. Immunol.* 195:89-122.

Montecucco & Schiavo (1995) "Structure and function of tetanus and botulinum neurotoxins" *Q. Rev. Biophys.* 28(4):423-472.

Montecucco (1986) "How do Tetanus and Botulinum Toxins Bind to Neuronal Membranes?" *Trends Biochem. Sci.* 11(8):314-317.

Montero-Julian, et al. (1995) "Pharmacokinetic study of anti-interleukin-6 (IL-6) therapy with monoclonal antibodies: enhancement of IL-6 clearance by cocktails of anti-IL-6 antibodies" *Blood* 85(4): 917-924.

Mowry, et al. (2004) "Production and purification of a chimeric monoclonal antibody against botulinum neurotoxin serotype A" *Protein Expr. Purif.* 37(2):399-408.

Mullaney, et al. (2001) "Epitope Mapping of Neutralizing Botulinum Neurotoxin A Antibodies by Ohage Display" *Infect. Immun.* 69(10):6511-6514.

Noah, et al. (1995) "Production of Monoclonal Antibodies Specific to *Clostridium botulinum* Type B Neurotoxin" *J. AOAC Int.* 78(2):381-385.

Nowakowski, et al. (2002) "Potent Neutralization of Botulinum Neurotoxin by Recombinant Oligoclonal Antibody" *PNAS USA* 99(17):11346-11350.

O'Connell, et al. (2007) "Production of a recombinant antibody fragment in whole insect larvae" *Mol Biotechnol.* 36(1): 44-51.

Oguma et al. (1990) "Infant botulism due to *Clostridium botulinum* type C toxin" *Lancet* 336(8728):1449-1450.

Oguma, et al. (1982) "Four different monoclonal antibodies against type C1 toxin of *Clostridium botulinum*" *Infect. Immun.* 38(1):14-20.

Oguma, et al. (1984) "Analysis of antigenicity of *Clostridium botulinum* type C1 and D toxins by polyclonal and monoclonal antibodies" *Infect Immun.* 43(2):584-588.

Oshima (1997) "Immune Recognition of Botulinum Neurotoxin Type A: Regions Recognized by T cells and Antibodies against the Protective H(C) Fragment (residues 855-1296) of Toxin" *Mol. Immunol.* 34(14):1031-1040.

Padlan et al. (1989) "Structure of an antibody-antigen complex: crystal structure of the HyHEL-10 Fab-lysozyme complex" *Proc Natl Acad Sci USA* 86:5938-5942.

Palys, et al. (2006) "Conversion of a mouse Fab into a whole humanized IgG antibody for detecting botulinum toxin" *Hum Antibodies* 15(4):125-132.

Park, et al. (2003) "Immunologic characterization of spasmodic dysphonia patients who develop resistance to botulinum toxin" *J. Voice.* 17(2):255-264.

Pless, et al. (2001) "High-affinity, protective antibodies to the binding domain of botulinum neurotoxin type A" *Infect. Immun.* 69(1):570-574.

Razai, et al. (2005) "Molecular evolution of antibody affinity for sensitive detection and neutralization of botulinum neurotoxin type A" *J. Mol. Biol.* 351(1):158-169.

Reichert (2001) "Monoclonal antibodies in the clinic" *Nat. Biotechnol.* 19(9):819-822.

Rudikoff, et al. (1982) "Single Amino Acid Substitution Altering Antigen-Binding Specificity" *PNAS USA* 79(6):1979-1983.

Schengrund (1999) "What is the Cell Surface Receptor(s) for the Different Serotypes of Botulinum Neurotoxin?" *J Toxicol.—Toxin Rev.* 18(1):35-44.

Schiavo, et al. (1992) "Tetanus and botulinum-B neurotoxins block neurotransmitter release by proteolytic cleavage of synaptobrevin" *Nature (London)* 359(6398):832-835.

Schiavo, et al. (1993) "Identification of the nerve terminal targets of botulinum neurotoxin serotypes A, D, and E" *J. Biol. Chem.* 268(32):23784-23787.

Schier, et al. (1995) "In vitro and in vivo characterization of a human anti-c-erbB-2 single-chain Fv isolated from a filamentous phage antibody library" *Immunotechnology*, 1(1):73-81.

Schier, et al. (1996) "Isolation of picomolar affinity anti-c-erbB-2 single-chain Fv by molecular evolution of the complementarity determining regions in the center of the antibody binding site" *J. Mol. Biol.* 263(4):551-567.

Schmidt & Stafford (2005) "Botulinum neurotoxin serotype F: identification of substrate recognition requirements and development of inhibitors with low nanomolar affinity" *Biochemistry* 44(10):4067-4073.

Scotcher, et al. (2009) "Characterization of the Epitope Region of F1-2 and F1-5, Two Monoclonal Antibodies to Botulinum Neurotoxin Type A" *Hybridoma* 28(5):315-325.

Sharma, et al. (2006) "Detection of type A, B, E, and F *Clostridium botulinum* neurotoxins in foods by using an amplified enzyme-linked immunosorbent assay with digoxigenin-labeled antibodies" *Appl Environ. Microbiol.* 72(2): 1231-1238.

Shone, et al. (1985) "Monoclonal antibody-based immunoassay for type A *Clostridium botulinum* toxin is comparable to the mouse bioassay" *Appl Environ Microbiol.* 50(1):63-67.

Simpson (1980) "Kinetic studies on the interaction between botulinum toxin type A and the cholinergic neuromuscular junction" *J. Pharmacol. Exp. Ther.* 212(1):16-21.

Smith, et al. (2005) "Sequence variation within botulinum neurotoxin serotypes impacts antibody binding and neutralization" *Infect. Immun.* 73(9):5450-5457.

Stark & Caton (1991) "Antibodies that are specific for a single amino acid interchange in a protein epitope use structurally distinct variable regions" *J. Exp. Med.* 174(3):613-624.

Swaminathan & Eswaramoorthy (2000) "Structural Analysis of the Catalytic and Binding Sites of Clostridium Botulinum Neurotoxin B" *Nat Struct Biol* 7(8):693-699.

Tacket et al. (1984) "Equine antitoxin use and other factors that predict outcome in type A foodborne botulism" *Am. J. Med.* 76(5):794-798.

Thanongsaksrikul et al. (2010) "A V H H That Neutralizes the Zinc Metalloproteinase Activity of Botulinum Neurotoxin Type A" *J Biol Chem* 285(13):9657-9666.

Tsuzuki, et al. (1988) "Establishment of a monoclonal antibody recognizing an antigenic site common to *Clostridium botulinum* type B, C1, D, and E toxins and tetanus toxin" *Infect Immun.* 56(4):898-902.

Volk, et al. (1984) "Neutralization of tetanus toxin by distinct monoclonal antibodies binding to multiple epitopes on the toxin molecule" *Infect. Immun.* 45(3):604-609.

Weigert, et al. (1978) "Rearrangement of genetic information may produce immunoglobulin diversity" *Nature* 276(5690):785-790.

Williams, et al. (1983) "Radioiodination of botulinum neurotoxin type A with retention of biological activity and its binding to brain synaptosomes" *Eur. J Biochem.*, 131(2):437-445.

Wu, et al. (2001) "Characterization of neutralizing antibodies and identification of neutralizing epitope mimics on the *Clostridium botulinum* neurotoxin type A" *Appl. Environ. Microbiol.* 67(7):3201-3207.

Yang et al. (2004) "Isolation and characterization of a neutralizing antibody specific to internalization domain of *Clostridium botulinum* neurotoxin type B" *Toxicon* 44(1):19-25.

Zwick, et al. (2001) "Neutralization synergy of human immunodeficiency virus type 1 primary isolates by cocktails of broadly neutralizing antibodies" *J. Virol.* 75(24):12198-12208.

Gessler, Frank, et al., (2005), "Sensitive Detection of Botulinum Neurotoxin Types C and D with an Immunoaffinity Chromatographic Column Test", Applied and Environmental Microbiology, 71(12):7897-7903.

Garcia, et al., (2013), "Human monoclonal antibodies binding botulinum neurotoxin types C, D, and mosaic neurotoxins C-D and D-C", Abstracts Toxins 2011 / Toxicon 68, 86-87, abstract only.

Lou, et al., (2015), "Human antibody engineering for prevention and treatment of botulinum neurotixin (BONT) intoxication", Abstracts / Toxicon 93 S40-S41, Abstract #131.

* cited by examiner

Deduced protein sequences of heavy and light chain variable regions of BoNT B binder

Fig. 2

| VL Clone | Framework1 | CDR1 | Framework 2 | CDR2 | Framework3 | CDR3 | Framework4 | Gene Family |
|---|---|---|---|---|---|---|---|---|
| A12 | DIQMTQSPSSLSASVGDRVTITC | RASQRISNYLN | WYQQKPGKAPKLLIY | AASSLQS | GVPSRFSGSGSGTDFTLTISSLQPEDFATYYC | QQSYREPLT | FGGGTKVEIKR | VK1 |
| 6A12 | DIQMTQSPSSVSASVGDRVTITC | RASQGISSWLA | WYQQKPGKAPKLLIY | AASSLQS | GVPSRFSGSGSGTDFTLTISSLQPEDFATYYC | QRANSPPLT | FGGGTKVEIKR | VK2 |
| B1.1 | DVMMTQSPSSLSASVGDRVTITC | RASQSISSYIN | WYQQKPGKAPKLLIY | AASSLQS | GVPSRFSGSGSGTDFTLTISSLQPEDFATYYC | QQSYSTPLT | FGGGTKLEIKR | VK1 |
| B6 | DVMMTQSPSSLSASVGDRIIITC | QASQDISNYLN | WYQQKPGKAPKLLIR | DASNLET | GVPSRFSGSGSGTHFTFTISSLHPEDIATYYC | QQYDNLPYT | FGQGTKLEIKR | VK1 |
| B6.1 | --IQ--------------------- | R-S-S--SY--- | ------T------- | S--S-QS | --------S---D--L-----Q---F--Y- | --SYST-FYT | --------- | VK1 |
| B8 | DIQMTQSPSSLSASVGDRVTITC | RASQRISNYLN | WYQQKPGKAPKLLIY | AASSLQS | GVPSRFSGSGSGTDFTLTISSLQPEDFATYYC | QQSYREPLT | FGGGTKVDIKR | VK1 |
| BB.1 | ------------------------ | ---------- | ------------- | ----Y-- | -------Y------------------------- | --------- | --------- | VK1 |
| B11 | DIVMTQSPSTLSASVGDRVTITC | RASQSINSWLA | WYQQKPGKAPKLLIY | EASSLES | GVPSRFSGSGSGTEFTLTISSLQPEDFATYYC | QQYDSWLT | FGGGTKVEIKR | VK1 |
| B11C3 | --Q--------SV---- | ---GYSK--- | ----E-R---- | G---Q-- | ---------D--- | ---FP--- | --- | VK1 |
| B11E8 | E--L---A---V-P-A-LS-- | ----VSKF-- | ----R-Q--R-- | G--TRAT | --I-A----------A------SE---D--- | ---NWPI-- | --Q---RL-- | VK1 |
| B12 | DIVMMTQSPSTLSASVGDRVTITC | RASQGISSWLA | WYQQKPGKAPKLLIY | KASSLES | GVPERFSGSNSGNTAILTITRVEAGEADYYC | LQHNSYPRA | FGGGTKLTVLG | VL3 |
| B12.1 | AVLNQPESVSAPGKTVAIHC | BGNNVGNRAVH | WYQQRPGQAPVLVVH | DDSDRPS | GIDERFSGSNSGNTAALTLTGLQAEDEADYYC | GYMDSSSAGWV | FGGGTKLTVLG | VL1 |
| B12.2 | ESVLTQPEVSARPGQKVTISC | SGSSSNIGNNYVS | WYQQLPGTAPKLLIY | ENSKRSS | GIDPRFSGSKSGTSASLATSGLQAEDEADYYC | GTWDSSLSAVV | FGGGTKLTVLG | VL1 |
| 1B1B | DVMMTQSPSSVSASVGDRVTITC | RASQSISSYIN | WYQQKPGKAPKLLIE | AASSLQS | AVPSRFSGSGSGTDFTLTISSLQPEDFATYYC | QQSYSEPPT | FGQGTKVEIKR | VK1 |
| 2B18.1 | --I---------L-------S-S- | ---------- | ----K------Y | KI--B-- | G-------T-------------------- | --------I-- | --G------- | VK1 |
| 4E19 | DIVLQSPSTLSASVGNRVTLSC | RASRLGYIN | WYQQRCKAPKLIY | AASSLEN | GVPSRFSGSGSGTDFTLTISSLQEDDFATYYC | QQAFGFPPNT | FGQGTKVEIKR | VK1 |
| 1E22 | DIQMTQSPSTLSASLGNRVTLSC | RASQSIQSWLA | WYQQKPGCAPKLLIY | SASVLQT | GVPSRFSGSGSGTDFTLTISSLQPEDFATYYC | QQYNSPLT | FGQGTKLEIKR | VK1 |

Fig. 2 cont'd

Deduced protein sequences of heavy and light chain variable regions of BoNT/E binder

| VH Clone | Framework1 | CDR1 | Framework2 | CDR2 | Framework3 | CDR3 | Framework4 | Gene Family |
|---|---|---|---|---|---|---|---|---|
| 2A10 | QVQLQQSGAEVKKPGSSVKVSCKASGGTFT | RYTIT | WVRQAPGQGLEWMG | GIIPIFDKANYAQKFQS | RVTFTADASTSTAYMELGSLRPEDTAVYYCAA | YSRGYVHFDY | WGPGTLVTVSS | VH1 |
| 3E1 | QVQLVESGAEVKKPGSSVKVSCKASGGTFS | NSGFT | WVRQVPGQGLEWMG | GIIPMFGPANYAQKFQG | RVTITADESTRMVYMELRSLRSEDTAVYYCAR | DQGEYTVGMLLYYAMDV | WGEGTTVTVSS | VH1 |
| 3E2 | QVQLQESGAEVKKPGSSVKVSCKASGGDLN | KYAIT | WLRQAPGQGFEWMG | GITPIFATTNYAQKFQG | RVMITADEVTSTVYMDLSSLGSEDTAIYFCAK | SPRGGIVGTFDT | WGQGTMVTVSS | VH1 |
| 3E3 | QVQLVESGGGLVKPGESLRLSCAASGFTFS | NYNMN | WVRQAPGKGLEWVS | SISDGGSYRYYAYSVKG | RFTISRDNTKNSLYLQMNSLRAEDTALYYCAR | DEMVHGILVYYGMDV | WGQGTTVTVSS | VH3 |
| 3E4 | QVQLQESGGGLVQPGGSLRLSCGASGFTFS | SDAMS | WVRQAPGKGLEWVA | AILPSGEATYYADSVKG | RFTISRHSSKNTLYLQMNSLRADDTAVYYCAR | DSYHSRLAAFDI | WGQGTMVTVSS | VH3 |
| 3E4.1 | ------------------------------ | ----- | -------------- | ----------------- | -------------------------------- | --------------- | ----------- | VH3 |
| 3E5 | QVQLVQSGGGVVQPGRPLRLSCAASTFNFR | DFYMS | WIRQAPGKGLEWVS | YIGSSGSALQYADSVKG | RFTISRDNDKNVLYLQMTSLRAEDTAVYYCAR | VASRYHDVLTDGFDI | WGQGTMVTVSS | VH3 |
| 3E6 | QVQLVQSGGGVVQPGKSLRLSCAASGFTFS | SYAMH | WVRQAPGKGLEWVA | VISYDGNKKYYADSVKG | RFTISRDNSKNTLYLQMNSLRAEDAAVFYCAR | ARLCTSTSCYWTFDP | WGQGTLVTVSS | VH3 |
| 3E6.1 | ------------------------------ | ----- | -------------- | ----------------- | -------------------------------- | --------------- | ----------- | VH3 |
| 4E11 | QVQLVQSGGGLVQPGGSLRLSCAASGFRFS | GYSFN | WVRQAPGKGLEWVA | YMSSGGSIKNYADSVKG | RFTISRDNAKNSLYLQVNSLRDEDTALYYCAR | GPPGRPNDAFDI | WGQGTMVTVSS | VH3 |
| 4E13 | EVQLVQSGGGLVQPGGSLRLSCAASGFTFS | SYAMT | WVRQAPGKGLEWVS | SISVSGDSTYYADSVKG | RFTISRDNSKNTVSLQMNSLRAEDTALYYCAK | GLSKADLFGMDV | WGQGTMVTVSS | VH3 |
| 4E16 | QVQLQESGPGLVKPSETLSLTCSVSGVSIS | DYYWS | WIRQPPGKGLEWIG | YIYYSGSTNYNPSLKS | RVTISVDTSKNQFSLNLSSVTAADTAVYYCAR | HTSGWSGGAFDI | WGQGTMVTVSS | VH4 |
| 4E16.1 | ------------------------------ | ----- | -------------- | ----------------- | -------------------------------- | ------------ | ----------- | VH4 |
| 4E17 | EVQLVQSGGNLVQPGGSLRLSCAATGPIGS | HWMT | WVRQAPGQGLEWVA | NINLDGTEKFYVDSVKG | RFTVSRDNRKSSVFLQMNNLRVDDTAVYYCAR | LQWGGYNGWLSP | WGQGTLVTVSS | VH3 |
| 4E17.1 | ------------------------------ | ---- | -------------- | ----------------- | -------------------------------- | ------------ | ----------- | VH3 |

Fig. 3

| VL Clone | Framework1 | CDR1 | Framework2 | CDR2 | Framework3 | CDR3 | Framework4 | Gene Family |
|---|---|---|---|---|---|---|---|---|
| 2A10 | DIVMTQSPSFLSASVGDRVTITC | RASQGISSYLA | WYQQKPGKAPKLLIY | AASTLQS | GVPSRFSGSGSGTEFTLTISSLQPEDFATYYC | QQLNSYPLT | FGGGTKVDIKR | VK1 |
| 3E1 | EIVLTQSPDSLSASVGDRVTITC | RASQGISGYLA | WYQHKAGKAPKLLIY | AASSLQS | GVPSRFSGSGTGTEFTLTISSLQPDDFATYYC | QQYNSYPPT | FGGGTKVEIKR | VK1 |
| 3E2 | EIVLTQSPSFLSAFVGDRVTITC | RISQSINNYLN | WYQQKAGKAPKLLIY | AASTLHT | GVPSRFSGSGSGTEFTLTISSLQPDDFATYYC | QQSYSIPLT | FGGGTKVEIKR | VK1 |
| 3E3 | DIVMTQSPDSLSASVGDRVTITC | RASQSFSSSYLA | WYQQKPGQAPRLLIY | AASSRAA | GVPDIGSVADSGTDFTLNISGLQPEDFAAYYC | QQSYSTPYT | FGGGTKVEIKR | VK1 |
| 3E4 | DIVMTQSPSFLSAFVGDRVTITC | RASQSISNWLA | WYQQKPGKAPKVLIY | KASSLEN | GVPSRFSGSGSGTDFTLTISSLQPDDFATYYC | QQYNAYPLT | FGGGTKVEIKR | VK1 |
| 3E4.1 | E--L---T---S-----A---- | ----R-GS--- | ------NP----- | --F---S | -----------R--E---S---------- | ---DS--Y- | ---Q----L--- | VK1 |
| 3E5 | DVVMTQSPSSLSASIGDRVTITC | QASQDISNRLN | WYQQKPGKVPKLLIS | DASNLET | GVPSRFSGSGSGTDFTFTISSLQPEDIATYYC | QQYDPLT | FGGGTKVEIKR | VK1 |
| 3E6 | DIQMTQSPSSVSASVGDRVTISC | RASQGISSWLA | WYQQKPGQAPTLLIY | AASSLQS | GVPSRFSGSGSGTDFTLTISSLQPEDFATYYC | QQAYRTPIT | FGGGTKVEIKR | VK1 |
| 3E6.1 | -------------R-S-T---- | Q---D--NY-N | -----P-K--- | ------- | ---------T----------------- | -SYN--P- | ---Q----L--- | VK1 |
| 4E11 | ASVLTQDPAVSVALGQTVRITC | QGDSLRSYYAS | WYQQKPGQAPVLVIY | GKSNRPS | GIPDRFSGSSSGNTASLTITGAQAEDEADYYC | NSRDSTGNQL | FGGGKVTVLG | VL3 |
| 4E13 | AELTQDPAVSVALGQTVRITC | QGDSLRSYYAS | WYQQKPGQAPVLVIY | GENSRPS | GIPDRFSGSSSGNTASLTIAGAQAEDEADYYC | NSPDSSGIHLV | FGGGKVTVLG | VL3 |
| 4E16 | EIVLTQSPDSLAVSLGERATINC | KSSQSTLYSSNNKNYLA | WYQQKPGQPPKLLFY | WASTRES | GVPDRFSGSGSGTDFTLTISSLQAEDVAVYYC | HQYISSPLT | FGGGTKLEIKR | VK4 |
| 4E16.1 | ---------N---------R-- | ----------G----I- | ----------I--- | | -------------E-------------- | Q----RWT | ---Q----- | VK4 |
| 4E17 | DIVMTQSPSSASVGDRVTITC | RASQSISSTLN | WYQQKPGRAPKLLIY | GTSNLQS | GVPSGFSGSGSGTDFTLTISSLQPEDFATYYC | QETYSTPPT | FGGGTKLEIKR | VK1 |
| 4E17.1 | ----------L---S------- | -----RH-V- | ---------- | KA-S-A- | -A--R---------------D------- | -QS--I-L- | -------V--- | VL1 |

BoNT A1 ────────(represents ~10% amino acid difference)──────── BoNT A2

NCTC 2916
62A
ATCC 3502
Hall hyper

Kyoto-F
FRI-honey

*Fig. 5* bivalent BoNT B (3.6-4.0% difference) BoNT B1

(4.6-5.0% difference) BoNT B2

(7.6-7.7% difference) nonproteolytic BoNT B (4.3% difference)

(7.2% difference)

(7.0% difference)

── Danish
── Strain 111
── Eklund 17B
── CDC 1436
── CDC 588
── CDC 593
── CDC 3281

*Fig. 6*

HuC25   $K_D = 8.44 \times 10^{-10}$ M

* Library constructed by error prone PCR of whole scFv
* 3 mutations, 1 VH FMW1 and 2 VL CDR3
* 5 fold affinity increase AR1   $K_D = 1.69 \times 10^{-10}$ M

* Library constructed by error prone PCR of whole scFv
* 1 mutation VH CDR1
* 2.8 fold affinity increase AR2   $K_D = 6.14 \times 10^{-11}$ M

* VH CDR1 was diversified by spiked oliog
* 3 mutations, 2 VH CDR1 and 1 VH CDR2
* 2.5 fold affinity increase AR4   $K_D = 2.26 \times 10^{-11}$ M

*Fig. 7A*

3D12   $K_D = 6.43 \times 10^{-10}$ M

* Library constructed by error prone PCR of whole scFv
* 5 mutations, 2 VL CDR1, 2 VL CDR2, and 1 VL CDR3
* 45 fold affinity increase RAZ1   $K_D = 2.1 \times 10^{-11}$ M

*Fig. 7B*

SEQUENCE LISTING

<160> NUMBER OF SEQ ID NOS: 522

<210> SEQ ID NO 1
<211> LENGTH: 15
<212> TYPE: PRT
<213> ORGANISM: Artificial Sequence
<220> FEATURE:
<223> OTHER INFORMATION: protein linker

<400> SEQUENCE: 1

Gly Gly Gly Gly Ser Gly Gly Gly Gly Ser Gly Gly Gly Gly Ser
1               5                   10                  15

<210> SEQ ID NO 2
<211> LENGTH: 5
<212> TYPE: PRT
<213> ORGANISM: Artificial Sequence
<220> FEATURE:
<223> OTHER INFORMATION: protein linker

<400> SEQUENCE: 2

Ser Ser Ser Ser Gly
1               5

<210> SEQ ID NO 3
<211> LENGTH: 15
<212> TYPE: PRT
<213> ORGANISM: Artificial Sequence
<220> FEATURE:
<223> OTHER INFORMATION: protein linker

<400> SEQUENCE: 3

Ser Ser Ser Ser Gly Ser Ser Ser Gly Ser Ser Ser Ser Gly
1               5                   10                  15

<210> SEQ ID NO 4
<211> LENGTH: 122
<212> TYPE: PRT
<213> ORGANISM: Artificial Sequence
<220> FEATURE:
<223> OTHER INFORMATION: single chain antibody

<400> SEQUENCE: 4

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Ser Asn Tyr Asp Tyr Tyr Gly Met Asp Val Trp
            100                 105                 110

Gly Gln Gly Thr Thr Val Thr Val Ser Ser
        115                 120

<210> SEQ ID NO 5
<211> LENGTH: 121
<212> TYPE: PRT
<213> ORGANISM: Artificial Sequence
<220> FEATURE:
<223> OTHER INFORMATION: single chain antibody

<400> SEQUENCE: 5

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val

```
                  50                  55                  60
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                     85                  90                  95

Ala Arg Val Ser Ile Val Gly Gly Pro Tyr Gly Met Asp Val Trp Gly
                100                 105                 110

Gln Gly Thr Thr Val Thr Val Ser Ser
                115                 120

<210> SEQ ID NO 6
<211> LENGTH: 123
<212> TYPE: PRT
<213> ORGANISM: Artificial Sequence
<220> FEATURE:
<223> OTHER INFORMATION: single chain antibody

<400> SEQUENCE: 6

Gln Val Gln Leu Val Gln Ser Gly Ala Glu Val Glu Lys Pro Gly Ser
  1               5                  10                  15

Ser Val Lys Val Ser Cys Lys Ala Ser Gly Gly Ser Phe Ser Ser Tyr
                 20                  25                  30

Ala Phe Thr Trp Val Arg Gln Ala Pro Gly Gln Gly Leu Glu Trp Met
                 35                  40                  45

Gly Arg Ile Val Pro Phe Leu Gly Val Pro Tyr Tyr Thr Gln Lys Phe
             50                  55                  60

Arg Gly Arg Val Thr Ile Thr Ala Asp Lys Ala Thr Ser Thr Val Tyr
 65                  70                  75                  80

Met Glu Leu Ser Ser Leu Thr Phe Asp Asp Thr Ala Val Tyr Tyr Cys
                 85                  90                  95

Ala Arg Asp Lys Arg Thr Tyr Glu Tyr Asn Trp Asn Ser Leu Trp Phe
                100                 105                 110

Trp Gly Arg Gly Thr Leu Val Thr Val Ser Ser
                115                 120

<210> SEQ ID NO 7
<211> LENGTH: 125
<212> TYPE: PRT
<213> ORGANISM: Artificial Sequence
<220> FEATURE:
<223> OTHER INFORMATION: single chain antibody

<400> SEQUENCE: 7

Gln Val Gln Leu Val Gln Ser Gly Ala Glu Val Lys Lys Pro Gly Glu
  1               5                  10                  15

Ser Leu Val Ile Ser Cys Lys Ala Ser Gly Asp Lys Asp Thr Phe Thr
                 20                  25                  30

Ser Phe Trp Ile Ala Trp Val Arg Gln Met Pro Gly Lys Gly Leu Glu
                 35                  40                  45

Trp Met Gly Ile Ile Tyr Ala Gly Asp Ser Asp Thr Arg Tyr Ser Pro
             50                  55                  60

Ser Phe Gln Gly His Val Asn Ile Ser Val Asp Arg Ser Thr Asn Thr
 65                  70                  75                  80

Ala Tyr Leu Gln Trp Ser Ser Leu Lys Ala Ser Asp Thr Ala Met Tyr
                 85                  90                  95

Tyr Cys Ala Arg His Asp Ser Arg Tyr Lys Tyr Phe Tyr Phe Gly Met
                100                 105                 110
```

Asp Val Trp Gly Gln Gly Thr Thr Val Thr Val Ser Ser
            115                 120                 125

<210> SEQ ID NO 8
<211> LENGTH: 125
<212> TYPE: PRT
<213> ORGANISM: Artificial Sequence
<220> FEATURE:
<223> OTHER INFORMATION: single chain antibody

<400> SEQUENCE: 8

Gln Val Gln Leu Val Gln Ser Gly Ala Glu Val Lys Lys Pro Gly Glu
  1               5                  10                  15

Ser Leu Val Ile Ser Cys Lys Ala Ser Gly Asp Lys Asp Thr Phe Thr
             20                  25                  30

Ser Phe Trp Ile Ala Trp Val Arg Gln Met Pro Gly Lys Gly Leu Glu
         35                  40                  45

Trp Met Gly Ile Ile Tyr Ala Gly Asp Ser Asp Thr Arg Tyr Ser Pro
     50                  55                  60

Ser Phe Gln Gly His Val Asn Ile Ser Val Asp Arg Ser Thr Asn Thr
 65                  70                  75                  80

Ala Tyr Leu Gln Trp Ser Ser Leu Lys Ala Ser Asp Thr Ala Met Tyr
                 85                  90                  95

Tyr Cys Ala Arg His Asp Ser Arg Tyr Lys Tyr Phe Tyr Phe Gly Met
            100                 105                 110

Asp Val Trp Gly Gln Gly Thr Thr Val Thr Val Ser Ser
            115                 120                 125

<210> SEQ ID NO 9
<211> LENGTH: 122
<212> TYPE: PRT
<213> ORGANISM: Artificial Sequence
<220> FEATURE:
<223> OTHER INFORMATION: single chain antibody

<400> SEQUENCE: 9

Gln Val Gln Leu Leu Glu Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
             20                  25                  30

Gly Met His Trp Val Arg Gln Ala Pro Gly Lys Gly Leu Glu Trp Val
         35                  40                  45

Ala Val Ile Trp Tyr Asp Gly Ser Asn Lys Tyr Tyr Ala Asp Ser Val
     50                  55                  60

Lys Gly Arg Phe Thr Ile Ser Arg Asp Asn Ser Lys Asp Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Tyr Ser Asn Tyr Asp Tyr Tyr Tyr Gly Met Asp Val Trp
            100                 105                 110

Gly Gln Gly Thr Thr Val Thr Val Ser Ser
        115                 120

<210> SEQ ID NO 10
<211> LENGTH: 122
<212> TYPE: PRT
<213> ORGANISM: Artificial Sequence
<220> FEATURE:
<223> OTHER INFORMATION: single chain antibody

```
<400> SEQUENCE: 10

Gln Val Gln Leu Leu Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Ser Asn Tyr Asp Tyr Tyr Gly Met Asp Val Trp
            100                 105                 110

Gly Gln Gly Thr Thr Val Thr Val Ser Ser
            115                 120

<210> SEQ ID NO 11
<211> LENGTH: 128
<212> TYPE: PRT
<213> ORGANISM: Artificial Sequence
<220> FEATURE:
<223> OTHER INFORMATION: single chain antibody

<400> SEQUENCE: 11

Gln Val Gln Leu Leu Gln Ser Ala Gly Gly Val Val Gln Pro Gly Arg
1               5                   10                  15

Ser Leu Arg Leu Ser Cys Ala Ala Ser Gly Phe Ile Phe Arg Thr Tyr
            20                  25                  30

Gly Met His Trp Val Arg Gln Ala Pro Gly Lys Gly Leu Glu Trp Val
        35                  40                  45

Ala Phe Val Ser Ser Asp Gly Asn Asn Lys Phe Tyr Ser Asp Ser Val
    50                  55                  60

Lys Gly Arg Phe Thr Ile Pro Arg Asp Asn Ala Lys Asn Thr Leu Tyr
65                  70                  75                  80

Leu Gln Met Asn Ser Leu Glu Thr Glu Asp Thr Ala Val Tyr Tyr Cys
                85                  90                  95

Ala Lys Asp Arg Tyr Pro Ile Asp Cys Ser Gly Ser Cys Phe Ser
            100                 105                 110

Tyr Gly Met Asp Val Trp Gly Gln Gly Thr Thr Val Thr Val Ser Ser
        115                 120                 125

<210> SEQ ID NO 12
<211> LENGTH: 128
<212> TYPE: PRT
<213> ORGANISM: Artificial Sequence
<220> FEATURE:
<223> OTHER INFORMATION: single chain antibody

<400> SEQUENCE: 12

Glu Val Gln Leu Val Glu Ser Gly Gly Gly Val Val Gln Pro Gly Arg
1               5                   10                  15

Ser Leu Arg Leu Ser Cys Ala Thr Ser Gly Phe Ile Leu Arg Thr Tyr
            20                  25                  30

Gly Met His Trp Val Arg Gln Ala Pro Gly Lys Gly Leu Glu Trp Val
        35                  40                  45
```

```
Ala Phe Val Ser Ser Asp Gly Asn Asn Lys Phe Tyr Ser Asp Ser Val
 50                  55                  60

Lys Gly Arg Phe Thr Ile Pro Arg Asp Asn Ala Lys Asn Thr Leu Tyr
 65                  70                  75                  80

Leu Gln Met Asn Ser Leu Glu Thr Glu Asp Thr Ala Val Tyr Tyr Cys
                 85                  90                  95

Ala Lys Asp Arg Tyr Pro Ile Asp Cys Ser Gly Gly Ser Cys Phe Ser
            100                 105                 110

Tyr Gly Met Asp Val Trp Gly Gln Gly Thr Leu Val Thr Val Ser Ser
        115                 120                 125
```

<210> SEQ ID NO 13
<211> LENGTH: 128
<212> TYPE: PRT
<213> ORGANISM: Artificial Sequence
<220> FEATURE:
<223> OTHER INFORMATION: single chain antibody

<400> SEQUENCE: 13

```
Glu Val Gln Leu Val Gln Ser Gly Gly Gly Val Val Gln Pro Gly Arg
 1               5                  10                  15

Ser Leu Arg Leu Ser Cys Ala Ala Ser Gly Phe Ile Phe Arg Thr Tyr
             20                  25                  30

Gly Met His Trp Val Arg Gln Ala Pro Gly Lys Gly Leu Glu Trp Val
         35                  40                  45

Ala Phe Val Ser Ser Asp Gly Asn Asn Lys Phe Tyr Ser Asp Ser Val
 50                  55                  60

Lys Gly Arg Phe Thr Ile Ser Arg Asp Asn Ala Lys Asn Thr Leu Tyr
 65                  70                  75                  80

Leu Gln Met Asn Ser Leu Glu Thr Glu Asp Thr Ala Met Tyr Tyr Cys
                 85                  90                  95

Ala Lys Asp Arg Tyr Pro Ile Asp Cys Ser Gly Gly Ser Cys Phe Ser
            100                 105                 110

Tyr Gly Met Asp Val Trp Gly Gln Gly Thr Thr Val Thr Val Ser Ser
        115                 120                 125
```

<210> SEQ ID NO 14
<211> LENGTH: 123
<212> TYPE: PRT
<213> ORGANISM: Artificial Sequence
<220> FEATURE:
<223> OTHER INFORMATION: single chain antibody

<400> SEQUENCE: 14

```
Gln Val Asn Leu Arg Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
             20                  25                  30

Ala Leu His Trp Val Arg Gln Thr Pro Gly Lys Gly Leu Glu Trp Val
         35                  40                  45

Ala Leu Ile Ser Tyr Asp Gly Ser Asn Lys Tyr Tyr Ala Asp Ser Val
 50                  55                  60

Lys Gly Arg Phe Thr Ile Ser Arg Asp Asn Ser Lys Asn Met Leu Tyr
 65                  70                  75                  80

Leu Gln Met Asn Ser Leu Arg Ala Glu Asp Thr Ala Val Tyr Tyr Cys
                 85                  90                  95

Ala Lys Asp Arg Ser His Tyr Gly Asp Tyr Val Gly Tyr Leu Asp Tyr
            100                 105                 110
```

Trp Gly Gln Gly Thr Leu Val Thr Val Ser Ser
        115                 120

<210> SEQ ID NO 15
<211> LENGTH: 123
<212> TYPE: PRT
<213> ORGANISM: Artificial Sequence
<220> FEATURE:
<223> OTHER INFORMATION: single chain antibody

<400> SEQUENCE: 15

Gln Val Asn Leu Arg Glu Ser Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Ala Leu His Trp Val Arg Gln Thr Pro Gly Lys Gly Leu Glu Trp Val
        35                  40                  45

Ala Leu Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Met Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Ser His Tyr Gly Asp Tyr Val Gly Tyr Leu Asp Tyr
            100                 105                 110

Trp Gly Gln Gly Thr Leu Val Thr Val Ser Ser
        115                 120

<210> SEQ ID NO 16
<211> LENGTH: 123
<212> TYPE: PRT
<213> ORGANISM: Artificial Sequence
<220> FEATURE:
<223> OTHER INFORMATION: single chain antibody

<400> SEQUENCE: 16

Gln Val Asn Leu Arg Glu Ser Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Ala Leu His Trp Val Arg Gln Thr Pro Gly Lys Gly Leu Glu Trp Val
        35                  40                  45

Ala Leu Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Met Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Ser His Tyr Gly Asp Tyr Val Gly Tyr Leu Asp Tyr
            100                 105                 110

Trp Gly Gln Gly Thr Leu Val Thr Val Ser Ser
        115                 120

<210> SEQ ID NO 17
<211> LENGTH: 121
<212> TYPE: PRT
<213> ORGANISM: Artificial Sequence
<220> FEATURE:
<223> OTHER INFORMATION: single chain antibody

<400> SEQUENCE: 17

Glu Val Gln Leu Val Gln Ser Gly Gly Gly Leu Val Gln Pro Gly Gly
1               5                   10                  15

Ser Arg Arg Leu Ser Cys Ala Ala Ser Gly Phe Tyr Phe Asn Ala Tyr
                20                  25                  30

Trp Met Thr Trp Val Arg Gln Ala Pro Gly Lys Gly Leu Glu Trp Val
            35                  40                  45

Ala Asn Ile Asn Leu Asp Gly Thr Glu Ile Tyr Tyr Leu Asp Ser Val
        50                  55                  60

Lys Gly Arg Phe Thr Val Ser Arg Asp Asn Val Lys Asn Ser Val Phe
65                  70                  75                  80

Leu Gln Met Ser Ser Leu Arg Val Glu Asp Thr Ala Val Tyr Phe Cys
                85                  90                  95

Ala Arg Leu Glu Trp Gly Gly Arg Asn Gly Trp Val Ser Pro Trp Gly
            100                 105                 110

Gln Gly Thr Leu Val Thr Val Ser Ser
        115                 120

<210> SEQ ID NO 18
<211> LENGTH: 121
<212> TYPE: PRT
<213> ORGANISM: Artificial Sequence
<220> FEATURE:
<223> OTHER INFORMATION: single chain antibody

<400> SEQUENCE: 18

Gln Val Gln Leu Val Gln Ser Gly Gly Gly Leu Val Gln Pro Gly Gly
1               5                   10                  15

Ser Arg Arg Leu Ser Cys Ala Ala Ser Gly Phe Tyr Phe Asn Ala Tyr
                20                  25                  30

Trp Met Thr Trp Val Arg Gln Ala Pro Gly Lys Gly Leu Glu Trp Val
            35                  40                  45

Ala Asn Ile Asn Leu Asp Gly Thr Glu Ile Tyr Tyr Leu Asp Ser Val
        50                  55                  60

Lys Gly Arg Phe Thr Val Ser Arg Asp Asn Val Lys Asn Ser Val Phe
65                  70                  75                  80

Leu Gln Met Ser Ser Leu Arg Val Glu Asp Thr Ala Val Tyr Phe Cys
                85                  90                  95

Ala Arg Leu Glu Trp Gly Gly Arg Asn Gly Trp Val Ser Pro Trp Gly
            100                 105                 110

Gln Gly Thr Leu Val Thr Val Ser Ser
        115                 120

<210> SEQ ID NO 19
<211> LENGTH: 120
<212> TYPE: PRT
<213> ORGANISM: Artificial Sequence
<220> FEATURE:
<223> OTHER INFORMATION: single chain antibody

<400> SEQUENCE: 19

Gln Val Gln Leu Val Gln Ser Gly Ala Glu Val Lys Lys Pro Gly Ala
1               5                   10                  15

Ser Val Asn Val Ser Cys Lys Ala Ser Gly Tyr Thr Phe Thr Gly Tyr
                20                  25                  30

Tyr Ile Tyr Trp Val Arg Gln Ala Pro Gly Gln Gly Leu Glu Trp Met
            35                  40                  45

Gly Trp Ile Asn Pro Asn Ser Gly Val Thr Lys Tyr Ala Gln Lys Phe
            50                  55                  60

Gln Gly Arg Val Thr Met Thr Ile Asp Thr Ser Thr Asn Thr Ala Tyr
 65                  70                  75                  80

Met Glu Leu Asn Arg Leu Arg Ala Asp Asp Thr Ala Val Tyr Tyr Cys
                 85                  90                  95

Ala Arg Glu Trp Thr Gln Leu Trp Ser Pro Tyr Asp Tyr Trp Gly Gln
            100                 105                 110

Gly Thr Thr Val Thr Val Ser Ser
            115                 120

<210> SEQ ID NO 20
<211> LENGTH: 127
<212> TYPE: PRT
<213> ORGANISM: Artificial Sequence
<220> FEATURE:
<223> OTHER INFORMATION: single chain antibody

<400> SEQUENCE: 20

Gln Val Gln Leu Gln Glu Ser Gly Ser Arg Leu Val Lys Pro Ser Gln
 1                   5                  10                  15

Thr Leu Ser Leu Thr Cys Gly Val Ser Gly Gly Ser Ile Ser Ser Ser
             20                  25                  30

Ser Tyr Ser Trp Ser Trp Ile Arg Gln Thr Pro Gly Lys Gly Leu Glu
         35                  40                  45

Trp Ile Gly Tyr Ile Tyr His Ser Gly Ser Thr Tyr Tyr Asn Pro Ser
     50                  55                  60

Leu Lys Ser Arg Val Thr Met Ser Val Asp Lys Ser Arg Asn Gln Phe
 65                  70                  75                  80

Ser Leu Asn Met Ser Ser Val Thr Ala Ala Asp Thr Ala Val Tyr Tyr
                 85                  90                  95

Cys Ala Arg Thr Ala Phe Tyr Tyr Glu Asn Thr Gly Pro Ile Arg Cys
            100                 105                 110

Tyr Leu Asp Phe Trp Gly Gln Gly Thr Leu Val Thr Val Ser Ser
            115                 120                 125

<210> SEQ ID NO 21
<211> LENGTH: 108
<212> TYPE: PRT
<213> ORGANISM: Artificial Sequence
<220> FEATURE:
<223> OTHER INFORMATION: single chain antibody

<400> SEQUENCE: 21

Asp Ile Gln Met Thr Gln Ser Pro Ser Ser Leu Ser Ala Ser Val Gly
 1                   5                  10                  15

Asp Arg Val Thr Ile Thr Cys Arg Ala Ser Gln Arg Ile Ser Asn Tyr
             20                  25                  30

Leu Asn Trp Tyr Gln Gln Lys Pro Gly Lys Ala Pro Lys Leu Leu Ile
         35                  40                  45

Tyr Ala Ala Ser Ser Leu Gln Ser Glu Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Arg Pro Pro Leu
                 85                  90                  95

Thr Phe Gly Gly Gly Thr Lys Val Glu Ile Lys Arg
            100                 105

<210> SEQ ID NO 22
<211> LENGTH: 108
<212> TYPE: PRT
<213> ORGANISM: Artificial Sequence
<220> FEATURE:
<223> OTHER INFORMATION: single chain antibody

<400> SEQUENCE: 22

```
Asp Ile Gln Met Thr Gln Ser Pro Ser Ser Val Ser Ala Ser Val Gly
 1               5                  10                  15

Asn Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Lys Ala Asn Ser Phe Pro Leu
                85                  90                  95

Thr Phe Gly Gly Gly Thr Lys Val Glu Ile Lys Arg
            100                 105
```

<210> SEQ ID NO 23
<211> LENGTH: 108
<212> TYPE: PRT
<213> ORGANISM: Artificial Sequence
<220> FEATURE:
<223> OTHER INFORMATION: single chain antibody

<400> SEQUENCE: 23

```
Asp Val Val Met Thr Gln Ser Pro Ser Leu Ser Ala Ser Val Gly
 1               5                  10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gln Gly Thr Lys Leu Glu Ile Lys Arg
            100                 105
```

<210> SEQ ID NO 24
<211> LENGTH: 108
<212> TYPE: PRT
<213> ORGANISM: Artificial Sequence
<220> FEATURE:
<223> OTHER INFORMATION: single chain antibody

<400> SEQUENCE: 24

```
Asp Val Val Met Thr Gln Ser Pro Ser Leu Ser Ala Ser Val Gly
 1               5                  10                  15

Asp Arg Ile Thr Ile Thr Cys Gln Ala Gly Gln Asp Ile Ser Asn Phe
            20                  25                  30
```

```
Leu Asn Trp Tyr Gln Gln Lys Pro Gly Lys Ala Pro Lys Leu Leu Ile
            35                  40                  45

Arg Asp Ala Ser Asn Leu Glu Thr Gly Val Pro Ser Arg Phe Ser Gly
 50                  55                  60

Gly Gly Ser Gly Thr His Phe Thr Phe Thr Ile Ser Ser Leu His Pro
 65                  70                  75                  80

Glu Asp Ile Ala Thr Tyr Phe Cys Gln Gln Tyr Asp Asn Leu Pro Tyr
                 85                  90                  95

Thr Phe Gly Gln Gly Thr Lys Leu Glu Ile Lys Arg
            100                 105
```

<210> SEQ ID NO 25
<211> LENGTH: 109
<212> TYPE: PRT
<213> ORGANISM: Artificial Sequence
<220> FEATURE:
<223> OTHER INFORMATION: single chain antibody

<400> SEQUENCE: 25

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
                20                  25                  30

Leu Asn Trp Tyr Gln Gln Glu Pro Gly Lys Ala Pro Lys Leu Leu Ile
            35                  40                  45

Tyr Ser Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Leu Pro
                 85                  90                  95

Tyr Thr Phe Gly Gln Gly Thr Lys Leu Glu Ile Lys Arg
            100                 105
```

<210> SEQ ID NO 26
<211> LENGTH: 108
<212> TYPE: PRT
<213> ORGANISM: Artificial Sequence
<220> FEATURE:
<223> OTHER INFORMATION: single chain antibody

<400> SEQUENCE: 26

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Arg Ile Ser Asn Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Glu Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Arg Pro Pro Leu
                 85                  90                  95

Thr Phe Gly Gly Gly Thr Lys Val Asp Ile Lys Arg
            100                 105
```

```
<210> SEQ ID NO 27
<211> LENGTH: 108
<212> TYPE: PRT
<213> ORGANISM: Artificial Sequence
<220> FEATURE:
<223> OTHER INFORMATION: single chain antibody

<400> SEQUENCE: 27
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Arg Ile Ser Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Glu Val Pro Ser Arg Phe Ser Gly
    50                  55                  60

Ser Gly Tyr Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Arg Pro Pro Leu
                85                  90                  95

Thr Phe Gly Gly Gly Thr Lys Val Asp Ile Lys Arg
            100                 105

```
<210> SEQ ID NO 28
<211> LENGTH: 108
<212> TYPE: PRT
<213> ORGANISM: Artificial Sequence
<220> FEATURE:
<223> OTHER INFORMATION: single chain antibody

<400> SEQUENCE: 28
```

Asp Ile Val Met Thr Gln Ser Pro Ser Thr Leu Ser Ala Ser Val Gly
1               5                   10                  15

Asp Arg Val Thr Val Thr Cys Arg Ala Ser Gln Ser Ile Asn Ser Trp
            20                  25                  30

Leu Ala Trp Tyr Gln Gln Lys Pro Gly Lys Ala Pro Lys Leu Leu Ile
        35                  40                  45

Tyr Glu Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Ser Tyr Trp Leu
                85                  90                  95

Thr Phe Gly Gly Gly Thr Lys Val Glu Ile Lys Arg
            100                 105

```
<210> SEQ ID NO 29
<211> LENGTH: 108
<212> TYPE: PRT
<213> ORGANISM: Artificial Sequence
<220> FEATURE:
<223> OTHER INFORMATION: single chain antibody

<400> SEQUENCE: 29
```

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Val Ser Arg Trp
            20                  25                  30

Leu Ala Trp Tyr Gln Gln Arg Pro Glu Lys Ala Pro Lys Leu Leu Ile
        35                  40                  45

```
Tyr Gly Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asp Ser Phe Pro Leu
                85                  90                  95

Thr Phe Gly Gly Gly Thr Lys Val Glu Ile Lys Arg
            100                 105

<210> SEQ ID NO 30
<211> LENGTH: 108
<212> TYPE: PRT
<213> ORGANISM: Artificial Sequence
<220> FEATURE:
<223> OTHER INFORMATION: single chain antibody

<400> SEQUENCE: 30

Glu Ile Val Leu Thr Gln Ser Pro Ala Thr Leu Ser Val Ser Pro Gly
 1               5                  10                  15

Glu Arg Ala Thr Leu Ser Cys Arg Ala Ser Gln Ser Val Ser Lys Phe
                20                  25                  30

Leu Ala Trp Tyr Gln Gln Lys Arg Gly Gln Ala Pro Arg Leu Leu Ile
            35                  40                  45

Tyr Gly Ala Ser Thr Arg Ala Thr Gly Ile Pro Ala Arg Phe Ser Gly
        50                  55                  60

Ser Gly Ser Gly Thr Glu Phe Ala Leu Thr Ile Ser Ser Leu Gln Ser
 65                  70                  75                  80

Glu Asp Phe Ala Asp Tyr Tyr Cys Gln Gln Tyr Asp Asn Trp Pro Ile
                85                  90                  95

Thr Phe Gly Gln Gly Thr Arg Leu Glu Ile Lys Arg
            100                 105

<210> SEQ ID NO 31
<211> LENGTH: 108
<212> TYPE: PRT
<213> ORGANISM: Artificial Sequence
<220> FEATURE:
<223> OTHER INFORMATION: single chain antibody

<400> SEQUENCE: 31

Asp Ile Val Met Thr Gln Ser Pro Ser Thr Leu Ser Ala Ser Val Gly
 1               5                  10                  15

Asp Arg Val Thr Ile Thr Cys Arg Ala Ser Gln Gly Ile Ser Ser Trp
                20                  25                  30

Leu Ala Trp Tyr Gln Gln Lys Pro Gly Lys Ala Pro Lys Leu Leu Ile
            35                  40                  45

Tyr Lys Ala Ser Ser Leu Glu Ser Gly Val Pro Ser Arg Phe Ser Gly
        50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Arg
                85                  90                  95

Ala Phe Gly Gln Gly Thr Lys Leu Glu Ile Lys Arg
            100                 105

<210> SEQ ID NO 32
<211> LENGTH: 109
<212> TYPE: PRT
```

<213> ORGANISM: Artificial Sequence
<220> FEATURE:
<223> OTHER INFORMATION: single chain antibody

<400> SEQUENCE: 32

Ala Tyr Val Leu Thr Gln Pro Pro Ser Val Ser Val Ala Pro Gly Lys
1               5                   10                  15

Thr Ala Ala Ile Thr Cys Glu Gly Asn Asn Val Gly Asn Lys Asn Val
            20                  25                  30

His Trp Tyr Gln Gln Arg Pro Gly Gln Ala Pro Val Leu Val Val His
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Asn Arg Val Glu Ala Gly
65                  70                  75                  80

Asp Glu Ala Asp Tyr Tyr Cys Gln Val Trp Asp Ser Ser Ala Gln
                85                  90                  95

Trp Val Phe Gly Gly Gly Thr Lys Leu Thr Val Leu Gly
            100                 105

<210> SEQ ID NO 33
<211> LENGTH: 111
<212> TYPE: PRT
<213> ORGANISM: Artificial Sequence
<220> FEATURE:
<223> OTHER INFORMATION: single chain antibody

<400> SEQUENCE: 33

Glu Ser Val Leu Thr Gln Pro Pro Leu Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Glu Asn Ser Lys Arg Ser Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Val Val Phe Gly Gly Gly Thr Lys Leu Thr Val Leu Gly
            100                 105                 110

<210> SEQ ID NO 34
<211> LENGTH: 108
<212> TYPE: PRT
<213> ORGANISM: Artificial Sequence
<220> FEATURE:
<223> OTHER INFORMATION: single chain antibody

<400> SEQUENCE: 34

Asp Val Val Met Thr Gln Ser Pro Ser Ser Val Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Arg Pro Gly Lys Ala Pro Lys Leu Leu Ile
        35                  40                  45

Phe Ala Ala Ser Ser Leu Gln Ser Ala Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Thr Phe Gly Gln Gly Thr Lys Val Glu Ile Lys Arg
            100                 105

<210> SEQ ID NO 35
<211> LENGTH: 108
<212> TYPE: PRT
<213> ORGANISM: Artificial Sequence
<220> FEATURE:
<223> OTHER INFORMATION: single chain antibody

<400> SEQUENCE: 35

Asp Ile Val Met Thr Gln Ser Pro Ser Ser Leu Ser Ala Ser Val Gly
1               5                   10                  15

Asp Arg Val Ser Ile Ser Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Lys Thr Ser Ser Leu Glu Ser Gly Val Pro Ser Arg Phe Ser Gly
        50                  55                  60

Arg Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys Arg
            100                 105

<210> SEQ ID NO 36
<211> LENGTH: 108
<212> TYPE: PRT
<213> ORGANISM: Artificial Sequence
<220> FEATURE:
<223> OTHER INFORMATION: single chain antibody

<400> SEQUENCE: 36

Asp Ile Val Leu Thr Gln Ser Pro Ser Thr Leu Ser Ala Ser Val Gly
1               5                   10                  15

Asp Arg Val Thr Ile Ser Cys Arg Ala Ser Arg Ser Ile Gly Trp Tyr
                20                  25                  30

Leu Asn Trp Tyr Gln Gln Arg Pro Gly Lys Ala Pro Lys Leu Leu Ile
            35                  40                  45

Tyr Ala Ala Ser Ser Leu His Asn Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Ala Phe Gly Phe Pro Arg
                85                  90                  95

Thr Phe Gly Gln Gly Thr Lys Val Glu Ile Lys Arg
            100                 105

<210> SEQ ID NO 37
<211> LENGTH: 108
<212> TYPE: PRT
<213> ORGANISM: Artificial Sequence
<220> FEATURE:
<223> OTHER INFORMATION: single chain antibody

```
<400> SEQUENCE: 37

Asp Ile Gln Met Thr Gln Ser Pro Ser Thr Leu Ser Ala Ser Ile Gly
1               5                   10                  15

Asp Arg Val Thr Ile Ser Cys Arg Ala Ser Gln Ser Ile Gln Ser Trp
            20                  25                  30

Leu Ala Trp Tyr Gln Gln Arg Pro Gly Glu Ala Pro Lys Leu Leu Ile
        35                  40                  45

Tyr Ser Ala Ser Thr Leu Gln Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gln Gly Thr Lys Leu Glu Ile Lys Arg
            100                 105

<210> SEQ ID NO 38
<211> LENGTH: 119
<212> TYPE: PRT
<213> ORGANISM: Artificial Sequence
<220> FEATURE:
<223> OTHER INFORMATION: single chain antibody

<400> SEQUENCE: 38

Gln Val Gln Leu Gln Gln Ser Gly Ala Glu Val Lys Lys Pro Gly Ser
1               5                   10                  15

Ser Val Lys Val Ser Cys Lys Ala Ser Gly Gly Thr Phe Thr Arg Tyr
            20                  25                  30

Thr Ile Thr Trp Val Arg Gln Ala Pro Gly Gln Gly Leu Glu Trp Met
        35                  40                  45

Gly Gly Ile Ile Pro Ile Phe Asp Lys Ala Asn Tyr Ala Gln Lys Phe
    50                  55                  60

Gln Ser Arg Val Thr Phe Thr Ala Asp Ala Ser Thr Ser Thr Ala Tyr
65                  70                  75                  80

Met Glu Leu Gly Ser Leu Arg Pro Glu Asp Thr Ala Val Tyr Tyr Cys
                85                  90                  95

Ala Ala Tyr Ser Arg Gly Tyr Val His Phe Asp Tyr Trp Gly Pro Gly
            100                 105                 110

Thr Leu Val Thr Val Ser Ser
        115

<210> SEQ ID NO 39
<211> LENGTH: 126
<212> TYPE: PRT
<213> ORGANISM: Artificial Sequence
<220> FEATURE:
<223> OTHER INFORMATION: single chain antibody

<400> SEQUENCE: 39

Gln Val Gln Leu Val Glu Ser Gly Ala Glu Val Lys Lys Pro Gly Ser
1               5                   10                  15

Ser Val Lys Val Ser Cys Lys Ala Ser Gly Gly Thr Phe Ser Asn Ser
            20                  25                  30

Gly Phe Thr Trp Val Arg Gln Val Pro Gly Gln Gly Leu Glu Trp Met
        35                  40                  45

Gly Gly Ile Ile Pro Met Phe Gly Pro Ala Asn Tyr Ala Gln Lys Phe
    50                  55                  60
```

Gln Gly Arg Val Thr Ile Thr Ala Asp Glu Ser Thr Arg Met Val Tyr
65                  70                  75                  80

Met Glu Leu Arg Ser Leu Arg Ser Glu Asp Thr Ala Val Tyr Tyr Cys
                85                  90                  95

Ala Arg Asp Gln Gly Glu Tyr Thr Val Gly Met Leu Tyr Tyr Ala
            100                 105                 110

Met Asp Val Trp Gly Glu Gly Thr Thr Val Thr Val Ser Ser
        115                 120                 125

<210> SEQ ID NO 40
<211> LENGTH: 121
<212> TYPE: PRT
<213> ORGANISM: Artificial Sequence
<220> FEATURE:
<223> OTHER INFORMATION: single chain antibody

<400> SEQUENCE: 40

Gln Val Gln Leu Gln Glu Ser Gly Ala Glu Val Lys Lys Pro Gly Ser
1               5                   10                  15

Ser Val Lys Val Ser Cys Lys Ala Ser Gly Gly Asp Leu Asn Lys Tyr
            20                  25                  30

Ala Ile Thr Trp Leu Arg Gln Ala Pro Gly Gln Gly Phe Glu Trp Met
        35                  40                  45

Gly Gly Ile Thr Pro Ile Phe Ala Thr Thr Asn Tyr Ala Gln Lys Phe
    50                  55                  60

Gln Gly Arg Val Met Ile Thr Ala Asp Glu Val Thr Ser Thr Val Tyr
65                  70                  75                  80

Met Asp Leu Ser Ser Leu Gly Ser Glu Asp Thr Ala Ile Tyr Phe Cys
                85                  90                  95

Ala Lys Ser Pro Arg Gly Gly Ile Val Gly Thr Phe Asp Thr Trp Gly
            100                 105                 110

Gln Gly Thr Met Val Thr Val Ser Ser
        115                 120

<210> SEQ ID NO 41
<211> LENGTH: 124
<212> TYPE: PRT
<213> ORGANISM: Artificial Sequence
<220> FEATURE:
<223> OTHER INFORMATION: single chain antibody

<400> SEQUENCE: 41

Gln Val Gln Leu Val Glu Ser Gly Gly Gly Leu Val Lys Pro Gly Glu
1               5                   10                  15

Ser Leu Arg Leu Ser Cys Ala Ala Ser Gly Phe Thr Phe Ser Asn Tyr
            20                  25                  30

Asn Met Asn Trp Val Arg Gln Ala Pro Gly Lys Gly Leu Glu Trp Val
        35                  40                  45

Ser Ser Ile Ser Asp Gly Gly Ser Tyr Arg Tyr Tyr Ala Tyr Ser Val
    50                  55                  60

Lys Gly Arg Phe Thr Ile Ser Arg Asp Asn Thr Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Glu Met Val His Gly Ile Leu Val Tyr Tyr Gly Met Asp
            100                 105                 110

Val Trp Gly Gln Gly Thr Thr Val Thr Val Ser Ser

<210> SEQ ID NO 42
<211> LENGTH: 121
<212> TYPE: PRT
<213> ORGANISM: Artificial Sequence
<220> FEATURE:
<223> OTHER INFORMATION: single chain antibody

<400> SEQUENCE: 42

```
Gln Val Gln Leu Gln Glu Ser Gly Gly Gly Leu Val Gln Pro Gly Gly
  1               5                  10                  15
Ser Leu Arg Leu Ser Cys Gly Ala Ser Gly Phe Thr Phe Ser Ser Asp
             20                  25                  30
Ala Met Ser Trp Val Arg Gln Ala Pro Gly Lys Gly Leu Glu Trp Val
         35                  40                  45
Ala Ala Ile Leu Pro Ser Gly Glu Ala Thr Tyr Tyr Ala Asp Ser Val
     50                  55                  60
Lys Gly Arg Phe Thr Ile Ser Arg His Ser Ser Lys Asn Thr Leu Tyr
 65                  70                  75                  80
Leu Gln Met Asn Ser Leu Arg Ala Asp Asp Thr Ala Val Tyr Tyr Cys
                 85                  90                  95
Ala Arg Asp Ser Tyr His Ser Arg Leu Ala Ala Phe Asp Ile Trp Gly
            100                 105                 110
Gln Gly Thr Met Val Thr Val Ser Ser
        115                 120
```

<210> SEQ ID NO 43
<211> LENGTH: 121
<212> TYPE: PRT
<213> ORGANISM: Artificial Sequence
<220> FEATURE:
<223> OTHER INFORMATION: single chain antibody

<400> SEQUENCE: 43

```
Gln Val Gln Leu Gln Glu Ser Gly Gly Gly Leu Val Gln Pro Gly Gly
  1               5                  10                  15
Ser Leu Arg Leu Ser Cys Gly Ala Ser Gly Phe Thr Phe Ser Ser Asp
             20                  25                  30
Ala Met Ser Trp Val Arg Gln Ala Pro Gly Lys Gly Leu Glu Trp Val
         35                  40                  45
Ala Ala Ile Leu Pro Ser Gly Glu Ala Thr Tyr Tyr Ala Asp Ser Val
     50                  55                  60
Lys Gly Arg Phe Thr Ile Ser Arg His Ser Ser Lys Asn Thr Leu Tyr
 65                  70                  75                  80
Leu Gln Met Asn Ser Leu Arg Ala Asp Asp Thr Ala Val Tyr Tyr Cys
                 85                  90                  95
Ala Arg Asp Ser Tyr His Ser Arg Leu Ala Ala Phe Asp Ile Trp Gly
            100                 105                 110
Gln Gly Thr Met Val Thr Val Ser Ser
        115                 120
```

<210> SEQ ID NO 44
<211> LENGTH: 124
<212> TYPE: PRT
<213> ORGANISM: Artificial Sequence
<220> FEATURE:
<223> OTHER INFORMATION: single chain antibody

<400> SEQUENCE: 44

```
Gln Val Gln Leu Val Gln Ser Gly Gly Gly Val Val Gln Pro Gly Arg
  1               5                  10                  15

Pro Leu Arg Leu Ser Cys Ala Ala Ser Thr Phe Asn Phe Arg Asp Phe
             20                  25                  30

Tyr Met Ser Trp Ile Arg Gln Ala Pro Gly Lys Gly Leu Glu Trp Val
         35                  40                  45

Ser Tyr Ile Gly Ser Ser Gly Ser Ala Leu Gln Tyr Ala Asp Ser Val
     50                  55                  60

Lys Gly Arg Phe Thr Ile Ser Arg Asp Asn Asp Lys Asn Val Leu Tyr
 65                  70                  75                  80

Leu Gln Met Thr Ser Leu Arg Ala Glu Asp Thr Ala Val Tyr Tyr Cys
             85                  90                  95

Ala Arg Val Ala Ser Arg Tyr His Asp Val Leu Thr Asp Gly Phe Asp
            100                 105                 110

Ile Trp Gly Gln Gly Thr Met Val Thr Val Ser Ser
            115                 120

<210> SEQ ID NO 45
<211> LENGTH: 124
<212> TYPE: PRT
<213> ORGANISM: Artificial Sequence
<220> FEATURE:
<223> OTHER INFORMATION: single chain antibody

<400> SEQUENCE: 45

Gln Val Gln Leu Val Gln Ser Gly Gly Gly Val Val Gln Pro Gly Lys
  1               5                  10                  15

Ser Leu Arg Leu Ser Cys Ala Ala Ser Gly Phe Thr Phe Ser Ser Tyr
             20                  25                  30

Ala Met His Trp Val Arg Gln Ala Pro Gly Lys Gly Leu Glu Trp Val
         35                  40                  45

Ala Val Ile Ser Tyr Asp Gly Asn Lys Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Ala Ala Val Phe Tyr Cys
             85                  90                  95

Ala Arg Ala Arg Leu Cys Thr Ser Thr Ser Cys Tyr Trp Thr Phe Asp
            100                 105                 110

Pro Trp Gly Gln Gly Thr Leu Val Thr Val Ser Ser
            115                 120

<210> SEQ ID NO 46
<211> LENGTH: 124
<212> TYPE: PRT
<213> ORGANISM: Artificial Sequence
<220> FEATURE:
<223> OTHER INFORMATION: single chain antibody

<400> SEQUENCE: 46

Gln Val Gln Leu Val Gln Ser Gly Gly Gly Val Val Gln Pro Gly Lys
  1               5                  10                  15

Ser Leu Arg Leu Ser Cys Ala Ala Ser Gly Phe Thr Phe Ser Ser Tyr
             20                  25                  30

Ala Met His Trp Val Arg Gln Ala Pro Gly Lys Gly Leu Glu Trp Val
         35                  40                  45

Ala Val Ile Ser Tyr Asp Gly Asn Lys Lys Tyr Tyr Ala Asp Ser Val
```

```
                 50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Ala Ala Val Phe Tyr Cys
                 85                  90                  95

Ala Arg Ala Arg Leu Cys Thr Ser Thr Ser Cys Tyr Trp Thr Phe Asp
                100                 105                 110

Pro Trp Gly Gln Gly Thr Leu Val Thr Val Ser Ser
            115                 120

<210> SEQ ID NO 47
<211> LENGTH: 121
<212> TYPE: PRT
<213> ORGANISM: Artificial Sequence
<220> FEATURE:
<223> OTHER INFORMATION: single chain antibody

<400> SEQUENCE: 47

Gln Val Gln Leu Val Gln Ser Gly Gly Gly Leu Val Gln Pro Gly Gly
  1               5                  10                  15

Ser Leu Arg Leu Ser Cys Ala Ala Ser Gly Phe Arg Phe Ser Gly Tyr
                 20                  25                  30

Ser Phe Asn Trp Val Arg Gln Ala Pro Gly Lys Gly Leu Glu Trp Val
             35                  40                  45

Ala Tyr Met Ser Ser Gly Gly Ser Ile Lys Asn Tyr Ala Asp Ser Val
         50                  55                  60

Lys Gly Arg Phe Thr Ile Ser Arg Asp Asn Ala Lys Asn Ser Leu Tyr
 65                  70                  75                  80

Leu Gln Val Asn Ser Leu Arg Asp Glu Asp Thr Ala Leu Tyr Tyr Cys
                 85                  90                  95

Ala Arg Gly Pro Pro Gly Arg Pro Asn Asp Ala Phe Asp Ile Trp Gly
                100                 105                 110

Gln Gly Thr Met Val Thr Val Ser Ser
            115                 120

<210> SEQ ID NO 48
<211> LENGTH: 121
<212> TYPE: PRT
<213> ORGANISM: Artificial Sequence
<220> FEATURE:
<223> OTHER INFORMATION: single chain antibody

<400> SEQUENCE: 48

Glu Val Gln Leu Val Gln Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
                 20                  25                  30

Ala Met Thr Trp Val Arg Gln Ala Pro Gly Lys Gly Leu Glu Trp Val
             35                  40                  45

Ser Ser Ile Ser Val Ser Gly Asp Ser Thr Tyr Tyr Ala Asp Ser Val
         50                  55                  60

Lys Gly Arg Phe Thr Ile Ser Arg Asp Asn Ser Lys Asn Thr Val Ser
 65                  70                  75                  80

Leu Gln Met Asn Ser Leu Arg Ala Glu Asp Thr Ala Leu Tyr Tyr Cys
                 85                  90                  95

Ala Lys Gly Leu Ser Lys Ala Asp Leu Phe Gly Met Asp Val Trp Gly
                100                 105                 110
```

-continued

```
Gln Gly Thr Met Val Thr Val Ser Ser
        115                 120

<210> SEQ ID NO 49
<211> LENGTH: 120
<212> TYPE: PRT
<213> ORGANISM: Artificial Sequence
<220> FEATURE:
<223> OTHER INFORMATION: single chain antibody

<400> SEQUENCE: 49

Gln Val Gln Leu Gln Glu Ser Gly Pro Gly Leu Val Lys Pro Ser Glu
1               5                   10                  15

Thr Leu Ser Leu Thr Cys Ser Val Ser Gly Val Ser Ile Ser Asp Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Asn Leu Ser Ser Val Thr Ala Ala Asp Thr Ala Val Tyr Tyr Cys Ala
                85                  90                  95

Arg His Thr Ser Gly Trp Ser Gly Gly Ala Phe Asp Ile Trp Gly Gln
            100                 105                 110

Gly Thr Met Val Thr Val Ser Ser
        115                 120

<210> SEQ ID NO 50
<211> LENGTH: 120
<212> TYPE: PRT
<213> ORGANISM: Artificial Sequence
<220> FEATURE:
<223> OTHER INFORMATION: single chain antibody

<400> SEQUENCE: 50

Gln Val Gln Leu Gln Glu Ser Gly Pro Gly Leu Val Lys Pro Ser Glu
1               5                   10                  15

Thr Leu Ser Leu Thr Cys Ser Val Ser Gly Val Ser Ile Ser Asp Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Asn Leu Ser Ser Val Thr Ala Ala Asp Thr Ala Val Tyr Tyr Cys Ala
                85                  90                  95

Arg His Thr Ser Gly Trp Ser Gly Gly Ala Phe Asp Ile Trp Gly Gln
            100                 105                 110

Gly Thr Met Val Thr Val Ser Ser
        115                 120

<210> SEQ ID NO 51
<211> LENGTH: 120
<212> TYPE: PRT
<213> ORGANISM: Artificial Sequence
<220> FEATURE:
<223> OTHER INFORMATION: single chain antibody
```

```
<400> SEQUENCE: 51

Glu Val Gln Leu Val Gln Ser Gly Gly Asn Leu Val Gln Pro Gly Gly
1               5                   10                  15

Ser Leu Arg Leu Ser Cys Ala Ala Thr Gly Pro Ile Gly Ser His Trp
            20                  25                  30

Met Thr Trp Val Arg Gln Ala Pro Gly Gln Gly Leu Glu Trp Val Ala
        35                  40                  45

Asn Ile Asn Leu Asp Gly Thr Glu Lys Phe Tyr Val Asp Ser Val Lys
    50                  55                  60

Gly Arg Phe Thr Val Ser Arg Asp Asn Arg Lys Ser Ser Val Phe Leu
65              70                  75                  80

Gln Met Asn Asn Leu Arg Val Asp Asp Thr Ala Val Tyr Tyr Cys Ala
                85                  90                  95

Arg Leu Gln Trp Gly Gly Tyr Asn Gly Trp Leu Ser Pro Trp Gly Gln
            100                 105                 110

Gly Thr Leu Val Thr Val Ser Ser
        115                 120

<210> SEQ ID NO 52
<211> LENGTH: 120
<212> TYPE: PRT
<213> ORGANISM: Artificial Sequence
<220> FEATURE:
<223> OTHER INFORMATION: single chain antibody

<400> SEQUENCE: 52

Glu Val Gln Leu Val Gln Ser Gly Gly Asn Leu Val Gln Pro Gly Gly
1               5                   10                  15

Ser Leu Arg Leu Ser Cys Ala Ala Thr Gly Pro Ile Gly Ser His Trp
            20                  25                  30

Met Thr Trp Val Arg Gln Ala Pro Gly Gln Gly Leu Glu Trp Val Ala
        35                  40                  45

Asn Ile Asn Leu Asp Gly Thr Glu Lys Phe Tyr Val Asp Ser Val Lys
    50                  55                  60

Gly Arg Phe Thr Val Ser Arg Asp Asn Arg Lys Ser Ser Val Phe Leu
65              70                  75                  80

Gln Met Asn Asn Leu Arg Val Asp Asp Thr Ala Val Tyr Tyr Cys Ala
                85                  90                  95

Arg Leu Gln Trp Gly Gly Tyr Asn Gly Trp Leu Ser Pro Trp Gly Gln
            100                 105                 110

Gly Thr Leu Val Thr Val Ser Ser
        115                 120

<210> SEQ ID NO 53
<211> LENGTH: 108
<212> TYPE: PRT
<213> ORGANISM: Artificial Sequence
<220> FEATURE:
<223> OTHER INFORMATION: single chain antibody

<400> SEQUENCE: 53

Asp Ile Val Met Thr Gln Ser Pro Ser Phe Leu Ser Ala Ser Val Gly
1               5                   10                  15

Asp Arg Val Thr Ile Thr Cys Trp Ala Ser Gln Gly Ile Ser Ser Tyr
            20                  25                  30

Leu Ala Trp Tyr Gln Gln Lys Pro Gly Lys Ala Pro Lys Leu Leu Ile
            35                  40                  45
```

Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Leu
                85                  90                  95

Thr Phe Gly Gly Gly Thr Lys Val Asp Ile Lys Arg
            100                 105

<210> SEQ ID NO 54
<211> LENGTH: 108
<212> TYPE: PRT
<213> ORGANISM: Artificial Sequence
<220> FEATURE:
<223> OTHER INFORMATION: single chain antibody

<400> SEQUENCE: 54

Glu Ile Val Leu Thr Gln Ser Pro Asp Ser Leu Ser Ala Ser Val Gly
1               5                   10                  15

Asp Arg Val Thr Ile Thr Cys Arg Ala Ser Gln Gly Ile Ser Gly Tyr
                20                  25                  30

Leu Ala Trp Tyr Gln His Lys Ala Gly Lys Ala Pro Lys Leu Leu Ile
            35                  40                  45

Tyr Ala Ala Ser Ser Leu Gln Ser Gly Val Pro Ser Arg Phe Ser Gly
    50                  55                  60

Ser Gly Tyr Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Pro Phe
                85                  90                  95

Thr Phe Gly Gly Gly Thr Lys Val Glu Ile Lys Arg
            100                 105

<210> SEQ ID NO 55
<211> LENGTH: 108
<212> TYPE: PRT
<213> ORGANISM: Artificial Sequence
<220> FEATURE:
<223> OTHER INFORMATION: single chain antibody

<400> SEQUENCE: 55

Glu Ile Val Leu Thr Gln Ser Pro Ser Phe Leu Ser Ala Phe Val Gly
1               5                   10                  15

Asp Arg Val Thr Ile Thr Cys Arg Thr Ser Gln Ser Ile Asn Asn Tyr
                20                  25                  30

Leu Asn Trp Tyr Gln Gln Lys Ala Gly Lys Ala Pro Lys Leu Leu Ile
            35                  40                  45

Tyr Ala Ala Ser Thr Leu His Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Ser Tyr Ser Ile Pro Leu
                85                  90                  95

Thr Phe Gly Gly Gly Thr Lys Val Glu Ile Lys Arg
            100                 105

<210> SEQ ID NO 56
<211> LENGTH: 109
<212> TYPE: PRT
<213> ORGANISM: Artificial Sequence

```
<220> FEATURE:
<223> OTHER INFORMATION: single chain antibody

<400> SEQUENCE: 56
```

Asp Ile Val Met Thr Gln Ser Pro Asp Ser Leu Ser Ala Ser Val Gly
 1               5                  10                  15

Asp Ser Val Thr Ile Thr Cys Arg Ala Ser Gln Ser Phe Ser Ser Ser
            20                  25                  30

Tyr Leu Ala Trp Tyr Gln Gln Lys Pro Gly Gln Ala Pro Arg Leu Leu
        35                  40                  45

Ile Tyr Ala Ala Ser Ser Arg Ala Ala Gly Val Pro Thr Gly Ser Val
 50                  55                  60

Ala Asp Gly Ser Gly Thr Asp Phe Thr Leu Thr Ile Ser Gly Leu Gln
 65                  70                  75                  80

Pro Glu Asp Phe Ala Ala Tyr Tyr Cys Gln Gln Ser Tyr Ser Thr Pro
                85                  90                  95

Tyr Thr Phe Gly Gly Gly Thr Lys Val Glu Ile Lys Arg
            100                 105

```
<210> SEQ ID NO 57
<211> LENGTH: 108
<212> TYPE: PRT
<213> ORGANISM: Artificial Sequence
<220> FEATURE:
<223> OTHER INFORMATION: single chain antibody

<400> SEQUENCE: 57
```

Asp Ile Val Met Thr Gln Ser Pro Ser Phe Leu Ser Ala Phe Val Gly
 1               5                  10                  15

Asp Arg Val Thr Ile Thr Cys Arg Ala Ser Gln Ser Ile Ser Asn Trp
            20                  25                  30

Leu Ala Trp Tyr Gln Gln Lys Pro Gly Lys Ala Pro Lys Val Leu Ile
        35                  40                  45

Tyr Lys Ala Ser Ser Leu Glu Asn Gly Val Pro Ser Arg Phe Ser Gly
 50                  55                  60

Ser Gly Ser Gly Thr Asp Phe Thr Leu Thr Ile Thr Ser Leu Gln Pro
 65                  70                  75                  80

Asp Asp Phe Ala Thr Tyr Tyr Cys Gln Gln Tyr Asn Ala Tyr Pro Leu
                85                  90                  95

Thr Phe Gly Gly Gly Thr Lys Val Glu Ile Lys Arg
            100                 105

```
<210> SEQ ID NO 58
<211> LENGTH: 108
<212> TYPE: PRT
<213> ORGANISM: Artificial Sequence
<220> FEATURE:
<223> OTHER INFORMATION: single chain antibody

<400> SEQUENCE: 58
```

Glu Ile Val Leu Thr Gln Ser Pro Ser Thr Leu Ser Ala Ser Val Gly
 1               5                  10                  15

Asp Arg Val Ala Ile Thr Cys Arg Ala Ser Gln Arg Ile Gly Ser Trp
            20                  25                  30

Leu Ala Trp Tyr Gln Gln Lys Pro Gly Lys Ala Pro Asn Pro Leu Ile
        35                  40                  45

Tyr Lys Ala Phe Ser Leu Glu Ser Gly Val Pro Ser Arg Phe Ser Gly
 50                  55                  60

```
Ser Arg Ser Gly Thr Glu Phe Thr Leu Thr Ile Ser Ser Leu Gln Pro
 65                  70                  75                  80

Asp Asp Phe Ala Thr Tyr Phe Cys Gln Gln Tyr Asp Ser Tyr Pro Tyr
                 85                  90                  95

Thr Phe Gly Gln Gly Thr Lys Leu Glu Ile Lys Arg
            100                 105
```

<210> SEQ ID NO 59
<211> LENGTH: 107
<212> TYPE: PRT
<213> ORGANISM: Artificial Sequence
<220> FEATURE:
<223> OTHER INFORMATION: single chain antibody

<400> SEQUENCE: 59

```
Asp Val Val Met Thr Gln Ser Pro Ser Ser Leu Ser Ala Ser Ile Gly
 1               5                  10                  15

Asp Arg Val Thr Phe Thr Cys Gln Ala Ser Gln Asp Ile Ser Asn Arg
                 20                  25                  30

Leu Asn Trp Tyr Gln Gln Lys Pro Gly Lys Val Pro Lys Leu Leu Ile
             35                  40                  45

Ser Asp Ala Ser Asn Leu Glu Thr Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Tyr Asp Pro Leu Leu Thr
                 85                  90                  95

Phe Gly Gly Gly Thr Lys Val Glu Ile Lys Arg
            100                 105
```

<210> SEQ ID NO 60
<211> LENGTH: 108
<212> TYPE: PRT
<213> ORGANISM: Artificial Sequence
<220> FEATURE:
<223> OTHER INFORMATION: single chain antibody

<400> SEQUENCE: 60

```
Asp Ile Gln Met Thr Gln Ser Pro Ser Ser Val Ser Ala Ser Val Gly
 1               5                  10                  15

Asp Thr Val Thr Ile Ser Cys Arg Ala Ser Gln Gly Ile Ser Ser Trp
                 20                  25                  30

Leu Ala Trp Tyr Gln Gln Lys Ser Gly Gln Ala Pro Thr Leu Leu Ile
             35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Ile Ile Ser Ser Leu Gln Pro
 65                  70                  75                  80

Glu Asp Phe Ala Thr Tyr Tyr Cys Gln Gln Ala Tyr Arg Thr Pro Ile
                 85                  90                  95

Thr Phe Gly Gly Gly Thr Lys Val Glu Ile Lys Arg
            100                 105
```

<210> SEQ ID NO 61
<211> LENGTH: 108
<212> TYPE: PRT
<213> ORGANISM: Artificial Sequence
<220> FEATURE:
<223> OTHER INFORMATION: single chain antibody

<400> SEQUENCE: 61

Asp Ile Gln Met Thr Gln Ser Pro Ser Ser Val Ser Ala Ser Val Gly
1               5                   10                  15

Asp Arg Val Ser Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Asn Thr Pro Pro
                85                  90                  95

Thr Phe Gly Gln Gly Thr Lys Leu Glu Ile Lys Arg
            100                 105

<210> SEQ ID NO 62
<211> LENGTH: 108
<212> TYPE: PRT
<213> ORGANISM: Artificial Sequence
<220> FEATURE:
<223> OTHER INFORMATION: single chain antibody

<400> SEQUENCE: 62

Ala Ser Val Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Ser Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Thr Gly Asn Gln
                85                  90                  95

Leu Phe Gly Gly Gly Thr Lys Val Thr Val Leu Gly
            100                 105

<210> SEQ ID NO 63
<211> LENGTH: 108
<212> TYPE: PRT
<213> ORGANISM: Artificial Sequence
<220> FEATURE:
<223> OTHER INFORMATION: single chain antibody

<400> SEQUENCE: 63

Ala Glu Leu Thr Gln Asp Pro Ala Val Ser Val Ala Leu Gly Gln Thr
1               5                   10                  15

Val Arg Ile Thr Cys Gln Gly Asp Ser Leu Arg Ser Tyr Tyr Ala Ser
            20                  25                  30

Trp Tyr Gln Gln Lys Pro Gly Gln Ala Pro Val Leu Val Ile Tyr Gly
        35                  40                  45

Glu Asn Ser Arg Pro Ser Gly Ile Pro Asp Arg Phe Ser Gly Ser Ser
    50                  55                  60

Ser Gly Asn Thr Ala Ser Leu Thr Ile Ala Gly Ala Gln Ala Glu Asp
65                  70                  75                  80

```
Glu Ala Asp Tyr Tyr Cys Asn Ser Pro Asp Ser Ser Gly Ile His Leu
                 85                  90                  95

Val Phe Gly Gly Gly Thr Lys Val Thr Val Leu Gly
            100                 105
```

<210> SEQ ID NO 64
<211> LENGTH: 114
<212> TYPE: PRT
<213> ORGANISM: Artificial Sequence
<220> FEATURE:
<223> OTHER INFORMATION: single chain antibody

<400> SEQUENCE: 64

```
Glu Ile Val Leu Thr Gln Ser Pro Asp Ser Leu Ala Val Ser Leu Gly
  1               5                  10                  15

Glu Arg Ala Thr Ile Asn Cys Lys Ser Ser Gln Ser Val Leu Tyr Ser
                 20                  25                  30

Ser Asn Asn Lys Asn Tyr Leu Ala Trp Tyr Gln Gln Lys Pro Gly Gln
             35                  40                  45

Pro Pro Lys Leu Leu Phe Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys His Gln
                 85                  90                  95

Tyr Tyr Ser Ser Pro Leu Thr Phe Gly Gly Gly Thr Lys Leu Glu Ile
            100                 105                 110

Lys Arg
```

<210> SEQ ID NO 65
<211> LENGTH: 114
<212> TYPE: PRT
<213> ORGANISM: Artificial Sequence
<220> FEATURE:
<223> OTHER INFORMATION: single chain antibody

<400> SEQUENCE: 65

```
Glu Ile Val Leu Thr Gln Ser Pro Asn Ser Leu Ala Val Ser Leu Gly
  1               5                  10                  15

Glu Arg Ala Thr Ile Arg Cys Lys Ser Ser Gln Ser Val Leu Tyr Ser
                 20                  25                  30

Gly Asn Asn Lys Asn Tyr Ile Ala Trp Tyr Gln Gln Lys Pro Gly Gln
             35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Glu Thr Asp Phe Thr Leu Thr
 65                  70                  75                  80

Ile Ser Ser Leu Arg Ala Glu Asp Val Ala Leu Tyr Tyr Cys Gln Gln
                 85                  90                  95

Tyr Tyr Ser Ser Arg Trp Thr Phe Gly Gln Gly Thr Lys Leu Glu Ile
            100                 105                 110

Lys Arg
```

<210> SEQ ID NO 66
<211> LENGTH: 108
<212> TYPE: PRT
<213> ORGANISM: Artificial Sequence
<220> FEATURE:
<223> OTHER INFORMATION: single chain antibody

<400> SEQUENCE: 66

Asp Ile Val Met Thr Gln Ser Pro Ser Ser Val Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Gly Thr Ser Asn Leu Gln Ser Gly Val Pro Ser Gly Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Glu Thr Tyr Ser Thr Pro Pro
                85                  90                  95

Thr Phe Gly Gly Gly Thr Lys Leu Glu Ile Lys Arg
            100                 105

<210> SEQ ID NO 67
<211> LENGTH: 108
<212> TYPE: PRT
<213> ORGANISM: Artificial Sequence
<220> FEATURE:
<223> OTHER INFORMATION: single chain antibody

<400> SEQUENCE: 67

Asp Ile Val Met Thr Gln Ser Pro Ser Ser Leu Ser Ala Ser Val Gly
1               5                   10                  15

Asp Arg Val Thr Ile Ser Cys Arg Ala Ser Gln Ser Ile Arg His Tyr
            20                  25                  30

Val Asn Trp Tyr Gln Gln Lys Pro Gly Lys Ala Pro Lys Leu Leu Ile
        35                  40                  45

Tyr Lys Ala Ser Ser Leu Ala Ser Gly Ala Pro Ser Arg Phe Ser Gly
    50                  55                  60

Ser Gly Ser Gly Thr Asp Phe Thr Leu Thr Ile Ser Ser Leu Gln Pro
65                  70                  75                  80

Asp Asp Phe Ala Thr Tyr Tyr Cys Gln Gln Ser Tyr Ser Ile Pro Leu
                85                  90                  95

Thr Phe Gly Gly Gly Thr Lys Val Glu Ile Lys Arg
            100                 105

<210> SEQ ID NO 68
<211> LENGTH: 30
<212> TYPE: PRT
<213> ORGANISM: Artificial Sequence
<220> FEATURE:
<223> OTHER INFORMATION: single chain antibody fragment

<400> SEQUENCE: 68

Gln Val Gln Leu Gln Gln Ser Gly Ala Glu Val Lys Lys Pro Gly Ser
1               5                   10                  15

Ser Val Lys Val Ser Cys Lys Ala Ser Gly Gly Thr Phe Thr
            20                  25                  30

<210> SEQ ID NO 69
<211> LENGTH: 5
<212> TYPE: PRT
<213> ORGANISM: Artificial Sequence
<220> FEATURE:
<223> OTHER INFORMATION: single chain antibody fragment

<400> SEQUENCE: 69

Arg Tyr Thr Ile Thr
1               5

<210> SEQ ID NO 70
<211> LENGTH: 14
<212> TYPE: PRT
<213> ORGANISM: Artificial Sequence
<220> FEATURE:
<223> OTHER INFORMATION: single chain antibody fragment

<400> SEQUENCE: 70

Trp Val Arg Gln Ala Pro Gly Gln Gly Leu Glu Trp Met Gly
1               5                   10

<210> SEQ ID NO 71
<211> LENGTH: 17
<212> TYPE: PRT
<213> ORGANISM: Artificial Sequence
<220> FEATURE:
<223> OTHER INFORMATION: single chain antibody fragment

<400> SEQUENCE: 71

Gly Ile Ile Pro Ile Phe Asp Lys Ala Asn Tyr Ala Gln Lys Phe Gln
1               5                   10                  15

Ser

<210> SEQ ID NO 72
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 72

Arg Val Thr Phe Thr Ala Asp Ala Ser Thr Ser Thr Ala Tyr Met Glu
1               5                   10                  15

Leu Gly Ser Leu Arg Pro Glu Asp Thr Ala Val Tyr Tyr Cys Ala Ala
            20                  25                  30

<210> SEQ ID NO 73
<211> LENGTH: 10
<212> TYPE: PRT
<213> ORGANISM: Artificial Sequence
<220> FEATURE:
<223> OTHER INFORMATION: single chain antibody fragment

<400> SEQUENCE: 73

Tyr Ser Arg Gly Tyr Val His Phe Asp Tyr
1               5                   10

<210> SEQ ID NO 74
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 74

Trp Gly Pro Gly Thr Leu Val Thr Val Ser Ser
1               5                   10

<210> SEQ ID NO 75
<211> LENGTH: 30
<212> TYPE: PRT
<213> ORGANISM: Artificial Sequence

```
<220> FEATURE:
<223> OTHER INFORMATION: single chain antibody fragment

<400> SEQUENCE: 75

Gln Val Gln Leu Val Glu Ser Gly Ala Glu Val Lys Lys Pro Gly Ser
 1               5                  10                  15

Ser Val Lys Val Ser Cys Lys Ala Ser Gly Gly Thr Phe Ser
            20                  25                  30

<210> SEQ ID NO 76
<211> LENGTH: 5
<212> TYPE: PRT
<213> ORGANISM: Artificial Sequence
<220> FEATURE:
<223> OTHER INFORMATION: single chain antibody fragment

<400> SEQUENCE: 76

Asn Ser Gly Phe Thr
 1               5

<210> SEQ ID NO 77
<211> LENGTH: 14
<212> TYPE: PRT
<213> ORGANISM: Artificial Sequence
<220> FEATURE:
<223> OTHER INFORMATION: single chain antibody fragment

<400> SEQUENCE: 77

Trp Val Arg Gln Val Pro Gly Gln Gly Leu Glu Trp Met Gly
 1               5                  10

<210> SEQ ID NO 78
<211> LENGTH: 17
<212> TYPE: PRT
<213> ORGANISM: Artificial Sequence
<220> FEATURE:
<223> OTHER INFORMATION: single chain antibody fragment

<400> SEQUENCE: 78

Gly Ile Ile Pro Met Phe Gly Pro Ala Asn Tyr Ala Gln Lys Phe Gln
 1               5                  10                  15

Gly

<210> SEQ ID NO 79
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 79

Arg Val Thr Ile Thr Ala Asp Glu Ser Thr Arg Met Val Tyr Met Glu
 1               5                  10                  15

Leu Arg Ser Leu Arg Ser Glu Asp Thr Ala Val Tyr Tyr Cys Ala Arg
            20                  25                  30

<210> SEQ ID NO 80
<211> LENGTH: 17
<212> TYPE: PRT
<213> ORGANISM: Artificial Sequence
<220> FEATURE:
<223> OTHER INFORMATION: single chain antibody fragment

<400> SEQUENCE: 80

Asp Gln Gly Glu Tyr Thr Val Gly Met Leu Leu Tyr Tyr Ala Met Asp
```

Val

<210> SEQ ID NO 81
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 81

Trp Gly Glu Gly Thr Thr Val Thr Val Ser Ser
1               5                   10

<210> SEQ ID NO 82
<211> LENGTH: 30
<212> TYPE: PRT
<213> ORGANISM: Artificial Sequence
<220> FEATURE:
<223> OTHER INFORMATION: single chain antibody fragment

<400> SEQUENCE: 82

Gln Val Gln Leu Gln Glu Ser Gly Ala Glu Val Lys Lys Pro Gly Ser
1               5                   10                  15

Ser Val Lys Val Ser Cys Lys Ala Ser Gly Gly Asp Leu Asn
            20                  25                  30

<210> SEQ ID NO 83
<211> LENGTH: 5
<212> TYPE: PRT
<213> ORGANISM: Artificial Sequence
<220> FEATURE:
<223> OTHER INFORMATION: single chain antibody fragment

<400> SEQUENCE: 83

Lys Tyr Ala Ile Thr
1               5

<210> SEQ ID NO 84
<211> LENGTH: 14
<212> TYPE: PRT
<213> ORGANISM: Artificial Sequence
<220> FEATURE:
<223> OTHER INFORMATION: single chain antibody fragment

<400> SEQUENCE: 84

Trp Leu Arg Gln Ala Pro Gly Gln Gly Phe Glu Trp Met Gly
1               5                   10

<210> SEQ ID NO 85
<211> LENGTH: 17
<212> TYPE: PRT
<213> ORGANISM: Artificial Sequence
<220> FEATURE:
<223> OTHER INFORMATION: single chain antibody fragment

<400> SEQUENCE: 85

Gly Ile Thr Pro Ile Phe Ala Thr Thr Asn Tyr Ala Gln Lys Phe Gln
1               5                   10                  15

Gly

<210> SEQ ID NO 86
<211> LENGTH: 32
<212> TYPE: PRT
<213> ORGANISM: Artificial Sequence

```
<220> FEATURE:
<223> OTHER INFORMATION: single chain antibody fragment

<400> SEQUENCE: 86

Arg Val Met Ile Thr Ala Asp Glu Val Thr Ser Thr Val Tyr Met Asp
 1               5                  10                  15

Leu Ser Ser Leu Gly Ser Glu Asp Thr Ala Ile Tyr Phe Cys Ala Lys
            20                  25                  30

<210> SEQ ID NO 87
<211> LENGTH: 12
<212> TYPE: PRT
<213> ORGANISM: Artificial Sequence
<220> FEATURE:
<223> OTHER INFORMATION: single chain antibody fragment

<400> SEQUENCE: 87

Ser Pro Arg Gly Gly Ile Val Gly Thr Phe Asp Thr
 1               5                  10

<210> SEQ ID NO 88
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 88

Trp Gly Gln Gly Thr Met Val Thr Val Ser Ser
 1               5                  10

<210> SEQ ID NO 89
<211> LENGTH: 30
<212> TYPE: PRT
<213> ORGANISM: Artificial Sequence
<220> FEATURE:
<223> OTHER INFORMATION: single chain antibody fragment

<400> SEQUENCE: 89

Gln Val Gln Leu Val Glu Ser Gly Gly Gly Leu Val Lys Pro Gly Glu
 1               5                  10                  15

Ser Leu Arg Leu Ser Cys Ala Ala Ser Gly Phe Thr Phe Ser
            20                  25                  30

<210> SEQ ID NO 90
<211> LENGTH: 5
<212> TYPE: PRT
<213> ORGANISM: Artificial Sequence
<220> FEATURE:
<223> OTHER INFORMATION: single chain antibody fragment

<400> SEQUENCE: 90

Asn Tyr Asn Met Asn
 1               5

<210> SEQ ID NO 91
<211> LENGTH: 14
<212> TYPE: PRT
<213> ORGANISM: Artificial Sequence
<220> FEATURE:
<223> OTHER INFORMATION: single chain antibody fragment

<400> SEQUENCE: 91

Trp Val Arg Gln Ala Pro Gly Lys Gly Leu Glu Trp Val Ser
 1               5                  10
```

<210> SEQ ID NO 92
<211> LENGTH: 17
<212> TYPE: PRT
<213> ORGANISM: Artificial Sequence
<220> FEATURE:
<223> OTHER INFORMATION: single chain antibody fragment

<400> SEQUENCE: 92

```
Ser Ile Ser Asp Gly Gly Ser Tyr Arg Tyr Tyr Ala Tyr Ser Val Lys
1               5                   10                  15

Gly
```

<210> SEQ ID NO 93
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 93

```
Arg Phe Thr Ile Ser Arg Asp Asn Thr Lys Asn Ser Leu Tyr Leu Gln
1               5                   10                  15

Met Asn Ser Leu Arg Ala Glu Asp Thr Ala Leu Tyr Tyr Cys Ala Arg
            20                  25                  30
```

<210> SEQ ID NO 94
<211> LENGTH: 15
<212> TYPE: PRT
<213> ORGANISM: Artificial Sequence
<220> FEATURE:
<223> OTHER INFORMATION: single chain antibody fragment

<400> SEQUENCE: 94

```
Asp Glu Met Val His Gly Ile Leu Val Tyr Tyr Gly Met Asp Val
1               5                   10                  15
```

<210> SEQ ID NO 95
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 95

```
Trp Gly Gln Gly Thr Thr Val Thr Val Ser Ser
1               5                   10
```

<210> SEQ ID NO 96
<211> LENGTH: 30
<212> TYPE: PRT
<213> ORGANISM: Artificial Sequence
<220> FEATURE:
<223> OTHER INFORMATION: single chain antibody fragment

<400> SEQUENCE: 96

```
Gln Val Gln Leu Gln Glu Ser Gly Gly Gly Leu Val Gln Pro Gly Gly
1               5                   10                  15

Ser Leu Arg Leu Ser Cys Gly Ala Ser Gly Phe Thr Phe Ser
            20                  25                  30
```

<210> SEQ ID NO 97
<211> LENGTH: 5
<212> TYPE: PRT
<213> ORGANISM: Artificial Sequence
<220> FEATURE:

<223> OTHER INFORMATION: single chain antibody fragment

<400> SEQUENCE: 97

Ser Asp Ala Met Ser
1               5

<210> SEQ ID NO 98
<211> LENGTH: 14
<212> TYPE: PRT
<213> ORGANISM: Artificial Sequence
<220> FEATURE:
<223> OTHER INFORMATION: single chain antibody fragment

<400> SEQUENCE: 98

Trp Val Arg Gln Ala Pro Gly Lys Gly Leu Glu Trp Val Ala
1               5                   10

<210> SEQ ID NO 99
<211> LENGTH: 17
<212> TYPE: PRT
<213> ORGANISM: Artificial Sequence
<220> FEATURE:
<223> OTHER INFORMATION: single chain antibody fragment

<400> SEQUENCE: 99

Ala Ile Leu Pro Ser Gly Glu Ala Thr Tyr Tyr Ala Asp Ser Val Lys
1               5                   10                  15

Gly

<210> SEQ ID NO 100
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 100

Arg Phe Thr Ile Ser Arg His Ser Ser Lys Asn Thr Leu Tyr Leu Gln
1               5                   10                  15

Met Asn Ser Leu Arg Ala Asp Asp Thr Ala Val Tyr Tyr Cys Ala Arg
            20                  25                  30

<210> SEQ ID NO 101
<211> LENGTH: 12
<212> TYPE: PRT
<213> ORGANISM: Artificial Sequence
<220> FEATURE:
<223> OTHER INFORMATION: single chain antibody fragment

<400> SEQUENCE: 101

Asp Ser Tyr His Ser Arg Leu Ala Ala Phe Asp Ile
1               5                   10

<210> SEQ ID NO 102
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 102

Trp Gly Gln Gly Thr Met Val Thr Val Ser Ser
1               5                   10

<210> SEQ ID NO 103

```
<211> LENGTH: 30
<212> TYPE: PRT
<213> ORGANISM: Artificial Sequence
<220> FEATURE:
<223> OTHER INFORMATION: single chain antibody fragment

<400> SEQUENCE: 103

Gln Val Gln Leu Gln Glu Ser Gly Gly Gly Leu Val Gln Pro Gly Gly
1               5                   10                  15

Ser Leu Arg Leu Ser Cys Gly Ala Ser Gly Phe Thr Phe Ser
            20                  25                  30

<210> SEQ ID NO 104
<211> LENGTH: 5
<212> TYPE: PRT
<213> ORGANISM: Artificial Sequence
<220> FEATURE:
<223> OTHER INFORMATION: single chain antibody fragment

<400> SEQUENCE: 104

Ser Asp Ala Met Ser
1               5

<210> SEQ ID NO 105
<211> LENGTH: 14
<212> TYPE: PRT
<213> ORGANISM: Artificial Sequence
<220> FEATURE:
<223> OTHER INFORMATION: single chain antibody fragment

<400> SEQUENCE: 105

Trp Val Arg Gln Ala Pro Gly Lys Gly Leu Glu Trp Val Ala
1               5                   10

<210> SEQ ID NO 106
<211> LENGTH: 17
<212> TYPE: PRT
<213> ORGANISM: Artificial Sequence
<220> FEATURE:
<223> OTHER INFORMATION: single chain antibody fragment

<400> SEQUENCE: 106

Ala Ile Leu Pro Ser Gly Glu Ala Thr Tyr Tyr Ala Asp Ser Val Lys
1               5                   10                  15

Gly

<210> SEQ ID NO 107
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 107

Arg Phe Thr Ile Ser Arg His Ser Ser Lys Asn Thr Leu Tyr Leu Gln
1               5                   10                  15

Met Asn Ser Leu Arg Ala Asp Asp Thr Ala Val Tyr Tyr Cys Ala Arg
            20                  25                  30

<210> SEQ ID NO 108
<211> LENGTH: 12
<212> TYPE: PRT
<213> ORGANISM: Artificial Sequence
<220> FEATURE:
<223> OTHER INFORMATION: single chain antibody fragment
```

-continued

<400> SEQUENCE: 108

Asp Ser Tyr His Ser Arg Leu Ala Ala Phe Asp Ile
1               5                   10

<210> SEQ ID NO 109
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 109

Trp Gly Gln Gly Thr Met Val Thr Val Ser Ser
1               5                   10

<210> SEQ ID NO 110
<211> LENGTH: 30
<212> TYPE: PRT
<213> ORGANISM: Artificial Sequence
<220> FEATURE:
<223> OTHER INFORMATION: single chain antibody fragment

<400> SEQUENCE: 110

Gln Val Gln Leu Val Gln Ser Gly Gly Gly Val Val Gln Pro Gly Arg
1               5                   10                  15

Pro Leu Arg Leu Ser Cys Ala Ala Ser Thr Phe Asn Phe Arg
            20                  25                  30

<210> SEQ ID NO 111
<211> LENGTH: 5
<212> TYPE: PRT
<213> ORGANISM: Artificial Sequence
<220> FEATURE:
<223> OTHER INFORMATION: single chain antibody fragment

<400> SEQUENCE: 111

Asp Phe Tyr Met Ser
1               5

<210> SEQ ID NO 112
<211> LENGTH: 14
<212> TYPE: PRT
<213> ORGANISM: Artificial Sequence
<220> FEATURE:
<223> OTHER INFORMATION: single chain antibody fragment

<400> SEQUENCE: 112

Trp Ile Arg Gln Ala Pro Gly Lys Gly Leu Glu Trp Val Ser
1               5                   10

<210> SEQ ID NO 113
<211> LENGTH: 17
<212> TYPE: PRT
<213> ORGANISM: Artificial Sequence
<220> FEATURE:
<223> OTHER INFORMATION: single chain antibody fragment

<400> SEQUENCE: 113

Tyr Ile Gly Ser Ser Gly Ser Ala Leu Gln Tyr Ala Asp Ser Val Lys
1               5                   10                  15

Gly

<210> SEQ ID NO 114
<211> LENGTH: 32
<212> TYPE: PRT

```
<213> ORGANISM: Artificial Sequence
<220> FEATURE:
<223> OTHER INFORMATION: single chain antibody fragment

<400> SEQUENCE: 114

Arg Phe Thr Ile Ser Arg Asp Asn Asp Lys Asn Val Leu Tyr Leu Gln
1               5                   10                  15

Met Thr Ser Leu Arg Ala Glu Asp Thr Ala Val Tyr Tyr Cys Ala Arg
                20                  25                  30

<210> SEQ ID NO 115
<211> LENGTH: 15
<212> TYPE: PRT
<213> ORGANISM: Artificial Sequence
<220> FEATURE:
<223> OTHER INFORMATION: single chain antibody fragment

<400> SEQUENCE: 115

Val Ala Ser Arg Tyr His Asp Val Leu Thr Asp Gly Phe Asp Ile
1               5                   10                  15

<210> SEQ ID NO 116
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 116

Trp Gly Gln Gly Thr Met Val Thr Val Ser Ser
1               5                   10

<210> SEQ ID NO 117
<211> LENGTH: 30
<212> TYPE: PRT
<213> ORGANISM: Artificial Sequence
<220> FEATURE:
<223> OTHER INFORMATION: single chain antibody fragment

<400> SEQUENCE: 117

Gln Val Gln Leu Val Gln Ser Gly Gly Gly Val Val Gln Pro Gly Lys
1               5                   10                  15

Ser Leu Arg Leu Ser Cys Ala Ala Ser Gly Phe Thr Phe Ser
                20                  25                  30

<210> SEQ ID NO 118
<211> LENGTH: 5
<212> TYPE: PRT
<213> ORGANISM: Artificial Sequence
<220> FEATURE:
<223> OTHER INFORMATION: single chain antibody fragment

<400> SEQUENCE: 118

Ser Tyr Ala Met His
1               5

<210> SEQ ID NO 119
<211> LENGTH: 14
<212> TYPE: PRT
<213> ORGANISM: Artificial Sequence
<220> FEATURE:
<223> OTHER INFORMATION: single chain antibody fragment

<400> SEQUENCE: 119

Trp Val Arg Gln Ala Pro Gly Lys Gly Leu Glu Trp Val Ala
1               5                   10
```

```
<210> SEQ ID NO 120
<211> LENGTH: 17
<212> TYPE: PRT
<213> ORGANISM: Artificial Sequence
<220> FEATURE:
<223> OTHER INFORMATION: single chain antibody fragment

<400> SEQUENCE: 120

Val Ile Ser Tyr Asp Gly Asn Lys Lys Tyr Tyr Ala Asp Ser Val Lys
1               5                   10                  15

Gly

<210> SEQ ID NO 121
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 121

Arg Phe Thr Ile Ser Arg Asp Asn Ser Lys Asn Thr Leu Tyr Leu Gln
1               5                   10                  15

Met Asn Ser Leu Arg Ala Glu Asp Ala Ala Val Phe Tyr Cys Ala Arg
            20                  25                  30

<210> SEQ ID NO 122
<211> LENGTH: 15
<212> TYPE: PRT
<213> ORGANISM: Artificial Sequence
<220> FEATURE:
<223> OTHER INFORMATION: single chain antibody fragment

<400> SEQUENCE: 122

Ala Arg Leu Cys Thr Ser Thr Ser Cys Tyr Trp Thr Phe Asp Pro
1               5                   10                  15

<210> SEQ ID NO 123
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 123

Trp Gly Gln Gly Thr Leu Val Thr Val Ser Ser
1               5                   10

<210> SEQ ID NO 124
<211> LENGTH: 30
<212> TYPE: PRT
<213> ORGANISM: Artificial Sequence
<220> FEATURE:
<223> OTHER INFORMATION: single chain antibody fragment

<400> SEQUENCE: 124

Gln Val Gln Leu Val Gln Ser Gly Gly Gly Val Val Gln Pro Gly Lys
1               5                   10                  15

Ser Leu Arg Leu Ser Cys Ala Ala Ser Gly Phe Thr Phe Ser
            20                  25                  30

<210> SEQ ID NO 125
<211> LENGTH: 5
<212> TYPE: PRT
<213> ORGANISM: Artificial Sequence
```

```
<220> FEATURE:
<223> OTHER INFORMATION: single chain antibody fragment

<400> SEQUENCE: 125

Ser Tyr Ala Met His
1               5

<210> SEQ ID NO 126
<211> LENGTH: 14
<212> TYPE: PRT
<213> ORGANISM: Artificial Sequence
<220> FEATURE:
<223> OTHER INFORMATION: single chain antibody fragment

<400> SEQUENCE: 126

Trp Val Arg Gln Ala Pro Gly Lys Gly Leu Glu Trp Val Ala
1               5                   10

<210> SEQ ID NO 127
<211> LENGTH: 17
<212> TYPE: PRT
<213> ORGANISM: Artificial Sequence
<220> FEATURE:
<223> OTHER INFORMATION: single chain antibody fragment

<400> SEQUENCE: 127

Val Ile Ser Tyr Asp Gly Asn Lys Lys Tyr Tyr Ala Asp Ser Val Lys
1               5                   10                  15
Gly

<210> SEQ ID NO 128
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 128

Arg Phe Thr Ile Ser Arg Asp Asn Ser Lys Asn Thr Leu Tyr Leu Gln
1               5                   10                  15
Met Asn Ser Leu Arg Ala Glu Asp Ala Ala Val Phe Tyr Cys Ala Arg
            20                  25                  30

<210> SEQ ID NO 129
<211> LENGTH: 15
<212> TYPE: PRT
<213> ORGANISM: Artificial Sequence
<220> FEATURE:
<223> OTHER INFORMATION: single chain antibody fragment

<400> SEQUENCE: 129

Ala Arg Leu Cys Thr Ser Thr Ser Cys Tyr Trp Thr Phe Asp Pro
1               5                   10                  15

<210> SEQ ID NO 130
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 130

Trp Gly Gln Gly Thr Leu Val Thr Val Ser Ser
1               5                   10
```

```
<210> SEQ ID NO 131
<211> LENGTH: 30
<212> TYPE: PRT
<213> ORGANISM: Artificial Sequence
<220> FEATURE:
<223> OTHER INFORMATION: single chain antibody fragment

<400> SEQUENCE: 131

Gln Val Gln Leu Val Gln Ser Gly Gly Gly Leu Val Gln Pro Gly Gly
 1               5                  10                  15

Ser Leu Arg Leu Ser Cys Ala Ala Ser Gly Phe Arg Phe Ser
            20                  25                  30

<210> SEQ ID NO 132
<211> LENGTH: 5
<212> TYPE: PRT
<213> ORGANISM: Artificial Sequence
<220> FEATURE:
<223> OTHER INFORMATION: single chain antibody fragment

<400> SEQUENCE: 132

Gly Tyr Ser Phe Asn
 1               5

<210> SEQ ID NO 133
<211> LENGTH: 14
<212> TYPE: PRT
<213> ORGANISM: Artificial Sequence
<220> FEATURE:
<223> OTHER INFORMATION: single chain antibody fragment

<400> SEQUENCE: 133

Trp Val Arg Gln Ala Pro Gly Lys Gly Leu Glu Trp Val Ala
 1               5                  10

<210> SEQ ID NO 134
<211> LENGTH: 17
<212> TYPE: PRT
<213> ORGANISM: Artificial Sequence
<220> FEATURE:
<223> OTHER INFORMATION: single chain antibody fragment

<400> SEQUENCE: 134

Tyr Met Ser Ser Gly Gly Ser Ile Lys Asn Tyr Ala Asp Ser Val Lys
 1               5                  10                  15

Gly

<210> SEQ ID NO 135
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 135

Arg Phe Thr Ile Ser Arg Asp Asn Ala Lys Asn Ser Leu Tyr Leu Gln
 1               5                  10                  15

Val Asn Ser Leu Arg Asp Glu Asp Thr Ala Leu Tyr Tyr Cys Ala Arg
            20                  25                  30

<210> SEQ ID NO 136
<211> LENGTH: 12
<212> TYPE: PRT
<213> ORGANISM: Artificial Sequence
<220> FEATURE:
<223> OTHER INFORMATION: single chain antibody fragment
```

-continued

```
<400> SEQUENCE: 136

Gly Pro Pro Gly Arg Pro Asn Asp Ala Phe Asp Ile
1               5                   10

<210> SEQ ID NO 137
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 137

Trp Gly Gln Gly Thr Met Val Thr Val Ser Ser
1               5                   10

<210> SEQ ID NO 138
<211> LENGTH: 30
<212> TYPE: PRT
<213> ORGANISM: Artificial Sequence
<220> FEATURE:
<223> OTHER INFORMATION: single chain antibody fragment

<400> SEQUENCE: 138

Glu Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 139
<211> LENGTH: 5
<212> TYPE: PRT
<213> ORGANISM: Artificial Sequence
<220> FEATURE:
<223> OTHER INFORMATION: single chain antibody fragment

<400> SEQUENCE: 139

Ser Tyr Ala Met Thr
1               5

<210> SEQ ID NO 140
<211> LENGTH: 14
<212> TYPE: PRT
<213> ORGANISM: Artificial Sequence
<220> FEATURE:
<223> OTHER INFORMATION: single chain antibody fragment

<400> SEQUENCE: 140

Trp Val Arg Gln Ala Pro Gly Lys Gly Leu Glu Trp Val Ser
1               5                   10

<210> SEQ ID NO 141
<211> LENGTH: 17
<212> TYPE: PRT
<213> ORGANISM: Artificial Sequence
<220> FEATURE:
<223> OTHER INFORMATION: single chain antibody fragment

<400> SEQUENCE: 141

Ser Ile Ser Val Ser Gly Asp Ser Thr Tyr Tyr Ala Asp Ser Val Lys
1               5                   10                  15

Gly

<210> SEQ ID NO 142
<211> LENGTH: 32
```

```
<212> TYPE: PRT
<213> ORGANISM: Artificial Sequence
<220> FEATURE:
<223> OTHER INFORMATION: single chain antibody fragment

<400> SEQUENCE: 142

Arg Phe Thr Ile Ser Arg Asp Asn Ser Lys Asn Thr Val Ser Leu Gln
 1               5                  10                  15

Met Asn Ser Leu Arg Ala Glu Asp Thr Ala Leu Tyr Tyr Cys Ala Lys
            20                  25                  30

<210> SEQ ID NO 143
<211> LENGTH: 12
<212> TYPE: PRT
<213> ORGANISM: Artificial Sequence
<220> FEATURE:
<223> OTHER INFORMATION: single chain antibody fragment

<400> SEQUENCE: 143

Gly Leu Ser Lys Ala Asp Leu Phe Gly Met Asp Val
 1               5                  10

<210> SEQ ID NO 144
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 144

Trp Gly Gln Gly Thr Met Val Thr Val Ser Ser
 1               5                  10

<210> SEQ ID NO 145
<211> LENGTH: 5
<212> TYPE: PRT
<213> ORGANISM: Artificial Sequence
<220> FEATURE:
<223> OTHER INFORMATION: single chain antibody fragment

<400> SEQUENCE: 145

Asp Tyr Tyr Trp Ser
 1               5

<210> SEQ ID NO 146
<211> LENGTH: 14
<212> TYPE: PRT
<213> ORGANISM: Artificial Sequence
<220> FEATURE:
<223> OTHER INFORMATION: single chain antibody fragment

<400> SEQUENCE: 146

Trp Ile Arg Gln Pro Pro Gly Lys Gly Leu Glu Trp Ile Gly
 1               5                  10

<210> SEQ ID NO 147
<211> LENGTH: 16
<212> TYPE: PRT
<213> ORGANISM: Artificial Sequence
<220> FEATURE:
<223> OTHER INFORMATION: single chain antibody fragment

<400> SEQUENCE: 147

Tyr Ile Tyr Tyr Ser Gly Ser Thr Asn Tyr Asn Pro Ser Leu Lys Ser
 1               5                  10                  15
```

```
<210> SEQ ID NO 148
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 148

Arg Val Thr Ile Ser Val Asp Thr Ser Lys Asn Gln Phe Ser Leu Asn
 1               5                  10                  15

Leu Ser Ser Val Thr Ala Ala Asp Thr Ala Val Tyr Tyr Cys Ala Arg
            20                  25                  30

<210> SEQ ID NO 149
<211> LENGTH: 12
<212> TYPE: PRT
<213> ORGANISM: Artificial Sequence
<220> FEATURE:
<223> OTHER INFORMATION: single chain antibody fragment

<400> SEQUENCE: 149

His Thr Ser Gly Trp Ser Gly Gly Ala Phe Asp Ile
 1               5                  10

<210> SEQ ID NO 150
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 150

Trp Gly Gln Gly Thr Met Val Thr Val Ser Ser
 1               5                  10

<210> SEQ ID NO 151
<211> LENGTH: 30
<212> TYPE: PRT
<213> ORGANISM: Artificial Sequence
<220> FEATURE:
<223> OTHER INFORMATION: single chain antibody fragment

<400> SEQUENCE: 151

Gln Val Gln Leu Gln Glu Ser Gly Pro Gly Leu Val Lys Pro Ser Glu
 1               5                  10                  15

Thr Leu Ser Leu Thr Cys Ser Val Ser Gly Val Ser Ile Ser
            20                  25                  30

<210> SEQ ID NO 152
<211> LENGTH: 5
<212> TYPE: PRT
<213> ORGANISM: Artificial Sequence
<220> FEATURE:
<223> OTHER INFORMATION: single chain antibody fragment

<400> SEQUENCE: 152

Asp Tyr Tyr Trp Ser
 1               5

<210> SEQ ID NO 153
<211> LENGTH: 14
<212> TYPE: PRT
<213> ORGANISM: Artificial Sequence
<220> FEATURE:
<223> OTHER INFORMATION: single chain antibody fragment

<400> SEQUENCE: 153
```

```
Trp Ile Arg Gln Pro Pro Gly Lys Gly Leu Glu Trp Ile Gly
1               5                   10

<210> SEQ ID NO 154
<211> LENGTH: 16
<212> TYPE: PRT
<213> ORGANISM: Artificial Sequence
<220> FEATURE:
<223> OTHER INFORMATION: single chain antibody fragment

<400> SEQUENCE: 154

Tyr Ile Tyr Tyr Ser Gly Ser Thr Asn Tyr Asn Pro Ser Leu Lys Ser
1               5                   10                  15

<210> SEQ ID NO 155
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 155

Arg Val Thr Ile Ser Val Asp Thr Ser Lys Asn Gln Phe Ser Leu Asn
1               5                   10                  15

Leu Ser Ser Val Thr Ala Ala Asp Thr Ala Val Tyr Tyr Cys Ala Arg
                20                  25                  30

<210> SEQ ID NO 156
<211> LENGTH: 12
<212> TYPE: PRT
<213> ORGANISM: Artificial Sequence
<220> FEATURE:
<223> OTHER INFORMATION: single chain antibody fragment

<400> SEQUENCE: 156

His Thr Ser Gly Trp Ser Gly Gly Ala Phe Asp Ile
1               5                   10

<210> SEQ ID NO 157
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 157

Trp Gly Gln Gly Thr Met Val Thr Val Ser Ser
1               5                   10

<210> SEQ ID NO 158
<211> LENGTH: 30
<212> TYPE: PRT
<213> ORGANISM: Artificial Sequence
<220> FEATURE:
<223> OTHER INFORMATION: single chain antibody fragment

<400> SEQUENCE: 158

Glu Val Gln Leu Val Gln Ser Gly Gly Asn Leu Val Gln Pro Gly Gly
1               5                   10                  15

Ser Leu Arg Leu Ser Cys Ala Ala Thr Gly Pro Ile Gly Ser
                20                  25                  30

<210> SEQ ID NO 159
<211> LENGTH: 4
<212> TYPE: PRT
```

```
<213> ORGANISM: Artificial Sequence
<220> FEATURE:
<223> OTHER INFORMATION: single chain antibody fragment

<400> SEQUENCE: 159

His Trp Met Thr
 1

<210> SEQ ID NO 160
<211> LENGTH: 14
<212> TYPE: PRT
<213> ORGANISM: Artificial Sequence
<220> FEATURE:
<223> OTHER INFORMATION: single chain antibody fragment

<400> SEQUENCE: 160

Trp Val Arg Gln Ala Pro Gly Gln Gly Leu Glu Trp Val Ala
 1               5                  10

<210> SEQ ID NO 161
<211> LENGTH: 17
<212> TYPE: PRT
<213> ORGANISM: Artificial Sequence
<220> FEATURE:
<223> OTHER INFORMATION: single chain antibody fragment

<400> SEQUENCE: 161

Asn Ile Asn Leu Asp Gly Thr Glu Lys Phe Tyr Val Asp Ser Val Lys
 1               5                  10                  15

Gly

<210> SEQ ID NO 162
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 162

Arg Phe Thr Val Ser Arg Asp Asn Arg Lys Ser Ser Val Phe Leu Gln
 1               5                  10                  15

Met Asn Asn Leu Arg Val Asp Asp Thr Ala Val Tyr Tyr Cys Ala Arg
                20                  25                  30

<210> SEQ ID NO 163
<211> LENGTH: 12
<212> TYPE: PRT
<213> ORGANISM: Artificial Sequence
<220> FEATURE:
<223> OTHER INFORMATION: single chain antibody fragment

<400> SEQUENCE: 163

Leu Gln Trp Gly Gly Tyr Asn Gly Trp Leu Ser Pro
 1               5                  10

<210> SEQ ID NO 164
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 164

Trp Gly Gln Gly Thr Leu Val Thr Val Ser Ser
 1               5                  10
```

<210> SEQ ID NO 165
<211> LENGTH: 30
<212> TYPE: PRT
<213> ORGANISM: Artificial Sequence
<220> FEATURE:
<223> OTHER INFORMATION: single chain antibody fragment

<400> SEQUENCE: 165

Glu Val Gln Leu Val Gln Ser Gly Gly Asn Leu Val Gln Pro Gly Gly
 1               5                  10                  15

Ser Leu Arg Leu Ser Cys Ala Ala Thr Gly Pro Ile Gly Ser
            20                  25                  30

<210> SEQ ID NO 166
<211> LENGTH: 4
<212> TYPE: PRT
<213> ORGANISM: Artificial Sequence
<220> FEATURE:
<223> OTHER INFORMATION: single chain antibody fragment

<400> SEQUENCE: 166

His Trp Met Thr
 1

<210> SEQ ID NO 167
<211> LENGTH: 14
<212> TYPE: PRT
<213> ORGANISM: Artificial Sequence
<220> FEATURE:
<223> OTHER INFORMATION: single chain antibody fragment

<400> SEQUENCE: 167

Trp Val Arg Gln Ala Pro Gly Gln Gly Leu Glu Trp Val Ala
 1               5                  10

<210> SEQ ID NO 168
<211> LENGTH: 17
<212> TYPE: PRT
<213> ORGANISM: Artificial Sequence
<220> FEATURE:
<223> OTHER INFORMATION: single chain antibody fragment

<400> SEQUENCE: 168

Asn Ile Asn Leu Asp Gly Thr Glu Lys Phe Tyr Val Asp Ser Val Lys
 1               5                  10                  15

Gly

<210> SEQ ID NO 169
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 169

Arg Phe Thr Val Ser Arg Asp Asn Arg Lys Ser Ser Val Phe Leu Gln
 1               5                  10                  15

Met Asn Asn Leu Arg Val Asp Asp Thr Ala Val Tyr Tyr Cys Ala Arg
            20                  25                  30

<210> SEQ ID NO 170
<211> LENGTH: 12
<212> TYPE: PRT
<213> ORGANISM: Artificial Sequence
<220> FEATURE:

<223> OTHER INFORMATION: single chain antibody fragment

<400> SEQUENCE: 170

Leu Gln Trp Gly Gly Tyr Asn Gly Trp Leu Ser Pro
1               5                   10

<210> SEQ ID NO 171
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 171

Trp Gly Gln Gly Thr Leu Val Thr Val Ser Ser
1               5                   10

<210> SEQ ID NO 172
<211> LENGTH: 23
<212> TYPE: PRT
<213> ORGANISM: Artificial Sequence
<220> FEATURE:
<223> OTHER INFORMATION: single chain antibody fragment

<400> SEQUENCE: 172

Asp Ile Val Met Thr Gln Ser Pro Ser Phe Leu Ser Ala Ser Val Gly
1               5                   10                  15

Asp Arg Val Thr Ile Thr Cys
            20

<210> SEQ ID NO 173
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 173

Trp Ala Ser Gln Gly Ile Ser Ser Tyr Leu Ala
1               5                   10

<210> SEQ ID NO 174
<211> LENGTH: 15
<212> TYPE: PRT
<213> ORGANISM: Artificial Sequence
<220> FEATURE:
<223> OTHER INFORMATION: single chain antibody fragment

<400> SEQUENCE: 174

Trp Tyr Gln Gln Lys Pro Gly Lys Ala Pro Lys Leu Leu Ile Tyr
1               5                   10                  15

<210> SEQ ID NO 175
<211> LENGTH: 7
<212> TYPE: PRT
<213> ORGANISM: Artificial Sequence
<220> FEATURE:
<223> OTHER INFORMATION: single chain antibody fragment

<400> SEQUENCE: 175

Ala Ala Ser Thr Leu Gln Ser
1               5

<210> SEQ ID NO 176
<211> LENGTH: 32
<212> TYPE: PRT

<213> ORGANISM: Artificial Sequence
<220> FEATURE:
<223> OTHER INFORMATION: single chain antibody fragment

<400> SEQUENCE: 176

Gly Val Pro Ser Arg Phe Ser Gly Ser Gly Ser Gly Thr Glu Phe Thr
1               5                   10                  15

Leu Thr Ile Ser Ser Leu Gln Pro Glu Asp Phe Ala Thr Tyr Tyr Cys
            20                  25                  30

<210> SEQ ID NO 177
<211> LENGTH: 9
<212> TYPE: PRT
<213> ORGANISM: Artificial Sequence
<220> FEATURE:
<223> OTHER INFORMATION: single chain antibody fragment

<400> SEQUENCE: 177

Gln Gln Leu Asn Ser Tyr Pro Leu Thr
1               5

<210> SEQ ID NO 178
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 178

Phe Gly Gly Gly Thr Lys Val Asp Ile Lys Arg
1               5                   10

<210> SEQ ID NO 179
<211> LENGTH: 23
<212> TYPE: PRT
<213> ORGANISM: Artificial Sequence
<220> FEATURE:
<223> OTHER INFORMATION: single chain antibody fragment

<400> SEQUENCE: 179

Glu Ile Val Leu Thr Gln Ser Pro Asp Ser Leu Ser Ala Ser Val Gly
1               5                   10                  15

Asp Arg Val Thr Ile Thr Cys
            20

<210> SEQ ID NO 180
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 180

Arg Ala Ser Gln Gly Ile Ser Gly Tyr Leu Ala
1               5                   10

<210> SEQ ID NO 181
<211> LENGTH: 15
<212> TYPE: PRT
<213> ORGANISM: Artificial Sequence
<220> FEATURE:
<223> OTHER INFORMATION: single chain antibody fragment

<400> SEQUENCE: 181

Trp Tyr Gln His Lys Ala Gly Lys Ala Pro Lys Leu Leu Ile Tyr
1               5                   10                  15

<210> SEQ ID NO 182
<211> LENGTH: 7
<212> TYPE: PRT
<213> ORGANISM: Artificial Sequence
<220> FEATURE:
<223> OTHER INFORMATION: single chain antibody fragment

<400> SEQUENCE: 182

Ala Ala Ser Ser Leu Gln Ser
 1               5

<210> SEQ ID NO 183
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 183

Gly Val Pro Ser Arg Phe Ser Gly Ser Gly Tyr Gly Thr Glu Phe Thr
 1               5                  10                  15

Leu Thr Ile Ser Ser Leu Gln Pro Asp Asp Phe Ala Thr Tyr Tyr Cys
             20                  25                  30

<210> SEQ ID NO 184
<211> LENGTH: 9
<212> TYPE: PRT
<213> ORGANISM: Artificial Sequence
<220> FEATURE:
<223> OTHER INFORMATION: single chain antibody fragment

<400> SEQUENCE: 184

Gln Gln Tyr Asn Ser Tyr Pro Phe Thr
 1               5

<210> SEQ ID NO 185
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 185

Phe Gly Gly Gly Thr Lys Val Glu Ile Lys Arg
 1               5                  10

<210> SEQ ID NO 186
<211> LENGTH: 23
<212> TYPE: PRT
<213> ORGANISM: Artificial Sequence
<220> FEATURE:
<223> OTHER INFORMATION: single chain antibody fragment

<400> SEQUENCE: 186

Glu Ile Val Leu Thr Gln Ser Pro Ser Phe Leu Ser Ala Phe Val Gly
 1               5                  10                  15

Asp Arg Val Thr Ile Thr Cys
             20

<210> SEQ ID NO 187
<211> LENGTH: 11
<212> TYPE: PRT
<213> ORGANISM: Artificial Sequence
<220> FEATURE:
<223> OTHER INFORMATION: single chain antibody fragment

```
<400> SEQUENCE: 187

Arg Thr Ser Gln Ser Ile Asn Asn Tyr Leu Asn
1               5                   10

<210> SEQ ID NO 188
<211> LENGTH: 15
<212> TYPE: PRT
<213> ORGANISM: Artificial Sequence
<220> FEATURE:
<223> OTHER INFORMATION: single chain antibody fragment

<400> SEQUENCE: 188

Trp Tyr Gln Gln Lys Ala Gly Lys Ala Pro Lys Leu Leu Ile Tyr
1               5                   10                  15

<210> SEQ ID NO 189
<211> LENGTH: 7
<212> TYPE: PRT
<213> ORGANISM: Artificial Sequence
<220> FEATURE:
<223> OTHER INFORMATION: single chain antibody fragment

<400> SEQUENCE: 189

Ala Ala Ser Thr Leu His Thr
1               5

<210> SEQ ID NO 190
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 190

Gly Val Pro Ser Arg Phe Ser Gly Ser Gly Ser Gly Thr Glu Phe Thr
1               5                   10                  15

Leu Thr Ile Ser Ser Leu Gln Pro Glu Asp Phe Ala Thr Tyr Tyr Cys
            20                  25                  30

<210> SEQ ID NO 191
<211> LENGTH: 9
<212> TYPE: PRT
<213> ORGANISM: Artificial Sequence
<220> FEATURE:
<223> OTHER INFORMATION: single chain antibody fragment

<400> SEQUENCE: 191

Gln Gln Ser Tyr Ser Ile Pro Leu Thr
1               5

<210> SEQ ID NO 192
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 192

Phe Gly Gly Gly Thr Lys Val Glu Ile Lys Arg
1               5                   10

<210> SEQ ID NO 193
<211> LENGTH: 23
<212> TYPE: PRT
<213> ORGANISM: Artificial Sequence
```

```
<220> FEATURE:
<223> OTHER INFORMATION: single chain antibody fragment

<400> SEQUENCE: 193

Asp Ile Val Met Thr Gln Ser Pro Asp Ser Leu Ser Ala Ser Val Gly
1               5                   10                  15

Asp Ser Val Thr Ile Thr Cys
            20

<210> SEQ ID NO 194
<211> LENGTH: 12
<212> TYPE: PRT
<213> ORGANISM: Artificial Sequence
<220> FEATURE:
<223> OTHER INFORMATION: single chain antibody fragment

<400> SEQUENCE: 194

Arg Ala Ser Gln Ser Phe Ser Ser Ser Tyr Leu Ala
1               5                   10

<210> SEQ ID NO 195
<211> LENGTH: 15
<212> TYPE: PRT
<213> ORGANISM: Artificial Sequence
<220> FEATURE:
<223> OTHER INFORMATION: single chain antibody fragment

<400> SEQUENCE: 195

Trp Tyr Gln Gln Lys Pro Gly Gln Ala Pro Arg Leu Leu Ile Tyr
1               5                   10                  15

<210> SEQ ID NO 196
<211> LENGTH: 7
<212> TYPE: PRT
<213> ORGANISM: Artificial Sequence
<220> FEATURE:
<223> OTHER INFORMATION: single chain antibody fragment

<400> SEQUENCE: 196

Ala Ala Ser Ser Arg Ala Ala
1               5

<210> SEQ ID NO 197
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 197

Gly Val Pro Thr Gly Ser Val Ala Asp Gly Ser Gly Thr Asp Phe Thr
1               5                   10                  15

Leu Thr Ile Ser Gly Leu Gln Pro Glu Asp Phe Ala Ala Tyr Tyr Cys
            20                  25                  30

<210> SEQ ID NO 198
<211> LENGTH: 9
<212> TYPE: PRT
<213> ORGANISM: Artificial Sequence
<220> FEATURE:
<223> OTHER INFORMATION: single chain antibody fragment

<400> SEQUENCE: 198

Gln Gln Ser Tyr Ser Thr Pro Tyr Thr
1               5
```

<210> SEQ ID NO 199
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 199

```
Phe Gly Gly Gly Thr Lys Val Glu Ile Lys Arg
1               5                   10
```

<210> SEQ ID NO 200
<211> LENGTH: 23
<212> TYPE: PRT
<213> ORGANISM: Artificial Sequence
<220> FEATURE:
<223> OTHER INFORMATION: single chain antibody fragment

<400> SEQUENCE: 200

```
Asp Ile Val Met Thr Gln Ser Pro Ser Phe Leu Ser Ala Phe Val Gly
1               5                   10                  15

Asp Arg Val Thr Ile Thr Cys
            20
```

<210> SEQ ID NO 201
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 201

```
Arg Ala Ser Gln Ser Ile Ser Asn Trp Leu Ala
1               5                   10
```

<210> SEQ ID NO 202
<211> LENGTH: 15
<212> TYPE: PRT
<213> ORGANISM: Artificial Sequence
<220> FEATURE:
<223> OTHER INFORMATION: single chain antibody fragment

<400> SEQUENCE: 202

```
Trp Tyr Gln Gln Lys Pro Gly Lys Ala Pro Lys Val Leu Ile Tyr
1               5                   10                  15
```

<210> SEQ ID NO 203
<211> LENGTH: 7
<212> TYPE: PRT
<213> ORGANISM: Artificial Sequence
<220> FEATURE:
<223> OTHER INFORMATION: single chain antibody fragment

<400> SEQUENCE: 203

```
Lys Ala Ser Ser Leu Glu Asn
1               5
```

<210> SEQ ID NO 204
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 204

```
Gly Val Pro Ser Arg Phe Ser Gly Ser Gly Ser Gly Thr Asp Phe Thr
```

```
                1               5                   10                  15
Leu Thr Ile Thr Ser Leu Gln Pro Asp Asp Phe Ala Thr Tyr Tyr Cys
                20                  25                  30
```

<210> SEQ ID NO 205
<211> LENGTH: 9
<212> TYPE: PRT
<213> ORGANISM: Artificial Sequence
<220> FEATURE:
<223> OTHER INFORMATION: single chain antibody fragment

<400> SEQUENCE: 205

```
Gln Gln Tyr Asn Ala Tyr Pro Leu Thr
1               5
```

<210> SEQ ID NO 206
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 206

```
Phe Gly Gly Gly Thr Lys Val Glu Ile Lys Arg
1               5                   10
```

<210> SEQ ID NO 207
<211> LENGTH: 23
<212> TYPE: PRT
<213> ORGANISM: Artificial Sequence
<220> FEATURE:
<223> OTHER INFORMATION: single chain antibody fragment

<400> SEQUENCE: 207

```
Glu Ile Val Leu Thr Gln Ser Pro Ser Thr Leu Ser Ala Ser Val Gly
1               5                   10                  15

Asp Arg Val Ala Ile Thr Cys
                20
```

<210> SEQ ID NO 208
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 208

```
Arg Ala Ser Gln Arg Ile Gly Ser Trp Leu Ala
1               5                   10
```

<210> SEQ ID NO 209
<211> LENGTH: 15
<212> TYPE: PRT
<213> ORGANISM: Artificial Sequence
<220> FEATURE:
<223> OTHER INFORMATION: single chain antibody fragment

<400> SEQUENCE: 209

```
Trp Tyr Gln Gln Lys Pro Gly Lys Ala Pro Asn Pro Leu Ile Tyr
1               5                   10                  15
```

<210> SEQ ID NO 210
<211> LENGTH: 7
<212> TYPE: PRT
<213> ORGANISM: Artificial Sequence
<220> FEATURE:

<223> OTHER INFORMATION: single chain antibody fragment

<400> SEQUENCE: 210

Lys Ala Phe Ser Leu Glu Ser
1               5

<210> SEQ ID NO 211
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 211

Gly Val Pro Ser Arg Phe Ser Gly Ser Arg Gly Thr Glu Phe Thr
1               5                   10                  15

Leu Thr Ile Ser Ser Leu Gln Pro Asp Asp Phe Ala Thr Tyr Phe Cys
            20                  25                  30

<210> SEQ ID NO 212
<211> LENGTH: 9
<212> TYPE: PRT
<213> ORGANISM: Artificial Sequence
<220> FEATURE:
<223> OTHER INFORMATION: single chain antibody fragment

<400> SEQUENCE: 212

Gln Gln Tyr Asp Ser Tyr Pro Tyr Thr
1               5

<210> SEQ ID NO 213
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 213

Phe Gly Gln Gly Thr Lys Leu Glu Ile Lys Arg
1               5                   10

<210> SEQ ID NO 214
<211> LENGTH: 23
<212> TYPE: PRT
<213> ORGANISM: Artificial Sequence
<220> FEATURE:
<223> OTHER INFORMATION: single chain antibody fragment

<400> SEQUENCE: 214

Asp Val Val Met Thr Gln Ser Pro Ser Ser Leu Ser Ala Ser Ile Gly
1               5                   10                  15

Asp Arg Val Thr Phe Thr Cys
            20

<210> SEQ ID NO 215
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 215

Gln Ala Ser Gln Asp Ile Ser Asn Arg Leu Asn
1               5                   10

```
<210> SEQ ID NO 216
<211> LENGTH: 15
<212> TYPE: PRT
<213> ORGANISM: Artificial Sequence
<220> FEATURE:
<223> OTHER INFORMATION: single chain antibody fragment

<400> SEQUENCE: 216

Trp Tyr Gln Gln Lys Pro Gly Lys Val Pro Lys Leu Leu Ile Ser
1               5                   10                  15

<210> SEQ ID NO 217
<211> LENGTH: 7
<212> TYPE: PRT
<213> ORGANISM: Artificial Sequence
<220> FEATURE:
<223> OTHER INFORMATION: single chain antibody fragment

<400> SEQUENCE: 217

Asp Ala Ser Asn Leu Glu Thr
1               5

<210> SEQ ID NO 218
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 218

Gly Val Pro Ser Arg Phe Ser Gly Ser Gly Ser Gly Thr Asp Phe Thr
1               5                   10                  15

Phe Thr Ile Ser Ser Leu Gln Pro Glu Asp Ile Ala Thr Tyr Tyr Cys
            20                  25                  30

<210> SEQ ID NO 219
<211> LENGTH: 8
<212> TYPE: PRT
<213> ORGANISM: Artificial Sequence
<220> FEATURE:
<223> OTHER INFORMATION: single chain antibody fragment

<400> SEQUENCE: 219

Gln Gln Tyr Asp Pro Leu Leu Thr
1               5

<210> SEQ ID NO 220
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 220

Phe Gly Gly Gly Thr Lys Val Glu Ile Lys Arg
1               5                   10

<210> SEQ ID NO 221
<211> LENGTH: 23
<212> TYPE: PRT
<213> ORGANISM: Artificial Sequence
<220> FEATURE:
<223> OTHER INFORMATION: single chain antibody fragment

<400> SEQUENCE: 221

Asp Ile Gln Met Thr Gln Ser Pro Ser Ser Val Ser Ala Ser Val Gly
1               5                   10                  15
```

Asp Thr Val Thr Ile Ser Cys
            20

<210> SEQ ID NO 222
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 222

Arg Ala Ser Gln Gly Ile Ser Ser Trp Leu Ala
1               5                   10

<210> SEQ ID NO 223
<211> LENGTH: 15
<212> TYPE: PRT
<213> ORGANISM: Artificial Sequence
<220> FEATURE:
<223> OTHER INFORMATION: single chain antibody fragment

<400> SEQUENCE: 223

Trp Tyr Gln Gln Lys Ser Gly Gln Ala Pro Thr Leu Leu Ile Tyr
1               5                   10                  15

<210> SEQ ID NO 224
<211> LENGTH: 7
<212> TYPE: PRT
<213> ORGANISM: Artificial Sequence
<220> FEATURE:
<223> OTHER INFORMATION: single chain antibody fragment

<400> SEQUENCE: 224

Ala Ala Ser Ser Leu Gln Ser
1               5

<210> SEQ ID NO 225
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 225

Gly Val Pro Ser Arg Phe Ser Gly Ser Gly Ser Gly Thr Asp Phe Thr
1               5                   10                  15

Leu Ile Ile Ser Ser Leu Gln Pro Glu Asp Phe Ala Thr Tyr Tyr Cys
            20                  25                  30

<210> SEQ ID NO 226
<211> LENGTH: 9
<212> TYPE: PRT
<213> ORGANISM: Artificial Sequence
<220> FEATURE:
<223> OTHER INFORMATION: single chain antibody fragment

<400> SEQUENCE: 226

Gln Gln Ala Tyr Arg Thr Pro Ile Thr
1               5

<210> SEQ ID NO 227
<211> LENGTH: 11
<212> TYPE: PRT
<213> ORGANISM: Artificial Sequence
<220> FEATURE:
<223> OTHER INFORMATION: single chain antibody fragment

```
<400> SEQUENCE: 227

Phe Gly Gly Gly Thr Lys Val Glu Ile Lys Arg
1               5                   10

<210> SEQ ID NO 228
<211> LENGTH: 23
<212> TYPE: PRT
<213> ORGANISM: Artificial Sequence
<220> FEATURE:
<223> OTHER INFORMATION: single chain antibody fragment

<400> SEQUENCE: 228

Asp Ile Gln Met Thr Gln Ser Pro Ser Ser Val Ser Ala Ser Val Gly
1               5                   10                  15

Asp Arg Val Ser Ile Thr Cys
            20

<210> SEQ ID NO 229
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 229

Gln Ala Ser Gln Asp Ile Ser Asn Tyr Leu Asn
1               5                   10

<210> SEQ ID NO 230
<211> LENGTH: 15
<212> TYPE: PRT
<213> ORGANISM: Artificial Sequence
<220> FEATURE:
<223> OTHER INFORMATION: single chain antibody fragment

<400> SEQUENCE: 230

Trp Tyr Gln Gln Lys Pro Gly Lys Ala Pro Lys Leu Leu Ile Tyr
1               5                   10                  15

<210> SEQ ID NO 231
<211> LENGTH: 7
<212> TYPE: PRT
<213> ORGANISM: Artificial Sequence
<220> FEATURE:
<223> OTHER INFORMATION: single chain antibody fragment

<400> SEQUENCE: 231

Ala Ala Ser Ser Leu Gln Ser
1               5

<210> SEQ ID NO 232
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 232

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 233
```

```
<211> LENGTH: 9
<212> TYPE: PRT
<213> ORGANISM: Artificial Sequence
<220> FEATURE:
<223> OTHER INFORMATION: single chain antibody fragment

<400> SEQUENCE: 233

Gln Gln Ser Tyr Asn Thr Pro Pro Thr
 1               5

<210> SEQ ID NO 234
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 234

Phe Gly Gln Gly Thr Lys Leu Glu Ile Lys Arg
 1               5                  10

<210> SEQ ID NO 235
<211> LENGTH: 22
<212> TYPE: PRT
<213> ORGANISM: Artificial Sequence
<220> FEATURE:
<223> OTHER INFORMATION: single chain antibody fragment

<400> SEQUENCE: 235

Ala Ser Val Leu Thr Gln Asp Pro Ala Val Ser Val Ala Leu Gly Gln
 1               5                  10                  15

Thr Val Arg Ile Thr Cys
             20

<210> SEQ ID NO 236
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 236

Gln Gly Asp Ser Leu Arg Ser Tyr Tyr Ala Ser
 1               5                  10

<210> SEQ ID NO 237
<211> LENGTH: 15
<212> TYPE: PRT
<213> ORGANISM: Artificial Sequence
<220> FEATURE:
<223> OTHER INFORMATION: single chain antibody fragment

<400> SEQUENCE: 237

Trp Tyr Gln Gln Lys Pro Gly Gln Ala Pro Val Leu Val Ile Tyr
 1               5                  10                  15

<210> SEQ ID NO 238
<211> LENGTH: 7
<212> TYPE: PRT
<213> ORGANISM: Artificial Sequence
<220> FEATURE:
<223> OTHER INFORMATION: single chain antibody fragment

<400> SEQUENCE: 238

Gly Lys Ser Asn Arg Pro Ser
 1               5
```

<210> SEQ ID NO 239
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 239

Gly Ile Pro Asp Arg Phe Ser Gly Ser Ser Gly Asn Thr Ala Ser
1               5                   10                  15

Leu Thr Ile Thr Gly Ala Gln Ala Glu Asp Glu Ala Asp Tyr Tyr Cys
            20                  25                  30

<210> SEQ ID NO 240
<211> LENGTH: 10
<212> TYPE: PRT
<213> ORGANISM: Artificial Sequence
<220> FEATURE:
<223> OTHER INFORMATION: single chain antibody fragment

<400> SEQUENCE: 240

Asn Ser Arg Asp Ser Thr Gly Asn Gln Leu
1               5                   10

<210> SEQ ID NO 241
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 241

Phe Gly Gly Gly Thr Lys Val Thr Val Leu Gly
1               5                   10

<210> SEQ ID NO 242
<211> LENGTH: 21
<212> TYPE: PRT
<213> ORGANISM: Artificial Sequence
<220> FEATURE:
<223> OTHER INFORMATION: single chain antibody fragment

<400> SEQUENCE: 242

Ala Glu Leu Thr Gln Asp Pro Ala Val Ser Val Ala Leu Gly Gln Thr
1               5                   10                  15

Val Arg Ile Thr Cys
            20

<210> SEQ ID NO 243
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 243

Gln Gly Asp Ser Leu Arg Ser Tyr Tyr Ala Ser
1               5                   10

<210> SEQ ID NO 244
<211> LENGTH: 15
<212> TYPE: PRT
<213> ORGANISM: Artificial Sequence
<220> FEATURE:
<223> OTHER INFORMATION: single chain antibody fragment

<400> SEQUENCE: 244

Trp Tyr Gln Gln Lys Pro Gly Gln Ala Pro Val Leu Val Ile Tyr
 1               5                  10                  15

<210> SEQ ID NO 245
<211> LENGTH: 7
<212> TYPE: PRT
<213> ORGANISM: Artificial Sequence
<220> FEATURE:
<223> OTHER INFORMATION: single chain antibody fragment

<400> SEQUENCE: 245

Gly Glu Asn Ser Arg Pro Ser
 1               5

<210> SEQ ID NO 246
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 246

Gly Ile Pro Asp Arg Phe Ser Gly Ser Ser Gly Asn Thr Ala Ser
 1               5                  10                  15

Leu Thr Ile Ala Gly Ala Gln Ala Glu Asp Glu Ala Asp Tyr Tyr Cys
         20                  25                  30

<210> SEQ ID NO 247
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 247

Asn Ser Pro Asp Ser Ser Gly Ile His Leu Val
 1               5                  10

<210> SEQ ID NO 248
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 248

Phe Gly Gly Gly Thr Lys Val Thr Val Leu Gly
 1               5                  10

<210> SEQ ID NO 249
<211> LENGTH: 23
<212> TYPE: PRT
<213> ORGANISM: Artificial Sequence
<220> FEATURE:
<223> OTHER INFORMATION: single chain antibody fragment

<400> SEQUENCE: 249

Glu Ile Val Leu Thr Gln Ser Pro Asp Ser Leu Ala Val Ser Leu Gly
 1               5                  10                  15

Glu Arg Ala Thr Ile Asn Cys
         20

<210> SEQ ID NO 250
<211> LENGTH: 17

```
<212> TYPE: PRT
<213> ORGANISM: Artificial Sequence
<220> FEATURE:
<223> OTHER INFORMATION: single chain antibody fragment

<400> SEQUENCE: 250

Lys Ser Ser Gln Ser Val Leu Tyr Ser Ser Asn Asn Lys Asn Tyr Leu
1               5                   10                  15

Ala

<210> SEQ ID NO 251
<211> LENGTH: 15
<212> TYPE: PRT
<213> ORGANISM: Artificial Sequence
<220> FEATURE:
<223> OTHER INFORMATION: single chain antibody fragment

<400> SEQUENCE: 251

Trp Tyr Gln Gln Lys Pro Gly Gln Pro Pro Lys Leu Leu Phe Tyr
1               5                   10                  15

<210> SEQ ID NO 252
<211> LENGTH: 7
<212> TYPE: PRT
<213> ORGANISM: Artificial Sequence
<220> FEATURE:
<223> OTHER INFORMATION: single chain antibody fragment

<400> SEQUENCE: 252

Trp Ala Ser Thr Arg Glu Ser
1               5

<210> SEQ ID NO 253
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 253

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 254
<211> LENGTH: 9
<212> TYPE: PRT
<213> ORGANISM: Artificial Sequence
<220> FEATURE:
<223> OTHER INFORMATION: single chain antibody fragment

<400> SEQUENCE: 254

His Gln Tyr Tyr Ser Ser Pro Leu Thr
1               5

<210> SEQ ID NO 255
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 255

Phe Gly Gly Gly Thr Lys Leu Glu Ile Lys Arg
1               5                   10
```

<210> SEQ ID NO 256
<211> LENGTH: 23
<212> TYPE: PRT
<213> ORGANISM: Artificial Sequence
<220> FEATURE:
<223> OTHER INFORMATION: single chain antibody fragment

<400> SEQUENCE: 256

Glu Ile Val Leu Thr Gln Ser Pro Asn Ser Leu Ala Val Ser Leu Gly
 1               5                  10                  15

Glu Arg Ala Thr Ile Arg Cys
            20

<210> SEQ ID NO 257
<211> LENGTH: 17
<212> TYPE: PRT
<213> ORGANISM: Artificial Sequence
<220> FEATURE:
<223> OTHER INFORMATION: single chain antibody fragment

<400> SEQUENCE: 257

Lys Ser Ser Gln Ser Val Leu Tyr Ser Gly Asn Asn Lys Asn Tyr Leu
 1               5                  10                  15

Ala

<210> SEQ ID NO 258
<211> LENGTH: 15
<212> TYPE: PRT
<213> ORGANISM: Artificial Sequence
<220> FEATURE:
<223> OTHER INFORMATION: single chain antibody fragment

<400> SEQUENCE: 258

Trp Tyr Gln Gln Lys Pro Gly Gln Pro Pro Lys Leu Leu Ile Tyr
 1               5                  10                  15

<210> SEQ ID NO 259
<211> LENGTH: 7
<212> TYPE: PRT
<213> ORGANISM: Artificial Sequence
<220> FEATURE:
<223> OTHER INFORMATION: single chain antibody fragment

<400> SEQUENCE: 259

Trp Ala Ser Thr Arg Glu Ser
 1               5

<210> SEQ ID NO 260
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 260

Gly Val Pro Asp Arg Phe Ser Gly Ser Gly Ser Glu Thr Asp Phe Thr
 1               5                  10                  15

Leu Thr Ile Ser Ser Leu Arg Ala Glu Asp Val Ala Leu Tyr Tyr Cys
            20                  25                  30

<210> SEQ ID NO 261
<211> LENGTH: 8
<212> TYPE: PRT
<213> ORGANISM: Artificial Sequence

```
<220> FEATURE:
<223> OTHER INFORMATION: single chain antibody fragment

<400> SEQUENCE: 261

Gln Gln Tyr Tyr Ser Arg Trp Thr
1               5

<210> SEQ ID NO 262
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 262

Phe Gly Gln Gly Thr Lys Leu Glu Ile Lys Arg
1               5                   10

<210> SEQ ID NO 263
<211> LENGTH: 23
<212> TYPE: PRT
<213> ORGANISM: Artificial Sequence
<220> FEATURE:
<223> OTHER INFORMATION: single chain antibody fragment

<400> SEQUENCE: 263

Asp Ile Val Met Thr Gln Ser Pro Ser Ser Val Ser Ala Ser Val Gly
1               5                   10                  15

Asp Arg Val Thr Ile Thr Cys
            20

<210> SEQ ID NO 264
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 264

Arg Ala Ser Gln Ser Ile Ser Ser Tyr Leu Asn
1               5                   10

<210> SEQ ID NO 265
<211> LENGTH: 15
<212> TYPE: PRT
<213> ORGANISM: Artificial Sequence
<220> FEATURE:
<223> OTHER INFORMATION: single chain antibody fragment

<400> SEQUENCE: 265

Trp Tyr Gln Gln Lys Pro Gly Lys Ala Pro Lys Leu Leu Ile Tyr
1               5                   10                  15

<210> SEQ ID NO 266
<211> LENGTH: 7
<212> TYPE: PRT
<213> ORGANISM: Artificial Sequence
<220> FEATURE:
<223> OTHER INFORMATION: single chain antibody fragment

<400> SEQUENCE: 266

Gly Thr Ser Asn Leu Gln Ser
1               5

<210> SEQ ID NO 267
<211> LENGTH: 32
```

```
<212> TYPE: PRT
<213> ORGANISM: Artificial Sequence
<220> FEATURE:
<223> OTHER INFORMATION: single chain antibody fragment

<400> SEQUENCE: 267

Gly Val Pro Ser Gly Phe Ser Gly Ser Gly Thr Asp Phe Thr
 1               5                  10                  15

Leu Thr Ile Ser Ser Leu Gln Pro Glu Asp Phe Ala Thr Tyr Tyr Cys
            20                  25                  30

<210> SEQ ID NO 268
<211> LENGTH: 9
<212> TYPE: PRT
<213> ORGANISM: Artificial Sequence
<220> FEATURE:
<223> OTHER INFORMATION: single chain antibody fragment

<400> SEQUENCE: 268

Gln Glu Thr Tyr Ser Thr Pro Pro Thr
 1               5

<210> SEQ ID NO 269
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 269

Phe Gly Gly Gly Thr Lys Leu Glu Ile Lys Arg
 1               5                  10

<210> SEQ ID NO 270
<211> LENGTH: 23
<212> TYPE: PRT
<213> ORGANISM: Artificial Sequence
<220> FEATURE:
<223> OTHER INFORMATION: single chain antibody fragment

<400> SEQUENCE: 270

Asp Ile Val Met Thr Gln Ser Pro Ser Ser Leu Ser Ala Ser Val Gly
 1               5                  10                  15

Asp Arg Val Thr Ile Ser Cys
            20

<210> SEQ ID NO 271
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 271

Arg Ala Ser Gln Ser Ile Arg His Tyr Val Asn
 1               5                  10

<210> SEQ ID NO 272
<211> LENGTH: 15
<212> TYPE: PRT
<213> ORGANISM: Artificial Sequence
<220> FEATURE:
<223> OTHER INFORMATION: single chain antibody fragment

<400> SEQUENCE: 272

Trp Tyr Gln Gln Lys Pro Gly Lys Ala Pro Lys Leu Leu Ile Tyr
 1               5                  10                  15
```

<210> SEQ ID NO 273
<211> LENGTH: 7
<212> TYPE: PRT
<213> ORGANISM: Artificial Sequence
<220> FEATURE:
<223> OTHER INFORMATION: single chain antibody fragment

<400> SEQUENCE: 273

Lys Ala Ser Ser Leu Ala Ser
1               5

<210> SEQ ID NO 274
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 274

Gly Ala Pro Ser Arg Phe Ser Gly Ser Gly Ser Gly Thr Asp Phe Thr
1               5                   10                  15

Leu Thr Ile Ser Ser Leu Gln Pro Asp Asp Phe Ala Thr Tyr Tyr Cys
            20                  25                  30

<210> SEQ ID NO 275
<211> LENGTH: 9
<212> TYPE: PRT
<213> ORGANISM: Artificial Sequence
<220> FEATURE:
<223> OTHER INFORMATION: single chain antibody fragment

<400> SEQUENCE: 275

Gln Gln Ser Tyr Ser Ile Pro Leu Thr
1               5

<210> SEQ ID NO 276
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 276

Phe Gly Gly Gly Thr Lys Val Glu Ile Lys Arg
1               5                   10

<210> SEQ ID NO 277
<211> LENGTH: 30
<212> TYPE: PRT
<213> ORGANISM: Artificial Sequence
<220> FEATURE:
<223> OTHER INFORMATION: single chain antibody fragment

<400> SEQUENCE: 277

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser
            20                  25                  30

<210> SEQ ID NO 278
<211> LENGTH: 5
<212> TYPE: PRT
<213> ORGANISM: Artificial Sequence
<220> FEATURE:

<223> OTHER INFORMATION: single chain antibody fragment

<400> SEQUENCE: 278

Ser Tyr Gly Met His
1               5

<210> SEQ ID NO 279
<211> LENGTH: 14
<212> TYPE: PRT
<213> ORGANISM: Artificial Sequence
<220> FEATURE:
<223> OTHER INFORMATION: single chain antibody fragment

<400> SEQUENCE: 279

Trp Val Arg Gln Ala Pro Gly Lys Gly Leu Glu Trp Val Ala
1               5                   10

<210> SEQ ID NO 280
<211> LENGTH: 17
<212> TYPE: PRT
<213> ORGANISM: Artificial Sequence
<220> FEATURE:
<223> OTHER INFORMATION: single chain antibody fragment

<400> SEQUENCE: 280

Val Ile Trp Tyr Asp Gly Ser Asn Lys Tyr Tyr Ala Asp Ser Val Lys
1               5                   10                  15

Gly

<210> SEQ ID NO 281
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 281

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 282
<211> LENGTH: 13
<212> TYPE: PRT
<213> ORGANISM: Artificial Sequence
<220> FEATURE:
<223> OTHER INFORMATION: single chain antibody fragment

<400> SEQUENCE: 282

Gly Tyr Ser Asn Tyr Asp Tyr Tyr Tyr Gly Met Asp Val
1               5                   10

<210> SEQ ID NO 283
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 283

Trp Gly Gln Gly Thr Thr Val Thr Val Ser Ser
1               5                   10

<210> SEQ ID NO 284

```
<211> LENGTH: 30
<212> TYPE: PRT
<213> ORGANISM: Artificial Sequence
<220> FEATURE:
<223> OTHER INFORMATION: single chain antibody fragment

<400> SEQUENCE: 284

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser
            20                  25                  30

<210> SEQ ID NO 285
<211> LENGTH: 5
<212> TYPE: PRT
<213> ORGANISM: Artificial Sequence
<220> FEATURE:
<223> OTHER INFORMATION: single chain antibody fragment

<400> SEQUENCE: 285

Ser Tyr Gly Met His
 1               5

<210> SEQ ID NO 286
<211> LENGTH: 14
<212> TYPE: PRT
<213> ORGANISM: Artificial Sequence
<220> FEATURE:
<223> OTHER INFORMATION: single chain antibody fragment

<400> SEQUENCE: 286

Trp Val Arg Gln Ala Pro Gly Lys Gly Leu Glu Trp Val Ser
 1               5                  10

<210> SEQ ID NO 287
<211> LENGTH: 17
<212> TYPE: PRT
<213> ORGANISM: Artificial Sequence
<220> FEATURE:
<223> OTHER INFORMATION: single chain antibody fragment

<400> SEQUENCE: 287

Tyr Ile Ser Ser Ser Gly Ser Thr Ile Tyr Tyr Ala Asp Ser Val Lys
 1               5                  10                  15

Gly

<210> SEQ ID NO 288
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 288

Arg Phe Thr Ile Ser Arg Asp Asn Ala Lys Asn Ser Leu Tyr Leu Gln
 1               5                  10                  15

Met Asn Ser Leu Arg Ala Glu Asp Thr Ala Val Tyr Tyr Cys Ala Arg
            20                  25                  30

<210> SEQ ID NO 289
<211> LENGTH: 12
<212> TYPE: PRT
<213> ORGANISM: Artificial Sequence
<220> FEATURE:
<223> OTHER INFORMATION: single chain antibody fragment
```

```
<400> SEQUENCE: 289

Val Ser Ile Val Gly Gly Pro Tyr Gly Met Asp Val
1               5                   10

<210> SEQ ID NO 290
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 290

Trp Gly Gln Gly Thr Thr Val Thr Val Ser Ser
1               5                   10

<210> SEQ ID NO 291
<211> LENGTH: 30
<212> TYPE: PRT
<213> ORGANISM: Artificial Sequence
<220> FEATURE:
<223> OTHER INFORMATION: single chain antibody fragment

<400> SEQUENCE: 291

Glu Val Gln Leu Val Gln Ser Gly Ala Glu Val Glu Lys Pro Gly Ser
1               5                   10                  15

Ser Val Lys Val Ser Cys Lys Ala Ser Gly Gly Ser Phe Ser
            20                  25                  30

<210> SEQ ID NO 292
<211> LENGTH: 5
<212> TYPE: PRT
<213> ORGANISM: Artificial Sequence
<220> FEATURE:
<223> OTHER INFORMATION: single chain antibody fragment

<400> SEQUENCE: 292

Ser Tyr Ala Phe Thr
1               5

<210> SEQ ID NO 293
<211> LENGTH: 14
<212> TYPE: PRT
<213> ORGANISM: Artificial Sequence
<220> FEATURE:
<223> OTHER INFORMATION: single chain antibody fragment

<400> SEQUENCE: 293

Trp Val Arg Gln Ala Pro Gly Gln Gly Leu Glu Trp Met Gly
1               5                   10

<210> SEQ ID NO 294
<211> LENGTH: 17
<212> TYPE: PRT
<213> ORGANISM: Artificial Sequence
<220> FEATURE:
<223> OTHER INFORMATION: single chain antibody fragment

<400> SEQUENCE: 294

Arg Ile Val Pro Phe Leu Gly Val Pro Tyr Tyr Thr Gln Lys Phe Arg
1               5                   10                  15

Gly

<210> SEQ ID NO 295
<211> LENGTH: 32
<212> TYPE: PRT
```

```
<213> ORGANISM: Artificial Sequence
<220> FEATURE:
<223> OTHER INFORMATION: single chain antibody fragment

<400> SEQUENCE: 295

Arg Val Thr Ile Thr Ala Asp Lys Ala Thr Ser Thr Val Tyr Met Glu
 1               5                  10                  15

Leu Ser Ser Leu Thr Phe Asp Asp Thr Ala Val Tyr Tyr Cys Ala Arg
            20                  25                  30

<210> SEQ ID NO 296
<211> LENGTH: 14
<212> TYPE: PRT
<213> ORGANISM: Artificial Sequence
<220> FEATURE:
<223> OTHER INFORMATION: single chain antibody fragment

<400> SEQUENCE: 296

Asp Lys Arg Thr Tyr Glu Tyr Asn Trp Asn Ser Leu Trp Phe
 1               5                  10

<210> SEQ ID NO 297
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 297

Trp Gly Arg Gly Thr Thr Val Thr Val Ser Ser
 1               5                  10

<210> SEQ ID NO 298
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 298

Gln Val Gln Leu Val Gln Ser Gly Ala Glu Val Lys Lys Pro Gly Glu
 1               5                  10                  15

Ser Leu Val Ile Ser Cys Lys Ala Ser Gly Asp Lys Asp Thr Phe Thr
            20                  25                  30

<210> SEQ ID NO 299
<211> LENGTH: 5
<212> TYPE: PRT
<213> ORGANISM: Artificial Sequence
<220> FEATURE:
<223> OTHER INFORMATION: single chain antibody fragment

<400> SEQUENCE: 299

Ser Phe Trp Ile Ala
 1               5

<210> SEQ ID NO 300
<211> LENGTH: 14
<212> TYPE: PRT
<213> ORGANISM: Artificial Sequence
<220> FEATURE:
<223> OTHER INFORMATION: single chain antibody fragment

<400> SEQUENCE: 300

Trp Val Arg Gln Met Pro Gly Lys Gly Leu Glu Trp Met Gly
 1               5                  10
```

```
<210> SEQ ID NO 301
<211> LENGTH: 17
<212> TYPE: PRT
<213> ORGANISM: Artificial Sequence
<220> FEATURE:
<223> OTHER INFORMATION: single chain antibody fragment

<400> SEQUENCE: 301

Ile Ile Tyr Ala Gly Asp Ser Asp Thr Arg Tyr Ser Pro Ser Phe Gln
1               5                   10                  15

Gly

<210> SEQ ID NO 302
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 302

His Val Asn Ile Ser Val Asp Arg Ser Thr Asn Thr Ala Tyr Leu Gln
1               5                   10                  15

Trp Ser Ser Leu Lys Ala Ser Asp Thr Ala Met Tyr Tyr Cys Ala Arg
            20                  25                  30

<210> SEQ ID NO 303
<211> LENGTH: 14
<212> TYPE: PRT
<213> ORGANISM: Artificial Sequence
<220> FEATURE:
<223> OTHER INFORMATION: single chain antibody fragment

<400> SEQUENCE: 303

His Asp Ser Arg Tyr Lys Tyr Phe Tyr Phe Gly Met Asp Val
1               5                   10

<210> SEQ ID NO 304
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 304

Trp Gly Gln Gly Thr Thr Val Thr Val Ser Ser
1               5                   10

<210> SEQ ID NO 305
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 305

Gln Val Gln Leu Val Gln Ser Gly Ala Glu Val Lys Lys Pro Gly Glu
1               5                   10                  15

Ser Leu Val Ile Ser Cys Lys Ala Ser Gly Asp Lys Asp Thr Phe Thr
            20                  25                  30

<210> SEQ ID NO 306
<211> LENGTH: 5
<212> TYPE: PRT
<213> ORGANISM: Artificial Sequence
```

```
<220> FEATURE:
<223> OTHER INFORMATION: single chain antibody fragment

<400> SEQUENCE: 306

Ser Phe Trp Ile Ala
1               5

<210> SEQ ID NO 307
<211> LENGTH: 14
<212> TYPE: PRT
<213> ORGANISM: Artificial Sequence
<220> FEATURE:
<223> OTHER INFORMATION: single chain antibody fragment

<400> SEQUENCE: 307

Trp Val Arg Gln Met Pro Gly Lys Gly Leu Glu Trp Met Gly
1               5                  10

<210> SEQ ID NO 308
<211> LENGTH: 17
<212> TYPE: PRT
<213> ORGANISM: Artificial Sequence
<220> FEATURE:
<223> OTHER INFORMATION: single chain antibody fragment

<400> SEQUENCE: 308

Ile Ile Tyr Ala Gly Asp Ser Asp Thr Arg Tyr Ser Pro Ser Phe Gln
1               5                  10                  15
Gly

<210> SEQ ID NO 309
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 309

His Val Asn Ile Ser Val Asp Arg Ser Thr Asn Thr Ala Tyr Leu Gln
1               5                  10                  15
Trp Ser Ser Leu Lys Ala Ser Asp Thr Ala Met Tyr Tyr Cys Ala Arg
            20                  25                  30

<210> SEQ ID NO 310
<211> LENGTH: 14
<212> TYPE: PRT
<213> ORGANISM: Artificial Sequence
<220> FEATURE:
<223> OTHER INFORMATION: single chain antibody fragment

<400> SEQUENCE: 310

His Asp Ser Arg Tyr Lys Tyr Phe Tyr Phe Gly Met Asp Val
1               5                  10

<210> SEQ ID NO 311
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 311

Trp Gly Gln Gly Thr Thr Val Thr Val Ser Ser
1               5                  10
```

```
<210> SEQ ID NO 312
<211> LENGTH: 30
<212> TYPE: PRT
<213> ORGANISM: Artificial Sequence
<220> FEATURE:
<223> OTHER INFORMATION: single chain antibody fragment

<400> SEQUENCE: 312

Gln Val Gln Leu Leu Glu Ser Gly Gly Gly Val Val Gln Pro Gly Arg
1               5                   10                  15

Ser Leu Arg Leu Ser Cys Ala Ala Ser Gly Phe Thr Phe Ser
            20                  25                  30

<210> SEQ ID NO 313
<211> LENGTH: 5
<212> TYPE: PRT
<213> ORGANISM: Artificial Sequence
<220> FEATURE:
<223> OTHER INFORMATION: single chain antibody fragment

<400> SEQUENCE: 313

Ser Tyr Gly Met His
1               5

<210> SEQ ID NO 314
<211> LENGTH: 14
<212> TYPE: PRT
<213> ORGANISM: Artificial Sequence
<220> FEATURE:
<223> OTHER INFORMATION: single chain antibody fragment

<400> SEQUENCE: 314

Trp Val Arg Gln Ala Pro Gly Lys Gly Leu Glu Trp Val Ala
1               5                   10

<210> SEQ ID NO 315
<211> LENGTH: 17
<212> TYPE: PRT
<213> ORGANISM: Artificial Sequence
<220> FEATURE:
<223> OTHER INFORMATION: single chain antibody fragment

<400> SEQUENCE: 315

Val Ile Trp Tyr Asp Gly Ser Asn Lys Tyr Tyr Ala Asp Ser Val Lys
1               5                   10                  15

Gly

<210> SEQ ID NO 316
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 316

Arg Phe Thr Ile Ser Arg Asp Asn Ser Lys Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 317
<211> LENGTH: 13
<212> TYPE: PRT
<213> ORGANISM: Artificial Sequence
<220> FEATURE:
<223> OTHER INFORMATION: single chain antibody fragment
```

<400> SEQUENCE: 317

Gly Tyr Ser Asn Tyr Asp Tyr Tyr Gly Met Asp Val
1               5                   10

<210> SEQ ID NO 318
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 318

Trp Gly Gln Gly Thr Thr Val Thr Val Ser Ser
1               5                   10

<210> SEQ ID NO 319
<211> LENGTH: 30
<212> TYPE: PRT
<213> ORGANISM: Artificial Sequence
<220> FEATURE:
<223> OTHER INFORMATION: single chain antibody fragment

<400> SEQUENCE: 319

Gln Val Gln Leu Leu Glu Ser Gly Gly Val Val Gln Pro Gly Arg
1               5                   10                  15

Ser Leu Arg Leu Ser Cys Ala Ala Ser Gly Phe Thr Phe Ser
            20                  25                  30

<210> SEQ ID NO 320
<211> LENGTH: 5
<212> TYPE: PRT
<213> ORGANISM: Artificial Sequence
<220> FEATURE:
<223> OTHER INFORMATION: single chain antibody fragment

<400> SEQUENCE: 320

Ser Tyr Gly Met His
1               5

<210> SEQ ID NO 321
<211> LENGTH: 14
<212> TYPE: PRT
<213> ORGANISM: Artificial Sequence
<220> FEATURE:
<223> OTHER INFORMATION: single chain antibody fragment

<400> SEQUENCE: 321

Trp Val Arg Gln Ala Pro Gly Lys Gly Leu Glu Trp Val Ala
1               5                   10

<210> SEQ ID NO 322
<211> LENGTH: 17
<212> TYPE: PRT
<213> ORGANISM: Artificial Sequence
<220> FEATURE:
<223> OTHER INFORMATION: single chain antibody fragment

<400> SEQUENCE: 322

Val Ile Trp Tyr Asp Gly Ser Asn Lys Tyr Tyr Ala Asp Ser Val Lys
1               5                   10                  15

Gly

<210> SEQ ID NO 323
<211> LENGTH: 32

-continued

```
<212> TYPE: PRT
<213> ORGANISM: Artificial Sequence
<220> FEATURE:
<223> OTHER INFORMATION: single chain antibody fragment

<400> SEQUENCE: 323

Arg Phe Thr Ile Ser Arg Asp Asn Ser Lys Asn Thr Leu Tyr Leu Gln
1               5                   10                  15
Met Asn Ser Leu Arg Ala Glu Asp Thr Ala Val Tyr Tyr Cys Ala Arg
            20                  25                  30

<210> SEQ ID NO 324
<211> LENGTH: 13
<212> TYPE: PRT
<213> ORGANISM: Artificial Sequence
<220> FEATURE:
<223> OTHER INFORMATION: single chain antibody fragment

<400> SEQUENCE: 324

Gly Tyr Ser Asn Tyr Asp Tyr Tyr Tyr Gly Met Asp Val
1               5                   10

<210> SEQ ID NO 325
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 325

Trp Gly Gln Gly Thr Thr Val Thr Val Ser Ser
1               5                   10

<210> SEQ ID NO 326
<211> LENGTH: 30
<212> TYPE: PRT
<213> ORGANISM: Artificial Sequence
<220> FEATURE:
<223> OTHER INFORMATION: single chain antibody fragment

<400> SEQUENCE: 326

Gln Val Gln Leu Leu Gln Ser Ala Gly Gly Val Val Gln Pro Gly Arg
1               5                   10                  15
Ser Leu Arg Leu Ser Cys Ala Ala Ser Gly Phe Ile Phe Arg
            20                  25                  30

<210> SEQ ID NO 327
<211> LENGTH: 5
<212> TYPE: PRT
<213> ORGANISM: Artificial Sequence
<220> FEATURE:
<223> OTHER INFORMATION: single chain antibody fragment

<400> SEQUENCE: 327

Thr Tyr Gly Met His
1               5

<210> SEQ ID NO 328
<211> LENGTH: 14
<212> TYPE: PRT
<213> ORGANISM: Artificial Sequence
<220> FEATURE:
<223> OTHER INFORMATION: single chain antibody fragment

<400> SEQUENCE: 328

Trp Val Arg Gln Ala Pro Gly Lys Gly Leu Glu Trp Val Ala
```

<210> SEQ ID NO 329
<211> LENGTH: 17
<212> TYPE: PRT
<213> ORGANISM: Artificial Sequence
<220> FEATURE:
<223> OTHER INFORMATION: single chain antibody fragment

<400> SEQUENCE: 329

Phe Val Ser Ser Asp Gly Asn Asn Lys Phe Tyr Ser Asp Ser Val Lys
 1               5                  10                  15
Gly

<210> SEQ ID NO 330
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 330

Arg Phe Thr Ile Pro Arg Asp Asn Ala Lys Asn Thr Leu Tyr Leu Gln
 1               5                  10                  15
Met Asn Ser Leu Glu Thr Glu Asp Thr Ala Val Tyr Tyr Cys Ala Lys
            20                  25                  30

<210> SEQ ID NO 331
<211> LENGTH: 19
<212> TYPE: PRT
<213> ORGANISM: Artificial Sequence
<220> FEATURE:
<223> OTHER INFORMATION: single chain antibody fragment

<400> SEQUENCE: 331

Asp Arg Tyr Pro Ile Asp Cys Ser Gly Gly Ser Cys Phe Ser Tyr Gly
 1               5                  10                  15
Met Asp Val

<210> SEQ ID NO 332
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 332

Trp Gly Gln Gly Thr Thr Val Thr Val Ser Ser
 1               5                  10

<210> SEQ ID NO 333
<211> LENGTH: 30
<212> TYPE: PRT
<213> ORGANISM: Artificial Sequence
<220> FEATURE:
<223> OTHER INFORMATION: single chain antibody fragment

<400> SEQUENCE: 333

Glu Val Gln Leu Val Glu Ser Gly Gly Gly Val Val Gln Pro Gly Arg
 1               5                  10                  15
Ser Leu Arg Leu Ser Cys Ala Thr Ser Gly Phe Ile Leu Arg
            20                  25                  30

<210> SEQ ID NO 334

<210> SEQ ID NO 334
<211> LENGTH: 5
<212> TYPE: PRT
<213> ORGANISM: Artificial Sequence
<220> FEATURE:
<223> OTHER INFORMATION: single chain antibody fragment

<400> SEQUENCE: 334

Thr Tyr Gly Met His
1               5

<210> SEQ ID NO 335
<211> LENGTH: 14
<212> TYPE: PRT
<213> ORGANISM: Artificial Sequence
<220> FEATURE:
<223> OTHER INFORMATION: single chain antibody fragment

<400> SEQUENCE: 335

Trp Val Arg Gln Ala Pro Gly Lys Gly Leu Glu Trp Val Ala
1               5                   10

<210> SEQ ID NO 336
<211> LENGTH: 17
<212> TYPE: PRT
<213> ORGANISM: Artificial Sequence
<220> FEATURE:
<223> OTHER INFORMATION: single chain antibody fragment

<400> SEQUENCE: 336

Phe Val Ser Ser Asp Gly Asn Asn Lys Phe Tyr Ser Asp Ser Val Lys
1               5                   10                  15

Gly

<210> SEQ ID NO 337
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 337

Arg Phe Thr Ile Pro Arg Asp Asn Ala Lys Asn Thr Leu Tyr Leu Gln
1               5                   10                  15

Met Asn Ser Leu Glu Thr Glu Asp Thr Ala Val Tyr Tyr Cys Ala Lys
            20                  25                  30

<210> SEQ ID NO 338
<211> LENGTH: 19
<212> TYPE: PRT
<213> ORGANISM: Artificial Sequence
<220> FEATURE:
<223> OTHER INFORMATION: single chain antibody fragment

<400> SEQUENCE: 338

Asp Arg Tyr Pro Ile Asp Cys Ser Gly Gly Ser Cys Phe Ser Tyr Gly
1               5                   10                  15

Met Asp Val

<210> SEQ ID NO 339
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 339

```
Trp Gly Gln Gly Thr Leu Val Thr Val Ser Ser
 1               5                  10

<210> SEQ ID NO 340
<211> LENGTH: 30
<212> TYPE: PRT
<213> ORGANISM: Artificial Sequence
<220> FEATURE:
<223> OTHER INFORMATION: single chain antibody fragment

<400> SEQUENCE: 340

Glu Val Gln Leu Val Gln Ser Gly Gly Val Val Gln Pro Gly Arg
 1               5                  10                  15

Ser Leu Arg Leu Ser Cys Ala Ala Ser Gly Phe Ile Phe Arg
            20                  25                  30

<210> SEQ ID NO 341
<211> LENGTH: 5
<212> TYPE: PRT
<213> ORGANISM: Artificial Sequence
<220> FEATURE:
<223> OTHER INFORMATION: single chain antibody fragment

<400> SEQUENCE: 341

Thr Tyr Gly Met His
 1               5

<210> SEQ ID NO 342
<211> LENGTH: 14
<212> TYPE: PRT
<213> ORGANISM: Artificial Sequence
<220> FEATURE:
<223> OTHER INFORMATION: single chain antibody fragment

<400> SEQUENCE: 342

Trp Val Arg Gln Ala Pro Gly Lys Gly Leu Glu Trp Val Ala
 1               5                  10

<210> SEQ ID NO 343
<211> LENGTH: 17
<212> TYPE: PRT
<213> ORGANISM: Artificial Sequence
<220> FEATURE:
<223> OTHER INFORMATION: single chain antibody fragment

<400> SEQUENCE: 343

Phe Val Ser Ser Asp Gly Asn Asn Lys Phe Tyr Ser Asp Ser Val Lys
 1               5                  10                  15

Gly

<210> SEQ ID NO 344
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 344

Arg Phe Thr Ile Ser Arg Asp Asn Ala Lys Asn Thr Leu Tyr Leu Gln
 1               5                  10                  15

Met Asn Ser Leu Glu Thr Glu Asp Thr Ala Met Tyr Tyr Cys Ala Lys
            20                  25                  30

<210> SEQ ID NO 345
```

```
<211> LENGTH: 19
<212> TYPE: PRT
<213> ORGANISM: Artificial Sequence
<220> FEATURE:
<223> OTHER INFORMATION: single chain antibody fragment

<400> SEQUENCE: 345

Asp Arg Tyr Pro Ile Asp Cys Ser Gly Gly Ser Cys Phe Ser Tyr Gly
 1               5                  10                  15
Met Asp Val

<210> SEQ ID NO 346
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 346

Trp Gly Gln Gly Thr Thr Val Thr Val Ser Ser
 1               5                  10

<210> SEQ ID NO 347
<211> LENGTH: 30
<212> TYPE: PRT
<213> ORGANISM: Artificial Sequence
<220> FEATURE:
<223> OTHER INFORMATION: single chain antibody fragment

<400> SEQUENCE: 347

Gln Val Asn Leu Arg Glu Ser Gly Gly Gly Val Val Gln Pro Gly Arg
 1               5                  10                  15
Ser Leu Arg Leu Ser Cys Ala Ala Ser Gly Phe Thr Phe Ser
            20                  25                  30

<210> SEQ ID NO 348
<211> LENGTH: 5
<212> TYPE: PRT
<213> ORGANISM: Artificial Sequence
<220> FEATURE:
<223> OTHER INFORMATION: single chain antibody fragment

<400> SEQUENCE: 348

Ser Tyr Ala Leu His
 1               5

<210> SEQ ID NO 349
<211> LENGTH: 14
<212> TYPE: PRT
<213> ORGANISM: Artificial Sequence
<220> FEATURE:
<223> OTHER INFORMATION: single chain antibody fragment

<400> SEQUENCE: 349

Trp Val Arg Gln Thr Pro Gly Lys Gly Leu Glu Trp Val Ala
 1               5                  10

<210> SEQ ID NO 350
<211> LENGTH: 17
<212> TYPE: PRT
<213> ORGANISM: Artificial Sequence
<220> FEATURE:
<223> OTHER INFORMATION: single chain antibody fragment

<400> SEQUENCE: 350

Leu Ile Ser Tyr Asp Gly Ser Asn Lys Tyr Tyr Ala Asp Ser Val Lys
```

```
                1               5                  10                  15
Gly

<210> SEQ ID NO 351
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 351

Arg Phe Thr Ile Ser Arg Asp Asn Ser Lys Asn Met Leu Tyr Leu Gln
 1               5                  10                  15

Met Asn Ser Leu Arg Ala Glu Asp Thr Ala Val Tyr Tyr Cys Ala Lys
                20                  25                  30

<210> SEQ ID NO 352
<211> LENGTH: 14
<212> TYPE: PRT
<213> ORGANISM: Artificial Sequence
<220> FEATURE:
<223> OTHER INFORMATION: single chain antibody fragment

<400> SEQUENCE: 352

Asp Arg Ser His Tyr Gly Asp Tyr Val Gly Tyr Leu Asp Tyr
 1               5                  10

<210> SEQ ID NO 353
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 353

Trp Gly Gln Gly Thr Leu Val Thr Val Ser Ser
 1               5                  10

<210> SEQ ID NO 354
<211> LENGTH: 30
<212> TYPE: PRT
<213> ORGANISM: Artificial Sequence
<220> FEATURE:
<223> OTHER INFORMATION: single chain antibody fragment

<400> SEQUENCE: 354

Gln Val Asn Leu Arg Glu Ser Gly Gly Val Val Gln Pro Gly Arg
 1               5                  10                  15

Ser Leu Arg Leu Ser Cys Ala Ala Ser Gly Phe Thr Phe Ser
                20                  25                  30

<210> SEQ ID NO 355
<211> LENGTH: 5
<212> TYPE: PRT
<213> ORGANISM: Artificial Sequence
<220> FEATURE:
<223> OTHER INFORMATION: single chain antibody fragment

<400> SEQUENCE: 355

Ser Tyr Ala Leu His
 1               5

<210> SEQ ID NO 356
<211> LENGTH: 14
<212> TYPE: PRT
```

```
<213> ORGANISM: Artificial Sequence
<220> FEATURE:
<223> OTHER INFORMATION: single chain antibody fragment

<400> SEQUENCE: 356

Trp Val Arg Gln Thr Pro Gly Lys Gly Leu Glu Trp Val Ala
1               5                   10

<210> SEQ ID NO 357
<211> LENGTH: 17
<212> TYPE: PRT
<213> ORGANISM: Artificial Sequence
<220> FEATURE:
<223> OTHER INFORMATION: single chain antibody fragment

<400> SEQUENCE: 357

Leu Ile Ser Tyr Asp Gly Ser Asn Lys Tyr Tyr Ala Asp Ser Val Lys
1               5                   10                  15

Gly

<210> SEQ ID NO 358
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 358

Arg Phe Thr Ile Ser Arg Asp Asn Ser Lys Asn Met Leu Tyr Leu Gln
1               5                   10                  15

Met Asn Ser Leu Arg Ala Glu Asp Thr Ala Val Tyr Tyr Cys Ala Lys
            20                  25                  30

<210> SEQ ID NO 359
<211> LENGTH: 14
<212> TYPE: PRT
<213> ORGANISM: Artificial Sequence
<220> FEATURE:
<223> OTHER INFORMATION: single chain antibody fragment

<400> SEQUENCE: 359

Asp Arg Ser His Tyr Gly Asp Tyr Val Gly Tyr Leu Asp Tyr
1               5                   10

<210> SEQ ID NO 360
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 360

Trp Gly Gln Gly Thr Leu Val Thr Val Ser Ser
1               5                   10

<210> SEQ ID NO 361
<211> LENGTH: 30
<212> TYPE: PRT
<213> ORGANISM: Artificial Sequence
<220> FEATURE:
<223> OTHER INFORMATION: single chain antibody fragment

<400> SEQUENCE: 361

Gln Val Asn Leu Arg Glu Ser Gly Gly Gly Val Val Gln Pro Gly Arg
1               5                   10                  15
```

```
Ser Leu Arg Leu Ser Cys Ala Ala Ser Gly Phe Thr Phe Ser
            20                  25                  30
```

<210> SEQ ID NO 362
<211> LENGTH: 5
<212> TYPE: PRT
<213> ORGANISM: Artificial Sequence
<220> FEATURE:
<223> OTHER INFORMATION: single chain antibody fragment

<400> SEQUENCE: 362

```
Ser Tyr Ala Leu His
 1               5
```

<210> SEQ ID NO 363
<211> LENGTH: 14
<212> TYPE: PRT
<213> ORGANISM: Artificial Sequence
<220> FEATURE:
<223> OTHER INFORMATION: single chain antibody fragment

<400> SEQUENCE: 363

```
Trp Val Arg Gln Thr Pro Gly Lys Gly Leu Glu Trp Val Ala
 1               5                  10
```

<210> SEQ ID NO 364
<211> LENGTH: 17
<212> TYPE: PRT
<213> ORGANISM: Artificial Sequence
<220> FEATURE:
<223> OTHER INFORMATION: single chain antibody fragment

<400> SEQUENCE: 364

```
Leu Ile Ser Tyr Asp Gly Ser Asn Lys Tyr Tyr Ala Asp Ser Val Lys
 1               5                  10                  15

Gly
```

<210> SEQ ID NO 365
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 365

```
Arg Phe Thr Ile Ser Arg Asp Asn Ser Lys Asn Met Leu Tyr Leu Gln
 1               5                  10                  15

Met Asn Ser Leu Arg Ala Glu Asp Thr Ala Val Tyr Tyr Cys Ala Lys
            20                  25                  30
```

<210> SEQ ID NO 366
<211> LENGTH: 14
<212> TYPE: PRT
<213> ORGANISM: Artificial Sequence
<220> FEATURE:
<223> OTHER INFORMATION: single chain antibody fragment

<400> SEQUENCE: 366

```
Asp Arg Ser His Tyr Gly Asp Tyr Val Gly Tyr Leu Asp Tyr
 1               5                  10
```

<210> SEQ ID NO 367
<211> LENGTH: 11
<212> TYPE: PRT
<213> ORGANISM: Artificial Sequence
<220> FEATURE:

<223> OTHER INFORMATION: single chain antibody fragment

<400> SEQUENCE: 367

Trp Gly Gln Gly Thr Leu Val Thr Val Ser Ser
1               5                   10

<210> SEQ ID NO 368
<211> LENGTH: 30
<212> TYPE: PRT
<213> ORGANISM: Artificial Sequence
<220> FEATURE:
<223> OTHER INFORMATION: single chain antibody fragment

<400> SEQUENCE: 368

Glu Val Gln Leu Val Gln Ser Gly Gly Gly Leu Val Gln Pro Gly Gly
1               5                   10                  15

Ser Arg Arg Leu Ser Cys Ala Ala Ser Gly Phe Tyr Phe Asn
            20                  25                  30

<210> SEQ ID NO 369
<211> LENGTH: 5
<212> TYPE: PRT
<213> ORGANISM: Artificial Sequence
<220> FEATURE:
<223> OTHER INFORMATION: single chain antibody fragment

<400> SEQUENCE: 369

Ala Tyr Trp Met Thr
1               5

<210> SEQ ID NO 370
<211> LENGTH: 14
<212> TYPE: PRT
<213> ORGANISM: Artificial Sequence
<220> FEATURE:
<223> OTHER INFORMATION: single chain antibody fragment

<400> SEQUENCE: 370

Trp Val Arg Gln Ala Pro Gly Lys Gly Leu Glu Trp Val Ala
1               5                   10

<210> SEQ ID NO 371
<211> LENGTH: 17
<212> TYPE: PRT
<213> ORGANISM: Artificial Sequence
<220> FEATURE:
<223> OTHER INFORMATION: single chain antibody fragment

<400> SEQUENCE: 371

Asn Ile Asn Leu Asp Gly Thr Glu Ile Tyr Tyr Leu Asp Ser Val Lys
1               5                   10                  15

Gly

<210> SEQ ID NO 372
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 372

Arg Phe Thr Val Ser Arg Asp Asn Val Lys Asn Ser Val Phe Leu Gln
1               5                   10                  15

Met Ser Ser Leu Arg Val Glu Asp Thr Ala Val Tyr Phe Cys Ala Arg
            20                  25                  30

<210> SEQ ID NO 373
<211> LENGTH: 12
<212> TYPE: PRT
<213> ORGANISM: Artificial Sequence
<220> FEATURE:
<223> OTHER INFORMATION: single chain antibody fragment

<400> SEQUENCE: 373

Leu Glu Trp Gly Gly Arg Asn Gly Trp Val Ser Pro
1               5                   10

<210> SEQ ID NO 374
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 374

Trp Gly Gln Gly Thr Leu Val Thr Val Ser Ser
1               5                   10

<210> SEQ ID NO 375
<211> LENGTH: 30
<212> TYPE: PRT
<213> ORGANISM: Artificial Sequence
<220> FEATURE:
<223> OTHER INFORMATION: single chain antibody fragment

<400> SEQUENCE: 375

Gln Val Gln Leu Val Gln Ser Gly Gly Gly Leu Val Gln Pro Gly Gly
1               5                   10                  15

Ser Arg Arg Leu Ser Cys Ala Ala Ser Gly Phe Tyr Phe Asn
            20                  25                  30

<210> SEQ ID NO 376
<211> LENGTH: 5
<212> TYPE: PRT
<213> ORGANISM: Artificial Sequence
<220> FEATURE:
<223> OTHER INFORMATION: single chain antibody fragment

<400> SEQUENCE: 376

Ala Tyr Trp Met Thr
1               5

<210> SEQ ID NO 377
<211> LENGTH: 14
<212> TYPE: PRT
<213> ORGANISM: Artificial Sequence
<220> FEATURE:
<223> OTHER INFORMATION: single chain antibody fragment

<400> SEQUENCE: 377

Trp Val Arg Gln Ala Pro Gly Lys Gly Leu Glu Trp Val Ala
1               5                   10

<210> SEQ ID NO 378
<211> LENGTH: 17
<212> TYPE: PRT
<213> ORGANISM: Artificial Sequence
<220> FEATURE:
<223> OTHER INFORMATION: single chain antibody fragment

<400> SEQUENCE: 378

```
Asn Ile Asn Leu Asp Gly Thr Glu Ile Tyr Tyr Leu Asp Ser Val Lys
 1               5                  10                  15
Gly
```

<210> SEQ ID NO 379
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 379

```
Arg Phe Thr Val Ser Arg Asp Asn Val Lys Asn Ser Val Phe Leu Gln
 1               5                  10                  15
Met Ser Ser Leu Arg Val Glu Asp Thr Ala Val Tyr Phe Cys Ala Arg
                20                  25                  30
```

<210> SEQ ID NO 380
<211> LENGTH: 12
<212> TYPE: PRT
<213> ORGANISM: Artificial Sequence
<220> FEATURE:
<223> OTHER INFORMATION: single chain antibody fragment

<400> SEQUENCE: 380

```
Leu Glu Trp Gly Gly Arg Asn Gly Trp Val Ser Pro
 1               5                  10
```

<210> SEQ ID NO 381
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 381

```
Trp Gly Gln Gly Thr Leu Val Thr Val Ser Ser
 1               5                  10
```

<210> SEQ ID NO 382
<211> LENGTH: 30
<212> TYPE: PRT
<213> ORGANISM: Artificial Sequence
<220> FEATURE:
<223> OTHER INFORMATION: single chain antibody fragment

<400> SEQUENCE: 382

```
Gln Val Gln Leu Val Gln Ser Gly Ala Glu Val Lys Lys Pro Gly Ala
 1               5                  10                  15
Ser Val Asn Val Ser Cys Lys Ala Ser Gly Tyr Thr Phe Thr
                20                  25                  30
```

<210> SEQ ID NO 383
<211> LENGTH: 5
<212> TYPE: PRT
<213> ORGANISM: Artificial Sequence
<220> FEATURE:
<223> OTHER INFORMATION: single chain antibody fragment

<400> SEQUENCE: 383

```
Gly Tyr Tyr Ile Tyr
 1               5
```

<210> SEQ ID NO 384
<211> LENGTH: 14

```
<212> TYPE: PRT
<213> ORGANISM: Artificial Sequence
<220> FEATURE:
<223> OTHER INFORMATION: single chain antibody fragment

<400> SEQUENCE: 384

Trp Val Arg Gln Ala Pro Gly Gln Gly Leu Glu Trp Met Gly
 1               5                  10

<210> SEQ ID NO 385
<211> LENGTH: 17
<212> TYPE: PRT
<213> ORGANISM: Artificial Sequence
<220> FEATURE:
<223> OTHER INFORMATION: single chain antibody fragment

<400> SEQUENCE: 385

Trp Ile Asn Pro Asn Ser Gly Val Thr Lys Tyr Ala Gln Lys Phe Gln
 1               5                  10                  15

Gly

<210> SEQ ID NO 386
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 386

Arg Val Thr Met Thr Ile Asp Thr Ser Thr Asn Thr Ala Tyr Met Glu
 1               5                  10                  15

Leu Asn Arg Leu Arg Ala Asp Asp Thr Ala Val Tyr Tyr Cys Ala Arg
                20                  25                  30

<210> SEQ ID NO 387
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 387

Glu Trp Thr Gln Leu Trp Ser Pro Tyr Asp Tyr
 1               5                  10

<210> SEQ ID NO 388
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 388

Trp Gly Gln Gly Thr Thr Val Thr Val Ser Ser
 1               5                  10

<210> SEQ ID NO 389
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 389

Gln Val Gln Leu Gln Glu Ser Gly Ser Arg Leu Val Lys Pro Ser Gln
 1               5                  10                  15
```

```
Thr Leu Ser Leu Thr Cys Gly Val Ser Gly Gly Ser Ile Ser Ser Ser
            20                  25                  30

<210> SEQ ID NO 390
<211> LENGTH: 5
<212> TYPE: PRT
<213> ORGANISM: Artificial Sequence
<220> FEATURE:
<223> OTHER INFORMATION: single chain antibody fragment

<400> SEQUENCE: 390

Ser Tyr Ser Trp Ser
1               5

<210> SEQ ID NO 391
<211> LENGTH: 14
<212> TYPE: PRT
<213> ORGANISM: Artificial Sequence
<220> FEATURE:
<223> OTHER INFORMATION: single chain antibody fragment

<400> SEQUENCE: 391

Trp Ile Arg Gln Thr Pro Gly Lys Gly Leu Glu Trp Ile Gly
1               5                   10

<210> SEQ ID NO 392
<211> LENGTH: 16
<212> TYPE: PRT
<213> ORGANISM: Artificial Sequence
<220> FEATURE:
<223> OTHER INFORMATION: single chain antibody fragment

<400> SEQUENCE: 392

Tyr Ile Tyr His Ser Gly Ser Thr Tyr Tyr Asn Pro Ser Leu Lys Ser
1               5                   10                  15

<210> SEQ ID NO 393
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 393

Arg Val Thr Met Ser Val Asp Lys Ser Arg Asn Gln Phe Ser Leu Asn
1               5                   10                  15

Met Ser Ser Val Thr Ala Ala Asp Thr Ala Val Tyr Tyr Cys Ala Arg
            20                  25                  30

<210> SEQ ID NO 394
<211> LENGTH: 17
<212> TYPE: PRT
<213> ORGANISM: Artificial Sequence
<220> FEATURE:
<223> OTHER INFORMATION: single chain antibody fragment

<400> SEQUENCE: 394

Thr Ala Phe Tyr Tyr Glu Asn Thr Gly Pro Ile Arg Cys Tyr Leu Asp
1               5                   10                  15

Phe

<210> SEQ ID NO 395
<211> LENGTH: 11
<212> TYPE: PRT
<213> ORGANISM: Artificial Sequence
```

```
<220> FEATURE:
<223> OTHER INFORMATION: single chain antibody fragment

<400> SEQUENCE: 395

Trp Gly Gln Gly Thr Leu Val Thr Val Ser Ser
1               5                   10

<210> SEQ ID NO 396
<211> LENGTH: 23
<212> TYPE: PRT
<213> ORGANISM: Artificial Sequence
<220> FEATURE:
<223> OTHER INFORMATION: single chain antibody fragment

<400> SEQUENCE: 396

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 397
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 397

Arg Ala Ser Gln Arg Ile Ser Asn Tyr Leu Asn
1               5                   10

<210> SEQ ID NO 398
<211> LENGTH: 15
<212> TYPE: PRT
<213> ORGANISM: Artificial Sequence
<220> FEATURE:
<223> OTHER INFORMATION: single chain antibody fragment

<400> SEQUENCE: 398

Trp Tyr Gln Gln Lys Pro Gly Lys Ala Pro Lys Leu Leu Ile Tyr
1               5                   10                  15

<210> SEQ ID NO 399
<211> LENGTH: 7
<212> TYPE: PRT
<213> ORGANISM: Artificial Sequence
<220> FEATURE:
<223> OTHER INFORMATION: single chain antibody fragment

<400> SEQUENCE: 399

Ala Ala Ser Ser Leu Gln Ser
1               5

<210> SEQ ID NO 400
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 400

Glu Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30
```

<210> SEQ ID NO 401
<211> LENGTH: 9
<212> TYPE: PRT
<213> ORGANISM: Artificial Sequence
<220> FEATURE:
<223> OTHER INFORMATION: single chain antibody fragment

<400> SEQUENCE: 401

Gln Gln Ser Tyr Arg Pro Pro Leu Thr
 1               5

<210> SEQ ID NO 402
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 402

Phe Gly Gly Gly Thr Lys Val Glu Ile Lys Arg
 1               5                  10

<210> SEQ ID NO 403
<211> LENGTH: 23
<212> TYPE: PRT
<213> ORGANISM: Artificial Sequence
<220> FEATURE:
<223> OTHER INFORMATION: single chain antibody fragment

<400> SEQUENCE: 403

Asp Ile Gln Met Thr Gln Ser Pro Ser Ser Val Ser Ala Ser Val Gly
 1               5                  10                  15

Asn Arg Val Thr Ile Thr Cys
            20

<210> SEQ ID NO 404
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 404

Arg Ala Ser Gln Gly Ile Ser Ser Trp Leu Ala
 1               5                  10

<210> SEQ ID NO 405
<211> LENGTH: 15
<212> TYPE: PRT
<213> ORGANISM: Artificial Sequence
<220> FEATURE:
<223> OTHER INFORMATION: single chain antibody fragment

<400> SEQUENCE: 405

Trp Tyr Gln Gln Lys Pro Gly Lys Ala Pro Lys Leu Leu Ile Tyr
 1               5                  10                  15

<210> SEQ ID NO 406
<211> LENGTH: 7
<212> TYPE: PRT
<213> ORGANISM: Artificial Sequence
<220> FEATURE:
<223> OTHER INFORMATION: single chain antibody fragment

<400> SEQUENCE: 406

Ala Ala Ser Ser Leu Gln Ser

```
1               5
```

<210> SEQ ID NO 407
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 407

```
Gly Val Pro Ser Arg Phe Ser Gly Ser Gly Ser Gly Thr Asp Phe Thr
1               5                   10                  15
Leu Thr Ile Ser Ser Leu Gln Pro Glu Asp Phe Ala Thr Tyr Tyr Cys
            20                  25                  30
```

<210> SEQ ID NO 408
<211> LENGTH: 9
<212> TYPE: PRT
<213> ORGANISM: Artificial Sequence
<220> FEATURE:
<223> OTHER INFORMATION: single chain antibody fragment

<400> SEQUENCE: 408

```
Gln Lys Ala Asn Ser Phe Pro Leu Thr
1               5
```

<210> SEQ ID NO 409
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 409

```
Phe Gly Gly Gly Thr Lys Val Glu Ile Lys Arg
1               5                   10
```

<210> SEQ ID NO 410
<211> LENGTH: 23
<212> TYPE: PRT
<213> ORGANISM: Artificial Sequence
<220> FEATURE:
<223> OTHER INFORMATION: single chain antibody fragment

<400> SEQUENCE: 410

```
Asp Val Val Met Thr Gln Ser Pro Ser Ser Leu Ser Ala Ser Val Gly
1               5                   10                  15
Asp Arg Val Thr Ile Thr Cys
            20
```

<210> SEQ ID NO 411
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 411

```
Arg Ala Ser Gln Ser Ile Ser Ser Tyr Leu Asn
1               5                   10
```

<210> SEQ ID NO 412
<211> LENGTH: 15
<212> TYPE: PRT
<213> ORGANISM: Artificial Sequence
<220> FEATURE:

<223> OTHER INFORMATION: single chain antibody fragment

<400> SEQUENCE: 412

Trp Tyr Gln Gln Lys Pro Gly Lys Ala Pro Lys Leu Leu Ile Tyr
1               5                   10                  15

<210> SEQ ID NO 413
<211> LENGTH: 7
<212> TYPE: PRT
<213> ORGANISM: Artificial Sequence
<220> FEATURE:
<223> OTHER INFORMATION: single chain antibody fragment

<400> SEQUENCE: 413

Ala Ala Ser Ser Leu Gln Ser
1               5

<210> SEQ ID NO 414
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 414

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 415
<211> LENGTH: 9
<212> TYPE: PRT
<213> ORGANISM: Artificial Sequence
<220> FEATURE:
<223> OTHER INFORMATION: single chain antibody fragment

<400> SEQUENCE: 415

Gln Gln Ser Tyr Ser Thr Pro Leu Thr
1               5

<210> SEQ ID NO 416
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 416

Phe Gly Gln Gly Thr Lys Leu Glu Ile Lys Arg
1               5                   10

<210> SEQ ID NO 417
<211> LENGTH: 23
<212> TYPE: PRT
<213> ORGANISM: Artificial Sequence
<220> FEATURE:
<223> OTHER INFORMATION: single chain antibody fragment

<400> SEQUENCE: 417

Asp Val Val Met Thr Gln Ser Pro Ser Ser Leu Ser Ala Ser Val Gly
1               5                   10                  15

Asp Arg Ile Thr Ile Thr Cys
            20

```
<210> SEQ ID NO 418
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 418

Gln Ala Gly Gln Asp Ile Ser Asn Phe Leu Asn
1               5                   10

<210> SEQ ID NO 419
<211> LENGTH: 15
<212> TYPE: PRT
<213> ORGANISM: Artificial Sequence
<220> FEATURE:
<223> OTHER INFORMATION: single chain antibody fragment

<400> SEQUENCE: 419

Trp Tyr Gln Gln Lys Pro Gly Lys Ala Pro Lys Leu Leu Ile Arg
1               5                   10                  15

<210> SEQ ID NO 420
<211> LENGTH: 7
<212> TYPE: PRT
<213> ORGANISM: Artificial Sequence
<220> FEATURE:
<223> OTHER INFORMATION: single chain antibody fragment

<400> SEQUENCE: 420

Asp Ala Ser Asn Leu Glu Thr
1               5

<210> SEQ ID NO 421
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 421

Gly Val Pro Ser Arg Phe Ser Gly Gly Ser Gly Thr His Phe Thr
1               5                   10                  15

Phe Thr Ile Ser Ser Leu His Pro Glu Asp Ile Ala Thr Tyr Phe Cys
                20                  25                  30

<210> SEQ ID NO 422
<211> LENGTH: 9
<212> TYPE: PRT
<213> ORGANISM: Artificial Sequence
<220> FEATURE:
<223> OTHER INFORMATION: single chain antibody fragment

<400> SEQUENCE: 422

Gln Gln Tyr Asp Asn Leu Pro Tyr Thr
1               5

<210> SEQ ID NO 423
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 423

Phe Gly Gln Gly Thr Lys Leu Glu Ile Lys Arg
1               5                   10
```

<210> SEQ ID NO 424
<211> LENGTH: 23
<212> TYPE: PRT
<213> ORGANISM: Artificial Sequence
<220> FEATURE:
<223> OTHER INFORMATION: single chain antibody fragment

<400> SEQUENCE: 424

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 425
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 425

Arg Ala Ser Gln Ser Ile Ser Ser Tyr Leu Asn
1               5                   10

<210> SEQ ID NO 426
<211> LENGTH: 15
<212> TYPE: PRT
<213> ORGANISM: Artificial Sequence
<220> FEATURE:
<223> OTHER INFORMATION: single chain antibody fragment

<400> SEQUENCE: 426

Trp Tyr Gln Gln Glu Pro Gly Lys Ala Pro Lys Leu Leu Ile Tyr
1               5                   10                  15

<210> SEQ ID NO 427
<211> LENGTH: 7
<212> TYPE: PRT
<213> ORGANISM: Artificial Sequence
<220> FEATURE:
<223> OTHER INFORMATION: single chain antibody fragment

<400> SEQUENCE: 427

Ser Ala Ser Ser Leu Gln Ser
1               5

<210> SEQ ID NO 428
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 428

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 429
<211> LENGTH: 10
<212> TYPE: PRT
<213> ORGANISM: Artificial Sequence
<220> FEATURE:
<223> OTHER INFORMATION: single chain antibody fragment

<400> SEQUENCE: 429

Gln Gln Ser Tyr Ser Thr Pro Pro Tyr Thr
1               5                   10

<210> SEQ ID NO 430
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 430

Phe Gly Gln Gly Thr Lys Leu Glu Ile Lys Arg
1               5                   10

<210> SEQ ID NO 431
<211> LENGTH: 23
<212> TYPE: PRT
<213> ORGANISM: Artificial Sequence
<220> FEATURE:
<223> OTHER INFORMATION: single chain antibody fragment

<400> SEQUENCE: 431

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 432
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 432

Arg Ala Ser Gln Arg Ile Ser Asn Tyr Leu Asn
1               5                   10

<210> SEQ ID NO 433
<211> LENGTH: 15
<212> TYPE: PRT
<213> ORGANISM: Artificial Sequence
<220> FEATURE:
<223> OTHER INFORMATION: single chain antibody fragment

<400> SEQUENCE: 433

Trp Tyr Gln Gln Lys Pro Gly Lys Ala Pro Lys Leu Leu Ile Tyr
1               5                   10                  15

<210> SEQ ID NO 434
<211> LENGTH: 7
<212> TYPE: PRT
<213> ORGANISM: Artificial Sequence
<220> FEATURE:
<223> OTHER INFORMATION: single chain antibody fragment

<400> SEQUENCE: 434

Ala Ala Ser Ser Leu Gln Ser
1               5

<210> SEQ ID NO 435
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 435

Glu Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 436
<211> LENGTH: 9
<212> TYPE: PRT
<213> ORGANISM: Artificial Sequence
<220> FEATURE:
<223> OTHER INFORMATION: single chain antibody fragment

<400> SEQUENCE: 436

Gln Gln Ser Tyr Arg Pro Pro Leu Thr
1               5

<210> SEQ ID NO 437
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 437

Phe Gly Gly Gly Thr Lys Val Asp Ile Lys Arg
1               5                   10

<210> SEQ ID NO 438
<211> LENGTH: 23
<212> TYPE: PRT
<213> ORGANISM: Artificial Sequence
<220> FEATURE:
<223> OTHER INFORMATION: single chain antibody fragment

<400> SEQUENCE: 438

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 439
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 439

Arg Ala Ser Gln Arg Ile Ser Asn Tyr Leu Asn
1               5                   10

<210> SEQ ID NO 440
<211> LENGTH: 15
<212> TYPE: PRT
<213> ORGANISM: Artificial Sequence
<220> FEATURE:
<223> OTHER INFORMATION: single chain antibody fragment

<400> SEQUENCE: 440

Trp Tyr Gln Gln Lys Pro Gly Lys Ala Pro Lys Leu Leu Ile Tyr
1               5                   10                  15

<210> SEQ ID NO 441
<211> LENGTH: 7
<212> TYPE: PRT
<213> ORGANISM: Artificial Sequence
<220> FEATURE:
<223> OTHER INFORMATION: single chain antibody fragment

<400> SEQUENCE: 441

Ala Ala Ser Ser Leu Gln Ser
1               5

<210> SEQ ID NO 442
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 442

Glu Val Pro Ser Arg Phe Ser Gly Ser Gly Tyr Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 443
<211> LENGTH: 9
<212> TYPE: PRT
<213> ORGANISM: Artificial Sequence
<220> FEATURE:
<223> OTHER INFORMATION: single chain antibody fragment

<400> SEQUENCE: 443

Gln Gln Ser Tyr Arg Pro Pro Leu Thr
1               5

<210> SEQ ID NO 444
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 444

Phe Gly Gly Gly Thr Lys Val Asp Ile Lys Arg
1               5                   10

<210> SEQ ID NO 445
<211> LENGTH: 23
<212> TYPE: PRT
<213> ORGANISM: Artificial Sequence
<220> FEATURE:
<223> OTHER INFORMATION: single chain antibody fragment

<400> SEQUENCE: 445

Asp Ile Val Met Thr Gln Ser Pro Ser Thr Leu Ser Ala Ser Val Gly
1               5                   10                  15

Asp Arg Val Thr Val Thr Cys
            20

<210> SEQ ID NO 446
<211> LENGTH: 11
<212> TYPE: PRT
<213> ORGANISM: Artificial Sequence
<220> FEATURE:
<223> OTHER INFORMATION: single chain antibody fragment -continued

```
<400> SEQUENCE: 446

Arg Ala Ser Gln Ser Ile Asn Ser Trp Leu Ala
1               5                   10

<210> SEQ ID NO 447
<211> LENGTH: 15
<212> TYPE: PRT
<213> ORGANISM: Artificial Sequence
<220> FEATURE:
<223> OTHER INFORMATION: single chain antibody fragment

<400> SEQUENCE: 447

Trp Tyr Gln Gln Lys Pro Gly Lys Ala Pro Lys Leu Leu Ile Tyr
1               5                   10                  15

<210> SEQ ID NO 448
<211> LENGTH: 7
<212> TYPE: PRT
<213> ORGANISM: Artificial Sequence
<220> FEATURE:
<223> OTHER INFORMATION: single chain antibody fragment

<400> SEQUENCE: 448

Glu Ala Ser Ser Leu Glu Ser
1               5

<210> SEQ ID NO 449
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 449

Gly Val Pro Ser Arg Phe Ser Gly Ser Gly Ser Gly Thr Glu Phe Thr
1               5                   10                  15

Leu Thr Ile Ser Ser Leu Gln Pro Asp Asp Phe Ala Thr Tyr Tyr Cys
            20                  25                  30

<210> SEQ ID NO 450
<211> LENGTH: 9
<212> TYPE: PRT
<213> ORGANISM: Artificial Sequence
<220> FEATURE:
<223> OTHER INFORMATION: single chain antibody fragment

<400> SEQUENCE: 450

Gln Gln Tyr Asp Ser Tyr Trp Leu Thr
1               5

<210> SEQ ID NO 451
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 451

Phe Gly Gly Gly Thr Lys Val Glu Ile Lys Arg
1               5                   10

<210> SEQ ID NO 452
<211> LENGTH: 23
<212> TYPE: PRT
<213> ORGANISM: Artificial Sequence
<220> FEATURE:
```

<223> OTHER INFORMATION: single chain antibody fragment

<400> SEQUENCE: 452

Asp Ile Gln Met Thr Gln Ser Pro Ser Ser Val Ser Ala Ser Val Gly
1               5                   10                  15

Asp Arg Val Thr Ile Thr Cys
            20

<210> SEQ ID NO 453
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 453

Arg Ala Ser Gln Gly Val Ser Arg Trp Leu Ala
1               5                   10

<210> SEQ ID NO 454
<211> LENGTH: 15
<212> TYPE: PRT
<213> ORGANISM: Artificial Sequence
<220> FEATURE:
<223> OTHER INFORMATION: single chain antibody fragment

<400> SEQUENCE: 454

Trp Tyr Gln Gln Arg Pro Glu Lys Ala Pro Lys Leu Leu Ile Tyr
1               5                   10                  15

<210> SEQ ID NO 455
<211> LENGTH: 7
<212> TYPE: PRT
<213> ORGANISM: Artificial Sequence
<220> FEATURE:
<223> OTHER INFORMATION: single chain antibody fragment

<400> SEQUENCE: 455

Gly Ala Ser Ser Leu Gln Ser
1               5

<210> SEQ ID NO 456
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 456

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 457
<211> LENGTH: 9
<212> TYPE: PRT
<213> ORGANISM: Artificial Sequence
<220> FEATURE:
<223> OTHER INFORMATION: single chain antibody fragment

<400> SEQUENCE: 457

Gln Gln Tyr Asp Ser Phe Pro Leu Thr
1               5

```
<210> SEQ ID NO 458
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 458

Phe Gly Gly Gly Thr Lys Val Glu Ile Lys Arg
 1               5                  10

<210> SEQ ID NO 459
<211> LENGTH: 23
<212> TYPE: PRT
<213> ORGANISM: Artificial Sequence
<220> FEATURE:
<223> OTHER INFORMATION: single chain antibody fragment

<400> SEQUENCE: 459

Glu Ile Val Leu Thr Gln Ser Pro Ala Thr Leu Ser Val Ser Pro Gly
 1               5                  10                  15

Glu Arg Ala Thr Leu Ser Cys
            20

<210> SEQ ID NO 460
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 460

Arg Ala Ser Gln Ser Val Ser Lys Phe Leu Ala
 1               5                  10

<210> SEQ ID NO 461
<211> LENGTH: 15
<212> TYPE: PRT
<213> ORGANISM: Artificial Sequence
<220> FEATURE:
<223> OTHER INFORMATION: single chain antibody fragment

<400> SEQUENCE: 461

Trp Tyr Gln Gln Lys Arg Gly Gln Ala Pro Arg Leu Leu Ile Tyr
 1               5                  10                  15

<210> SEQ ID NO 462
<211> LENGTH: 7
<212> TYPE: PRT
<213> ORGANISM: Artificial Sequence
<220> FEATURE:
<223> OTHER INFORMATION: single chain antibody fragment

<400> SEQUENCE: 462

Gly Ala Ser Thr Arg Ala Thr
 1               5

<210> SEQ ID NO 463
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 463

Gly Ile Pro Ala Arg Phe Ser Gly Ser Gly Ser Gly Thr Glu Phe Ala
 1               5                  10                  15
```

```
Leu Thr Ile Ser Ser Leu Gln Ser Glu Asp Phe Ala Asp Tyr Tyr Cys
            20                  25                  30

<210> SEQ ID NO 464
<211> LENGTH: 9
<212> TYPE: PRT
<213> ORGANISM: Artificial Sequence
<220> FEATURE:
<223> OTHER INFORMATION: single chain antibody fragment

<400> SEQUENCE: 464

Gln Gln Tyr Asp Asn Trp Pro Ile Thr
 1               5

<210> SEQ ID NO 465
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 465

Phe Gly Gln Gly Thr Arg Leu Glu Ile Lys Arg
 1               5                  10

<210> SEQ ID NO 466
<211> LENGTH: 23
<212> TYPE: PRT
<213> ORGANISM: Artificial Sequence
<220> FEATURE:
<223> OTHER INFORMATION: single chain antibody fragment

<400> SEQUENCE: 466

Asp Ile Val Met Thr Gln Ser Pro Ser Thr Leu Ser Ala Ser Val Gly
 1               5                  10                  15

Asp Arg Val Thr Ile Thr Cys
            20

<210> SEQ ID NO 467
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 467

Arg Ala Ser Gln Gly Ile Ser Ser Trp Leu Ala
 1               5                  10

<210> SEQ ID NO 468
<211> LENGTH: 15
<212> TYPE: PRT
<213> ORGANISM: Artificial Sequence
<220> FEATURE:
<223> OTHER INFORMATION: single chain antibody fragment

<400> SEQUENCE: 468

Trp Tyr Gln Gln Lys Pro Gly Lys Ala Pro Lys Leu Leu Ile Tyr
 1               5                  10                  15

<210> SEQ ID NO 469
<211> LENGTH: 7
<212> TYPE: PRT
<213> ORGANISM: Artificial Sequence
<220> FEATURE:
<223> OTHER INFORMATION: single chain antibody fragment
```

-continued

<400> SEQUENCE: 469

Lys Ala Ser Ser Leu Glu Ser
1               5

<210> SEQ ID NO 470
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 470

Gly Val Pro Ser Arg Phe Ser Gly Ser Gly Ser Gly Thr Glu Phe Thr
1               5                   10                  15

Leu Thr Ile Ser Ser Leu Gln Pro Glu Asp Phe Ala Thr Tyr Tyr Cys
            20                  25                  30

<210> SEQ ID NO 471
<211> LENGTH: 9
<212> TYPE: PRT
<213> ORGANISM: Artificial Sequence
<220> FEATURE:
<223> OTHER INFORMATION: single chain antibody fragment

<400> SEQUENCE: 471

Leu Gln His Asn Ser Tyr Pro Arg Ala
1               5

<210> SEQ ID NO 472
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 472

Phe Gly Gln Gly Thr Lys Leu Glu Ile Lys Arg
1               5                   10

<210> SEQ ID NO 473
<211> LENGTH: 22
<212> TYPE: PRT
<213> ORGANISM: Artificial Sequence
<220> FEATURE:
<223> OTHER INFORMATION: single chain antibody fragment

<400> SEQUENCE: 473

Ala Tyr Val Leu Thr Gln Pro Pro Ser Val Ser Val Ala Pro Gly Lys
1               5                   10                  15

Thr Ala Ala Ile Thr Cys
            20

<210> SEQ ID NO 474
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 474

Glu Gly Asn Asn Val Gly Asn Lys Asn Val His
1               5                   10

<210> SEQ ID NO 475

```
<211> LENGTH: 15
<212> TYPE: PRT
<213> ORGANISM: Artificial Sequence
<220> FEATURE:
<223> OTHER INFORMATION: single chain antibody fragment

<400> SEQUENCE: 475

Trp Tyr Gln Gln Arg Pro Gly Gln Ala Pro Val Leu Val Val His
1               5                   10                  15

<210> SEQ ID NO 476
<211> LENGTH: 7
<212> TYPE: PRT
<213> ORGANISM: Artificial Sequence
<220> FEATURE:
<223> OTHER INFORMATION: single chain antibody fragment

<400> SEQUENCE: 476

Asp Asp Ser Asp Arg Pro Ser
1               5

<210> SEQ ID NO 477
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 477

Gly Ile Pro Glu Arg Phe Ser Gly Ser Asn Ser Gly Asn Thr Ala Thr
1               5                   10                  15

Leu Thr Ile Asn Arg Val Glu Ala Gly Asp Glu Ala Asp Tyr Tyr Cys
            20                  25                  30

<210> SEQ ID NO 478
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 478

Gln Val Trp Asp Ser Ser Ser Ala Gln Trp Val
1               5                   10

<210> SEQ ID NO 479
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 479

Phe Gly Gly Gly Thr Lys Leu Thr Val Leu Gly
1               5                   10

<210> SEQ ID NO 480
<211> LENGTH: 22
<212> TYPE: PRT
<213> ORGANISM: Artificial Sequence
<220> FEATURE:
<223> OTHER INFORMATION: single chain antibody fragment

<400> SEQUENCE: 480

Glu Ser Val Leu Thr Gln Pro Pro Leu Val Ser Ala Ala Pro Gly Gln
1               5                   10                  15
```

Lys Val Thr Ile Ser Cys
            20

<210> SEQ ID NO 481
<211> LENGTH: 13
<212> TYPE: PRT
<213> ORGANISM: Artificial Sequence
<220> FEATURE:
<223> OTHER INFORMATION: single chain antibody fragment

<400> SEQUENCE: 481

Ser Gly Ser Ser Ser Asn Ile Gly Asn Asn Tyr Val Ser
1               5                   10

<210> SEQ ID NO 482
<211> LENGTH: 15
<212> TYPE: PRT
<213> ORGANISM: Artificial Sequence
<220> FEATURE:
<223> OTHER INFORMATION: single chain antibody fragment

<400> SEQUENCE: 482

Trp Tyr Gln Gln Leu Pro Gly Thr Ala Pro Lys Leu Leu Ile Tyr
1               5                   10                  15

<210> SEQ ID NO 483
<211> LENGTH: 7
<212> TYPE: PRT
<213> ORGANISM: Artificial Sequence
<220> FEATURE:
<223> OTHER INFORMATION: single chain antibody fragment

<400> SEQUENCE: 483

Glu Asn Ser Lys Arg Ser Ser
1               5

<210> SEQ ID NO 484
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 484

Gly Ile Pro Asp Arg Phe Ser Gly Ser Lys Ser Gly Thr Ser Ala Thr
1               5                   10                  15

Leu Gly Ile Thr Gly Leu Gln Thr Gly Asp Glu Ala Asp Tyr Tyr Cys
            20                  25                  30

<210> SEQ ID NO 485
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 485

Gly Thr Trp Asp Ser Ser Leu Ser Ala Val Val
1               5                   10

<210> SEQ ID NO 486
<211> LENGTH: 11
<212> TYPE: PRT
<213> ORGANISM: Artificial Sequence
<220> FEATURE:
<223> OTHER INFORMATION: single chain antibody fragment -continued

```
<400> SEQUENCE: 486

Phe Gly Gly Gly Thr Lys Leu Thr Val Leu Gly
 1               5                  10

<210> SEQ ID NO 487
<211> LENGTH: 23
<212> TYPE: PRT
<213> ORGANISM: Artificial Sequence
<220> FEATURE:
<223> OTHER INFORMATION: single chain antibody fragment

<400> SEQUENCE: 487

Asp Val Val Met Thr Gln Ser Pro Ser Ser Val Ser Ala Ser Val Gly
 1               5                  10                  15

Asp Arg Val Thr Ile Thr Cys
            20

<210> SEQ ID NO 488
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 488

Arg Ala Ser Gln Ser Ile Ser Ser Tyr Leu Asn
 1               5                  10

<210> SEQ ID NO 489
<211> LENGTH: 15
<212> TYPE: PRT
<213> ORGANISM: Artificial Sequence
<220> FEATURE:
<223> OTHER INFORMATION: single chain antibody fragment

<400> SEQUENCE: 489

Trp Tyr Gln Gln Arg Pro Gly Lys Ala Pro Lys Leu Leu Ile Phe
 1               5                  10                  15

<210> SEQ ID NO 490
<211> LENGTH: 7
<212> TYPE: PRT
<213> ORGANISM: Artificial Sequence
<220> FEATURE:
<223> OTHER INFORMATION: single chain antibody fragment

<400> SEQUENCE: 490

Ala Ala Ser Ser Leu Gln Ser
 1               5

<210> SEQ ID NO 491
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 491

Ala Val Pro Ser Arg Phe Ser Gly Ser Gly Ser Gly Thr Asp Phe Thr
 1               5                  10                  15

Leu Thr Ile Ser Ser Leu Gln Pro Glu Asp Phe Ala Thr Tyr Tyr Cys
            20                  25                  30

<210> SEQ ID NO 492
<211> LENGTH: 9
```

```
<212> TYPE: PRT
<213> ORGANISM: Artificial Sequence
<220> FEATURE:
<223> OTHER INFORMATION: single chain antibody fragment

<400> SEQUENCE: 492

Gln Gln Ser Tyr Ser Thr Pro Pro Thr
1               5

<210> SEQ ID NO 493
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 493

Phe Gly Gln Gly Thr Lys Val Glu Ile Lys Arg
1               5                   10

<210> SEQ ID NO 494
<211> LENGTH: 23
<212> TYPE: PRT
<213> ORGANISM: Artificial Sequence
<220> FEATURE:
<223> OTHER INFORMATION: single chain antibody fragment

<400> SEQUENCE: 494

Asp Ile Val Met Thr Gln Ser Pro Ser Ser Leu Ser Ala Ser Val Gly
1               5                   10                  15

Asp Arg Val Ser Ile Ser Cys
            20

<210> SEQ ID NO 495
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 495

Arg Ala Ser Gln Ser Ile Ser Ser Tyr Leu Asn
1               5                   10

<210> SEQ ID NO 496
<211> LENGTH: 15
<212> TYPE: PRT
<213> ORGANISM: Artificial Sequence
<220> FEATURE:
<223> OTHER INFORMATION: single chain antibody fragment

<400> SEQUENCE: 496

Trp Tyr Gln Gln Lys Pro Gly Lys Ala Pro Lys Leu Leu Ile Tyr
1               5                   10                  15

<210> SEQ ID NO 497
<211> LENGTH: 7
<212> TYPE: PRT
<213> ORGANISM: Artificial Sequence
<220> FEATURE:
<223> OTHER INFORMATION: single chain antibody fragment

<400> SEQUENCE: 497

Lys Thr Ser Ser Leu Glu Ser
1               5
```

```
<210> SEQ ID NO 498
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 498

Gly Val Pro Ser Arg Phe Ser Gly Arg Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 499
<211> LENGTH: 9
<212> TYPE: PRT
<213> ORGANISM: Artificial Sequence
<220> FEATURE:
<223> OTHER INFORMATION: single chain antibody fragment

<400> SEQUENCE: 499

Gln Gln Ser Tyr Ser Thr Pro Leu Thr
1               5

<210> SEQ ID NO 500
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 500

Phe Gly Gly Gly Thr Lys Val Glu Ile Lys Arg
1               5                   10

<210> SEQ ID NO 501
<211> LENGTH: 23
<212> TYPE: PRT
<213> ORGANISM: Artificial Sequence
<220> FEATURE:
<223> OTHER INFORMATION: single chain antibody fragment

<400> SEQUENCE: 501

Asp Ile Gln Met Thr Gln Ser Pro Ser Thr Leu Ser Ala Ser Ile Gly
1               5                   10                  15

Asp Arg Val Thr Ile Ser Cys
            20

<210> SEQ ID NO 502
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 502

Arg Ala Ser Gln Ser Ile Gln Ser Trp Leu Ala
1               5                   10

<210> SEQ ID NO 503
<211> LENGTH: 15
<212> TYPE: PRT
<213> ORGANISM: Artificial Sequence
<220> FEATURE:
<223> OTHER INFORMATION: single chain antibody fragment

<400> SEQUENCE: 503
```

Trp Tyr Gln Gln Arg Pro Gly Glu Ala Pro Lys Leu Leu Ile Tyr
1               5                   10                  15

<210> SEQ ID NO 504
<211> LENGTH: 7
<212> TYPE: PRT
<213> ORGANISM: Artificial Sequence
<220> FEATURE:
<223> OTHER INFORMATION: single chain antibody fragment

<400> SEQUENCE: 504

Ser Ala Ser Thr Leu Gln Thr
1               5

<210> SEQ ID NO 505
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 505

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 506
<211> LENGTH: 9
<212> TYPE: PRT
<213> ORGANISM: Artificial Sequence
<220> FEATURE:
<223> OTHER INFORMATION: single chain antibody fragment

<400> SEQUENCE: 506

Gln Gln Tyr Asn Ser Tyr Pro Leu Thr
1               5

<210> SEQ ID NO 507
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 507

Phe Gly Gln Gly Thr Lys Leu Glu Ile Lys Arg
1               5                   10

<210> SEQ ID NO 508
<211> LENGTH: 23
<212> TYPE: PRT
<213> ORGANISM: Artificial Sequence
<220> FEATURE:
<223> OTHER INFORMATION: single chain antibody fragment

<400> SEQUENCE: 508

Asp Ile Val Leu Thr Gln Ser Pro Ser Thr Leu Ser Ala Ser Val Gly
1               5                   10                  15

Asp Arg Val Thr Ile Ser Cys
            20

<210> SEQ ID NO 509
<211> LENGTH: 11
<212> TYPE: PRT

<213> ORGANISM: Artificial Sequence
<220> FEATURE:
<223> OTHER INFORMATION: single chain antibody fragment

<400> SEQUENCE: 509

Arg Ala Ser Arg Ser Ile Gly Trp Tyr Leu Asn
1               5                   10

<210> SEQ ID NO 510
<211> LENGTH: 15
<212> TYPE: PRT
<213> ORGANISM: Artificial Sequence
<220> FEATURE:
<223> OTHER INFORMATION: single chain antibody fragment

<400> SEQUENCE: 510

Trp Tyr Gln Gln Arg Pro Gly Lys Ala Pro Lys Leu Leu Ile Tyr
1               5                   10                  15

<210> SEQ ID NO 511
<211> LENGTH: 7
<212> TYPE: PRT
<213> ORGANISM: Artificial Sequence
<220> FEATURE:
<223> OTHER INFORMATION: single chain antibody fragment

<400> SEQUENCE: 511

Ala Ala Ser Ser Leu His Asn
1               5

<210> SEQ ID NO 512
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 512

Gly Val Pro Ser Arg Phe Ser Gly Ser Gly Ser Gly Thr Glu Phe Thr
1               5                   10                  15

Leu Thr Ile Ser Ser Leu Gln Pro Asp Asp Phe Ala Thr Tyr Tyr Cys
            20                  25                  30

<210> SEQ ID NO 513
<211> LENGTH: 9
<212> TYPE: PRT
<213> ORGANISM: Artificial Sequence
<220> FEATURE:
<223> OTHER INFORMATION: single chain antibody fragment

<400> SEQUENCE: 513

Gln Gln Ala Phe Gly Phe Pro Arg Thr
1               5

<210> SEQ ID NO 514
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 514

Phe Gly Gln Gly Thr Lys Val Glu Ile Lys Arg
1               5                   10

<210> SEQ ID NO 515

```
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 515

Asp Asp Pro Tyr Tyr Tyr Ser Tyr Met Asp Val
1               5                   10

<210> SEQ ID NO 516
<211> LENGTH: 9
<212> TYPE: PRT
<213> ORGANISM: Artificial Sequence
<220> FEATURE:
<223> OTHER INFORMATION: single chain antibody fragment

<400> SEQUENCE: 516

Gln Gln Tyr Tyr Ser Thr Pro Phe Thr
1               5

<210> SEQ ID NO 517
<211> LENGTH: 17
<212> TYPE: PRT
<213> ORGANISM: Artificial Sequence
<220> FEATURE:
<223> OTHER INFORMATION: single chain antibody fragment

<400> SEQUENCE: 517

Glu Ala Ser Phe Gly Trp Ser Tyr Leu Gly His Asp Asp Ala Phe Asp
1               5                   10                  15

Ile

<210> SEQ ID NO 518
<211> LENGTH: 9
<212> TYPE: PRT
<213> ORGANISM: Artificial Sequence
<220> FEATURE:
<223> OTHER INFORMATION: single chain antibody fragment

<400> SEQUENCE: 518

Gln Gln Tyr Gly Ser Ser Leu Trp Thr
1               5

<210> SEQ ID NO 519
<211> LENGTH: 17
<212> TYPE: PRT
<213> ORGANISM: Artificial Sequence
<220> FEATURE:
<223> OTHER INFORMATION: single chain antibody fragment

<400> SEQUENCE: 519

Asp Pro Gly Trp Ile Tyr Ser Asp Thr Ser Ala Ala Gly Trp Phe Asp
1               5                   10                  15

Pro

<210> SEQ ID NO 520
<211> LENGTH: 9
<212> TYPE: PRT
<213> ORGANISM: Artificial Sequence
<220> FEATURE:
<223> OTHER INFORMATION: single chain antibody fragment

<400> SEQUENCE: 520

Gln Gln Ser Tyr Asp Thr Pro Arg Thr
1               5
```

```
<210> SEQ ID NO 521
<211> LENGTH: 15
<212> TYPE: PRT
<213> ORGANISM: Artificial Sequence
<220> FEATURE:
<223> OTHER INFORMATION: protein linker

<400> SEQUENCE: 521

Gly Gly Gly Gly Ser Gly Gly Gly Gly Ser Gly Gly Gly Gly Ser
 1               5                  10                  15

<210> SEQ ID NO 522
<211> LENGTH: 5
<212> TYPE: PRT
<213> ORGANISM: Artificial Sequence
<220> FEATURE:
<223> OTHER INFORMATION: protein linker

<400> SEQUENCE: 522

Gly Gly Gly Gly Ser
 1               5
```

THERAPEUTIC MONOCLONAL ANTIBODIES THAT NEUTRALIZE BOTULINUM NEUROTOXINS

CROSS-REFERENCE TO RELATED APPLICATIONS

This application is a continuation application of U.S. Ser. No. 12/528,601, filed Nov. 12, 2009, now issued as U.S. Pat. No. 8,598,321, which application is a U.S. national stage application of international application serial no. PCT/US08/03767, filed on Mar. 21, 2008, which application claims benefit of and priority to U.S. Ser. No. 60/896,332, filed on Mar. 22, 2007, and U.S. Ser. No. 60/942,173, filed on Jun. 5, 2007, both of which are incorporated herein by reference in their entirety for all purposes.

STATEMENT AS TO RIGHTS TO INVENTIONS MADE UNDER FEDERALLY SPONSORED RESEARCH AND DEVELOPMENT

This invention was made with Government support by Grant No: U01 AI056493, awarded by the National Institutes of Health, and by Department of Defense Grant DAMD17-98-C-8030. The Government of the United States of America has certain rights in this invention.

FIELD OF THE INVENTION

This invention relates antibodies that neutralize *botulinum* neurotoxins (e.g., BoNT/A) and their use in the treatment of botulism.

BACKGROUND OF THE INVENTION

Botulism is caused by *botulinum* neurotoxin secreted by members of the genus *Clostridium* and is characterized by flaccid paralysis, which if not immediately fatal requires prolonged hospitalization in an intensive care unit and mechanical ventilation. Naturally occurring botulism is found in infants or adults whose gastrointestinal tracts become colonized by Clostridial bacteria (infant or intestinal botulism), after ingestion of contaminated food products (food botulism), or in anaerobic wound infections (wound botulism) (Center for Disease Control (1998) Botulism in the United States, 1899-1998. Handbook for epidemiologists, clinicians, and laboratory workers. Atlanta, Ga. U.S. Department of Health and Human Services, Public Health Service: downloadable at (worldwidewweb(dot)bt(dot)cdc(dot)gov/agent/botulism/index.asp). Botulism neurotoxins (BoNTs) are also classified by the Centers for Disease Control (CDC) as one of the six highest-risk threat agents for bioterrorism (the "Category A agents"), due to their extreme potency and lethality, ease of production and transport, and need for prolonged intensive care (Arnon et al. (2001) *JAMA* 285: 1059-1070). Both Iraq and the former Soviet Union produced BoNT for use as weapons (United Nations Security Council (1995) Tenth report of the executive committee of the special commission established by the secretary-general pursuant to paragraph 9(b)(I) of security council resolution 687 (1991), and paragraph 3 of resolution 699 (1991) on the activities of the Special Commision; Bozheyeva et al. (1999) Former soviet biological weapons facilities in Kazakhstan: past, present, and future. Center for Nonproliferation Studies, Monterey Institute of International Studies), and the Japanese cult Aum Shinrikyo attempted to use BoNT for bioterrorism (Arnon et al. (2001) supra). As a result of these threats, specific pharmaceutical agents are needed for prevention and treatment of intoxication.

No specific small molecule drugs exist for prevention or treatment of botulism, but an investigational pentavalent toxoid vaccine is available from the CDC (Siegel (1988) *J. Clin. Microbiol.* 26: 2351-2356) and a recombinant vaccine is under development (Smith (1998) *Toxicon* 36: 1539-1548). Regardless, mass civilian or military vaccination is unlikely due to the rarity of disease or exposure and the fact that vaccination would prevent subsequent medicinal use of BoNT. Post-exposure vaccination is useless, due to the rapid onset of disease. Toxin neutralizing antibody (Ab) can be used for pre- or post-exposure prophylaxis or for treatment (Franz et al. (1993) Pp. 473-476 In B. R. DasGupta (ed.), *Botulinum* and Tetanus Neurotoxins: Neurotransmission and Biomedical Aspects. Plenum Press, New York). Small quantities of both equine antitoxin and human *botulinum* immune globulin exist and are currently used to treat adult (Black and Gunn. (1980) *Am. J. Med.,* 69: 567-570; Hibbs et al. (1996) *Clin. Infect. Dis.,* 23: 337-340) and infant botulism (Arnon (1993). Clinical trial of human botulism immune globulin, p. 477-482. In B. R. DasGupta (ed.), *Botulinum* and Tetanus Neurotoxins: Neurotransmission and Biomedical Aspects. Plenum Press, New York) respectively.

Recombinant monoclonal antibody (mAb) could provide an unlimited supply of antitoxin free of infectious disease risk and not requiring human donors for plasmapheresis. Given the extreme lethality of the BoNTs, mAbs must be of high potency in order to provide an adequate number of doses at reasonable cost. The development of such mAbs has become a high priority research aim of the National Institute of Allergy and Infectious Diseases. While to date no single highly potent mAbs have been described, we recently reported that combining two to three mAbs could yield highly potent BoNT neutralization (Nowakowski et al. (2002) *Proc. Natl. Acad. Sci. USA,* 99: 11346-50).

The development of mAb therapy for botulism is complicated by the fact that there are at least seven BoNT serotypes (A-G) (Hatheway (1995) *Curr. Top. Microbio. Immunol,* 195: 55-75.) that show little, if any, antibody cross-reactivity. While only four of the BoNT serotypes routinely cause human disease (A, B, E, and F), there has been one reported case of infant botulism caused by BoNT C (Oguma et al. (1990) *Lancet* 336: 1449-1450), one outbreak of foodborne botulism linked to BoNT D (Demarchi, et al. (1958) *Bull. Acad. Nat. Med.,* 142: 580-582), and several cases of suspicious deaths where BoNT G was isolated (Sonnabend et al. (1981) *J. Infect. Dis.,* 143: 22-27). Aerosolized BoNT/C, D, and G have also been shown to produce botulism in primates by the inhalation route (Middlebrook and Franz (1997) *Botulinum* Toxins, chapter 33. In F. R. Sidell, E. T. Takafuji, D. R. Franz (eds.), Medical Aspects of Chemical and Biological Warfare. TMM publications, Washington, D.C.), and would most likely also affect humans. Thus it is likely that any one of the seven BoNT serotypes can be used as a biothreat agent.

Variability of the BoNT gene and protein sequence within serotypes has also been reported and there is evidence that such variability can affect the binding of monoclonal antibodies to BoNT/A (Kozaki et al. (1998) *Infect. Immun.,* 66: 4811-4816; Kozaki et al. (1995) *Microbiol. Immunol.,* 39: 767-774).

SUMMARY OF THE INVENTION

This invention pertains to antibodies that bind to and neutralize *botulinum* neurotoxin(s). We have discovered that particularly effective neutralization of a Botulism neurotoxin (BoNT) serotype can be achieved by the use of neutralizing antibodies that bind two or more subtypes of the particular neurotoxin serotype with high affinity and/or by combinations of such antibodies. In certain embodiments this invention provides improved antibodies that bind BoNT subtypes BoNT/A, BoNT/B, and BoNT/E. In certain embodiments this invention provides for compositions comprising neutralizing antibodies that bind two or more BoNT subtypes (e.g., BoNT/A1, BoNT/A2, BoNT/A3, etc.) with high affinity.

In certain embodiments this invention provides a neutralizing antibody for Botulinuym neurotoxin (BoNT). The antibody typically comprises at least one VH complementarity determining region (CDR) selected from the group consisting of a 2A10 VH CDR, a 3E1VH CDR, a 3E2VH CDR, a 3E3VH CDR, a 3E4VH CDR, a 3E4.1VH CDR, a 3E5VH CDR, a 3E6VH CDR, a 3E6.1VH CDR, a 4E11VH CDR, a 4E13VH CDR, a 4E16VH CDR, a 4E16.1VH CDR, a 4E17VH CDR, a 4E17.1VH CDR, an A12 VH CDR, a 6A12 VH CDR, a B1.1 VH CDR, a B6 VH CDR, a B6.1 VH CDR, a B8 VH CDR, a B8.1 VH CDR, a B11 VH CDR, a B11C3 VH CDR, a B11E8 VH CDR, a B12 VH CDR, a B12.1 VH CDR, a B12.2 VH CDR, a 1B18 VH CDR, a 2B18.1 VH CDR, a 4B19 VH CDR, and a 1B22 VH CDR; and/or at least one VL complementarity determining region selected from the group consisting of a 2A10 VL CDR, a 3E1VL CDR, a 3E2VL CDR, a 3E3VL CDR, a 3E4VL CDR, a 3E4.1VL CDR, a 3E5VL CDR, a 3E6VL CDR, a 3E6.1VL CDR, a 4E11VL CDR, a 4E13VL CDR, a 4E16VL CDR, a 4E16.1VL CDR, a 4E17VL CDR, a 4E17.1VL CDR, an A12 VL CDR, a 6A12 VL CDR, a B1.1 VL CDR, a B6 VL CDR, a B6.1 VL CDR, a B8 VL CDR, a B8.1 VL CDR, a B11 VL CDR, a B11C3 VL CDR, a B11E8 VL CDR, a B12 VL CDR, a B12.1. VL CDR, a B12.2 VL CDR, a 1B18 VL CDR, a 2B18.1 VL CDR, a 4B19 VL CDR, and a 1B22 VL CDR. In various embodiments the antibody comprises the VH CDRs of an antibody selected from the group consisting of 2A10, 3E1VH CDR, 3E2VH CDR, 3E3VH CDR, 3E4VH CDR, 3E4.1VH CDR, 3E5VH CDR, 3E6VH CDR, 3E6.1VH CDR, 4E11VH CDR, 4E13VH CDR, 4E16VH CDR, 4E16.1VH CDR, 4E17VH CDR, 4E17.1VH CDR, A12, 6A12, B1.1, B6, B6.1, B8, B8.1, B11, B11C3, B11E8, B12, B12.1, B12.2, 1818, 2818.1, 4819, and 1822; and/or the VL CDRs of an antibody selected from the group consisting of 2A10, 3E1VH CDR, 3E2VH CDR, 3E3VH CDR, 3E4VH CDR, 3E4.1VH CDR, 3E5VH CDR, 3E6VH CDR, 3E6.1VH CDR, 4E11VH CDR, 4E13VH CDR, 4E16VH CDR, 4E16.1VH CDR, 4E17VH CDR, 4E17.1VH CDR, A12, 6A12, B1.1, B6, B6.1, B8, B8.1, B11, B11C3, B11E8, B12, B12.1, B12.2, 1818, 2B18.1, 4B19, and 1B22. In various embodiments the antibody comprises the VH and VL CDRs of an antibody selected from the group consisting of 2A10, 3E1VH CDR, 3E2VH CDR, 3E3VH CDR, 3E4VH CDR, 3E4.1VH CDR, 3E5VH CDR, 3E6VH CDR, 3E6.1VH CDR, 4E11VH CDR, 4E13VH CDR, 4E16VH CDR, 4E16.1VH CDR, 4E17VH CDR, 4E17.1VH CDR, A12, 6A12, B1.1, B6, B6.1, B8, B8.1, B11, B11C3, B11E8, B12, B12.1, B12.2, 1818, 2B18.1, 4B1319, and 1B22. In various embodiments the antibody comprises the VH and VL domains of an antibody selected from the group consisting of 2A10, 3E1VH CDR, 3E2VH CDR, 3E3VH CDR, 3E4VH CDR, 3E4.1VH CDR, 3E5VH CDR, 3E6VH CDR, 3E6.1VH CDR, 4E11VH CDR, 4E13VH CDR, 4E16VH CDR, 4E16.1VH CDR, 4E17VH CDR, 4E17.1VH CDR, A12, 6A12, B1.1, B6, B6.1, B8, B8.1, B11, B11C3, B11E8, B12, B12.1, B12.2, 1818, 2818.1, 4819, and 1B22. In certain embodiments the antibody is a single chain Fv (scFv), a FAB, a (Fab')$_2$, an (ScFv)$_2$, and the like. In certain embodiments the antibody is an IgG. In certain embodiments the antibody is selected from the group consisting of 2A10, 3E1VH CDR, 3E2VH CDR, 3E3VH CDR, 3E4VH CDR, 3E4.1VH CDR, 3E5VH CDR, 3E6VH CDR, 3E6.1VH CDR, 4E11VH CDR, 4E13VH CDR, 4E16VH CDR, 4E16.1VH CDR, 4E17VH CDR, 4E17.1VH CDR, A12, 6A12, B1.1, B6, B6.1, B8, B8.1, B11, B11C3, B11E8, B12, B12.1, B12.2, 1B18, 2B18.1, 4B19, and 1B22. In various embodiments the antibody is in a pharmaceutically acceptable excipient (e.g., in a unit dosage formulation).

In various embodiments method of method of inhibiting the activity of Botulinum neurotoxin in a mammal are provided. The methods typically involve administering to a mammal in need thereof a composition comprising at least one neutralizing anti-BoNT antibody as described herein. In certain embodiments the composition comprises at least two different antibodies that each bind different BoNT serotypes. In certain embodiments the composition comprises at least three different antibodies that each bind different BoNT epitopes.

In certain embodiments compositions are provided that partially or fully neutralize a Botulinum neurotoxin (BoNT). The compositions typically comprise a first antibody that binds a BoNT/B or a BoNT/E serotype, e.g., one or more antibodies as described above, and a second antibody that binds a BoNT serotype selected from the group consisting of BoNT/A, BoNT/B, BoNT/C, BoNT/D, BoNT/E, and BoNT/F.

In various embodiments nucleic acids are provided that encode one or more antibodies as described herein. In certain embodiments cells containing such antibodies are also provided herein. Kits are also provided for neutralizing a Botulinum neurotoxin. The kits typically comprise a composition comprising one or more antibodies as described herein. The kits optionally also include instructional materials teaching the use of the composition to neutralize a Botulinum neurotoxin. In certain embodiments the composition is stored in a disposable syringe.

Definitions.

A "BoNT polypeptide" refers to a Botulinum neurotoxin polypeptide (e.g., a BoNT/A polypeptide, a BoNT/B polypeptide, a BoNT/C polypeptide, and so forth). The BoNT polypeptide can refer to a full-length polypeptide or to a fragment thereof. Thus, for example, the term "BoNT/A polypeptide" refers to either a full-length BoNT/A (a neurotoxin produced by Clostridium botulinum of the type A serotype) or a fragment thereof (e.g. the Hc fragment). The $H_C$ fragment approximately a 50 Da C-terminal fragment (residues 873-1296) of BoNT/A (Lacy and Stevens (1999) J. Mol. Biol., 291: 1091-1104).

A "BoNT" serotype refers one of the standard known BoNT serotypes (e.g. BoNT/A, BoNT/C, BoNT/D, BoNT/E, BoNT/F, etc.). BoNT serotypes differ from each other by as little as about 35% at the amino acid level (e.g., between BoNT/E and BoNT/F) up to about 66% at the amino acid level, (e.g., for BoNT/A vs BoNT/C or D). Thus, BoNT serotypes differ from each other by about 35-66% at the amino acid level.

The term "BoNT subtype" (e.g., a BoNT/A1A subtype) refers to botulinum neurotoxin gene sequences of a particular serotype (e.g., A, C, D, F, etc.) that differ from each other sufficiently to produce differential antibody binding. In certain embodiments, the subtypes differ from each other by at least 2.5%, preferably by at least 5%, or 10%, more preferably by at least 15% or 20% at the amino acid level. In certain embodiments, the subtypes differ from each other by nor more than 35%, preferably by no more than 31.6%, still more preferably by no more than 30%, or 25%, more preferably by less than about 20% or 16% at the amino acid level. In certain embodiments, BoNT subtypes differ from each other by at least 2.6%, more preferably by at least 3%, and most preferably by at least 3.6% at the amino acid level. BoNT subtypes typically differ from each other by less than about 31.6%, more preferably by less than about 16%, at the amino acid level.

An "anti-BoNT antibody" refers to an antibody that binds a BoNT polypeptide, preferably specifically binds a BoNT polypeptide with a KD less than $10^{-7}$, preferably less than $10^{-8}$, or $10^{-9}$, more preferably less than $10^{-10}$, $10^{-11}$, or $10^{-12}$.

"Neutralization" refers to a measurable decrease in the toxicity of a *Botulinum* neurotoxin (e.g., BoNT/A).

The term "high affinity" when used with respect to an antibody refers to an antibody that specifically binds to its target(s) with an affinity ($K_D$) of at least about $10^{-8}$ M, preferably at least about $10^{-9}$M, more preferably at least about $10^{-10}$M, and most preferably at last about $10^{-11}$ M. In certain embodiments "high affinity" antibodies have a $K_D$ that ranges from about 1 nM to about 5 pM.

The following abbreviations are used herein: AMP, ampicillin; BIG, *botulinum* immune globulin; BoNT, *botulinum* neurotoxin; BoNT/A, BoNT type A; CDR, complementarity determining region; ELISA, enzyme-linked immunosorbent assay; GLU, glucose; HBS, HEPES-buffered saline (10 mM HEPES, 150 mM NaCl [pH 7.4]); $H_c$, c-terminal domain of BoNT heavy chain (binding domain); $H_N$, N-terminal domain of BoNT heavy chain (translocation domain); IgG, immunoglobutin G; IMAC, immobilized-metal affinity chromatography; IPTG, isopropyl-β-D-thiogalactopyranoside; KAN, kanamycin; $K_d$, equilibrium constant; $k_{off}$, dissociation rate constant; $k_{on}$, association rate constant; MPBS, skim milk powder in PBS; NTA, nitrilotriacetic acid; PBS, phosphate-buffered saline (25 mM $NaH_2PO_4$, 125 mM NaCl [pH 7.0]; RU, resonance units; scFv, single-chain Fv antibody fragments; TPBS, 0.05% (vol/vol) Tween 20 in PBS; TMPBS, 0.05% (vol/vol) Tween 20 in MPBS; TU, transducing units; $V_H$, immunoglobulin heavy-chain variable region; $V_K$, immunoglobulin kappa light-chain variable region; $V_L$ immunoglobulin light-chain variable region; wt, wild type.

The terms "polypeptide", "peptide", or "protein" are used interchangeably herein to designate a linear series of amino acid residues connected one to the other by peptide bonds between the alpha-amino and carboxy groups of adjacent residues. The amino acid residues are preferably in the natural "L" isomeric form. However, residues in the "D" isomeric form can be substituted for any L-amino acid residue, as long as the desired functional property is retained by the polypeptide. In addition, the amino acids, in addition to the 20 "standard" amino acids, include modified and unusual amino acids, which include, but are not limited to those listed in 37 CFR (1.822(b)(4). Furthermore, it should be noted that a dash at the beginning or end of an amino acid residue sequence indicates either a peptide bond to a further sequence of one or more amino acid residues or a covalent bond to a carboxyl or hydroxyl end group.

As used herein, an "antibody" refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist as intact immunoglobulins or as a number of well characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region thereby converting the (Fab')$_2$ dimer into an Fab' monomer. The Fab' monomer is essentially an Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies. Preferred antibodies include, but are not limited to, Fab'$_2$, IgG, IgM, IgA, and single chain antibodies, more preferably single chain Fv (scFv) antibodies in which a variable heavy and a variable light chain are joined together (directly or through a peptide linker) to form a continuous polypeptide.

An "antigen-binding site" or "binding portion" refers to the part of an immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions" or "FRs". Thus, the term "FR" refers to amino acid sequences that are naturally found between and adjacent to hypervariable regions in immunoglobulins. In an antibody molecule, the three hypervariable regions of a light chain and the three hypervariable regions of a heavy chain are disposed relative to each other in three dimensional space to form an antigen binding "surface". This surface mediates recognition and binding of the target antigen. The three hypervariable regions of each of the heavy and light chains are referred to as "complementarity determining regions" or "CDRs" and are characterized, for example by Kabat et al. *Sequences of proteins of immunological interest,* 4th ed. U.S. Dept. Health and Human Services, Public Health Services, Bethesda, Md. (1987).

An S25 antibody refers to an antibody expressed by clone S25 or to an antibody synthesized in other manners, but having the same CDRs and preferably, but not necessarily, the same framework regions as the antibody expressed by clone s25. Similarly, antibodies C25, 1C6, 3D12, B4, 1F3, HuC25, AR1, AR2, AR3, AR4, WR1(V), WR1(T), 3-1, 3-8, 3-10, ING1, CR1, RAZZ, or ING2 refer to antibodies expressed by the corresponding clone(s) and/or to antibodies synthesized in other manners, but having the same CDRs and preferably, but not necessarily, the same framework regions as the referenced antibodies.

As used herein, the terms "immunological binding" and "immunological binding properties" refer to the non-covalent interactions of the type which occur between an immunoglobulin molecule and an antigen for which the immunoglobulin is specific. The strength or affinity of immunological binding interactions can be expressed in terms of the dissociation constant ($K_d$) of the interaction, wherein a smaller Kd represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and on geometric parameters that equally influence the rate in both directions. Thus, both the "on rate constant" ($K_{on}$) and the "off rate constant" ($K_{off}$) can be determined by calculation of the concentrations and the actual rates of association and dissociation. The ratio of $K_{off}/K_{on}$ enables cancellation of all parameters not related to affinity and is thus equal to the dissociation constant $K_d$ (see, generally, Davies et al. (1990) *Ann. Rev. Biochem.*, 59: 439-473).

A "BoNT-neutralizing antibody" refers to an antibody that binds to one or more *Botulinum* neurotoxin(s) (e.g., BoNT/A1, BoNT/A2, etc.) and that by so-binding reduces the toxicity of that BoNT neurotoxin. Thus, for example the term "BoNT/A-neutralizing antibody", as used herein refers to an antibody that specifically binds to a BoNT/A polypeptide (e.g. a BoNT/A1 polypeptide), in certain embodiments, to an $H_C$ domain of a BoNT/A polypeptide and that by so-binding reduces the toxicity of the BoNT/A polypeptide. Reduced toxicity can be measured as an increase in the time that paralysis developed and/or as a lethal dosage (e.g., $LD_{50}$) as described herein. Antibodies derived from BoNT-neutralizing antibodies include, but are not limited to, the antibodies whose sequence is expressly provided herein.

Antibodies derived from BoNT-neutralizing antibodies preferably have a binding affinity of about $1.6\times10^{-8}$ or better and can be derived by screening libraries of single chain Fv fragments displayed on phage or yeast constructed from heavy (VH) and light (VL) chain variable region genes obtained from mammals, including mice and humans, immunized with *botulinum* toxoid, toxin, or BoNT fragments. Antibodies can also be derived by screening phage or yeast display libraries in which a known BoNT-neutralizing variable heavy ($V_H$) chain is expressed in combination with a multiplicity of variable light ($V_L$) chains or conversely a known BoNT-neutralizing variable light chain is expressed in combination with a multiplicity of variable heavy ($V_H$) chains. BoNT-neutralizing antibodies also include those antibodies produced by the introduction of mutations into the variable heavy or variable light complementarity determining regions (CDR1, CDR2 or CDR3) as described herein. Finally BoNT-neutralizing antibodies include those antibodies produced by any combination of these modification methods as applied to the BoNT-neutralizing antibodies described herein and their derivatives.

A neutralizing epitope refers to the epitope specifically bound by a neutralizing antibody.

A single chain Fv ("scFv" or "scFv") polypeptide is a covalently linked $V_H:V_L$ heterodimer which may be expressed from a nucleic acid including $V_H$- and $V_L$-encoding sequences either joined directly or joined by a peptide-encoding linker. Huston, et al. (1988) *Proc. Nat. Acad. Sci. USA*, 85: 5879-5883. A number of structures for converting the naturally aggregated—but chemically separated light and heavy polypeptide chains from an antibody V region into an scFv molecule which will fold into a three dimensional structure substantially similar to the structure of an antigen-binding site. See, e.g. U.S. Pat. Nos. 5,091,513 and 5,132,405 and 4,956,778.

In one class of embodiments, recombinant design methods can be used to develop suitable chemical structures (linkers) for converting two naturally associated—but chemically separate—heavy and light polypeptide chains from an antibody variable region into a scFv molecule which will fold into a three-dimensional structure that is substantially similar to native antibody structure.

Design criteria include determination of the appropriate length to span the distance between the C-terminal of one chain and the N-terminal of the other, wherein the linker is generally formed from small hydrophilic amino acid residues that do not tend to coil or form secondary structures. Such methods have been described in the art. See, e.g., U.S. Pat. Nos. 5,091,513 and 5,132,405 to Huston et al.; and U.S. Pat. No. 4,946,778 to Ladner et al.

In this regard, the first general step of linker design involves identification of plausible sites to be linked. Appropriate linkage sites on each of the $V_H$ and $V_L$ polypeptide domains include those which will result in the minimum loss of residues from the polypeptide domains, and which will necessitate a linker comprising a minimum number of residues consistent with the need for molecule stability. A pair of sites defines a "gap" to be linked. Linkers connecting the C-terminus of one domain to the N-terminus of the next generally comprise hydrophilic amino acids which assume an unstructured configuration in physiological solutions and preferably are free of residues having large side groups which might interfere with proper folding of the $V_H$ and $V_L$ chains. Thus, suitable linkers under the invention generally comprise polypeptide chains of alternating sets of glycine and serine residues, and may include glutamic acid and lysine residues inserted to enhance solubility. One particular linker under the invention has the amino acid sequence [(Gly)$_4$Ser]$_3$ (SEQ ID NO:1). Another particularly preferred linker has the amino acid sequence comprising 2 or 3 repeats of [(Ser)$_4$Gly] (SEQ ID NO:2), such as [(Ser)$_4$Gly]$_3$ (SEQ ID NO:3), and the like. Nucleotide sequences encoding such linker moieties can be readily provided using various oligonucleotide synthesis techniques known in the art (see, e.g., Sambrook, supra.).

The phrase "specifically binds to a protein" or "specifically immunoreactive with", when referring to an antibody refers to a binding reaction which is determinative of the presence of the protein in the presence of a heterogeneous population of proteins and other biologics. Thus, under designated immunoassay conditions, the specified antibodies bind to a particular protein and do not bind in a significant amount to other proteins present in the sample. Specific binding to a protein under such conditions may require an antibody that is selected for its specificity for a particular protein. For example, BoNT/A-neutralizing antibodies can be raised to BoNT/A protein(s) that specifically bind to BoNT/A protein(s), and not to other proteins present in a tissue sample. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988) Antibodies, A Laboratory Manual, Cold Spring Harbor Publications, New York, for a description of immunoassay formats and conditions that can be used to determine specific immunoreactivity.

The term "conservative substitution" is used in reference to proteins or peptides to reflect amino acid substitutions that do not substantially alter the activity (specificity or binding affinity) of the molecule. Typically conservative amino acid substitutions involve substitution one amino acid for another amino acid with similar chemical properties (e.g. charge or hydrophobicity). The following six groups each contain amino acids that are typical conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W).

BRIEF DESCRIPTION OF THE DRAWINGS

FIG. 2 shows deduced protein sequences of heavy (VH) and light (VL) chain variable regions of BoNT B binders. VH domains: A12 (SEQ ID NO:4), 6A12 (SEQ ID NO:5), B1.1 (SEQ ID NO:6), B6 (SEQ ID NO:7), B6.1 (SEQ ID NO:8), B8 (SEQ ID NO:9), B8.1 (SEQ ID NO:10), B11 (SEQ ID NO:11), B11C3 (SEQ ID NO:12), B11E8 (SEQ ID NO:13), B12 (SEQ ID NO:14), B12.1 (SEQ ID NO:15), B12.2 (SEQ ID NO:16), 1B18 (SEQ ID NO:17), 2B18.1 (SEQ ID NO:18), 41319 (SEQ ID NO:19), 1B22 (SEQ ID NO:20). VL domains: A12 (SEQ ID NO:21), 6A12 (SEQ ID NO:22), B1.1 (SEQ ID NO:23), B6 (SEQ ID NO:24), B6.1 (SEQ ID NO:25), B8 (SEQ ID NO:26), B8.1 (SEQ ID NO:27), B11 (SEQ ID NO:28), B11C3 (SEQ ID NO:29), B11E8 (SEQ ID NO:30), B12 (SEQ ID NO:31), B12.1 (SEQ ID NO:32), B12.2 (SEQ ID NO:33), 1B18 (SEQ ID NO:34), 2B18.1 (SEQ ID NO:35), 4B19 (SEQ ID NO:36), 1B22 (SEQ ID NO:37). Dashes indicate conserved residues. Letters indicate mutated residues.

FIG. 3 shows deduced protein sequences of heavy and light chain variable regions of BoNT/E binders. VH domains: 2A10 (SEQ ID NO:38), 3E1 (SEQ ID NO:39), 3E2 (SEQ ID NO:40), 3E3 (SEQ ID NO:41), 3E4 (SEQ ID NO:42), 3E4.1 (SEQ ID NO:43), 3E5 (SEQ ID NO:44), 3E6 (SEQ ID NO:45), 3E6.1 (SEQ ID NO:46), 4E11 (SEQ ID NO:47), 4E13 (SEQ ID NO:48), 4E16 (SEQ ID NO:49), 4E16.1 (SEQ ID NO:50), 4E17 (SEQ ID NO:51), 4E17.1 (SEQ ID NO:52); VL domains: 2A10 (SEQ ID NO:53), 3E1 (SEQ ID NO:54), 3E2 (SEQ ID NO:55), 3E3 (SEQ ID NO:56), 3E4 (SEQ ID NO:57), 3E4.1 (SEQ ID NO:58), 3E5 (SEQ ID NO:59), 3E6 (SEQ ID NO:60), 3E6.1 (SEQ ID NO:61), 4E11 (SEQ ID NO:62), 4E13 (SEQ ID NO:63), 4E16 (SEQ ID NO:64), 4E16.1 (SEQ ID NO:65), 4E17 (SEQ ID NO:66), 4E17.1 (SEQ ID NO:67) Dashes indicate conserved residues. Letters indicate mutated residues.

FIG. 4 shows a phylogenetic tree of published *botulinum* neurotoxin genes. The phylogenetic tree was constructed from the DNA sequences of published Clostridial neurotoxin genes using Vector NTI software.

FIG. 5 shows an analysis of BoNT/A gene sequences. The phylogenetic tree of BoNT/A genes reveals two clusters, A1 and A2.

FIG. 6 shows an analysis of BoNT/B gene sequences. A phylogenetic tree of BoNT/B genes reveals four clusters: BoNT/B1, BoNT/B2, nonproteolytic BoNT/B, and bivalent BoNT/B. Percent differences between clusters range from 3.6 to 7.7%. As with BoNT/A, the greatest differences are seen in the heavy chain.

FIGS. 7A and 7B show a scheme used for affinity maturation of HuC25 (FIG. 7A) and 3D12 (FIG. 7B) scFv using yeast display.

DETAILED DESCRIPTION

Figure 1:
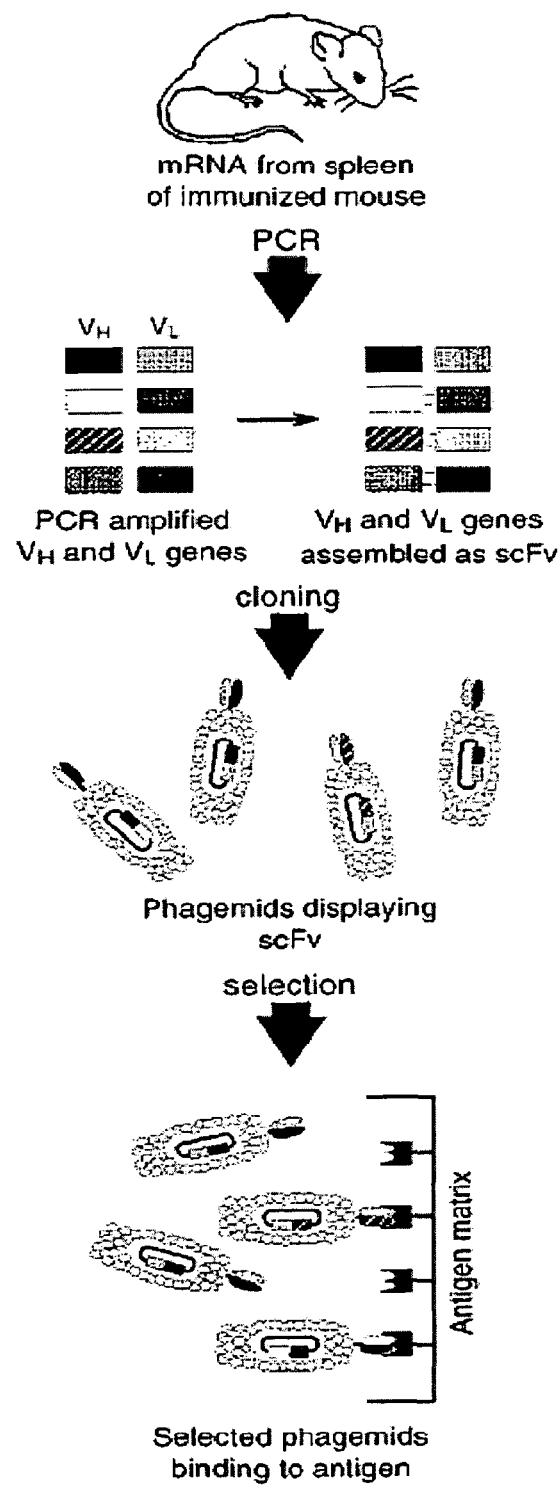
FIG. 1 illustrates one strategy for in vitro antibody production using phage libraries. mRNA is prepared from splenocytes, first-strand cDNA is prepared, and antibody $V_H$ and $V_L$ genes are amplified by PCR. $V_H$ and $V_L$ genes are spliced together randomly using PCR to create a repertoire of scFv genes. The scFv gene repertoire is cloned into a phagemid vector in frame with a gene (gIII) encoding a phagemid minor coat protein (pIII). Each phage in the resulting phage antibody library expresses and scFv-pIII fusion protein on its surface and contains the gene encoding the scFv inside. Phage antibodies binding a specific antigen can be separated from nonbinding phage antibodies by affinity chromatography on immobilized antigen. A single round of selection increases the number of antigen-binding phage antibodies by a factor ranging from 20 to 10,000 depending on the affinity of the antibody. Eluted phage antibodies are used to infect *E. coli*, which then produce more phage antibodies for the next round of selection. Repeated rounds of selection make it possible to isolate antigen-binding phage antibodies that were originally present at frequencies of less than one in a billion.

This invention provides novel antibodies that specifically bind to and neutralize *botulinum* neurotoxin type B and E, and in certain embodiments, other *botulinum* neurotoxin serotypes (e.g., A, C, D, F, etc., see, e.g., FIGS. 4-6). *Botulinum* neurotoxin is produced by the anaerobic bacterium *Clostridium botulinum*. Botulinum neurotoxin poisoning (botulism) arises in a number of contexts including, but not limited to food poisoning (food borne botulism), infected wounds (wound botulism), "infant botulism" from ingestion of spores and production of toxin in the intestine of infants, and as aa chemical/biological warfare agent. Botulism is a paralytic disease that typically begins with cranial nerve involvement and progresses caudally to involve the extremities. In acute cases, botulism can prove fatal.

Botulism neurotoxins (BoNTs) are classified by the Centers for Disease Control (CDC) as one of the six highest-risk threat agents for bioterrorism (the "Category A agents"), due to their extreme potency and lethality, ease of production and transport, and the need for prolonged intensive care (Amon et al. (2001) *JAMA* 285: 1059-1070). Both Iraq and the former Soviet Union produced BoNT for use as weapons (UN Security Council (1995) supra; Bozheyeva (1999) supra.) and the Japanese cult Aum Shinrikyo attempted to use BoNT for bioterrorism (Arnon (2001) supra.). As a result of these threats, specific pharmaceutical agents are needed for prevention and treatment of intoxication.

It has recently been discovered that there are multiple subtypes of various BoNT serotypes. Moreover, we have further discovered that many antibodies that bind, for example the BoNT/A1 subtype will not bind the BoNT/A2 subtype, and so forth.

In certain embodiments this invention pertains to the discovery that that particularly efficient neutralization of a botulism neurotoxin (BoNT) subtype is achieved by the use of neutralizing antibodies that bind two or more subtypes of the particular BoNT serotype with high affinity. In various embodiments this can be accomplished by using two or more different antibodies directed against each of the subtypes, or alternatively, by the use of antibodies that are cross-reactive for different BoNT subtypes, or by bispecific or polyspecific antibodies with specificities for two or more BoNT epitopes, and/or serotypes, and/or subtypes.

It was also a surprising discovery that when one starts combining neutralizing antibodies that the potency of the antibody combination increases dramatically. This increase makes it possible to generate a multi-antibody, and/or multi-specific antibodies of the required potency for therapeutic use. It was also surprising that as one begins combining two and three monoclonal antibodies, the particular BoNT epitope that is recognized becomes less important. Thus, in certain embodiments, this invention contemplates compositions comprising at least two, more preferably at least three high affinity antibodies that bind non-overlapping epitopes on the BoNT.

Thus, in certain embodiments, this invention contemplates compositions comprising two or more, in certain embodiments preferably three or more different antibodies selected from the antibodies described herein (see, e.g., FIGS. 2, and 3) and/or antibodies comprising one or more CDRs from these antibodies, and/or one or more antibodies comprising mutants of these antibodies.

As indicated above, in certain embodiments, the antibodies provided by this invention bind to and neutralize one or more *botulinum* neurotoxin type B, E, and in certain instances Bont/A subtypes. Neutralization, in this context, refers to a measurable decrease in the toxicity of the target neurotoxin. Such a decrease in toxicity can be measured in vitro by a number of methods well known to those of skill in the art. One such assay involves measuring the time to a given percentage (e.g., 50%) twitch tension reduction in a hemidiaphragm preparation. Toxicity can be determined in vivo, e.g. as an $LD_{50}$ in a test animal (e.g. mouse) *botulinum* neurotoxin type A in the presence of one or more putative neutralizing antibodies. The neutralizing antibody or antibody combination can be combined with the *botulinum* neurotoxin prior to administration, or the animal can be administered the antibody prior to, simultaneously with, or after administration of the neurotoxin.

As the antibodies of this invention act to neutralize *botulinum* neurotoxins, they are useful in the treatment of pathologies associated with *botulinum* neurotoxin poisoning. The treatments essentially comprise administering to the poisoned organism (e.g. human or non-human mammal) a quantity of one or more neutralizing antibodies sufficient to neutralize (e.g. mitigate or eliminate) symptoms of BoNT poisoning.

Such treatments are most desired and efficacious in acute cases (e.g. where vital capacity is less than 30-40 percent of predicted and/or paralysis is progressing rapidly and/or hypoxemia with absolute or relative hypercarbia is present. These antibodies can also be used to treat early cases with symptoms milder than indicated (to prevent progression) or even prophylactically (a use the military envisions for soldiers going in harms way). Treatment with the neutralizing antibody can be provided as an adjunct to other therapies (e.g. antibiotic treatment).

The antibodies provided by this invention can also be used for the rapid detection/diagnosis of botulism (type B, E, or A toxin(s)) and thereby supplement and/or replace previous laboratory diagnostics.

In another embodiment this invention provides the epitopes specifically bound by *botulinum* neurotoxin antibodies described herein. These epitopes can be used to isolate, and/or identify and/or screen for other antibodies BoNT neutralizing antibodies as described herein.

I. Potency of *Botulinum* Neurotoxin (BoNT)-neutralizing Antibodies.

Without being bound to a particular theory, it is believed that the current antitoxins used to treat botulism (horse and human) have a potency of about 5000 mouse LD50s/mg (human) and 55,000 mouse LD50s mg (horse).

Based on our calculations, we believe a commercially desirable antitoxin will have a have a potency greater than about 10,000 to 100,000 LD50s/mg. Combinations of the antibodies described herein (e.g., two or three antibodies) can meet this potency. Thus, in certain embodiments, this invention provides antibodies and/or antibody combinations that neutralize at least about 10,000 mouse LD50s/mg of antibody, preferably at least about 15,000 mouse LD50s/mg of antibody, more preferably at least about 20,000 mouse LD50s/mg of antibody, and most preferably at least about 25,000 mouse LD50s/mg of antibody.

II. *Botulinum* Neurotoxin (BoNT)-neutralizing Antibodies.

In certain preferred embodiments, BoNT neutralizing antibodies are selected that bind to or more BoNT subtypes. A number of subtypes are known for each BoNT serotype. Thus, for example, BoNT/A subtypes include, but are not limited to, BoNT/A1, BoNT/A2, BoNT/A3, and the like (see, e.g., FIG. 4). It is also noted, for example, that the BoNT/A1 subtype includes, but is not limited to 62A, NCTC 2916, ATCC 3502, and Hall hyper (Hall Allergan) and are identical (99.9-100% identity at the amino acid level.) and have been classified as subtype A1 (FIG. 5A). The BoNT/A2 sequences (Kyoto-F and FRI-A2H) (Willems, et al. (1993) *Res. Microbiol.* 144:547-556) are 100% identical at the amino acid level. Another BoNT/A subtype, (that we are calling A3) is produced by a strain called Loch Maree that killed a number of people in an outbreak in Scotland.

Figure 4:
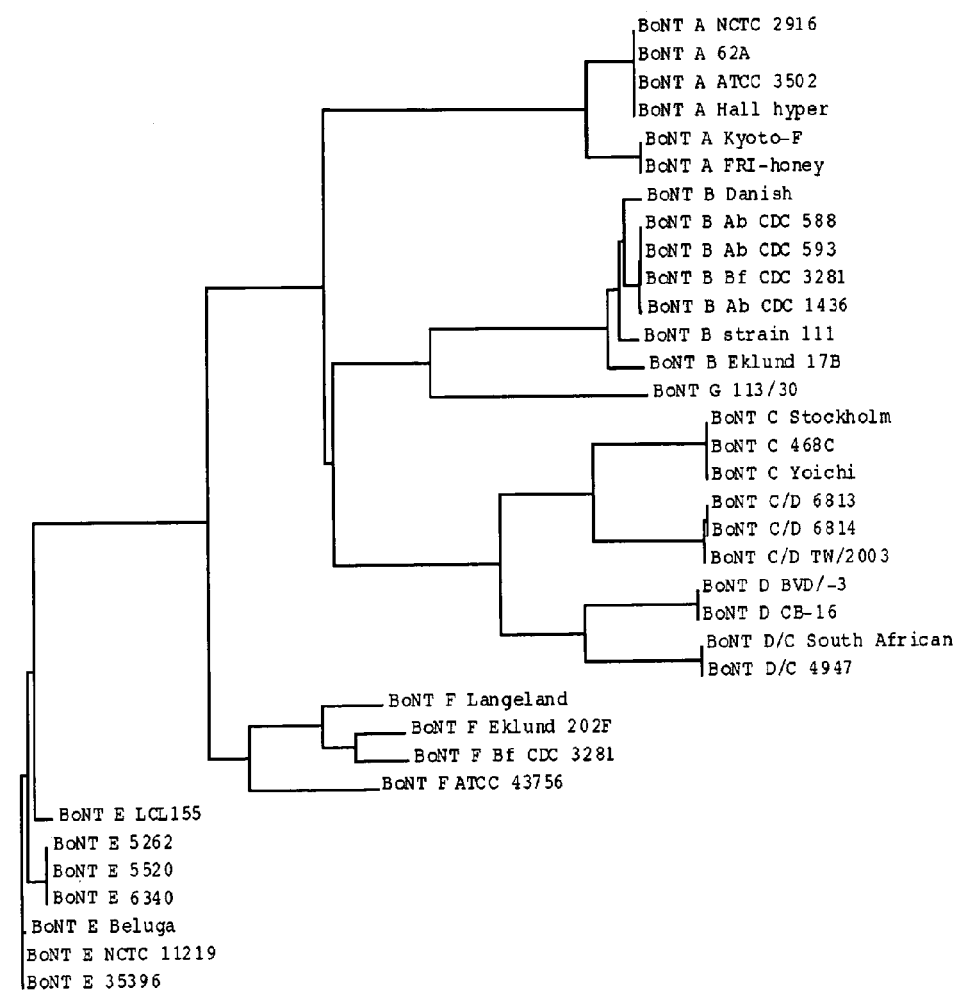

Similarly, as shown in FIG. 4, a number of subtypes are also known for serotypes B, C, E, and F. Using, the methods described herein, it was discovered that high-affinity antibodies that are cross-reactive with two or more subtypes within a serotype can also be produced (e.g., selected/engineered). Moreover, without being bound to a particular theory, it appears that these cross-reactive antibodies can substantially more efficient in neutralizing *Botulinum* neurotoxin, particularly when used in combination one or more different neutralizing antibodies.

The sequences of the variable heavy (VH) and variable light (VL) domains for a number of prototypical BoNT/B and BoNT/E antibodies are illustrated in Tables 1-4, and in FIGS. 2-3.

These antibodies can be used individually, and/or in combination with each other, and/or in combination with other known anti-BoNT antibodies (see, e.g., copending application Ser. No. 11/342,27, filed on Jan. 26, 2006, Ser. No. 09/144,886, filed in Aug. 31, 1998, Ser. No. 10/632,706, filed on Aug. 1, 2003, and PCT application Nos: PCT/US2006/003070 and PCT/US03/24371, which are incorporated herein by reference for all purposes) to form bispecific or polyspecific antibodies

TABLE 1

Deduced protein sequences of heavy chain variable regions of BoNT/E binders.

| VH Clone/ Gene Family | Framework 1 | CDR1 | Framework 2 | CDR2 | Framework 3 | CDR3 | Framework 4 |
|---|---|---|---|---|---|---|---|
| 2A10 VH1 | QVQLQQSGAEVKKPGSSVKVSCKASGGTFT (SEQ ID NO: 68) | RYTIT (SEQ ID NO: 69) | WVRQAPGQGLEWMG (SEQ ID NO: 70) | GIIPIFDKANYAQKFQS (SEQ ID NO: 71) | RVTFTADASTSTAYMELGSLRPEDTAVYYCAA (SEQ ID NO: 72) | YSRGYVHFDY (SEQ ID NO: 73) | WGPGTLVTVSS (SEQ ID NO: 74) |
| 3E1 VH1 | QVQLVESGAEVKKPGSSVKVSCKASGGTFS (SEQ ID NO: 75) | NSGFT (SEQ ID NO: 76) | WVRQVPGQGLEWMG (SEQ ID NO: 77) | GIIPMFGPANYAQKFQG (SEQ ID NO: 78) | RVTITADESTRMVYMELRSLRSEDTAVYYCAR (SEQ ID NO: 79) | DQGEYTVGMLLYYAMDV (SEQ ID NO: 80) | WGEGTTVTVSS (SEQ ID NO: 81) |
| 3E2 VH1 | QVQLQESGAEVKKPGSSVKVSCKASGGDLN (SEQ ID NO: 82) | KYAIT (SEQ ID NO: 83) | WLRQAPGQGFEWMG (SEQ ID NO: 84) | GITPIFATTNYAQKFQG (SEQ ID NO: 85) | RVMITADEVTSTVYMDLSSLGSEDTAIYFCAK (SEQ ID NO: 86) | SPRGGIVGTFDT (SEQ ID NO: 87) | WGQGTMVTVSS (SEQ ID NO: 88) |
| 3E3 VH3 | QVQLVESGGGLVKPGESLRLSCAASGFTFS (SEQ ID NO: 89) | NYNMN (SEQ ID NO: 90) | WVRQAPGKGLEWVS (SEQ ID NO: 91) | SISDGGSYRYYAYSVKG (SEQ ID NO: 92) | RFTISRDNTKNSLYLQMNSLRAEDTALYYCAR (SEQ ID NO: 93) | DEMVHGILVYYGMDV (SEQ ID NO: 94) | WGQGTTVTVSS (SEQ ID NO: 95) |
| 3E4 VH3 | QVQLQESGGGLVQPGGSLRLSCGASGFTFS (SEQ ID NO: 96) | SDAMS (SEQ ID NO: 97) | WVRQAPGKGLEWVA (SEQ ID NO: 98) | AILPSGEATYYADSVKG (SEQ ID NO: 99) | RFTISRHSSKNTLYLQMNSLRADDTAVYYCAR (SEQ ID NO: 100) | DSYHSRLAAFDI (SEQ ID NO: 101) | WGQGTMVTVSS (SEQ ID NO: 102) |
| 3E4.1 VH3 | QVQLQESGGGLVQPGGSLRLSCGASGFTFS (SEQ ID NO: 103) | SDAMS (SEQ ID NO: 104) | WVRQAPGKGLEWVA (SEQ ID NO: 105) | AILPSGEATYYADSVKG (SEQ ID NO: 106) | RFTISRHSSKNTLYLQMNSLRADDTAVYYCAR (SEQ ID NO: 107) | DSYHSRLAAFDI (SEQ ID NO: 108) | WGQGTMVTVSS (SEQ ID NO: 109) |
| 3E5 VH3 | QVQLVQSGGGVVQPGRPLRLSCAASTFNFR (SEQ ID NO: 110) | DFYMS (SEQ ID NO: 111) | WIRQAPGKGLEWVS (SEQ ID NO: 112) | YIGSSGSALQYADSVKG (SEQ ID NO: 113) | RFTISRDNDKNVLYLQMTSLRAEDTAVYYCAR (SEQ ID NO: 114) | VASRYHDVLTDGFDI (SEQ ID NO: 115) | WGQGTMVTVSS (SEQ ID NO: 116) |
| 3E6 VH3 | QVQLVQSGGGVVQPGKSLRLSCAASGFTFS (SEQ ID NO: 117) | SYAMH (SEQ ID NO: 118) | WVRQAPGKGLEWVA (SEQ ID NO: 119) | VISYDGNKKYYADSVKG (SEQ ID NO: 120) | RFTISRDNSKNTLYLQMNSLRAEDAAVFYCAR (SEQ ID NO: 121) | ARLCTSTSCYWTFDP (SEQ ID NO: 122) | WGQGTLVTVSS (SEQ ID NO: 123) |
| 3E6.1 VH3 | QVQLVQSGGGVVQPGKSLRLSCAASGFTFS (SEQ ID NO: 124) | SYAMH (SEQ ID NO: 125) | WVRQAPGKGLEWVA (SEQ ID NO: 126) | VISYDGNKKYYADSVKG (SEQ ID NO: 127) | RFTISRDNSKNTLYLQMNSLRAEDAAVFYCAR (SEQ ID NO: 128) | ARLCTSTSCYWTFDP (SEQ ID NO: 129) | WGQGTLVTVSS (SEQ ID NO: 130) |

TABLE 1-continued

Deduced protein sequences of heavy chain variable regions of BoNT/E binders.

| VH Clone/ Gene Family | Framework 1 | CDR1 | Framework 2 | CDR2 | Framework 3 | CDR3 | Framework 4 |
|---|---|---|---|---|---|---|---|
| 4E11 VH3 | QVQLVQS GGGLVQP GGSLRLSC AASGFRFS (SEQ ID NO: 131) | GYSFN (SEQ ID NO: 132) | WVRQAPG KGLEWVA (SEQ ID NO: 133) | YMSSGGSI KNYADSV KG (SEQ ID NO: 134) | RFTISRDN AKNSLYL QVNSLRD EDTALYY CAR (SEQ ID NO: 135) | GPPGRP NDAFDI (SEQ ID NO: 136) | WGQGTM VTVSS (SEQ ID NO: 137) |
| 4E13 VH3 | EVQLVQS GGGLVQP GGSLRLSC AASGFTFS (SEQ ID NO: 138) | SYAMT (SEQ ID NO: 139) | WVRQAPG KGLEWVS (SEQ ID NO: 140) | SISVSGDS TYYADSV KG (SEQ ID NO: 141) | RFTISRDN SKNTVSL QMNSLRA EDTALYY CAK (SEQ ID NO: 142) | GLSKA DLFGM DV (SEQ ID NO: 143) | WGQGTM VTVSS (SEQ ID NO: 144) |
| 4E16 VH4 | QVQLQES GPGLVKPS ETLSLTCS VSGVSIS (SEQ ID NO: 151) | DYYWS (SEQ ID NO: 145) | WIRQPPG KGLEWIG (SEQ ID NO: 146) | YIYYSGST NYNPSLKS (SEQ ID NO: 147) | RVTISVDT SKNQFSLN LSSVTAA DTAVYYC AR (SEQ ID NO: 148) | HTSGW SGGAF DI (SEQ ID NO: 149) | WGQGTM VTVSS (SEQ ID NO: 150) |
| 4E16.1 VH4 | QVQLQES GPGLVKPS ETLSLTCS VSGVSIS (SEQ ID NO: 151) | DYYWS (SEQ ID NO: 152) | WIRQPPG KGLEWIG (SEQ ID NO: 153) | YIYYSGST NYNPSLKS (SEQ ID NO: 154) | RVTISVDT SKNQFSLN LSSVTAA DTAVYYC AR (SEQ ID NO: 155) | HTSGW SGGAF DI (SEQ ID NO: 156) | WGQGTM VTVSS (SEQ ID NO: 157) |
| 4E17 VH3 | EVQLVQS GGNLVQP GGSLRLSC AATGPIGS (SEQ ID NO: 158) | HWMT (SEQ ID NO: 159) | WVRQAPG QGLEWVA (SEQ ID NO: 160) | NINLDGTE KFYVDSV KG (SEQ ID NO: 161) | RFTVSRD NRKSSVFL QMNNLRV DDTAVYY CAR (SEQ ID NO: 162) | LQWGG YNGWL SP (SEQ ID NO: 163) | WGQGTL VTVSS (SEQ ID NO: 164) |
| 4E17.1 | EVQLVQS GGNLVQP GGSLRLSC AATGPIGS (SEQ ID NO: 165) | HWMT (SEQ ID NO: 166) | WVRQAPG QGLEWVA (SEQ ID NO: 167) | NINLDGTE KFYVDSV KG (SEQ ID NO: 168) | RFTVSRD NRKSSVFL QMNNLRV DDTAVYY CAR (SEQ ID NO: 169) | LQWGG YNGWL SP (SEQ ID NO: 170) | WGQGTL VTVSS (SEQ ID NO: 171) |

TABLE 2

Deduced protein sequences of light chain variable regions (VL) of BoNT/E binders.

| VL Clone/ Gene Family | Framework 1 | CDR1 | Framework 2 | CDR2 | Framework 3 | CDR3 | Framework 4 |
|---|---|---|---|---|---|---|---|
| E1 VK1 (ZA1D VK1) | DIVMTQSP SFLSASVG DRVTITC (SEQ ID NO: 172) | WASQG ISSYLA (SEQ ID NO: 173) | WYQQKPG KAPKLLIY (SEQ ID NO: 174) | AASTLQ S (SEQ ID NO: 175) | GVPSRFSGS GSGTEFTLTI SSLQPEDFA TYYC (SEQ ID NO: 176) | QQLNSY PLT (SEQ ID NO: 177) | FGGGTK VDIKR (SEQ ID NO: 178) |
| 3E1 VK1 | EIVLTQSP DSLSASVG DRVTITC (SEQ ID NO: 179) | RASQGI SGYLA (SEQ ID NO: 180) | WYQHKA GKAPKLLI Y (SEQ ID NO: 181) | AASSLQ S (SEQ ID NO: 182) | GVPSRFSGS GYGTEFTLTI SSLQPDDFA TYYC (SEQ ID NO: 183) | QQYNSY PFT (SEQ ID NO: 184) | FGGGTK VEIKR (SEQ ID NO: 185) |

TABLE 2-continued

Deduced protein sequences of light chain variable regions (VL) of BoNT/E binders.

| VL Clone/ Gene Family | Framework 1 | CDR1 | Framework 2 | CDR2 | Framework 3 | CDR3 | Framework 4 |
|---|---|---|---|---|---|---|---|
| 3E2 VK1 | EIVLTQSP SFLSAFVG DRVTITC (SEQ ID NO: 186) | RTSQSI NNYLN (SEQ ID NO: 187) | WYQQKA GKAPKLLI Y (SEQ ID NO: 188) | AASTLH T (SEQ ID NO: 189) | GVPSRFSGS GSGTEFTLTI SSLQPEDFA TYYC (SEQ ID NO: 190) | QQSYSIP LT (SEQ ID NO: 191) | FGGGTK VEIKR (SEQ ID NO: 192) |
| 3E3 VK3 | DIVMTQSP DSLSASVG DSVTITC (SEQ ID NO: 193) | RASQSF SSSYLA (SEQ ID NO: 194) | WYQQKPG QAPRLLIY (SEQ ID NO: 195) | AASSRA A (SEQ ID NO: 196) | GVPTGSVAD GSGTGFTLTI SGLQPEDFA AYYC (SEQ ID NO: 197) | QQSYST PYT (SEQ ID NO: 198) | FGGGTK VEIKR (SEQ ID NO: 199) |
| 3E4 VK1 | DIVMTQSP SFLSAFVG DRVTITC (SEQ ID NO: 200) | RASQSI SNWLA (SEQ ID NO: 201) | WYQQKPG KAPKVLIY (SEQ ID NO: 202) | KASSLE N (SEQ ID NO: 203) | GVPSRFSGS GSGTDFTLTI TSLQPDDFA TYYC (SEQ ID NO: 204) | QQYNA YPLT (SEQ ID NO: 205) | FGGGTK VEIKR (SEQ ID NO: 206) |
| 3E4.1 VK1 | EIVLTQSP STLSASVG DRVAITC (SEQ ID NO: 207) | RASQRI GSWLA (SEQ ID NO: 208) | WYQQKPG KAPNPLIY (SEQ ID NO: 209) | KAFSLE S (SEQ ID NO: 210) | GVPSRFSGS RSGTEFTLTI SSLQPDDFA TYFC (SEQ ID NO: 211) | QQYDSY PYT (SEQ ID NO: 212) | FGQGTKL EIKR (SEQ ID NO: 213) |
| EK5 VK1 | DVVMTQS PSSLSASIG DRVTFTC (SEQ ID NO: 214) | QASQDI SNRLN (SEQ ID NO: 215) | WYQQKPG KVPKLLIS (SEQ ID NO: 216) | DASNLE T (SEQ ID NO: 217) | GVPSRFSGS GSGTDFTFTI SSLQPEDIAT YYC (SEQ ID NO: 218) | QQYDPL LT (SEQ ID NO: 219) | FGGGTK VEIKR (SEQ ID NO: 220) |
| 3E6 VK1 | DIQMTQSP SSVSASVG DTVTISC (SEQ ID NO: 221) | RASQGI SSWLA (SEQ ID NO: 222) | WYQQKSG QAPTLLIY (SEQ ID NO: 223) | AASSLQ S (SEQ ID NO: 224) | GVPSRFSGS GSGTDFTLII SSLQPEDFA TYYC (SEQ ID NO: 225) | QQAYRT PIT (SEQ ID NO: 226) | FGGGTK VEIKR (SEQ ID NO: 227) |
| 3E6.1 VK1 | DIQMTQSP SSVSASVG DRVSITC (SEQ ID NO: 228) | QASQDI SNYLN (SEQ ID NO: 229) | WYQQKPG KAPKLLIY (SEQ ID NO: 230) | AASSLQ S (SEQ ID NO: 231) | GVPSRFSGS GSGTDFTLTI SSLQPEDFA TYYC (SEQ ID NO: 232) | QQSYNT PPT (SEQ ID NO: 233) | FGQGTKL EIKR (SEQ ID NO: 234) |
| 4E11 VL3 | ASVLTQD PAVSVAL GQTVRITC (SEQ ID NO: 235) | QGDSL RSYYA S (SEQ ID NO: 236) | WYQQKPG QAPVLVIY (SEQ ID NO: 237) | GKSNRP S (SEQ ID NO: 238) | GIPDRFSGSS SGNTASLTTI GAQAEDEA DYYC (SEQ ID NO: 239) | NSRDST GNQL (SEQ ID NO: 240) | FGGGTK VTVLG (SEQ ID NO: 241) |
| 4E13 VL3 | AELTQDP AVSVALG QTVRITC (SEQ ID NO: 242) | QGDSL RSYYA S (SEQ ID NO: 243) | WYQQKPG QAPVLVIY (SEQ ID NO: 244) | GENSRP S (SEQ ID NO: 245) | GIPDRFSGSS SGNTASLTI AGAQAEDE ADYYC (SEQ ID NO: 246) | NSPDSS GIHLV (SEQ ID NO: 247) | FGGGTK VTVLG (SEQ ID NO: 248) |
| 4E16 VK4 | EIVLTQSP DSLSVSL GERATINC (SEQ ID NO: 249) | KSSQSV LYSSN NKNYL A (SEQ ID NO: 250) | WYQQKPG QPPKLLFY (SEQ ID NO: 251) | WASTRE S (SEQ ID NO: 252) | GVPDRFSGS GSGTDFTLTI SSLQAEDVA VYYC (SEQ ID NO: 253) | HQYYSS PLY (SEQ ID NO: 254) | FGGGTKL EIKR (SEQ ID NO: 255) |
| 4E16.1 VK4 | EIVLTQSP NSLAVSL GERATIRC (SEQ ID NO: 256) | KSSQSV LYSGN NKNYI A (SEQ ID NO: 257) | WYQQKPG QPPKLLIY (SEQ ID NO: 258) | WASTRE S (SEQ ID NO: 259) | GVPDRFSGS GSETDFTLTI SSLRAEDVA LYYC (SEQ ID NO: 260) | QQYYS RWT (SEQ ID NO: 261) | FGQGTKL EIKR (SEQ ID NO: 262) |

TABLE 2-continued

Deduced protein sequences of light chain variable regions (VL) of BoNT/E binders.

| VL Clone/ Gene Family | Framework 1 | CDR1 | Framework

TABLE 3-continued

Deduced protein sequences of heavy chain variable regions of BoNT/B binders.

| VH Clone/ Gene Family | Framework 1 | CDR1 | Framework 2 | CDR2 | Framework 3 | CDR3 | Framework 4 |
|---|---|---|---|---|---|---|---|
| B11 VH3 | QVQLLQS AGGVVQP GRSLRLSC AASGFIFR (SEQ ID NO: 326) | TYGMH (SEQ ID NO: 327) | WVRQAP GKGLEW VA (SEQ ID NO: 328) | FVSSDG NNKFY SDSVK G (SEQ ID NO: 329) | RFTIPRDNA KNTLYLQM NSLETEDTA VYYCAK (SEQ ID NO: 330) | DRYPID CSGGSC FSYGMD V (SEQ ID NO: 331) | WGQGTT VTVSS (SEQ ID NO: 332) |
| B11C3 VH3 | EVQLVES GGGVVQP GRSLRLSC ATSGFILR (SEQ ID NO: 333) | TYGMH (SEQ ID NO: 334) | WVRQAP GKGLEW VA (SEQ ID NO: 335) | FVSSDG NNKFY SDSVK G (SEQ ID NO: 336) | RFTIPRDNA KNTLYLQM NSLETEDTA VYYCAK (SEQ ID NO: 337) | DRYPID CSGGSC FSYGMD V (SEQ ID NO: 338) | WGQGTL VTVSS (SEQ ID NO: 339) |
| B11E8 VH3 | EVQLVQS GGGVVQP GRSLRLSC AASGFIFR (SEQ ID NO: 340) | TYGMH (SEQ ID NO: 341) | WVRQAP GKGLEW VA (SEQ ID NO: 342) | FVSSDG NNKFY SDSVK G (SEQ ID NO: 343) | RFTISRDNA KNTLYLQM NSLETEDTA MYYCAK (SEQ ID NO: 344) | DRYPID CSGGSC FSYGMD V (SEQ ID NO: 345) | WGQGTT VTVSS (SEQ ID NO: 346) |
| B12 VH3 | QVNLRES GGGVVQP GRSLRLSC AASGFTFS (SEQ ID NO: 347) | SYALH (SEQ ID NO: 348) | WVRQTP GKGLEW VA (SEQ ID NO: 349) | LISYDG SNKYY ADSVK G (SEQ ID NO: 350) | RFTISRDNSK NMLYLQMN SLRAEDTAV YYCAK (SEQ ID NO: 351) | DRSHYG DYVGYL DY (SEQ ID NO: 352) | WGQGTL VTVSS (SEQ ID NO: 353) |
| B12.1 VH3 | QVNLRES GGGVVQP GRSLRLSC AASGFTFS (SEQ ID NO: 354) | SYALH (SEQ ID NO: 355) | WVRQTP GKGLEW VA (SEQ ID NO: 356) | LISYDG SNKYY ADSVK G (SEQ ID NO: 357) | RFTISRDNSK NMLYLQMN SLRAEDTAV YYCAK (SEQ ID NO: 358) | DRSHYG DYVGYL DY (SEQ ID NO: 359) | WGQGTL VTVSS (SEQ ID NO: 360) |
| B12.2 VH3 | QVNLRES GGGVVQP GRSLRLSC AASGFTFS (SEQ ID NO: 361) | SYALH (SEQ ID NO: 362) | WVRQTP GKGLEW VA (SEQ ID NO: 363) | LISYDG SNKYY ADSVK G (SEQ ID NO: 364) | RFTISRDNSK NMLYLQMN SLRAEDTAV YYCAK (SEQ ID NO: 365) | DRSHYG DYVGYL DY (SEQ ID NO: 366) | WGQGTL VTVSS (SEQ ID NO: 367) |
| 1B18 VH3 | EVQLVQS GGGLVQP GGSRRLSC AASGFYF N (SEQ ID NO: 368) | AYWM T (SEQ ID NO: 369) | WVRQAP GKGLEW VA (SEQ ID NO: 370) | NINLDG TEIYYL DSVKG (SEQ ID NO: 371) | RFTVSRDNV KNSVFLQMS SLRVEDTAV YFCAR (SEQ ID NO: 372) | LEWGGR NGWVSP (SEQ ID NO: 373) | WGQGTL VTVSS (SEQ ID NO: 374) |
| 2B18.1 VH3 | QVQLVQS GGGLVQP GGSRRLSC AASGFYF N (SEQ ID NO: 375) | AYWM T (SEQ ID NO: 376) | WVRQAP GKGLEW VA (SEQ ID NO: 377) | NINLDG TEIYYL DSVKG (SEQ ID NO: 378) | RFTVSRDNV KNSVFLQMS SLRVEDTAV YFCAR (SEQ ID NO: 379) | LEWGGR NGWVSP (SEQ ID NO: 380) | WGQGTL VTVSS (SEQ ID NO: 381) |
| 4B19 VH1 | QVQLVQS GAEVKKP GASVNVS CKASGYT FT (SEQ ID NO: 382) | GYYIY (SEQ ID NO: 383) | WVRQAP GQGLEW MG (SEQ ID NO: 384) | WINPNS GVTKY AQKFQ G (SEQ ID NO: 385) | RVTMTIDTS TNTAYMEL NRLRADDT AVYYCAR (SEQ ID NO: 386) | EWTQL WSPYDY (SEQ ID NO: 387) | WGQGTT VTVSS (SEQ ID NO: 388) |
| 1B22 VH4 | QVQLQES GSRLVKPS QTLSLTCG VSGGSISS S (SEQ ID NO: 389) | SYSWS (SEQ ID NO: 390) | WIRQTPG KGLEWIG (SEQ ID NO: 391) | YIYHSG STYYN PSLKS (SEQ ID NO: 392) | RVTMSVDK SRNQFSLNM SSVTAADTA VYYCAR (SEQ ID NO: 393) | TAFYYE NTGPIRC YLDF (SEQ ID NO: 394) | WGQGTL VTVSS (SEQ ID NO: 395) |

TABLE 4

Deduced protein sequences of light chain variable regions (VL) of BoNT/B binders.

| VL/Clone/Gene Family | Framework 1 | CDR1 | Framework 2 | CDR2 | Framework 3 | CDR3 | Framework 4 |
|---|---|---|---|---|---|---|---|
| A12 VK1 | DIQMTQSPSSLSASVGDRVTITC (SEQ ID NO: 396) | RASQRISNYLN (SEQ ID NO: 397) | WYQQKPGKAPKLLIY (SEQ ID NO: 398) | AASSLQS (SEQ ID NO: 399) | EVPSRFSGSGSGTDFTLTISSLQPEDFATYYC (SEQ ID NO: 400) | QQSYRPPLT (SEQ ID NO: 401) | FGGGTKVEIKR (SEQ ID NO: 402) |
| 6A12 VK2 | DIQMTQSPSSVSASVGNRVTITC (SEQ ID NO: 403) | RASQGISSWLA (SEQ ID NO: 404) | WYQQKPGKAPKLLIY (SEQ ID NO: 405) | AASSLQS (SEQ ID NO: 406) | GVPSRFSGSGSGTDFTLTISSLQPEDFATYYC (SEQ ID NO: 407) | QKANSFPLT (SEQ ID NO: 408) | FGGGTKVEIKR (SEQ ID NO: 409) |
| B1.1 VK1 | DVVMTQSPSSLSASVGDRVTITC (SEQ ID NO: 410) | RASQSISSYLN (SEQ ID NO: 411) | WYQQKPGKAPKLLIY (SEQ ID NO: 412) | AASSLQS (SEQ ID NO: 413) | GVPSRFSGSGSGTDFTLTISSLQPEDFATYYC (SEQ ID NO: 414) | QQSYSTPLT (SEQ ID NO: 415) | FGQGTKLEIKR (SEQ ID NO: 416) |
| B6 VK1 | DVVMTQSPSSLSASVGDRITITC (SEQ ID NO: 417) | QAGQDISNFLN (SEQ ID NO: 418) | WYQQKPGKAPKLLIR (SEQ ID NO: 419) | DASNLET (SEQ ID NO: 420) | GVPSRFSGGGSGTHFTFTISSLHPEDIATTFC (SEQ ID NO: 421) | QQYDNLPYT (SEQ ID NO: 422) | FGQGTKLEIKR (SEQ ID NO: 423) |
| B6.1 VK1 | DIQMTQSPSSLSASVGDRVTITC (SEQ ID NO: 424) | RASQSISSYLN (SEQ ID NO: 425) | WYQQEPGKAPKLLIY (SEQ ID NO: 426) | SASSLQS (SEQ ID NO: 427) | GVPSRFSGSGSGTDFTLTISSLQPEDFATYYC (SEQ ID NO: 428) | QQSYSTPPYT (SEQ ID NO: 429) | FGQGTKLEIKR (SEQ ID NO: 430) |
| B8 VK1 | DIQMTQSPSSLSASVGDRVTITC (SEQ ID NO: 431) | RASQRISNYLN (SEQ ID NO: 432) | WYQQKPGKAPKLLIY (SEQ ID NO: 433) | AASSLQS (SEQ ID NO: 434) | EVPSRFSGSGSGTDFTLTISSLQPEDFATYYC (SEQ ID NO: 435) | QQSYRPPYT (SEQ ID NO: 436) | FGGGTKVDIKR (SEQ ID NO: 437) |
| B8.1 VK1 | DIQMTQSPSSLSASVGDRVTITC (SEQ ID NO: 438) | RASQRISNYLN (SEQ ID NO: 439) | WYQQKPGKAPKLLIY (SEQ ID NO: 440) | AASSLQS (SEQ ID NO: 441) | EVPSRFSGSGYGTDFTLTISSLQPEDFATYYC (SEQ ID NO: 442) | QQSYRPPLT (SEQ ID NO: 443) | FGGGTKVDIKR (SEQ ID NO: 444) |
| B11 VK1 | DIVMTQSPSTLSASVGDRVTVTC (SEQ ID NO: 445) | RASQSINSWLA (SEQ ID NO: 446) | WYQQKPGKAPKLLIY (SEQ ID NO: 447) | EASSLES (SEQ ID NO: 448) | GVPSRFSGSGSGTEFTLTISSLQPDDFATYYC (SEQ ID NO: 449) | QQYDSYWLT (SEQ ID NO: 450) | FGGGTKVEIKR (SEQ ID NO: 451) |
| B11C3 VK1 | DIQMTQSPSSVSASVGDRVTITC (SEQ ID NO: 452) | RASQGVSRWLA (SEQ ID NO: 453) | WYQQRPEKAPKLLIY (SEQ ID NO: 454) | GASSLQS (SEQ ID NO: 455) | GVPSRFSGSGSGTDFTLTISSLQPEDFATYYC (SEQ ID NO: 456) | QQYDSFPYT (SEQ ID NO: 457) | FGGGTKVEIKR (SEQ ID NO: 458) |
| B11E8 VK1 | EIVLTQSPATLSVSPGERATLSC (SEQ ID NO: 459) | RASQSVSKFLA (SEQ ID NO: 460) | WYQQKRGQAPRLLIY (SEQ ID NO: 461) | GASTRAT (SEQ ID NO: 462) | GIPARFSGSGSGTEFALTISSLQSEDFADYYC (SEQ ID NO: 463) | QQYDNWPIT (SEQ ID NO: 464) | FGQGTRLEIKR (SEQ ID NO: 465) |
| B12 VK1 | DIVMTQSPSTLSASVGDRVTITC (SEQ ID NO: 466) | RASQGISSWLA (SEQ ID NO: 467) | WYQQKPGKAPKLLIY (SEQ ID NO: 468) | KASSLES (SEQ ID NO: 469) | GVPSRFSGSGSGTEFTLTISSLQPEDFATYYC (SEQ ID NO: 470) | LQHNSYPRA (SEQ ID NO: 471) | FGQGTKLEIKR (SEQ ID NO: 472) |
| B12.1 VL3 | AYVLTQPPSVSVAPGKTAAITC (SEQ ID NO: 473) | EGNNVGNKNVH (SEQ ID NO: 474) | WYQQRPGQAPVLVVH (SEQ ID NO: 475) | DDSDRPS (SEQ ID NO: 476) | GIPERFSGSNSGNTATLTINRVEAGDEADYYC (SEQ ID NO: 477) | QVWDSSSAQWV (SEQ ID NO: 478) | FGGGTKLTVLG (SEQ ID NO: 479) |

TABLE 4-continued

Deduced protein sequences of light chain variable regions (VL) of BoNT/B binders.

| VL/Clone/Gene Family | Framework 1 | CDR1 | Framework 2 | CDR2 | Framework 3 | CDR3 | Framework 4 |
|---|---|---|---|---|---|---|---|
| B12.2 VL1 | ESVLTQPP LVSAAPG QKVTISC (SEQ ID NO: 480) | SGSSSN IGNNY VS (SEQ ID NO: 481) | WYQQLP GTAPKLL IY (SEQ ID NO: 482) | ENSKRS S (SEQ ID NO: 483) | GIPDRFSGSK SGTSATLGIT GLQTGDEA DYYC (SEQ ID NO: 484) | GTWDSS LSAVV (SEQ ID NO: 485) | FGGGTKL TVLG (SEQ ID NO: 486) |
| 1B18 VK1 | DVVMTQS PSSVSASV GDRVTITC (SEQ ID NO: 487) | RASQSI SSYLN (SEQ ID NO: 488) | WYQQRP GKAPKLL IF (SEQ ID NO: 489) | AASSL QS (SEQ ID NO: 490) | AVPSRFSGS GSGTDFTLTI SSLQPEDFA TYYC (SEQ ID NO: 491) | QQSYST PPT (SEQ ID NO: 492) | FGQGTK VEIKR (SEQ ID NO: 493) |
| 2B18.1 VK1 | DIVMTQSP SSLSASVG DRVSISC (SEQ ID NO: 494) | RASQSI SSYLN (SEQ ID NO: 495) | WYQQKP GKAPKLL IY (SEQ ID NO: 496) | KTSSLE S (SEQ ID NO: 497) | GVPSRFSGR GSGTDFTLTI SSLQPEDFA TYYC (SEQ ID NO: 498) | QQSYST PLT (SEQ ID NO: 499) | FGGGTK VEIKR (SEQ ID NO: 500) |
| 1B22 VK1 | DIQMTQSP STLSASIG DRVTISC (SEQ ID NO: 501) | RASQSI QSWLA (SEQ ID NO: 502) | WYQQRP GEAPKLL IY (SEQ ID NO: 503) | SASTLQ T (SEQ ID NO: 504) | GVPSRFSGS GSGTDFTLTI SSLQPEDFA TYYC (SEQ ID NO: 505) | QQYNSY PLT (SEQ ID NO: 506) | FGQGTKL EIKR (SEQ ID NO: 507) |
| 4B19 VK1 | DIVLTQSP STLSASVG DRVTISC (SEQ ID NO: 508) | RASRSI GWYLN (SEQ ID NO: 509) | WYQQRP GKAPKLL IY (SEQ ID NO: 510) | AASSL HN (SEQ ID NO: 511) | GVPSRFSGS GSGTEFTLTI SSLQPDDFA TYYC (SEQ ID NO: 512) | QQAFGF PRT (SEQ ID NO: 513) | FGQGTK VEIKR (SEQ ID NO: 514) |

TABLE 5

Unique BoNT/A light chain antibodies. Shown are the clone name, VH CDR3, VL CDR3, KD for BoNT/A light chain, and epitope recognized. Epitopes are assigned sequential numbers, if the epitope does not overlap with other light chain antibodies. Affinities are for BoNT/A1 as determined using yeast displayed scFv and soluble BoNT/A1.

| Clone | VH CDR3 | VL CDR3 | KD | Epitope |
|---|---|---|---|---|
| ING2 | DPYYYSYMDV (SEQ ID NO: 515) | QQYYSTPFT (SEQ ID NO: 516) | 0.25 | 1 |
| 5A20 | EASFGWSYLGHDDAFDI (SEQ IDNO: 517) | QQYGSSLWT (SEQ ID NO: 518) | 0.34 | 2 |
| CON1 (4A1.1) | DPGWIYSDTSAAGWFDP (SEQ ID NO: 519) | QQSYDTPRT (SEQ ID NO: 520) | 10 | 3 |

Using the teachings and the sequence information provided herein, the variable light and variable heavy chains can be joined directly or through a linker (e.g., (Gly$_4$Ser)$_3$, SEQ ID NO:521) to form a single-chain Fv antibody. The various CDRs and/or framework regions can be used to form full human antibodies, chimeric antibodies, antibody fragments, polyvalent antibodies, and the like.

In certain embodiments, the anti-BoNT antibodies of this invention have a binding affinity (K$_D$) for a BoNT protein of at least $10^{-8}$, preferably at least $10^{-9}$, more preferably at least $10^{-10}$, and most preferably at least $10^{-11}$, or $10^{-12}$.

III. Preparation of BoNT Neutralizing Antibodies.

A) Recombinant Expression of BoNT-neutralizing Antibodies.

Using the information provided herein, the *botulinum* neurotoxin-neutralizing antibodies of this invention are prepared using standard techniques well known to those of skill in the art.

For example, the polypeptide sequences provided herein (see, e.g., Tables 1-5, and/or FIGS. 2-3) can be used to determine appropriate nucleic acid sequences encoding the BoNT-neutralizing antibodies and the nucleic acids sequences then used to express one or more BoNT-neutralizing antibodies. The nucleic acid sequence(s) can be optimized to reflect particular codon "preferences" for various expression systems according to standard methods well known to those of skill in the art.

Using the sequence information provided, the nucleic acids may be synthesized according to a number of standard methods known to those of skill in the art. Oligonucleotide synthesis, is preferably carried out on commercially available solid phase oligonucleotide synthesis machines (Needham-VanDevanter et al. (1984) *Nucleic Acids Res.* 12:6159-6168) or manually synthesized using, for example, the solid phase phosphoramidite triester method described by Beaucage et. al. (1981) *Tetrahedron Letts.* 22(20): 1859-1862.

Once a nucleic acid encoding an anti-BoNT antibody is synthesized it can be amplified and/or cloned according to standard methods. Molecular cloning techniques to achieve these ends are known in the art. A wide variety of cloning and in vitro amplification methods suitable for the construction of recombinant nucleic acids are known to persons of skill. Examples of these techniques and instructions sufficient to direct persons of skill through many cloning exercises are found in Berger and Kimmel, *Guide to Molecular Cloning Techniques, Methods in Enzymology* volume 152 Academic Press, Inc., San Diego, Calif. (Berger); Sambrook et al. (1989) *Molecular Cloning—A Laboratory Manual* (2nd ed.) Vol. 1-3, Cold Spring Harbor Laboratory, Cold Spring Harbor Press, NY, (Sambrook); and *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel). Methods of producing recombinant immunoglobulins are also known in the art. See, Cabilly, U.S. Pat. No. 4,816,567; and Queen et al. (1989) *Proc. Nat'l Acad. Sci. USA* 86: 10029-10033.

Examples of techniques sufficient to direct persons of skill through in vitro amplification methods, including the polymerase chain reaction (PCR) the ligase chain reaction (LCR), Qβ-replicase amplification and other RNA polymerase mediated techniques are found in Berger, Sambrook, and Ausubel, as well as Mullis et al., (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) C&EN 36-47; *The Journal Of NIH Research* (1991) 3, 81-94; (Kwoh et al. (1989) *Proc. Natl. Acad. Sci. USA* 86, 1173; Guatelli et al. (1990) *Proc. Natl. Acad. Sci. USA* 87, 1874; Lomell et al. (1989) *J. Clin. Chem* 35, 1826; Landegren et al., (1988) *Science* 241, 1077-1080; Van Brunt (1990) *Biotechnology* 8, 291-294; Wu and Wallace, (1989) *Gene* 4, 560; and Barringer et al. (1990) *Gene* 89, 117. Improved methods of cloning in vitro amplified nucleic acids are described in Wallace et al., U.S. Pat. No. 5,426,039.

Once the nucleic acid for an anti-BoNT antibody is isolated and cloned, one can express the gene in a variety of recombinantly engineered cells known to those of skill in the art. Examples of such cells include bacteria, yeast, filamentous fungi, insect (especially employing baculoviral vectors), and mammalian cells. It is expected that those of skill in the art are knowledgeable in the numerous expression systems available for expression of antibodies.

In brief summary, the expression of natural or synthetic nucleic acids encoding anti-BoNT antibodies will typically be achieved by operably linking a nucleic acid encoding the antibody to a promoter (which is either constitutive or inducible), and incorporating the construct into an expression vector. The vectors can be suitable for replication and integration in prokaryotes, eukaryotes, or both. Typical cloning vectors contain transcription and translation terminators, initiation sequences, and promoters useful for regulation of the expression of the nucleic acid encoding the anti-BoNT antibody. The vectors optionally comprise generic expression cassettes containing at least one independent terminator sequence, sequences permitting replication of the cassette in both eukaryotes and prokaryotes, i.e., shuttle vectors, and selection markers for both prokaryotic and eukaryotic systems. See Sambrook.

To obtain high levels of expression of a cloned nucleic acid it is common to construct expression plasmids which typically contain a strong promoter to direct transcription, a ribosome binding site for translational initiation, and a transcription/translation terminator. Examples of regulatory regions suitable for this purpose in *E. coli* are the promoter and operator region of the *E. coli* tryptophan biosynthetic pathway as described by Yanofsky (1984) *J. Bacteriol.*, 158:1018-1024 and the leftward promoter of phage lambda (PO as described by Herskowitz and Hagen (1980) *Ann. Rev. Genet.*, 14:399-445. The inclusion of selection markers in DNA vectors transformed in *E. coli* is also useful. Examples of such markers include genes specifying resistance to ampicillin, tetracycline, or chloramphenicol. See Sambrook for details concerning selection markers, e.g., for use in *E. coli*.

Expression systems for expressing anti-BoNT antibodies are available using, for example, *E. coli*, *Bacillus* sp. (see, e.g., Palva, et al. (1983) *Gene* 22:229-235; Mosbach et al. (1983) *Nature*, 302: 543-545), and *Salmonella*. In certain embodiments, *E. coli* systems are preferred.

The anti-BoNT antibodies produced by prokaryotic cells may require exposure to chaotropic agents for proper folding. During purification from, e.g., *E. coli*, the expressed protein is optionally denatured and then renatured. This can be accomplished, e.g., by solubilizing the bacterially produced antibodies in a chaotropic agent such as guanidine HCl. The antibody is then renatured, either by slow dialysis or by gel filtration (see, e.g., U.S. Pat. No. 4,511,503).

Methods of transfecting and expressing genes in mammalian cells are known in the art. Transducing cells with nucleic acids can involve, for example, incubating viral vectors containing anti-BoNT nucleic acids with cells within the host range of the vector (see, e.g., Goeddel (1990) *Methods in Enzymology*, vol. 185, Academic Press, Inc., San Diego, Calif. or Krieger (1990) *Gene Transfer and Expression—A Laboratory Manual*, Stockton Press, New York, N.Y. and the references cited therein).

The culture of cells used in the present invention, including cell lines and cultured cells from tissue or blood samples is well known in the art (see, e.g., Freshney (1994) *Culture of Animal Cells, a Manual of Basic Technique, third edition*, Wiley-Liss, N. Y. and the references cited therein).

Techniques for using and manipulating antibodies are found in Coligan (1991) *Current Protocols in Immunology* Wiley/Greene, NY; Harlow and Lane (1989) *Antibodies: A Laboratory Manual* Cold Spring Harbor Press, NY; Stites et al. (eds.) *Basic and Clinical Immunology* (4th ed.) Lange Medical Publications, Los Altos, Calif., and references cited therein; Goding (1986) *Monoclonal Antibodies: Principles and Practice* (2d ed.) Academic Press, New York, N.Y.; and Kohler and Milstein (1975) *Nature* 256: 495-497.

In one preferred embodiment the BoNT/A-neutralizing antibody gene (e.g. BoNT/A-neutralizing scFv gene) is subcloned into the expression vector pUC119mycHis (Tomlinson et al. (1996) *J. Mol. Biol.*, 256: 813-817) or pSYN3, resulting in the addition of a hexahistidine tag at the C-terminal end of the scFv to facilitate purification. Detailed protocols for the cloning and purification of certain BoNT-neutralizing antibodies are found, for example, in Amersdorfer et al. (1997) *Infect. Immunity*, 65(9): 3743-3752, and the like.

B) Preparation of Whole Polyclonal or Monoclonal Antibodies.

The anti-BoNT antibodies of this invention include individual, allelic, strain, or species variants, and fragments thereof, both in their naturally occurring (full-length) forms and in recombinant forms. In certain embodiments, preferred antibodies are selected to bind one or more epitopes bound by the antibodies described herein (e.g., 2A10, 3E1, 3E2, 3E3, 3E4, 3E4.1, 3E5, 3E6, 3E6.1, 4E11, 4E13, 4E16, 4E16.1, 4E17, 4E17.1, n A12, 6A12, B1.1, B6, B6.1, B8, B8.1, B11, B11C3, B11E8, B12, B12.1, B12.2, 1B18, 2B18.1, 4B19, and 1B22). The antibodies can be raised in their native configurations or in non-native configurations. Anti-idiotypic antibodies can also be generated. Many methods of making antibodies that specifically bind to a particular epitope are known to persons of skill. The following discussion is presented as a general overview of the techniques available; however, one of skill will recognize that many variations upon the following methods are known.

1) Polyclonal Antibody Production.

Methods of producing polyclonal antibodies are known to those of skill in the art. In brief, an immunogen (e.g., BoNT/A, BoNT/B, BoNT/E, etc.) subsequences including, but not limited to subsequences comprising epitopes specifically bound by antibodies expressed by clones 2A10, 3E1, 3E2, 3E3, 3E4, 3E4.1, 3E5, 3E6, 3E6.1, 4E11, 4E13, 4E16, 4E16.1, 4E17, 4E17.1, n A12, 6A12, B1.1, B6, B6.1, B8, B8.1, B11, B11C3, B11E8, B12, B12.1, B12.2, 1B18, 2B18.1, 4B19, and 1B22 disclosed herein, preferably a purified polypeptide, a polypeptide coupled to an appropriate carrier (e.g., GST, keyhole limpet hemanocyanin, etc.), or a polypeptide incorporated into an immunization vector such as a recombinant vaccinia virus (see, U.S. Pat. No. 4,722,848) is mixed with an adjuvant and animals are immunized with the mixture (see, e.g., FIG. 1). The animal's immune response to the immunogen preparation is monitored by taking test bleeds and determining the titer of reactivity to the polypeptide of interest. When appropriately high titers of antibody to the immunogen are obtained, blood is collected from the animal and antisera are prepared. Further fractionation of the antisera to enrich for antibodies reactive to the BoNT/A polypeptide is performed where desired (see, e.g., Coligan (1991) *Current Protocols in Immunology* Wiley/Greene, NY; and Harlow and Lane (1989) *Antibodies: A Laboratory Manual* Cold Spring Harbor Press, NY).

Antibodies that specifically bind to the neutralizing epitopes described herein can be selected from polyclonal sera using the selection techniques described herein.

2) Monoclonal Antibody Production.

In some instances, it is desirable to prepare monoclonal antibodies from various mammalian hosts, such as mice, rodents, primates, humans, etc. Descriptions of techniques for preparing such monoclonal antibodies are found in, e.g., Stites et al. (eds.) *Basic and Clinical Immunology* (4th ed.) Lange Medical Publications, Los Altos, Calif., and references cited therein; Harlow and Lane, supra; Goding (1986) *Monoclonal Antibodies: Principles and Practice* (2d ed.) Academic Press, New York, N.Y.; and Kohler and Milstein (1975) *Nature* 256: 495-497.

Summarized briefly, monoclonal antibody production proceeds by injecting an animal with an (e.g., BoNT/A, BoNT/B, BoNT/E, etc.) subsequences including, but not limited to subsequences comprising epitopes specifically bound by antibodies expressed by clones 2A10, 3E1, 3E2, 3E3, 3E4, 3E4.1, 3E5, 3E6, 3E6.1, 4E11, 4E13, 4E16, 4E16.1, 4E17, 4E17.1, n A12, 6A12, B1.1, B6, B6.1, B8, B8.1, B11, B11C3, B11E8, B12, B12.1, B12.2, 1B18, 2B18.1, 4B19, and 1B22 disclosed herein. The animal is then sacrificed and cells taken from its spleen, which are fused with myeloma cells. The result is a hybrid cell or "hybridoma" that is capable of reproducing in vitro. The population of hybridomas is then screened to isolate individual clones, each of which secrete a single antibody species to the immunogen. In this manner, the individual antibody species obtained are the products of immortalized and cloned single B cells from the immune animal generated in response to a specific site recognized on the immunogenic substance.

Alternative methods of immortalization include transformation with Epstein Barr Virus, oncogenes, or retroviruses, or other methods known in the art. Colonies arising from single immortalized cells are screened for production of antibodies of the desired specificity and affinity for the BoNT antigen, and yield of the monoclonal antibodies produced by such cells is enhanced by various techniques, including injection into the peritoneal cavity of a vertebrate (preferably mammalian) host. The antibodies of the present invention are used with or without modification, and include chimeric antibodies such as humanized murine antibodies.

IV. Modification of BoNT Neutralizing Antibodies.

A) Phage Display can be Used to Increase Antibody Affinity.

To create higher affinity antibodies, mutant scFv gene repertories, based on the sequence of a binding scFv (see, e.g., Tables 1-5, and/or FIGS. 2, and/or 3), can be created and expressed on the surface of phage. Display of antibody fragments on the surface of viruses which infect bacteria (bacteriophage or phage) makes it possible to produce human or other mammalian antibodies (e.g., scFvs) with a wide range of affinities and kinetic characteristics. To display antibody fragments on the surface of phage (phage display), an antibody fragment gene is inserted into the gene encoding a phage surface protein (e.g., pIII) and the antibody fragment-pIII fusion protein is expressed on the phage surface (McCafferty et al. (1990) *Nature*, 348: 552-554; Hoogenboom et al. (1991) *Nucleic Acids Res.*, 19: 4133-4137).

Since the antibody fragments on the surface of the phage are functional, those phage bearing antigen binding antibody fragments can be separated from non-binding or lower affinity phage by antigen affinity chromatography (McCafferty et al. (1990) *Nature*, 348: 552-554). Mixtures of phage are allowed to bind to the affinity matrix, non-binding or lower affinity phage are removed by washing, and bound phage are eluted by treatment with acid or alkali. Depending on the affinity of the antibody fragment, enrichment factors of 20 fold-1,000,000 fold are obtained by single round of affinity selection.

By infecting bacteria with the eluted phage or modified variants of the eluted phage as described below, more phage can be grown and subjected to another round of selection. In this way, an enrichment of 1000 fold in one round becomes 1,000,000 fold in two rounds of selection (see, e.g., McCafferty et al. (1990) *Nature*, 348: 552-554). Thus, even when enrichments in each round are low, multiple rounds of affinity selection leads to the isolation of rare phage and the genetic material contained within which encodes the sequence of the binding antibody (see, e.g., Marks et al. (1991) *J. Mol. Biol.*, 222: 581-597). The physical link between genotype and phenotype provided by phage display makes it possible to test every member of an antibody fragment library for binding to antigen, even with libraries as large as 100,000,000 clones. For example, after multiple rounds of selection on antigen, a binding scFv that occurred with a frequency of only 1/30,000,000 clones was recovered (Id).

1) Chain Shuffling.

One approach for creating mutant scFv gene repertoires involves replacing either the $V_H$ or $V_L$ gene from a binding scFv with a repertoire of $V_H$ or $V_L$ genes (chain shuffling) (see, e.g., Clackson et al. (1991) *Nature*, 352: 624-628). Such gene repertoires contain numerous variable genes derived from the same germline gene as the binding scFv, but with point mutations (see, e.g., Marks et al. (1992) *Bio/Technology*, 10: 779-783). Using light or heavy chain shuffling and phage display, the binding avidities of, e.g., BoNT/E or BoNT/B-neutralizing antibody fragment can be dramatically increased (see, e.g., Marks et al. (1992) *Bio/Technology*, 10: 779-785 in which the affinity of a human scFv antibody fragment which bound the hapten phenyloxazolone (phox) was increased from 300 nM to 15 nM (20 fold)).

Thus, to alter the affinity of BoNT-neutralizing antibody a mutant scFv gene repertoire is created containing the $V_H$ gene of a known BoNT-neutralizing antibody (e.g., 2A10, 3E1, 3E2, 3E3, 3E4, 3E4.1, 3E5, 3E6, 3E6.1, 4E11, 4E13, 4E16, 4E16.1, 4E17, 4E17.1, n A12, 6A12, B1.1, B6,136:1, B8, B8.1, BI 1, B11C3, B11E8, B12, B12.1, B12.2, 1B18, 2B18.1, 4B19, and 1B22) and a $V_L$ gene repertoire (light chain shuffling). Alternatively, an scFv gene repertoire is created containing the $V_L$ gene of a known BoNT-neutralizing antibody (e.g 2A10, 3E1, 3E2, 3E3, 3E4, 3E4.1, 3E5, 3E6, 3E6.1, 4E11, 4E13, 4E16, 4E16.1, 4E17, 4E17.1, n A12, 6A12, B1.1, B6, B6.1, B8, B8.1, B11, B11C3, B11E8, B12, B12.1, B12.2, 1B18, 2B18.1, 4B19, and 1B22) and a $V_H$ gene repertoire (heavy chain shuffling). The scFv gene repertoire is cloned into a phage display vector (e.g., pHEN-1, Hoogenboom et al. (1991) *Nucleic Acids Res.*, 19: 4133-4137) and after transformation a library of transformants is obtained. Phage are prepared and concentrated and selections are performed. In addition to chain shuffling, it is also possible to shuffle individual complementarity determining regions (CDRs).

In certain embodiments, the antigen concentration is decreased in each round of selection, reaching a concentration less than the desired $K_d$ by the final rounds of selection. This results in the selection of phage on the basis of affinity (Hawkins et al. (1992) *J. Mol. Biol.* 226: 889-896).

2) Increasing the Affinity of Anti-BoNT Antibodies by Site Directed Mutagenesis.

The majority of antigen contacting amino acid side chains are located in the complementarity determining regions (CDRs), three in the $V_H$ (CDR1, CDR2, and CDR3) and three in the $V_L$ (CDR1, CDR2, and CDR3) (see, e.g., Chothia et al. (1987) *J. Mol. Biol.*, 196: 901-917; Chothia et al. (1986) *Science*, 233: 755-8; Nhan et al. (1991) *J. Mol. Biol.*, 217: 133-151). Without being bound to a theory, it is believed that these residues contribute the majority of binding energetics responsible for antibody affinity for antigen. In other molecules, mutating amino acids that contact ligand has been shown to be an effective means of increasing the affinity of one protein molecule for its binding partner (Lowman et al. (1993) *J. Mol. Biol.*, 234: 564-578; Wells (1990) *Biochemistry*, 29: 8509-8516). Thus mutation (randomization) of the CDRs and screening against, for example, BoNT/A, BoNT/E, BoNT/B, or the epitopes thereof, can be used to generate anti-BoNT antibodies having improved binding affinity.

In certain embodiments, each CDR is randomized in a separate library, using, for example, A 12 as a template. To simplify affinity measurement, A12, or other lower affinity anti-BoNT antibodies, are used as a template, rather than a higher affinity scFv. The CDR sequences of the highest affinity mutants from each CDR library are combined to obtain an additive increase in affinity. A similar approach has been used to increase the affinity of human growth hormone (hGH) for the growth hormone receptor over 1500 fold from $3.4 \times 10^{-10}$ to $9.0 \times 10^{-13}$ M (see, e.g., Lowman et al. (1993) *J. Mol. Biol.*, 234: 564-578).

To increase the affinity of BoNT-neutralizing antibodies, amino acid residues located in one or more CDRs (e.g., 9 amino acid residues located in $V_L$ CDR3) are partially randomized by synthesizing a "doped" oligonucleotide in which the wild type nucleotide occurred with a frequency of, e.g. 49%. The oligonucleotide is used to amplify the remainder of the BoNT-neutralizing scFv gene(s) using PCR.

For example in one embodiment, to create a library in which $V_H$ CDR3 is randomized an oligonucleotide is synthesized which anneals to the BoNT-neutralizing antibody $V_H$ framework 3 and encodes $V_H$ CDR3 and a portion of framework 4. At the four positions to be randomized, the sequence NNS can be used, where N is any of the 4 nucleotides, and S is "C" or "T". The oligonucleotide is used to amplify the BoNT/A-neutralizing antibody $V_H$ gene using PCR, creating a mutant BoNT-neutralizing antibody $V_H$ gene repertoire. PCR is used to splice the $V_H$ gene repertoire with the BoNT-neutralizing antibody light chain gene, and the resulting scFv gene repertoire cloned into a phage display vector (e.g., pHEN-1 or pCANTAB5E). Ligated vector DNA is used to transform electrocompetent *E. coli* to produce a phage antibody library.

To select higher affinity mutant scFv, each round of selection of the phage antibody libraries is conducted on decreasing amounts of one or more BoNT subtypes. Clones from the third and fourth round of selection can screened for binding to the desired antigen(s) (e.g., BoNT/B BoNT/E, etc.) by ELISA on 96 well plates. scFv from, e.g., twenty to forty ELISA positive clones can be expressed, e.g. in 10 ml cultures, the periplasm harvested, and the scFv $k_{off}$ determined by BIACORE™. Clones with the slowest $k_{off}$ are sequenced, and each unique scFv subcloned into an appropriate vector (e.g., pUC119 mycHis). The scFv are expressed in culture, and purified. Affinities of purified scFv can be determined by BIACORE™.

By way of illustration, FIG. 7 show a scheme used for affinity maturation of HuC25 (FIG. 7A) and 3D12 (FIG. 7B) scFv using yeast display (see, e.g.: Ser. No. 11/342,27, filed on Jan. 26, 2006, Ser. No. 09/144,886, filed in Aug. 31, 1998, Ser. No. 10/632,706, filed on Aug. 1, 2003, and PCT application Nos: PCT/US2006/003070 and PCT/US03/24371, which are incorporated herein by reference for all purposes).

3) Creation of Anti-BoNT (scFv')2 Homodimers.

To create anti-BoNT (e.g., BoNT-neutralizing) (scFv')$_2$ antibodies, two ANTI-BoNT scFvs are joined, either through a linker (e.g., a carbon linker, a peptide, etc.) or through a disulfide bond between, for example, two cysteines. Thus, for example, to create disulfide linked scFv, a cysteine residue can be introduced by site directed mutagenesis between a myc tag and a hexahistidine tag at the carboxy-terminus of an anti-BoNT/A. Introduction of the correct sequence can be verified by DNA sequencing. In certain embodiments, the construct is in pUC119, so that the pelB leader directs expressed scFv to the periplasm and cloning sites (NcoI and NotI) exist to introduce anti-BoNT mutant scFv. Expressed scFv has the myc tag at the C-terminus, followed by two glycines, a cysteine, and then 6 histidines to facilitate purification by IMAC. After disulfide bond formation between the two cysteine residues, the two scFv can be separated from each other by 26 amino acids (two 11 amino acid myc tags and 4 glycines). An scFv was expressed from this construct, purified by IMAC may predominantly comprise monomeric scFv. To produce (scFv')$_2$ dimers, the cysteine can be reduced by incubation with 1 mM beta-mercaptoethanol, and half of the scFv blocked by the addition of DTNB. Blocked and unblocked scFvs can be incubated together to form (scFv')$_2$ and the resulting material can optionally be analyzed by gel filtration. The affinity of the anti-BoNT scFv' monomer and (scFv')$_2$ dimer can optionally be determined by BIACORE™.

In certain embodiments, the (scFv')$_2$ dimer is created by joining the scFv fragments through a linker, more preferably through a peptide linker. This can be accomplished by a wide variety of means well known to those of skill in the art. For example, one preferred approach is described by Holliger et al. (1993) *Proc. Natl. Acad. Sci. USA*, 90: 6444-6448 (see also WO 94/13804).

Typically, linkers are introduced by PCR cloning. For example, synthetic oligonucleotides encoding the 5 amino acid linker (Gly$_4$Ser, SEQ ID NO:522) can be used to PCR amplify the BoNT/A-neutralizing antibody $V_H$ and $V_L$ genes which are then spliced together to create the BoNT/A-neutralizing diabody gene. The gene can then be cloned into an appropriate vector, expressed, and purified according to standard methods well known to those of skill in the art.

4) Preparation of anti-BoNT (scFv)$_2$, Fab, and Fab' Molecules.

Anti-BoNT antibodies such as anti-BoNT/E or anti-BoN/B scFv, or variant(s) with higher affinity, are suitable templates for creating size and valency variants. For example, an anti-BoNT (scFv')$_2$ can be created from the parent scFv (e.g., 2A10, 3E1, 3E2, 3E3, 3E4, 3E4.1, 3E5, 3E6, 3E6.1, 4E11, 4E13, 4E16, 4E16.1, 4E17, 4E17.1, n A12, 6A12, B1.1, B6, B6.1, B8, B8.1, B11, B11C3, B11E8, B12, B12.1, B12.2, 1B18, 2B18.1, 4B19, 1B22, etc.) as described above. An scFv gene can be excised using appropriate restriction enzymes and cloned into another vector as described herein.

In one embodiment, expressed scFv has a myc tag at the C-terminus, followed by two glycines, a cysteine, and six histidines to facilitate purification. In certain embodiments, after disulfide bond formation between the two cystine residues, the two scFv are separated from each other by 26 amino acids (e.g., two eleven amino acid myc tags and four glycines). Single-chain Fv (scFv) can be expressed from this construct and purified.

To produce (scFv')$_2$ dimers, the cysteine is reduced by incubation with 1 mM β-mercaptoethanol, and half of the scFv blocked by the addition of DTNB. Blocked and unblocked scFv are incubated together to form (scFv')$_2$, which is purified. As higher affinity scFv are isolated, their genes are similarly used to construct (scFv')$_2$.

In certain embodiments, anti-BoNT Fab are expressed in *E. coli* using an expression vector similar to the one described by Better et. al. (1988) *Science,* 240: 1041-1043. For example, to create a BoNT/B or BoNT/E-neutralizing Fab, the $V_H$ and $V_L$ genes are amplified from the scFv using PCR. The $V_H$ gene is cloned into an expression vector (e.g., a PUC119 based bacterial expression vector) that provides an IgG $C_H1$ domain downstream from, and in frame with, the $V_H$ gene. The vector also contains the lac promoter, a pelb leader sequence to direct expressed $V_H$-$C_H1$ domain into the periplasm, a gene 3 leader sequence to direct expressed light chain into the periplasm, and cloning sites for the light chain gene. Clones containing the correct VH gene are identified, e.g., by PCR fingerprinting. The $V_L$ gene is spliced to the $C_L$ gene using PCR and cloned into the vector containing the $V_H C_H1$ gene.

B) Selection of Neutralizing Antibodies.

In certain embodiments, selection of anti-BoNT antibodies (whether produced by phage display, yeast display, immunization methods, hybridoma technology, etc.) involves screening the resulting antibodies for specific binding to an appropriate antigen(s). In the instant case, suitable antigens can include, but are not limited to BoNT/E, BoNT/B, BoNT/A1, BoNT/A2, BoNT/A3 $H_C$, a C-terminal domain of BoNT heavy chain (binding domain), BoNT/A3 holotoxins, r recombinant BoNT domains such as HC (binding domain), HN (translocation domain), or LC (light chain), and the like. In certain embodiments the neutralizing antibodies are selected for specific binding of an epitope recognized by one or more of the antibodies described herein.

Selection can be by any of a number of methods well known to those of skill in the art. In an illustrative embodiment, selection is by immunochromatography (e.g., using immunotubes, Maxisorp, Nunc) against the desired target, e.g., BoNT/E, BoNT/B, etc. In another embodiment, selection is against a BoNT protein in a surface plasmon resonance system (e.g., BIACORE™, Pharmacia) either alone or in combination with an antibody that binds to an epitope specifically bound by one or more of the antibodies described herein. Selection can also be done using flow cytometry for yeast display libraries. In one embodiment, yeast display libraries are sequentially selected, first on BoNT/A1, then on BoNT/A2 to obtain antibodies that bind with high affinity to both subtypes of BoNT/A. This can be repeated for other subtypes.

For phage display, analysis of binding can be simplified by including an amber codon between the antibody fragment gene and gene III. This makes it possible to easily switch between displayed and soluble antibody fragments simply by changing the host bacterial strain. When phage are grown in a supE suppresser strain of *E. coli*, the amber stop codon between the antibody gene and gene III is read as glutamine and the antibody fragment is displayed on the surface of the phage. When eluted phage are used to infect a non-suppressor strain, the amber codon is read as a stop codon and soluble antibody is secreted from the bacteria into the periplasm and culture media (Hoogenboom et al. (1991) *Nucleic Acids Res.,* 19: 4133-4137). Binding of soluble scFv to antigen can be detected, e.g., by ELISA using a murine IgG monoclonal antibody (e.g., 9E10) which recognizes a C-terminal myc peptide tag on the scFv (Evan et al. (1985) *Mol. Cell Biol.,* 5: 3610-3616; Munro et al. (1986) *Cell,* 46: 291-300), e.g., followed by incubation with polyclonal anti-mouse Fc conjugated to a detectable label (e.g., horseradish peroxidase).

As indicated above, purification of the anti-BoNT antibody can be facilitated by cloning of the scFv gene into an expression vector (e.g., expression vector pUC119mycHIS) that results in the addition of the myc peptide tag followed by a hexa-histidine tag at the C-terminal end of the scFv. The vector also preferably encodes the pectate lyase leader sequence that directs expression of the scFv into the bacterial periplasm where the leader sequence is cleaved. This makes it possible to harvest native properly folded scFv directly from the bacterial periplasm. The BoNT-neutralizing antibody is then expressed and purified from the bacterial supernatant using immobilized metal affinity chromatography.

C) Measurement of Anti-BoNT Antibody Affinity for One or More BoNT Subtypes.

As explained above, selection for increased avidity involves measuring the affinity of an anti-BoNT (e.g., a BoNT-neutralizing) antibody (or a modified BoNT-neutralizing antibody) for one or more targets of interest (e.g. BoNT/E subtype(s) or domains thereof. For example, the $K_d$ of a BoNT/E-neutralizing antibody and the kinetics of binding to BoNT/E are determined in a BIACORE™, a biosensor based on surface plasmon resonance. For this technique, antigen is coupled to a derivatized sensor chip capable of detecting changes in mass. When antibody is passed over the sensor chip, antibody binds to the antigen resulting in an increase in mass that is quantifiable. Measurement of the rate of association as a function of antibody concentration can be used to calculate the association rate constant ($k_{on}$). After the association phase, buffer is passed over the chip and the rate of dissociation of antibody ($k_{off}$) determined. $K_{on}$, is typically measured in the range $1.0 \times 10^2$ to $5.0 \times 10^6$ and $k_{off}$ in the range $1.0 \times 10^{-1}$ to $1.0 \times 10^{-6}$. The equilibrium constant $K_d$ is then calculated as $k_{off}/k_{on}$ and thus is typically measured in the range $10^{-5}$ to $10^{-12}$. Affinities measured in this manner correlate well with affinities measured in solution by fluorescence quench titration.

Phage display and selection generally results in the selection of higher affinity mutant scFvs (Marks et al. (1992) *Bio/Technology,* 10: 779-783; Hawkins et al. (1992) 1 *Mol. Biol.* 226: 889-896; Riechmann et al. (1993) *Biochemistry,* 32: 8848-8855; Clackson et al. (1991) *Nature,* 352: 624-628), but probably does not result in the separation of mutants with less than a 6 fold difference in affinity (Riechmann et al.

(1993) *Biochemistry*, 32: 8848-8855). Thus a rapid method is needed to estimate the relative affinities of mutant scFvs isolated after selection. Since increased affinity results primarily from a reduction in the $k_{off}$, measurement of $k_{off}$ should identify higher affinity scFv. $k_{off}$ can be measured in the BIA-CORE™ on unpurified scFv in bacterial periplasm, since expression levels are high enough to give an adequate binding signal and $k_{off}$ is independent of concentration. The value of $k_{off}$ for periplasmic and purified scFv is typically in close agreement.

V. Human or Humanized (Chimeric) Antibody Production.

As indicated above, the anti-BoNT antibodies of this invention can be administered to an organism (e.g., a human patient) for therapeutic purposes (e.g., the treatment of botulism). Antibodies administered to an organism other than the species in which they are raised can be immunogenic. Thus, for example, murine antibodies repeatedly administered to a human often induce an immunologic response against the antibody (e.g., the human anti-mouse antibody (HAMA) response). While this is typically not a problem for the use of non-human antibodies of this invention as they are typically not utilized repeatedly, the immunogenic properties of the antibody are reduced by altering portions, or all, of the antibody into characteristically human sequences thereby producing chimeric or human antibodies, respectively.

A) Chimeric Antibodies.

Chimeric) antibodies are immunoglobulin molecules comprising a human and non-human portion. More specifically, the antigen combining region (or variable region) of a chimeric antibody is derived from a non-human source (e.g., murine) and the constant region of the chimeric antibody (which confers biological effector function to the immunoglobulin) is derived from a human source. The chimeric antibody should have the antigen binding specificity of the non-human antibody molecule and the effector function conferred by the human antibody molecule. A large number of methods of generating chimeric antibodies are well known to those of skill in the art (see, e.g., U.S. Pat. Nos. 5,502,167, 5,500,362, 5,491,088, 5,482,856, 5,472,693, 5,354,847, 5,292,867, 5,231,026, 5,204,244, 5,202,238, 5,169,939, 5,081,235, 5,075,431, and 4,975,369).

In general, the procedures used to produce chimeric antibodies consist of the following steps (the order of some steps may be interchanged): (a) identifying and cloning the correct gene segment encoding the antigen binding portion of the antibody molecule; this gene segment (known as the VDJ, variable, diversity and joining regions for heavy chains or VJ, variable, joining regions for light chains (or simply as the V or variable region) may be in either the cDNA or genomic form; (b) cloning the gene segments encoding the constant region or desired part thereof; (c) ligating the variable region to the constant region so that the complete chimeric antibody is encoded in a transcribable and translatable form; (d) ligating this construct into a vector containing a selectable marker and gene control regions such as promoters, enhancers and poly (A) addition signals; (e) amplifying this construct in a host cell (e.g., bacteria); (f) introducing the DNA into eukaryotic cells (transfection) most often mammalian lymphocytes; and culturing the host cell under conditions suitable for expression of the chimeric antibody.

Antibodies of several distinct antigen binding specificities have been manipulated by these protocols to produce chimeric proteins (e.g., anti-TNP: Boulianne et al. (1984) *Nature*, 312: 643; and anti-tumor antigens: Sahagan et al. (1986) *J. Immunol.*, 137: 1066). Likewise several different effector functions have been achieved by linking new sequences to those encoding the antigen binding region. Some of these include enzymes (Neuberger et al. (1984) *Nature* 312: 604), immunoglobulin constant regions from another species and constant regions of another immunoglobulin chain (Sharon et al. (1984) *Nature* 309: 364; Tan et al., (1985) *J. Immunol.* 135: 3565-3567).

In one preferred embodiment, a recombinant DNA vector is used to transfect a cell line that produces an anti-BoNT antibody. The novel recombinant DNA vector contains a "replacement gene" to replace all or a portion of the gene encoding the immunoglobulin constant region in the cell line (e.g., a replacement gene may encode all or a portion of a constant region of a human immunoglobulin, a specific immunoglobulin class, or an enzyme, a toxin, a biologically active peptide, a growth factor, inhibitor, or a linker peptide to facilitate conjugation to a drug, toxin, or other molecule, etc.), and a "target sequence" which allows for targeted homologous recombination with immunoglobulin sequences within the antibody producing cell.

In another embodiment, a recombinant DNA vector is used to transfect a cell line that produces an antibody having a desired effector function, (e.g., a constant region of a human immunoglobulin) in which case, the replacement gene contained in the recombinant vector may encode all or a portion of a region of an BoNT/A-neutralizing antibody and the target sequence contained in the recombinant vector allows for homologous recombination and targeted gene modification within the antibody producing cell. In either embodiment, when only a portion of the variable or constant region is replaced, the resulting chimeric antibody may define the same antigen and/or have the same effector function yet be altered or improved so that the chimeric antibody may demonstrate a greater antigen specificity, greater affinity binding constant, increased effector function, or increased secretion and production by the transfected antibody producing cell line, etc.

Regardless of the embodiment practiced, the processes of selection for integrated DNA (via a selectable marker), screening for chimeric antibody production, and cell cloning, can be used to obtain a clone of cells producing the chimeric antibody.

Thus, a piece of DNA which encodes a modification for a monoclonal antibody can be targeted directly to the site of the expressed immunoglobulin gene within a B-cell or hybridoma cell line. DNA constructs for any particular modification may be used to alter the protein product of any monoclonal cell line or hybridoma. Such a procedure circumvents the costly and time consuming task of cloning both heavy and light chain variable region genes from each B-cell clone expressing a useful antigen specificity. In addition to circumventing the process of cloning variable region genes, the level of expression of chimeric antibody should be higher when the gene is at its natural chromosomal location rather than at a random position. Detailed methods for preparation of chimeric (humanized) antibodies can be found in U.S. Pat. No. 5,482,856.

B) Human and Humanized Antibodies.

In another embodiment, this invention provides for humanized or fully human anti-BoNT-neutralizing antibodies (e.g., 2A10, 3E1, 3E2, 3E3, 3E4, 3E4.1, 3E5, 3E6, 3E6.1, 4E11, 4E13, 4E16, 4E16.1, 4E17, 4E17.1, n A12, 6A12, B1.1, B6, B6.1, B8, B8.1, B11, B11C3, B11E8, B12, B12.1, B12.2, 1B18, 2B18.1, 4B19, and 1B22, etc.). Human antibodies consist entirely of characteristically human polypeptide sequences. The human BoNT-neutralizing antibodies of this invention can be produced in using a wide variety of methods (see, e.g., Larrick et al., U.S. Pat. No. 5,001,065, for review).

In certain preferred embodiments, fully human scFv antibodies of this invention are obtained by modification and screening of fully human single-chain (e.g. scFv) libraries. Thus, in certain embodiments, fully human antibodies are produced using phage and/or yeast display methods as described herein. Methods of producing fully human gene libraries are well known to those of skill in the art (see, e.g., Vaughn et al. (1996) *Nature Biotechnology*, 14(3): 309-314, Marks et al. (1991) *J. Mol. Biol.*, 222: 581-597, and PCT/US96/10287).

In another embodiment, human BoNT-neutralizing antibodies of the present invention are can be produced in trioma cells. Genes encoding the antibodies are then cloned and expressed in other cells, particularly, nonhuman mammalian cells.

The general approach for producing human antibodies by trioma technology has been described by Ostberg et al. (1983) *Hybridoma* 2: 361-367, Ostberg, U.S. Pat. No. 4,634,664, and Engelman et al., U.S. Pat. No. 4,634,666. The antibody-producing cell lines obtained by this method are called triomas because they are descended from three cells; two human and one mouse. Triomas have been found to produce antibody more stably than ordinary hybridomas made from human cells.

Preparation of trioma cells requires an initial fusion of a mouse myeloma cell line with unimmunized human peripheral B lymphocytes. This fusion generates a xenogenic hybrid cell containing both human and mouse chromosomes (see, Engelman, supra.). Xenogenic cells that have lost the capacity to secrete antibodies are selected. Preferably, a xenogenic cell is selected that is resistant to 8-azaguanine. Such cells are unable to propagate on hypoxanthine-aminopterin-thymidine (HAT) or azaserine-hypoxanthine (AH) media.

The capacity to secrete antibodies is conferred by a further fusion between the xenogenic cell and B-lymphocytes immunized against a BoNT polypeptide (e.g., BoNT/A, BoNT/A $H_c$, BoNT/A subsequences including, but not limited to subsequences comprising epitopes specifically bound by the antibodies described herein, etc.). The B-lymphocytes are obtained from the spleen, blood or lymph nodes of human donor. If antibodies against a specific antigen or epitope are desired, it is preferable to use that antigen or epitope thereof as the immunogen rather than the entire polypeptide. Alternatively, B-lymphocytes are obtained from an unimmunized individual and stimulated with a BoNT polypeptide, or a epitope thereof, in vitro. In a further variation, B-lymphocytes are obtained from an infected, or otherwise immunized individual, and then hyperimmunized by exposure to a BoNT polypeptide for about seven to fourteen days, in vitro.

The immunized B-lymphocytes prepared by one of the above procedures are fused with a xenogenic hybrid cell by well known methods. For example, the cells are treated with 40-50% polyethylene glycol of MW 1000-4000, at about 37° C. for about 5-10 min. Cells are separated from the fusion mixture and propagated in media selective for the desired hybrids. When the xenogenic hybrid cell is resistant to 8-azaguanine, immortalized trioma cells are conveniently selected by successive passage of cells on HAT or AH medium. Other selective procedures are, of course, possible depending on the nature of the cells used in fusion. Clones secreting antibodies having the required binding specificity are identified by assaying the trioma culture medium for the ability to bind to the BoNT polypeptide or an epitope thereof. Triomas producing human antibodies having the desired specificity are subcloned by the limiting dilution technique and grown in vitro in culture medium, or are injected into selected host animals and grown in vivo.

The trioma cell lines obtained are then tested for the ability to bind a BoNT polypeptide or an epitope thereof. Antibodies are separated from the resulting culture medium or body fluids by conventional antibody-fractionation procedures, such as ammonium sulfate precipitation, DEAE cellulose chromatography and affinity chromatography.

Although triomas are genetically stable they do not produce antibodies at very high levels. Expression levels can be increased by cloning antibody genes from the trioma into one or more expression vectors, and transforming the vector into a cell line such as the cell lines typically used for expression of recombinant or humanized immunoglobulins. As well as increasing yield of antibody, this strategy offers the additional advantage that immunoglobulins are obtained from a cell line that does not have a human component, and does not therefore need to be subjected to the especially extensive viral screening required for human cell lines.

The genes encoding the heavy and light chains of immunoglobulins secreted by trioma cell lines are cloned according to methods, including but not limited to, the polymerase chain reaction (PCR), known in the art (see, e.g., Sambrook et al., *Molecular Cloning: A Laboratory Manual*, 2nd ed., Cold Spring Harbor, N.Y., 1989; Berger & Kimmel, *Methods in Enzymology, Vol. 152: Guide to Molecular Cloning Techniques*, Academic Press, Inc., San Diego, Calif., 1987; Co et al. (1992) *J. Immunol.*, 148: 1149). For example, genes encoding heavy and light chains are cloned from a trioma's genomic DNA or cDNA produced by reverse transcription of the trioma's RNA. Cloning is accomplished by conventional techniques including the use of PCR primers that hybridize to the sequences flanking or overlapping the genes, or segments of genes, to be cloned.

Typically, recombinant constructs comprise DNA segments encoding a complete human immunoglobulin heavy chain and/or a complete human immunoglobulin light chain of an immunoglobulin expressed by a trioma cell line. Alternatively, DNA segments encoding only a portion of the primary antibody genes are produced, which portions possess binding and/or effector activities. Other recombinant constructs contain segments of trioma cell line immunoglobulin genes fused to segments of other immunoglobulin genes, particularly segments of other human constant region sequences (heavy and/or light chain). Human constant region sequences can be selected from various reference sources, including but not limited to those listed in Kabat et al. (1987) *Sequences of Proteins of Immunological Interest*, U.S. Department of Health and Human Services.

In addition to the DNA segments encoding anti-BoNT immunoglobulins or fragments thereof, other substantially homologous modified immunoglobulins can be readily designed and manufactured utilizing various recombinant DNA techniques known to those skilled in the art such as site-directed mutagenesis (see Gillman & Smith (1979) *Gene*, 8: 81-97; Roberts et al. (1987) *Nature* 328: 731-734). Such modified segments will usually retain antigen binding capacity and/or effector function. Moreover, the modified segments are usually not so far changed from the original trioma genomic sequences to prevent hybridization to these sequences under stringent conditions. Because, like many genes, immunoglobulin genes contain separate functional regions, each having one or more distinct biological activities, the genes may be fused to functional regions from other genes to produce fusion proteins (e.g., immunotoxins) having novel properties or novel combinations of properties.

The genomic sequences can be cloned and expressed according to standard methods as described herein.

Other approaches to antibody production include in vitro immunization of human blood. In this approach, human blood lymphocytes capable of producing human antibodies are produced. Human peripheral blood is collected from the patient and is treated to recover mononuclear cells. The suppressor T-cells then are removed and remaining cells are suspended in a tissue culture medium to which is added the antigen and autologous serum and, preferably, a nonspecific lymphocyte activator. The cells then are incubated for a period of time so that they produce the specific antibody desired. The cells then can be fused to human myeloma cells to immortalize the cell line, thereby to permit continuous production of antibody (see U.S. Pat. No. 4,716,111).

In another approach, mouse-human hybridomas which produce human BoNT-neutralizing antibodies are prepared (see, e.g., U.S. Pat. No. 5,506,132). Other approaches include immunization of murines transformed to express human immunoglobulin genes, and phage display screening (Vaughan et al. supra.).

Vi. Assaying for Cross-reactivity at a Neutralizing Epitope.

In a preferred embodiment, the antibodies of this invention specifically bind to one or more epitopes recognized by antibodies described herein (e.g., 2A10, 3E1, 3E2, 3E3, 3E4, 3E4.1, 3E5, 3E6, 3E6.1, 4E11, 4E13, 4E16, 4E16.1, 4E17, 4E17.1, nA12, 6A12, B1.1, B6, B6.1, B8, B8.1, B11, B11C3, B11E8, B12, B12.1, B12.2, 1B18, 2B18.1, 4B19, and 1B22, etc.). In other words, particularly preferred antibodies are cross-reactive with one of more of these antibodies. Means of assaying for cross-reactivity are well known to those of skill in the art (see, e.g., Dowbenko et al. (1988), *J. Virol.* 62: 4703-4711).

This can be ascertained by providing one or more isolated target BoNT polypeptide(s) (e.g. BoNT/A1 and/or BoNT/A2, or recombinant domains of said toxin, such as $H_c$) attached to a solid support and assaying the ability of a test antibody to compete with, e.g., 2A10, 3E1, 3E2, 3E3, 3E4, 3E4.1, 3E5, 3E6, 3E6.1, 4E11, 4E13, 4E16, 4E16.1, 4E17, 4E17.1, nA12, 6A12, B1.1, B6, B6.1, B8, B8.1, B11, B11C3, B11E8, B12, B12.1, B12.2, 1B18, 2B18.1, 4B19, and 1B22, etc for binding to the target BoNT peptide. Thus, immunoassays in a competitive binding format are preferably used for crossreactivity determinations. For example, in one embodiment, a BoNT/E and/or BoNT/B polypeptide is immobilized to a solid support. Antibodies to be tested (e.g. generated by selection from a phage-display library) added to the assay compete with 2A10, 3E1, 3E2, 3E3, 3E4, 3E4.1, 3E5, 3E6, 3E6.1, 4E11, 4E13, 4E16, 4E16.1, 4E17, 4E17.1, n A12, 6A12, B1.1, B6, B6.1, B8, B8.1, B11, B11C3, B11E8, B12, B12.1, B12.2, 1B18, 2B18.1, 4B19, and 1B22, etc antibodies binding to the immobilized BoNT polypeptide(s). The ability of test antibodies to compete with the binding of the 2A10, 3E1, 3E2, 3E3, 3E4, 3E4.1, 3E5, 3E6, 3E6.1, 4E11, 4E13, 4E16, 4E16.1, 4E17, 4E17.1, n A12, 6A12, B1.1, B6, B6.1, B8, B8.1, B11, B11C3, B11E8, B12, B12.1, B12.2, 1B18, 2B18.1, 4B19, and 1B22, etc antibodies to the immobilized protein(s) are compared. The percent crossreactivity above proteins is then calculated, using standard calculations.

If the test antibody competes with one or more of the 2A10, 3E1, 3E2, 3E3, 3E4, 3E4.1, 3E5, 3E6, 3E6.1, 4E11, 4E13, 4E16, 4E16.1, 4E17, 4E17.1, n A12, 6A12, B1.1, B6, B6.1, B8, B8.1, B11, B11C3, B11E8, B12, B12.1, B12.2, 1B18, 2B18.1, 4B19, and 1B22, etc antibodies and has a binding affinity comparable to or greater than about $1 \times 10^{-8}$ M with the same target then the test antibody is expected to be a BoNT-neutralizing antibody.

In a particularly preferred embodiment, cross-reactivity is performed by using surface Plasmon resonance in a BIACORE™. In a BIACORE™ flow cell, the BoNT polypeptide(s) (e.g., BoNT/B and/or BoNT/E) are coupled to a sensor chip (e.g. CM5) as described in the examples. With a flow rate of 5 µl/min, a titration of 100 nM to 1 µM antibody is injected over the flow cell surface for about 5 minutes to determine an antibody concentration that results in near saturation of the surface. Epitope mapping or cross-reactivity is then evaluated using pairs of antibodies at concentrations resulting in near saturation and at least 100 RU of antibody bound. The amount of antibody bound is determined for each member of a pair, and then the two antibodies are mixed together to give a final concentration equal to the concentration used for measurements of the individual antibodies. Antibodies recognizing different epitopes show an essentially additive increase in the RU bound when injected together, while antibodies recognizing identical epitopes show only a minimal increase in RU (see the examples). In a particularly preferred embodiment, antibodies are said to be cross-reactive if, when "injected" together they show an essentially additive increase (preferably an increase by at least a factor of about 1.4, more preferably an increase by at least a factor of about 1.6, and most preferably an increase by at least a factor of about 1.8 or 2.

Cross-reactivity at the desired epitopes can ascertained by a number of other standard techniques (see, e.g., Geysen et al (1987) *J. Immunol. Meth.* 102, 259-274). This technique involves the synthesis of large numbers of overlapping BoNT peptides. The synthesized peptides are then screened against one or more of the prototypical antibodies (e.g., CR1, RAZ1, ING1, ING2, etc.) and the characteristic epitopes specifically bound by these antibodies can be identified by binding specificity and affinity. The epitopes thus identified can be conveniently used for competitive assays as described herein to identify cross-reacting antibodies.

The peptides for epitope mapping can be conveniently prepared using "Multipin" peptide synthesis techniques (see, e.g., Geysen et al (1987) *Science,* 235: 1184-1190). Using the known sequence of one or more BoNT subtypes (see, e.g., Atassi et al. (1996) *J. Prot. Chem.,* 7: 691-700 and references cited therein), overlapping BoNT polypeptide sequences can be synthesized individually in a sequential manner on plastic pins in an array of one or more 96-well microtest plate(s).

The procedure for epitope mapping using this multipin peptide system is described in U.S. Pat. No. 5,739,306. Briefly, the pins are first treated with a pre-coat buffer containing 2% bovine serum albumin and 0.1% Tween 20 in PBS for 1 hour at room temperature. Then the pins are then inserted into the individual wells of 96-well microtest plate containing the antibodies in the pre-coat buffer, e.g. at 2 µg/ml. The incubation is preferably for about 1 hour at room temperature. The pins are washed in PBST (e.g., 3 rinses for every 10 minutes), and then incubated in the wells of a 96-well microtest plate containing 100 mu 1 of HRP-conjugated goat anti-mouse IgG (Fc) (Jackson ImmunoResearch Laboratories) at a 1:4,000 dilution for 1 hour at room temperature. After the pins are washed as before, the pins are put into wells containing peroxidase substrate solution of diammonium 2,2'-azino-bis[3-ethylbenzthiazoline-b-sulfonate] (ABTS) and $H_2O_2$ (Kirkegaard & Perry Laboratories Inc., Gaithersburg, Md.) for 30 minutes at room temperature for color reaction. The plate is read at 405 nm by a plate reader (e.g., BioTek ELISA plate reader) against a background absorption wavelength of 492 nm. Wells showing color development indicated reactivity of the BoNT/A $H_C$ peptides in such wells with S25, C25, C39, 1C6, or 1F3 antibodies.

VII. Assaying for Neutralizing Activity of Anti-BoNT Antibodies.

Preferred antibodies of this invention act, individually or in combination, to neutralize (reduce or eliminate) the toxicity of *botulinum* neurotoxin type. Neutralization can be evaluated in vivo or in vitro. In vivo neutralization measurements simply involve measuring changes in the lethality (e.g., $LD_{50}$ or other standard metric) due to a BoNT neurotoxin administration due to the presence of one or more antibodies being tested for neutralizing activity. The neurotoxin can be directly administered to the test organism (e.g. mouse) or the organism can harbor a botulism infection (e.g., be infected with *Clostridium botulinum*). The antibody can be administered before, during, or after the injection of BoNT neurotoxin or infection of the test animal. A decrease in the rate of progression, or mortality rate indicates that the antibody(s) have neutralizing activity.

One suitable in vitro assay for neutralizing activity uses a hemidiaphragm preparation (Deshpande et al. (1995) *Toxicon*, 33: 551-557). Briefly, left and right phrenic nerve hemidiaphragm preparations are suspended in physiological solution and maintained at a constant temperature (e.g. 36° C.). The phrenic nerves are stimulated supramaximally (e.g. at 0.05 Hz with square waves of 0.2 ms duration). Isometric twitch tension is measured with a force displacement transducer (e.g., GrassModel FT03) connected to a chart recorder.

Purified antibodies are incubated with purified BoNT (e.g. BoNT/A1, BoNT/A2, BoNT/B, etc.) for 30 min at room temperature and then added to the tissue bath, resulting in a final antibody concentration of about $2.0 \times 10^{-8}$ M and a final BoNT concentration of about $2.0 \times 10^{-11}$ M. For each antibody studied, time to 50% twitch tension reduction is determined (e.g., three times for BoNT alone and three times for antibody plus BoNT). Differences between times to a given (arbitrary) percentage (e.g. 50%) twitch reduction are determined by standard statistical analyses (e.g. two-tailed t test) at standard levels of significance (e.g., a P value of <0.05 considered significant).

VIII. Diagnostic Assays.

As explained above, the anti-BoNT antibodies of this invention can be used for the in vivo or in vitro detection of BoNT toxin (e.g. BoNT/E toxin) and thus, are useful in the diagnosis (e.g. confirmatory diagnosis) of botulism. The detection and/or quantification of BoNT in a biological sample obtained from an organism is indicative of a *Clostridium botulinum* infection of that organism.

The BoNT antigen can be quantified in a biological sample derived from a patient such as a cell, or a tissue sample derived from a patient. As used herein, a biological sample is a sample of biological tissue or fluid that contains a BoNT concentration that may be correlated with and indicative of a *Clostridium botulinum* infection. Preferred biological samples include blood, urine, saliva, and tissue biopsies.

Although the sample is typically taken from a human patient, the assays can be used to detect BoNT antigen in cells from mammals in general, such as dogs, cats, sheep, cattle and pigs, and most particularly primates such as humans, chimpanzees, gorillas, macaques, and baboons, and rodents such as mice, rats, and guinea pigs.

Tissue or fluid samples are isolated from a patient according to standard methods well known to those of skill in the art, most typically by biopsy or venipuncture. The sample is optionally pretreated as necessary by dilution in an appropriate buffer solution or concentrated, if desired. Any of a number of standard aqueous buffer solutions, employing one of a variety of buffers, such as phosphate, Tris, or the like, at physiological pH can be used.

A) Immunological Binding Assays

The BoNT polypeptide (e.g., BoNT/E, BoNT/B, etc.) can be detected in an immunoassay utilizing one or more of the anti-BoNT antibodies of this invention as a capture agent that specifically binds to the BoNT polypeptide.

As used herein, an immunoassay is an assay that utilizes an antibody (e.g. a anti-BoNT/E antibody) to specifically bind an analyte (e.g., BoNT/E). The immunoassay is characterized by the binding of one or more anti-BoNT antibodies to a target (e.g. one or more BoNT/A subtypes) as opposed to other physical or chemical properties to isolate, target, and quantify the BoNT analyte.

The BoNT marker can be detected and quantified using any of a number of well recognized immunological binding assays (see, e.g., U.S. Pat. Nos. 4,366,241; 4,376,110; 4,517,288; and 4,837,168, and the like) For a review of the general immunoassays, see also *Methods in Cell Biology Volume 37: Antibodies in Cell Biology*, Asai, ed. Academic Press, Inc. New York (1993); *Basic and Clinical Immunology* 7th Edition, Stites & Ten, eds. (1991)).

The immunoassays of the present invention can be performed in any of a number of configurations (see, e.g., those reviewed in Maggio (ed.) (1980) *Enzyme Immunoassay* CRC Press, Boca Raton, Fla.; Tijan (1985) "Practice and Theory of Enzyme Immunoassays," *Laboratory Techniques in Biochemistry and Molecular Biology*, Elsevier Science Publishers B.V., Amsterdam; Harlow and Lane, supra; Chan (ed.) (1987) *Immunoassay: A Practical Guide* Academic Press, Orlando, Fla.; Price and Newman (eds.) (1991) *Principles and Practice of Immunoassays* Stockton Press, NY; and Ngo (ed.) (1988) *Non isotopic Immunoassays* Plenum Press, NY).

Immunoassays often utilize a labeling agent to specifically bind to and label the binding complex formed by the capture agent and the analyte (e.g., an anti-BoNT/E antibody/BoNT/E complex). The labeling agent can itself be one of the moieties comprising the antibody/analyte complex. Thus, for example, the labeling agent can be a labeled BoNT/E polypeptide or a labeled anti-BoNT/E antibody. Alternatively, the labeling agent is optionally a third moiety, such as another antibody, that specifically binds to the BoNT antibody, the BoNT peptide(s), the antibody/polypeptide complex, or to a modified capture group (e.g., biotin) which is covalently linked to BoNT polypeptide or to the anti-BoNT antibody.

In one embodiment, the labeling agent is an antibody that specifically binds to the anti-BoNT antibody. Such agents are well known to those of skill in the art, and most typically comprise labeled antibodies that specifically bind antibodies of the particular animal species from which the anti-BoNT antibody is derived (e.g., an anti-species antibody). Thus, for example, where the capture agent is a human derived BoNT/E antibody, the label agent may be a mouse anti-human IgG, i.e., an antibody specific to the constant region of the human antibody.

Other proteins capable of specifically binding immunoglobulin constant regions, such as streptococcal protein A or protein G are also used as the labeling agent. These proteins are normal constituents of the cell walls of streptococcal bacteria. They exhibit a strong non immunogenic reactivity with immunoglobulin constant regions from a variety of species (see generally Kronval, et al., (1973) *J. Immunol.*, 111: 1401-1406, and Akerstrom, et al., (1985) *J. Immunol.*, 135: 2589-2542, and the like).

Throughout the assays, incubation and/or washing steps may be required after each combination of reagents. Incubation steps can vary from about 5 seconds to several hours, preferably from about 5 minutes to about 24 hours. However, the incubation time will depend upon the assay format, analyte, volume of solution, concentrations, and the like. Usually, the assays are carried out at ambient temperature, although they can be conducted over a range of temperatures, such as 5° C. to 45° C.

1) Non Competitive Assay Formats.

Immunoassays for detecting BoNT neurotoxins (e.g. BoNT serotypes and/or subtypes) are, in certain embodiments, either competitive or noncompetitive. Noncompetitive immunoassays are assays in which the amount of captured analyte (in this case, BoNT polypeptide) is directly measured. In one preferred "sandwich" assay, for example, the capture agent (e.g., an anti-BoNT antibody) is bound directly or indirectly to a solid substrate where it is immobilized. These immobilized anti-BoNT antibodies capture BoNT polypeptide(s) present in a test sample (e.g., a blood sample). The BoNT polypeptide(s) thus immobilized are then bound by a labeling agent, e.g.; an anti-BoNT/E antibody bearing a label. Alternatively, the second antibody may lack a label, but it may, in turn, be bound by a labeled third antibody specific to antibodies of the species from which the second antibody is derived. Free labeled antibody is washed away and the remaining bound labeled antibody is detected (e.g., using a gamma detector where the label is radioactive).

2) Competitive Assay Formats.

In competitive assays, the amount of analyte (e.g., BoNT/E) present in the sample is measured indirectly by measuring the amount of an added (exogenous) analyte displaced (or competed away) from a capture agent (e.g., anti-BoNT/E antibody) by the analyte present in the sample. For example, in one competitive assay, a known amount of BoNT/E is added to a test sample with an unquantified amount of BoNT/E, and the sample is contacted with a capture agent, e.g., an anti-BoNT/E antibody that specifically binds BoNT/E. The amount of added BoNT/E that binds to the anti-BoNT/E-neutralizing antibody is inversely proportional to the concentration of BoNT/E present in the test sample.

The anti-BoNT/E antibody can be immobilized on a solid substrate. The amount of BoNT/E bound to the anti-BoNT/E antibody is determined either by measuring the amount of BoNT/E present in a BoNT/E-anti-BoNT/E antibody complex, or alternatively by measuring the amount of remaining uncomplexed BoNT/E.

B) Reduction of Non Specific Binding.

One of skill will appreciate that it is often desirable to reduce non specific binding in immunoassays and during analyte purification. Where the assay involves, for example BoNT/E polypeptide(s), BoNT/E-neutralizing antibody, or other capture agent(s) immobilized on a solid substrate, it is desirable to minimize the amount of non specific binding to the substrate. Means of reducing such non specific binding are well known to those of skill in the art. Typically, this involves coating the substrate with a proteinaceous composition. In particular, protein compositions such as bovine serum albumin (BSA), nonfat powdered milk, and gelatin are widely used.

C) Substrates.

As mentioned above, depending upon the assay, various components, including the BoNT polypeptide(s), anti-BoNT antibodies, etc., are optionally bound to a solid surface. Many methods for immobilizing biomolecules to a variety of solid surfaces are known in the art. For instance, the solid surface may be a membrane (e.g., nitrocellulose), a microtiter dish (e.g., PVC, polypropylene, or polystyrene), a test tube (glass or plastic), a dipstick (e.g., glass, PVC, polypropylene, polystyrene, latex, and the like), a microcentrifuge tube, or a glass, silica, plastic, metallic or polymer bead. The desired component may be covalently bound, or noncovalently attached through nonspecific bonding.

A wide variety of organic and inorganic polymers, both natural and synthetic may be employed as the material for the solid surface. Illustrative polymers include polyethylene, polypropylene, poly(4-methylbutene), polystyrene, polymethacrylate, poly(ethylene terephthalate), rayon, nylon, poly(vinyl butyrate), polyvinylidene difluoride (PVDF), silicones, polyformaldehyde, cellulose, cellulose acetate, nitrocellulose, and the like. Other materials which may be employed, include paper, glasses, ceramics, metals, metalloids, semiconductive materials, cements or the like. In addition, substances that form gels, such as proteins (e.g., gelatins), lipopolysaccharides, silicates, agarose and polyacrylamides can be used. Polymers which form several aqueous phases, such as dextrans, polyalkylene glycols or surfactants, such as phospholipids, long chain (12-24 carbon atoms) alkyl ammonium salts and the like are also suitable. Where the solid surface is porous, various pore sizes may be employed depending upon the nature of the system.

In preparing the surface, a plurality of different materials may be employed, e.g., as laminates, to obtain various properties. For example, protein coatings, such as gelatin can be used to avoid non specific binding, simplify covalent conjugation, enhance signal detection or the like.

If covalent bonding between a compound and the surface is desired, the surface will usually be polyfunctional or be capable of being polyfunctionalized. Functional groups which may be present on the surface and used for linking can include carboxylic acids, aldehydes, amino groups, cyano groups, ethylenic groups, hydroxyl groups, mercapto groups and the like. The manner of linking a wide variety of compounds to various surfaces is well known and is amply illustrated in the literature. See, for example, Immobilized Enzymes, Ichiro Chibata, Halsted Press, New York, 1978, and Cuatrecasas, (1970) *J. Biol. Chem.* 245 3059.

In addition to covalent bonding, various methods for non-covalently binding an assay component can be used. Noncovalent binding is typically nonspecific absorption of a compound to the surface. Typically, the surface is blocked with a second compound to prevent nonspecific binding of labeled assay components. Alternatively, the surface is designed such that it nonspecifically binds one component but does not significantly bind another. For example, a surface bearing a lectin such as concanavalin A will bind a carbohydrate containing compound but not a labeled protein that lacks glycosylation. Various solid surfaces for use in noncovalent attachment of assay components are reviewed in U.S. Pat. Nos. 4,447,576 and 4,254,082.

D) Other Assay Formats

BoNT polypeptides or anti-BoNT antibodies (e.g. BoNT/E neutralizing antibodies) can also be detected and quantified by any of a number of other means well known to those of skill in the art. These include analytic biochemical methods such as spectrophotometry, radiography, electrophoresis, capillary electrophoresis, high performance liquid chromatography (HPLC), thin layer chromatography (TLC), hyperdiffusion chromatography, and the like, and various immunological methods such as fluid or gel precipitin reactions, immunodiffusion (single or double), immunoelectrophoresis, radioimmunoassays (RIAs), enzyme-linked immunosorbent assays (ELISAs), immunofluorescent assays, and the like.

Western blot analysis and related methods can also be used to detect and quantify the presence of BoNT polypeptides in a sample. The technique generally comprises separating sample products by gel electrophoresis on the basis of molecular weight, transferring the separated products to a suitable solid support, (such as a nitrocellulose filter, a nylon filter, or derivatized nylon filter), and incubating the sample with the antibodies that specifically bind either the BoNT polypeptide. The antibodies specifically bind to the biological agent of interest on the solid support. These antibodies are directly labeled or alternatively are subsequently detected using labeled antibodies (e.g., labeled sheep anti-human antibodies where the antibody to a marker gene is a human antibody) which specifically bind to the antibody which binds the BoNT polypeptide.

Other assay formats include liposome immunoassays (LIAs), which use liposomes designed to bind specific molecules (e.g., antibodies) and release encapsulated reagents or markers. The released chemicals are then detected according to standard techniques (see, Monroe et al., (1986) *Amer. Clin. Prod. Rev.* 5:34-41).

E) Labeling of Anti-BoNT Anti-BoNT/E) Antibodies.

Anti-BoNT antibodies can be labeled by any of a number of methods known to those of skill in the art. Thus, for example, the labeling agent can be, e.g., a monoclonal antibody, a polyclonal antibody, a protein or complex such as those described herein, or a polymer such as an affinity matrix, carbohydrate or lipid. Detection proceeds by any known method, including immunoblotting, western analysis, gel-mobility shift assays, tracking of radioactive or bioluminescent markers, nuclear magnetic resonance, electron paramagnetic resonance, stopped-flow spectroscopy, column chromatography, capillary electrophoresis, or other methods which track a molecule based upon an alteration in size and/or charge. The particular label or detectable group used in the assay is not a critical aspect of the invention. The detectable group can be any material having a detectable physical or chemical property. Such detectable labels have been well-developed in the field of immunoassays and, in general, any label useful in such methods can be applied to the present invention. Thus, a label is any composition detectable by spectroscopic, photochemical, biochemical, immunochemical, electrical, optical or chemical means. Useful labels in the present invention include magnetic beads (e.g. DYNABEADS™), fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., LacZ, CAT, horse radish peroxidase, alkaline phosphatase and others, commonly used as detectable enzymes, either as marker gene products or in an ELISA), and colorimetric labels such as colloidal gold or colored glass or plastic (e.g. polystyrene, polypropylene, latex, etc.) beads.

The label may be coupled directly or indirectly to the desired component of the assay according to methods well known in the art. As indicated above, a wide variety of labels may be used, with the choice of label depending on the sensitivity required, ease of conjugation of the compound, stability requirements, available instrumentation, and disposal provisions.

Non radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with the labeled, naturally occurring anti-ligands. Alternatively, any haptenic or antigenic compound can be used in combination with an antibody.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems which may be used, see, U.S. Pat. No. 4,391,904, which is incorporated herein by reference.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence, e.g., by microscopy, visual inspection, via photographic film, by the use of electronic detectors such as charge coupled devices (CCDs) or photomultipliers and the like. Similarly, enzymatic labels may be detected by providing appropriate substrates for the enzyme and detecting the resulting reaction product. Finally, simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of BoNT peptides. In this case, antigen-coated particles are agglutinated by samples comprising the target antibodies. In this format, none of the components need be labeled and the presence of the target antibody is detected by simple visual inspection.

IX. Pharmaceutical Compositions.

The BoNT-neutralizing antibodies of this invention are useful in mitigating the progression of botulisum produced, e.g., by endogenous disease processes or by chemical/biological warfare agents. Typically compositions comprising one or preferably two or more different antibodies are administered to a mammal (e.g., to a human) in need thereof.

We have discovered that particularly efficient neutralization of a botulism neurotoxin (BoNT) subtype is achieved by the use of neutralizing antibodies that bind two or more subtypes of the particular BoNT serotype with high affinity. In certain embodiments, this can be accomplished by using two or more different antibodies directed against each of the subtypes and/or neutralizing antibodies that bind two or more BoNT subtypes (e.g., BoNT/A1, BoNT/A2, BoNT/A3, etc.) with high affinity.

It was also a surprising discovery that when one starts combining neutralizing antibodies that the potency of the antibody combination increases dramatically. This increase makes it possible to generate a *botulinum* antibody compositions of the required potency for therapeutic use. It was also surprising that as one begins combining two and three monoclonal antibodies, the particular BoNT epitope that is recognized becomes less important. Thus, in certain embodiments, this invention contemplates compositions comprising at least two, more preferably at least three high affinity antibodies that bind non-overlapping epitopes on the BoNT.

In certain embodiments, this invention contemplates compositions comprising two or more, preferably three or more different antibodies selected from the group consisting of 2A10, 3E1, 3E2, 3E3, 3E4, 3E4.1, 3E5, 3E6, 3E6.1, 4E11, 4E13, 4E16, 4E16.1, 4E17, 4E17.1, nA12, 6A12, B1.1, B6, B6.1, B8, B8.1, B11, B11C3, B11E8, B12, B12.1, B12.2, 1B18, 2B18.1, 4B19, and 1B22, an/or antibodies comprising one or more CDRs from these antibodies, and/or one or more antibodies comprising mutants of these antibodies.

The BoNT-neutralizing antibodies of this invention are useful for parenteral, topical, oral, or local administration, such as by aerosol or transdermally, for prophylactic and/or therapeutic treatment. The pharmaceutical compositions can be administered in a variety of unit dosage forms depending upon the method of administration. For example, unit dosage forms suitable for oral administration include powder, tablets, pills, capsules and lozenges. The antibodies comprising the pharmaceutical compositions of this invention, when administered orally, are preferably protected from digestion. This is typically accomplished either by complexing the antibodies with a composition to render them resistant to acidic and enzymatic hydrolysis or by packaging the antibodies in an appropriately resistant carrier such as a liposome. Means of protecting proteins from digestion are well known in the art.

The pharmaceutical compositions of this invention are particularly useful for parenteral administration, such as intravenous administration or administration into a body cavity or lumen of an organ. The compositions for administration will commonly comprise a solution of one or more BoNT-neutralizing antibody dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of BoNT/A-neutralizing antibody in these formulations can vary widely, and will be selected primarily based on fluid volumes, viscosities, body weight and the like in accordance with the particular mode of administration selected and the patient's needs.

Thus, a typical pharmaceutical composition for intravenous administration would be about 0.1 to 10 mg per patient per day. Dosages from about 1 mg up to about 200 mg per patient per day can be used. Methods for preparing parenterally administrable compositions will be known or apparent to those skilled in the art and are described in more detail in such publications as *Remington's Pharmaceutical Science*, 15th ed., Mack Publishing Company, Easton, Pa. (1980).

The compositions containing the BoNT-neutralizing antibodies of this invention or a cocktail thereof are generally administered for therapeutic treatments. Preferred pharmaceutical compositions are administered in a dosage sufficient to neutralize (mitigate or eliminate) the BoNT toxin(s) (i.e., reduce or eliminate a symptom of BoNT poisoning (botulism)). An amount adequate to accomplish this is defined as a "therapeutically effective dose." Amounts effective for this use will depend upon the severity of the disease and the general state of the patient's health.

Single or multiple administrations of the compositions may be administered depending on the dosage and frequency as required and tolerated by the patient. In any event, the composition should provide a sufficient quantity of the antibodies of this invention to effectively treat the patient.

X. Kits For Diagnosis or Treatment.

In another embodiment, this invention provides for kits for the treatment of botulism or for the detection/confirmation of a *Clostridium botulinum* infection. Kits will typically comprise one or more anti-BoNT antibodies (e.g., BoNT-neutralizing antibodies for pharmaceutical use) of this invention. For diagnostic purposes, the antibody(s) can optionally be labeled. In addition the kits will typically include instructional materials disclosing means of use BoNT-neutralizing antibodies in the treatment of symptoms of botulism. The kits may also include additional components to facilitate the particular application for which the kit is designed. Thus, for example, where a kit contains one or more anti-BoNT antibodies for detection of diagnosis of BoNT subtype, the antibody can be labeled, and the kit can additionally contain means of detecting the label (e.g. enzyme substrates for enzymatic labels, filter sets to detect fluorescent labels, appropriate secondary labels such as a sheep anti-human antibodies, or the like). The kits may additionally include buffers and other reagents routinely used for the practice of a particular method. Such kits and appropriate contents are well known to those of skill in the art.

In certain embodiments, kits provided for the treatment of botulisum comprise one or more BoNT neutralizing antibodies. The antibodies can be provided separately or mixed together. Typically the antibodies will be provided in a sterile pharmacologically acceptable excipient. In certain embodiments, the antibodies can be provided pre-loaded into a delivery device (e.g., a disposable syringe).

The kits can optionally include instructional materials teaching the use of the antibodies, recommended dosages, contraindications, and the like.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. An isolated antibody, or antigen-binding fragment thereof, that specifically binds an epitope of a *Botulinum* neurotoxin (BoNT), wherein the antibody or antigen-binding fragment comprises:
   a) a $V_H$ CDR1 comprising the amino acid sequence of SEQ ID NO:166;
   b) a $V_H$ CDR2 comprising the amino acid sequence of SEQ ID NO:168;
   c) a $V_H$ CDR3 comprising the amino acid sequence of SEQ ID NO:170;
   d) a $V_L$ CDR1 comprising the amino acid sequence of SEQ ID NO:271;
   e) a $V_L$ CDR2 comprising the amino acid sequence of SEQ ID NO:273; and
   f) a $V_L$ CDR3 comprising the amino acid sequence of SEQ ID NO:275.

2. A composition comprising the isolated antibody or antigen-binding fragment of claim 1 and a pharmaceutically acceptable carrier.

3. The isolated antibody or antigen-binding fragment of claim 1, wherein said antibody is a humanized antibody.

4. The isolated antibody or antigen-binding fragment of claim 1, wherein said antibody is a human monoclonal antibody.

5. The isolated antibody or antigen-binding fragment of claim 1, wherein said antibody is a single chain Fv (scFv), Fab, (Fab')$_2$ or (scFv')$_2$.

6. The isolated antibody or antigen-binding fragment of claim 1, wherein said antibody is an IgG.

7. A method of specifically binding a *botulinum* neurotoxin in a mammal, said method comprising administering to said mammal the isolated antibody or antigen-binding fragment of claim 1.

8. A kit for specifically binding a *Botulinum* neurotoxin, said kit comprising:
   a composition according to claim 1.

9. The isolated antibody or antigen-binding fragment of claim 1, wherein said antibody comprises:
   a heavy chain comprising the amino acid sequence of SEQ ID NO:52.

10. A composition comprising the isolated antibody or antigen-binding fragment of claim 9 and a pharmaceutically acceptable carrier.

11. The isolated antibody or antigen-binding fragment of claim 9, wherein said antibody is a humanized antibody.

12. The isolated antibody or antigen-binding fragment of claim 9, wherein said antibody is a human monoclonal antibody.

13. The isolated antibody or antigen-binding fragment of claim 9, wherein said antibody is a single chain Fv (scFv), Fab, (Fab)$_2$ or (scFv')$_2$.

14. The isolated antibody or antigen-binding fragment of claim 9, wherein said antibody is an IgG.

15. A method of specifically binding a *botulinum* neurotoxin in a mammal, said method comprising administering to said mammal the isolated antibody or antigen-binding fragment of claim 9.

16. A kit for specifically binding a *Botulinum* neurotoxin, said kit comprising:
   a composition according to claim 9.

17. The isolated antibody or antigen-binding fragment of claim 1, wherein said antibody comprises:
   a light chain comprising the amino acid sequence of SEQ ID NO:67.

18. The isolated antibody or antigen-binding fragment of claim 1, wherein said antibody comprises:
   a) a heavy chain comprising the amino acid sequence of SEQ ID NO:52; and
   b) a light chain comprising the amino acid sequence of SEQ ID NO:67.

19. A composition comprising the isolated antibody or antigen-binding fragment of claim 18 and a pharmaceutically acceptable carrier.

20. The isolated antibody or antigen-binding fragment of claim 18, wherein said antibody is a humanized antibody.

21. The isolated antibody or antigen-binding fragment of claim 18, wherein said antibody is a human monoclonal antibody.

22. The isolated antibody or antigen-binding fragment of claim 18, wherein said antibody is a single chain Fv (scFv), Fab, (Fab')$_2$ or (scFv')$_2$.

23. The isolated antibody or antigen-binding fragment of claim 18, wherein said antibody is an IgG.

24. A method of specifically binding a *botulinum* neurotoxin in a mammal, said method comprising administering to said mammal the isolated antibody or antigen-binding fragment of claim 18.

25. A kit for specifically binding a *Botulinum* neurotoxin, said kit comprising:
   a composition according to claim 18.

* * * * *